United States Patent
Bugdahn et al.

(10) Patent No.: US 12,303,468 B2
(45) Date of Patent: *May 20, 2025

(54) COMPOSITIONS COMPRISING ONE OR MORE (BIO)-ALKANEDIOLS WITH ANTIOXIDANTS

(71) Applicant: Symrise AG, Holzminden (DE)

(72) Inventors: Nikolas Bugdahn, Holzminden (DE); Sven Siegel, Hoexter (DE); Sabine Lange, Holzminden (DE); Dominik Stuhlmann, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/009,298

(22) PCT Filed: Dec. 9, 2021

(86) PCT No.: PCT/EP2021/084953
§ 371 (c)(1),
(2) Date: Dec. 8, 2022

(87) PCT Pub. No.: WO2022/122896
PCT Pub. Date: Jun. 16, 2022

(65) Prior Publication Data
US 2023/0293408 A1  Sep. 21, 2023

(30) Foreign Application Priority Data

Dec. 9, 2020 (WO) .................. PCT/EP2020/085172

(51) Int. Cl.
| | | |
|---|---|---|
| A61K 31/047 | (2006.01) | |
| A61K 8/34 | (2006.01) | |
| A61K 8/35 | (2006.01) | |
| A61K 8/37 | (2006.01) | |
| A61K 8/39 | (2006.01) | |
| A61K 8/42 | (2006.01) | |
| A61K 8/43 | (2006.01) | |

(Continued)

(52) U.S. Cl.
CPC ............ *A61K 31/047* (2013.01); *A61K 8/345* (2013.01); *A61K 8/347* (2013.01); *A61K 8/35* (2013.01); *A61K 8/375* (2013.01); *A61K 8/39* (2013.01); *A61K 8/42* (2013.01); *A61K 8/43* (2013.01); *A61K 8/4946* (2013.01); *A61K 8/671* (2013.01); *A61K 8/676* (2013.01); *A61K 8/678* (2013.01); *A61K 8/9789* (2017.08); *A61K 8/9794* (2017.08); *A61K 31/07* (2013.01); *A61K 31/167* (2013.01); *A61K 31/198* (2013.01); *A61K 31/222* (2013.01); *A61K 31/23* (2013.01); *A61K 31/355* (2013.01); *A61K 31/375* (2013.01); *A61K 31/4172* (2013.01); *A61K 31/658* (2023.05); *A61K 36/82* (2013.01); *A61K 36/9068* (2013.01); *A61K 47/08* (2013.01); *A61K 47/10* (2013.01); *A61K 47/14* (2013.01); *A61K 47/18* (2013.01); *A61K 47/183* (2013.01); *A61K 47/22* (2013.01); *A61K 47/46* (2013.01); *A61P 17/18* (2018.01); *A61Q 5/006* (2013.01); *A61Q 5/02* (2013.01); *A61Q 5/12* (2013.01); *A61Q 9/02* (2013.01); *A61Q 15/00* (2013.01); *A61Q 17/04* (2013.01); *A61Q 19/002* (2013.01); *A61Q 19/007* (2013.01); *A61Q 19/02* (2013.01); *A61Q 19/08* (2013.01); *A61K 2800/10* (2013.01); *A61K 2800/49* (2013.01); *A61K 2800/522* (2013.01); *A61K 2800/524* (2013.01); *A61K 2800/5922* (2013.01)

(58) Field of Classification Search
None
See application file for complete search history.

(56) References Cited

U.S. PATENT DOCUMENTS

| | | |
|---|---|---|
| 8,945,516 B2 | 2/2015 | Tamarkin et al. |
| 10,738,265 B2 | 8/2020 | Company |

(Continued)

FOREIGN PATENT DOCUMENTS

| | | | |
|---|---|---|---|
| AU | 2010100972 A4 | 10/2010 | |
| EP | 852949 A2 | 7/1998 | |
| EP | 1206933 B1 * | 5/2006 | ............. A61K 47/10 |
| EP | 2774481 A1 | 9/2014 | |
| EP | 2842607 A1 | 4/2015 | |

(Continued)

*Primary Examiner* — Robert A Wax
*Assistant Examiner* — Quanglong N Truong
(74) *Attorney, Agent, or Firm* — McDonnell Boehnen Hulbert & Berghoff LLP

(57) ABSTRACT

The present invention is in the field of antioxidants and relates to cosmetic or pharmaceutical, preferably dermatological, compositions or homecare product comprising or consisting of a synergistic combination of a specific antioxidant and an effective amount of 1,2-heptanediol and/or 2,3-heptanediol or of a specific alkanediol or a mixture of two or more different specific alkanediols and the use of said compositions as a cosmetic, for personal care, as a pharmaceutical or homecare product, in particular for scavenging reactive oxygen species (ROS), for inhibition matrix metalloproteinases expression and/or for inhibiting interleukin 8 (IL-8) secretion. Additionally, the present invention relates to the use of 1,2-heptanediol and/or 2,3-heptanediol or of a specific alkanediol or a mixture of two or more different specific alkanediols for enhancing the antioxidative effect of an antioxidant in a cosmetic or pharmaceutical, preferably dermatological, composition or homecare product, and/or for enhancing the antioxidative effect of a cosmetic or pharmaceutical, preferably dermatological, composition upon application.

8 Claims, 21 Drawing Sheets

(51) Int. Cl.
*A61K 8/49* (2006.01)
*A61K 8/67* (2006.01)
*A61K 8/9789* (2017.01)
*A61K 8/9794* (2017.01)
*A61K 31/00* (2006.01)
*A61K 31/07* (2006.01)
*A61K 31/167* (2006.01)
*A61K 31/198* (2006.01)
*A61K 31/222* (2006.01)
*A61K 31/23* (2006.01)
*A61K 31/355* (2006.01)
*A61K 31/375* (2006.01)
*A61K 31/4172* (2006.01)
*A61K 36/82* (2006.01)
*A61K 36/9068* (2006.01)
*A61K 47/08* (2006.01)
*A61K 47/10* (2017.01)
*A61K 47/14* (2017.01)
*A61K 47/18* (2017.01)
*A61K 47/22* (2006.01)
*A61K 47/46* (2006.01)
*A61P 17/18* (2006.01)
*A61Q 5/00* (2006.01)
*A61Q 5/02* (2006.01)
*A61Q 5/12* (2006.01)
*A61Q 9/02* (2006.01)
*A61Q 15/00* (2006.01)
*A61Q 17/04* (2006.01)
*A61Q 19/00* (2006.01)
*A61Q 19/02* (2006.01)
*A61Q 19/08* (2006.01)

(56) References Cited

U.S. PATENT DOCUMENTS

| | | | |
|---|---|---|---|
| 2005/0222276 | A1 | 10/2005 | Schmaus et al. |
| 2014/0142175 | A1 | 5/2014 | S. A. |
| 2015/0258079 | A1 | 9/2015 | Neufang et al. |
| 2015/0342854 | A1* | 12/2015 | Shibuya ............... A61K 8/9761 424/769 |
| 2018/0207068 | A1 | 7/2018 | Doering |
| 2019/0166834 | A1 | 6/2019 | Thomas et al. |
| 2019/0241491 | A1 | 8/2019 | Burgo et al. |
| 2020/0189995 | A1 | 6/2020 | Burgo et al. |

FOREIGN PATENT DOCUMENTS

| | | | |
|---|---|---|---|
| JP | 2007161668 | A | 6/2007 |
| JP | 2014172908 | A | 9/2014 |
| JP | 2016104809 | A | 6/2016 |
| JP | 2018090631 | A | 6/2018 |
| JP | 2019500381 | A | 1/2019 |
| JP | 2019048796 | A | 3/2019 |
| WO | 2004026840 | A1 | 4/2004 |
| WO | 2004047833 | A2 | 6/2004 |
| WO | 2006069953 | A1 | 7/2006 |
| WO | 2010149798 | A2 | 12/2010 |
| WO | 2018099570 | A1 | 6/2018 |
| WO | 2018154145 | A2 | 8/2018 |
| WO | 2019152569 | A2 | 8/2019 |
| WO | 2019185923 | A1 | 10/2019 |
| WO | 2020043269 | A1 | 3/2020 |
| WO | 2020160905 | A1 | 8/2020 |

* cited by examiner

COMPOSITIONS COMPRISING ONE OR MORE (BIO)-ALKANEDIOLS WITH ANTIOXIDANTS

CROSS-REFERENCE TO RELATED APPLICATIONS

This application is the US national phase under 35 U.S.C. § 371 of International Application No. PCT/EP2021/084953, filed Dec. 9, 2021, which claims priority to International Application No. PCT/EP2020/085172, filed Dec. 9, 2020, the contents of each of which are hereby incorporated by reference in their entirety.

TECHNICAL FIELD

The present invention is in the field of antioxidants and relates to cosmetic or pharmaceutical, preferably dermatological, compositions or homecare products comprising or consisting of a synergistic combination of a specific antioxidant and an effective amount of 1,2-heptanediol and/or 2,3-heptanediol or of a specific alkanediol or a mixture of two or more different specific alkanediols and the use of said compositions as a cosmetic, for personal care, as a pharmaceutical or a homecare product, in particular for scavenging reactive oxygen species (ROS), for inhibition matrix metalloproteinases expression and/or for inhibiting interleukin 8 (IL-8) secretion. Additionally, the present invention relates to the use of 1,2-heptanediol and/or 2,3-heptanediol or of a specific alkanediol or a mixture of two or more different specific alkanediols for enhancing the antioxidative effect of an antioxidant in a cosmetic or pharmaceutical, preferably dermatological, composition or homecare product, and/or for enhancing the antioxidative effect of a cosmetic or pharmaceutical, preferably dermatological, composition upon application.

BACKGROUND ART

Oxidation of lipids, primarily unsaturated fatty acids, in cosmetic or pharmaceutical or food is a key factor that needs to be controlled and prevented, because it affects both the nutritional value of the product and the health of the consumer. Oxidation of unsaturated fatty acids by the action of atmospheric oxygen begins with free radical chain reactions, generating highly reactive peroxides and hydroperoxides.

In turn, these peroxides and hydroperoxides react with substrates present in the matrix and result in carboxylic acids, aldehydes and ketones, among other, which alter the sensory properties of the productions and potentially compromise the consumer health. For this reason, antioxidants are widely used by the industry to prevent or delay the onset of oxidative breakdown.

Oxidative cell damage, particularly damage to the genetic material, is one of the most dangerous environmental influences, constituting a particular danger to the human organism. High-energy radiation, particularly in combination with oxygen, creates highly reactive radicals which are also referred to as "reactive oxygen species (ROS)", which are, for example, capable of changing the DNA such that thymine is oxidized to form thymine glycol, or guanine is oxidized to form 8-oxoguanine (8-OxoG). Specifically, the latter one is an aggressive mutagenic substance, because during the replication opposite an 8-OxoG both the normal cytosine nucleotide and, preferably, an adenine nucleotide may be incorporated. Incorrect transversion is one of the causes of cell defects and, eventually, of cancer. Oxidative stress triggered by ROS will also lead to accelerated skin ageing, which is regularly observed when people excessively expose themselves to UV radiation (for example, in tanning centers).

It is therefore obvious that there is considerable interest in protecting the human organism against such oxidative damage. For example, this may be performed by administering substances which quench radicals, whereby these so-called antioxidants can be ingested orally, either together with the food or separately as dietary supplements, or be topically applied, for example, in cosmetic products that are brought in contact with the skin.

Various natural or synthetic substances have proven their effectiveness as antioxidants. Besides vitamin C (ascorbic acid) the most well-known include the different carotene derivatives (e.g. beta carotene, lycopene, luteine) and, particularly, vitamin E and its derivatives (tocopherol, tocopheryl acetate and tocopheryl palmitate). Another important group is constituted by the polyphenols, specifically the anthocyanins and isoflavones, which are contained, for example, in a variety of red fruits.

There is continued interest in the market to improve both the potential and the range of efficiency of such antioxidants, either by achieving a higher performance with the same amounts or, vice versa, by achieving the same performance with lower amounts.

When searching for antioxidant agents it must be taken into account that the substances used in the cosmetic or pharmaceutical sector must be toxicologically acceptable, well tolerated by the skin, stable, especially in the customary cosmetic and/or pharmaceutical formulations, substantially and preferably odourless and able to be prepared inexpensively, i.e. using standard methods.

However, there is no clear dependency between the chemical structure of a substance, on the one hand, and its capability in reducing autoxidation, on the other hand, which makes the search for suitable substances more difficult. Furthermore, there is no predictable relationship between antioxidant performance, toxicological acceptability, tolerability and the stability of a substance.

It is therefore an object of the present invention to provide a cosmetic or pharmaceutical, preferably dermatological, composition or homecare product comprising an antioxidant such that is shows an increased antioxidant performance either in order to prevent the composition itself from oxidation or to protect the human organism, for example skin, upon application against oxidative damage.

A further object of the present invention is to provide a substance, which enhances the antioxidative effect of an antioxidant, for example in a cosmetic or pharmaceutical, preferably dermatological, composition, and/or which enhance the antioxidative effect of a cosmetic or pharmaceutical, preferably dermatological, composition upon application.

Furthermore, it is an object of the present invention to provide a substance by which the amount of an antioxidant in a cosmetic or pharmaceutical, preferably dermatological, composition or homecare product can be reduced.

Surprisingly it has been found that the addition of an effective amount of 1,2-heptanediol and/or 2,3-heptanediol or a specific alkanediol or a mixture of two or more different specific alkanediols as defined herein to a composition comprising an antioxidant show a strong synergy with respect to the antioxidant performance as demonstrated by the tests in the following examples.

Additionally, it has been observed that the overall amount of antioxidant in a composition comprising an antioxidant can be significantly reduced by the addition of an effective amount of 1,2-heptanediol and/or 2,3-heptanediol or a specific alkanediol or a mixture of two or more different specific alkanediols as defined herein.

SUMMARY OF THE INVENTION

In order to accomplish the above problem, the present invention provides in a first aspect a cosmetic or pharmaceutical, preferably dermatological, composition or homecare product, comprising or consisting of
- (a1) 1,2-heptanediol;
- (b1) at least one antioxidant; and
- (c1) optionally at least one active substance for a cosmetic or pharmaceutical composition or homecare product and/or additive;

or
- (a2) 2,3-heptanediol;
- (b2) at least one antioxidant; and
- (c2) optionally at least one active substance for a cosmetic or pharmaceutical composition or homecare product and/or additive;

or
- (a3) a mixture comprising 1,2-heptanediol and 2,3-heptanediol;
- (b3) at least one antioxidant; and
- (c3) optionally at least one active substance for a cosmetic or pharmaceutical composition or homecare product and/or additive.

In a second aspect, the present invention provides a cosmetic or pharmaceutical composition or homecare product, comprising or consisting of
- (a) at least one linear alkanediol having a carbon chain of 5 to 14 carbon atoms or a mixture comprising at least one first linear alkanediol having a carbon chain of 5 to 14 carbon atoms and one or more second linear alkanediol having a carbon chain of 5 to 14 carbon atoms which is different from the first linear alkanediol;
- (b) at least one antioxidant; and
- (c) optionally at least one active substance for a cosmetic or pharmaceutical composition or homecare product and/or additive.

In a further aspect, the present invention provides for the use of the composition as a cosmetic, for personal care, in particular for skin, hair, scalp and nail care, as a pharmaceutical, as a homecare product or for animal care.

In a further aspect, the present invention provides for the use of 1,2-heptanediol and/or 2,3-heptanediol or at least one linear alkanediol or a mixture comprising at least one first linear alkanediol and one or more second linear alkanediol for enhancing the antioxidative effect of an antioxidant in a cosmetic or pharmaceutical composition or homecare product and/or for enhancing the antioxidative effect of a cosmetic or pharmaceutical composition or homecare product upon application, and/or for enhancing the ROS scavenging performance of an antioxidant as defined in claim 10; and/or for enhancing the inhibition of the interleukin 8 (IL-8) secretion by an antioxidant; and/or for enhancing the inhibition of the matrix metal proteinases expression by an antioxidant.

DETAILED DESCRIPTION OF THE INVENTION

Figure 1A:
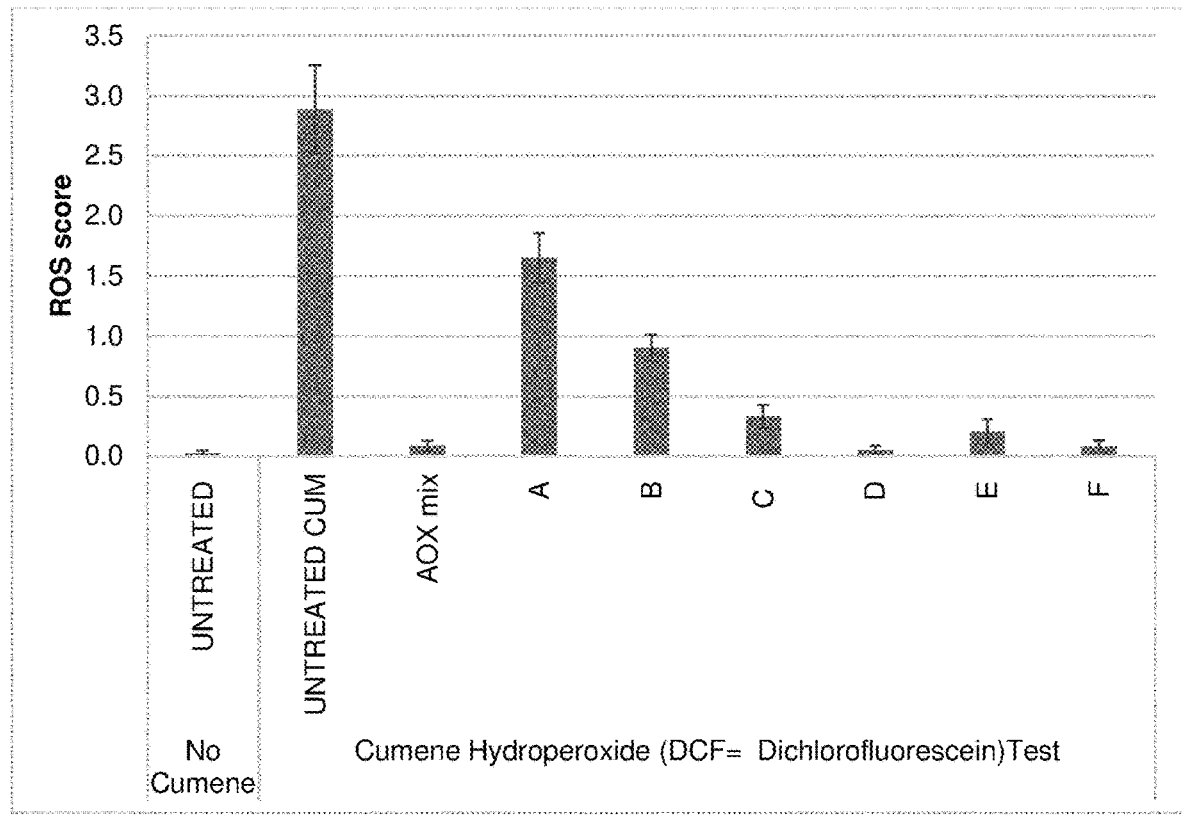
FIGS. 1a and 1b are diagrams showing the ROS scores of different compositions comprising tocopherol and/or a 1,2-alkanediol or a 2,3-alkanediol according to the present invention in a lipophilic test system.

The present invention is specified in the appended claims. The invention itself, and its preferred variants, other objects and advantages, are however also apparent from the following detailed description in conjunction with the accompanying examples and figures.

In a first aspect, the present invention relates to a cosmetic or pharmaceutical composition or homecare product, comprising or consisting of:
(a1) 1,2-heptanediol;
(b2) at least one antioxidant; and
(c3) optionally at least one active substance for a cosmetic or pharmaceutical composition or homecare product and/or additive.

Alternatively, the present invention relates in a first aspect to a cosmetic or pharmaceutical composition or homecare product, comprising or consisting of:
(a2) 2,3-heptanediol;
(b2) at least one antioxidant; and
(c2) optionally at least one active substance for a cosmetic or pharmaceutical composition or homecare product and/or additive.

In a further alternative, the present invention relates in a first aspect to a cosmetic or pharmaceutical composition or homecare product, comprising or consisting of:

(a1) a mixture comprising 1,2-heptanediol and 2,3-heptanediol;
(b2) at least one antioxidant; and
(c3) optionally at least one active substance for a cosmetic or pharmaceutical composition or homecare product and/or additive.

In a second aspect, the present invention relates to a cosmetic or pharmaceutical composition or homecare product, comprising or consisting of:
(a) at least one linear alkanediol having a carbon chain of 5 to 14 carbon atoms or a mixture comprising at least one first linear alkanediol having a carbon chain of 5 to 14 carbon atoms and one or more second linear alkanediol having a carbon chain of 5 to 14 carbon atoms which is different from the first linear alkanediol;
(b) at least one antioxidant; and
(c) optionally at least one active substance for a cosmetic or pharmaceutical composition or homecare product and/or additive.

In a more preferred variant of the second aspect of the present invention, the present invention relates to a cosmetic or pharmaceutical composition, comprising or consisting of:
(a') a mixture comprising at least one first linear alkanediol having a carbon chain of 5 to 14 carbon atoms and one or more second linear alkanediol having a carbon chain of 5 to 14 carbon atoms, wherein the number of the carbon atoms of the first and the second alkanediol is either same or different;
(b') at least one antioxidant; and
(c') optionally at least one active substance for a cosmetic or pharmaceutical composition or homecare product and/or additive.

The term "comprising" means that the named components are essential, but other components may be added and is still embraced by the present invention.

The term "consisting of" as used according to the present invention means that the total amount of components (a) to (c) adds up to 100% by weight, based on the total weight of the cosmetic or pharmaceutical composition or homecare product, and signifies that the subject matter is closed-ended and can only include the limitations that are expressly recited.

Whenever reference is made to "comprising" it is intended to cover both meanings as alternatives, that is the meaning can be either "comprising" or "consisting of", unless the context dictates otherwise.

The term "at least one . . . " means that the cosmetic or pharmaceutical composition or homecare product according to the present invention can comprise either one or a mixture of two, three, four, five, six or even more different of the respective components following said term.

The term "optionally" means that the subsequently described compound may but need not to be present in the composition, and that the description includes variants, were the compound is included or variants, were the compound is absent.

Alkanediols are glycols, i.e. any of a class of organic compounds belonging to the alcohol family; in the molecule of a glycol, two hydroxyl (—OH) groups are attached to different carbon atoms of a carbon chain.

The component (a) in the cosmetic or pharmaceutical composition or homecare product according to the first aspect of the present invention is either 1,2-heptanediol (a1) or 2,3-heptanediol (a2), or a mixture of both heptanediols, i.e. 1,2-heptanediol plus 2,3-heptanediol (a3).

1,2-heptandediol belongs to the category of alkanediols and is a straight chain alkanediol with the general formula:

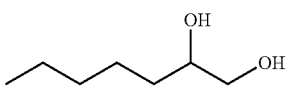

It has a carbon chain with 7 carbon atoms and the two functional OH groups of the alkanediol are in alpha, beta position and chemically bonded to the C1 and C2 carbon atoms in the alkanediol chain.

2,3-heptanediol belongs to the category of alkanediols and is a straight chain alkanediol with the general formula:

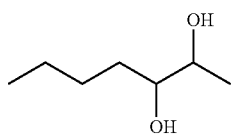

It has a carbon chain with 7 carbon atoms and the two functional OH groups of the alkanediol are in beta,gamma position and chemically bonded to the C2 and C3 carbon atoms in the alkanediol chain.

Straight chain 1,2-alkanediols have been used for more than 15 years as multifunctional actives. Short chain 1,2-alkanediols are amphiphilic compounds and thus, like 1,2-pentanediol and 1,2-hexanediol, are soluble both in water and cosmetic oils. In contrast, 1,2-octanediol tends to precipitate or recrystallize in oily solutions. On the other hand, 1,2-decanediol is a solid and soluble only in cosmetic oils. Apart from moisturizing, some 1,2-alkanediols are used as viscosity modifiers.

The component (a) in the cosmetic or pharmaceutical composition or homecare product according to the second aspect of the present invention is in a first alternative at least one linear alkanediol having a carbon chain of 5 to 14 carbon atoms.

Moreover, in a second alternative of this second aspect, the component (a) may include a first linear alkanediol in combination with a second linear alkanediol, preferably at least one first linear alkanediol having a carbon chain of 5 to 14 carbon atoms and at least one second linear alkanediol having a carbon chain of 5 to 14 carbon atoms. Therefore, the invention also entails a mixture of a first and a second alkanediol as described herein.

Since the first linear alkanediol of the invention can be selected from the same lists and types of compounds as the linear alkanediol according to the first alternative of the second aspect, in the following, reference is made to the linear alkanediol in general, which can also be the first linear alkanediol. In mixtures of first and second linear alkanediols, where these are specifically different, the specific terms "first" and "second" will be used to distinguish the two alkanediol components.

As used in this document, the phrase "at least one linear alkanediol" or "at least one first linear alkanediol" means that the composition can comprise one linear alkanediol having a carbon chain of 5 to 14 carbon atoms or can comprise one first linear alkanediol having a carbon chain of 5 to 14 carbon atoms or can comprise more than one linear alkanediol or can comprise more than one first linear alkanediol having a carbon chain of 5 to 14 carbon atoms, i.e. two, three, four or more different linear alkanediols or first linear alkanediols having a carbon chain of 5 to 14 carbon atoms.

The linear alkanediol or the first linear alkanediol consist of a chain of 5 to 14 carbon atoms joined to each other by single covalent bonds with two OH functional groups attached to two different carbon atoms in the chain.

The at least one linear alkanediol or the at least one first linear alkanediol having a carbon chain of 5 to 14 carbon atoms in the cosmetic or pharmaceutical composition or homecare product according to the second aspect of the present invention is preferably selected from the group consisting of pentanediol, hexanediol heptanediol, octanediol, nonanediol, decanediol, undecanediol, dodecanediol, tridecanediol, tetradecanediol, and mixtures thereof.

In a preferred variant, the at least one linear alkanediol or the at least one first linear alkanediol is selected from the group consisting of pentanediol, hexanediol, heptanediol, octanediol, nonanediol, decanediol, undecanediol, dodecanediol and tridecanediol.

In a more preferred variant, the at least one linear alkanediol or the at least one first linear alkanediol is selected from the group consisting of alkanediols having an uneven number of carbon atoms of 5 to 13, i.e. pentanediol, heptanediol, nonanediol, undecanediol and tridecanediol.

In a still more preferred variant, the at least one linear alkanediol or the at least one first linear alkanediol is selected from the group consisting of alkanediols having an uneven number of carbon atoms of 7, 9, 11 and 13, i.e. heptanediol, nonanediol, undecanediol and tridecanediol, or is selected from the group consisting of alkanediols having an uneven number of carbon atoms of 9 and 11, i.e. nonanediol and undecanediol, or is selected from the group consisting of alkanediols having an uneven number of carbon atoms of 9 and 13, i.e. nonanediol and tridecanediol, or is selected from the group consisting of alkanediols having an uneven number of carbon atoms of 11 and 13, i.e. undecanediol and tridecanediol.

In a still more preferred variant, the at least one linear alkanediol or the at least one first linear alkanediol is either pentanediol, hexanediol, heptanediol, nonanediol or octanediol.

In a most preferred variant, the at least one linear alkanediol or the at least first linear alkanediol is heptanediol or nonanediol.

In an alternative, the cosmetic or pharmaceutical composition or homecare product according to the second aspect of the present invention comprises a mixture comprising at least one first linear alkanediol having a carbon chain of 5 to 14 carbon atoms with one or more second linear alkanediol having a carbon chain of 5 to 14 carbon atoms which is different from the first linear alkanediol.

This means that the alkanediol mixture is a mixture of at least one first linear alkanediol having a carbon chain of 5 to 14 carbon atoms and one or more, i.e., two, three, four or more second linear alkanediol having a carbon chain of 5 to 14 carbon atoms. In this alternative, the first linear alkanediol can be any of the alkanediols as described herein for the linear alkanediol in general and in particular for the first alternative of the second aspect.

For example, the mixture can include one first linear alkanediol with one, two, three or more second linear alkanediols; or the mixture can include two first linear alkanediols with one, two, three or more second linear alkanediols, etc. with the proviso, that in each mixture, the first linear alkanediol and the second linear alkanediol are different from each other.

The phrase "different from each other means" that the first linear alkanediol and the second linear alkanediol in the mixture are either different with regard to the length of their carbon chain, i.e., number of the carbon atoms, and/or with regard to their constitutional isomerism or with regard to their stereoisomerism.

Likewise, the number of the carbon atoms of the first linear alkanediol and the second linear alkanediol in the mixture can also be same. For example, the first linear alkanediol and the second linear alkanediol have a carbon chain of 7 carbon atoms, but the first linear alkanediol and the second linear alkanediol are different with regard to their constitutional isomerism or with regard to their stereoisomerism.

The second linear alkanediol preferably consists of a chain of 5 to 14 carbon atoms joined to each other by single covalent bonds with two OH functional groups attached to two different carbon atoms in the chain.

The at least one second linear alkanediol having a carbon chain of 5 to 14 carbon atoms in the cosmetic or pharmaceutical composition or homecare product according to the second aspect of the present invention is selected from the group consisting of pentanediol, hexanediol, heptanediol, octanediol, nonanediol, decanediol, undecanediol, dodecanediol, tridecanediol and tetradecanediol.

In a preferred variant, the at least one second linear alkanediol is selected from the group consisting of pentanediol, hexanediol, heptanediol, octanediol, nonanediol, decanediol, undecanediol, dodecanediol and tridecanediol. If both the first and the second alkanediol is for example heptanediol, then the second linear alkanediol heptanediol is a different constitutional isomer or stereoisomer from the first linear alkanediol.

In a more preferred variant, the at least one second linear alkanediol is selected from the group consisting of pentanediol, hexanediol, heptanediol, octanediol and nonanediol, most preferably heptanediol, octanediol and nonanediol.

The term "alkanediol" within the context of the present invention also includes its constitutional isomers or position isomers. Constitutional isomers are compounds that have the same molecular formula and different connectivity. Position isomers, a particular form of constitutional isomerism, are structural isomers that can be viewed as differing only on the position of a functional group on a parent structure, which in this case is the position of the two alcohol functions.

Depending on the number of the carbon atoms of the carbon chain of the alkanediol, there are various position isomers of the alkanediol: (x,x+1) constitutional isomers; (x,x+2) constitutional isomers; (x,x+3) constitutional isomers; etc. and alpha,omega constitutional isomers when the alcohol functions are at the terminal ends of the carbon chain, wherein x stands for the number of the carbon atom in the alkanediol chain, to which the OH groups of the alkanediol are chemically bonded. For example: if x is 1, the two OH groups of the alkanediol are chemically bonded to the C1 and C2 carbon atoms in the alkanediol chain; if x is 2, the two OH groups of the alkanediol are chemically bonded to the C2 and C3 carbon atoms in the alkanediol chain, etc.

In the (x,x+1) constitutional isomers, the two OH functional groups are vicinal attached to two different adjacent carbon atoms in the chain. In the (x,x+2) constitutional isomers, the two OH functional groups are attached to two different carbon atoms in the chain where the two carbon atoms are separated by one C atom. In the (x,x+3) constitutional isomers, the two OH functional groups are attached to two different carbon atoms in the chain where the two carbon atoms are separated by two C atoms. In the alpha, omega constitutional isomers, the two functional groups are attached to the first C atom and to the terminal C atom.

In a preferred variant of the cosmetic or pharmaceutical composition or homecare product according to the second aspect of the present invention, the linear alkanediol having a carbon chain of 5 to 14 carbon atoms, is preferably a vicinal (x,x+1) diol, selected from the group consisting of a 1,2-diol, 2,3-diol, 3,4-diol, 4,5-diol, further (x,x+1) diols, and mixtures thereof, preferably an alpha,beta 1,2 constitutional isomer.

In a preferred variant of the cosmetic or pharmaceutical composition or homecare product according to the second aspect of the present invention, the first linear alkanediol and/or the second linear alkanediol having a carbon chain of 5 to 14 carbon atoms is a vicinal (x,x+1) diol, selected from the group consisting of a 1,2-diol, 2,3-diol, 3,4-diol, 4,5-diol, further (x,x+1) diols, and mixtures thereof, preferably an alpha,beta 1,2 constitutional isomer.

In a further preferred variant of the cosmetic or pharmaceutical composition or homecare product according to the second aspect of the present invention, the linear alkanediol having a carbon chain of 5 to 14 carbon atoms, is preferably a non-vicinal (x,x+2) diol, selected from the group consisting of a 1,3-diol, 2,4-diol, 3,5-diol, further (x,x+2) diols, and mixtures thereof, preferably an alpha,gamma 1,3 constitutional isomer.

In a preferred variant of the cosmetic or pharmaceutical composition or homecare product according to the second aspect of the present invention, the first linear alkanediol and/or the second linear alkanediol having a carbon chain of 5 to 14 carbon atoms is a non-vicinal (x,x+2) diol, selected from the group consisting of a 1,3-diol, 2,4-diol, 3,5-diol, 4,6-diol, further (x,x+2) diols, and mixtures thereof, preferably an alpha,gamma 1,3-consitutional isomer.

In a further preferred variant of the cosmetic or pharmaceutical composition or homecare product according to the second aspect of the present invention, the linear alkanediol having a carbon chain of 5 to 14 carbon atoms, is preferably a non-vicinal (x,x+3) diol, selected from the group consisting of a 1,4 diol, 2,5 diol, further (x,x+3) diols, and mixtures thereof, preferably an alpha,delta 1,4 constitutional isomer.

In a preferred variant of the cosmetic or pharmaceutical composition or homecare product according to the second aspect of the present invention, the first linear alkanediol and/or the second linear alkanediol having a carbon chain of 5 to 14 carbon atoms is a non-vicinal (x,x+3) diol, selected from the group consisting of a 1,4 diol, 2,5 diol, further (x,x+3) diols, and mixtures thereof, preferably an alpha,delta 1,4 constitutional isomer.

In a preferred variant of the cosmetic or pharmaceutical composition or homecare product according to the second aspect of the invention, the linear alkanediol or the first linear alkanediol and/or the second linear alkanediol is preferably an alpha,omega alkanediol, more preferably, 1,7-heptanediol or 1,8-octanediol.

According to the present invention, vicinal (x,x+1) diols are most preferred, such as alpha,beta or beta,gamma or gamma,delta etc.

Particularly preferred are non-vicinal (x,x+2) diols such as alpha,gamma, beta,delta etc. due to their steric arrangement optimum of the two OH groups and the conjugate system resulting therefrom, which makes them particularly suitable for stabilizing or quenching or scavenging of the radicals generated in oxidative processes as described above.

In a still preferred variant of the cosmetic or pharmaceutical composition or homecare product according to the second aspect of the present invention, the linear alkanediol and in particular the first linear alkanediol and/or the second linear alkanediol, is a 1,2-alkanediol, a 2,3-alkanediol, a 3,4-alkanediol, a 1,3-alkanediol, or mixtures thereof, more preferred a 2,3-alkanediol or a 1,3-alkanediol.

The 1,2-alkanediols of the linear alkanediol, in particular the first linear alkanediol having a carbon chain of 5 to 14 carbon atoms and/or the second linear alkanediol having a carbon chain of 5 to 14 carbon atoms, can preferably be those as represented by the following formulae:

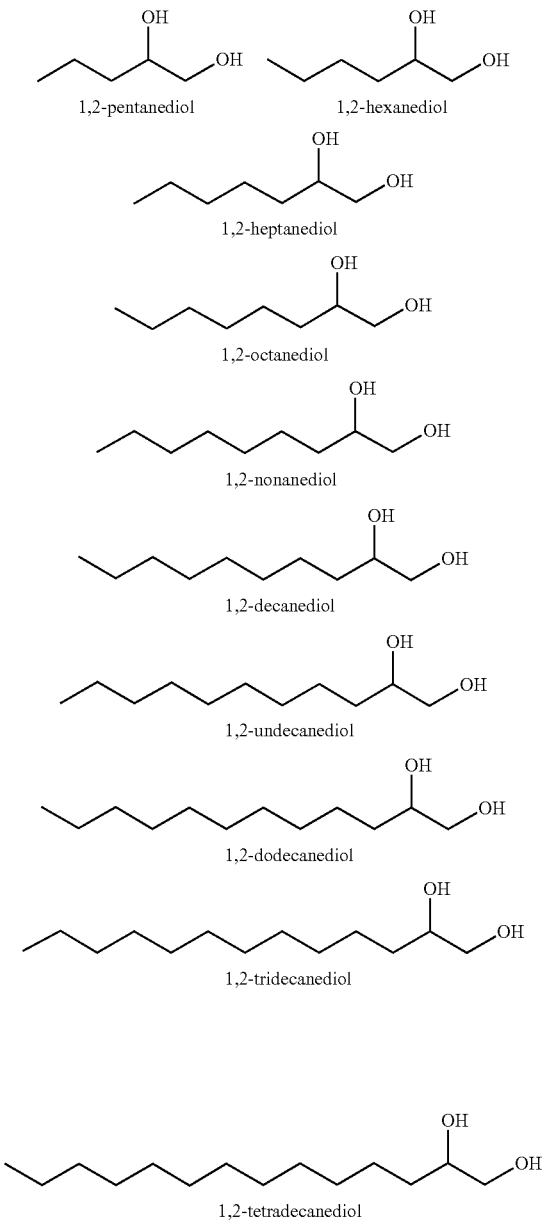

The 2,3-alkanediols of the linear alkanediol of the invention, in particular the first linear alkanediol having a carbon chain of 5 to 14 carbon atoms and/or the second linear alkanediol having a carbon chain of 5 to 14 carbon atoms, can preferably be those as represented by the following formulae:

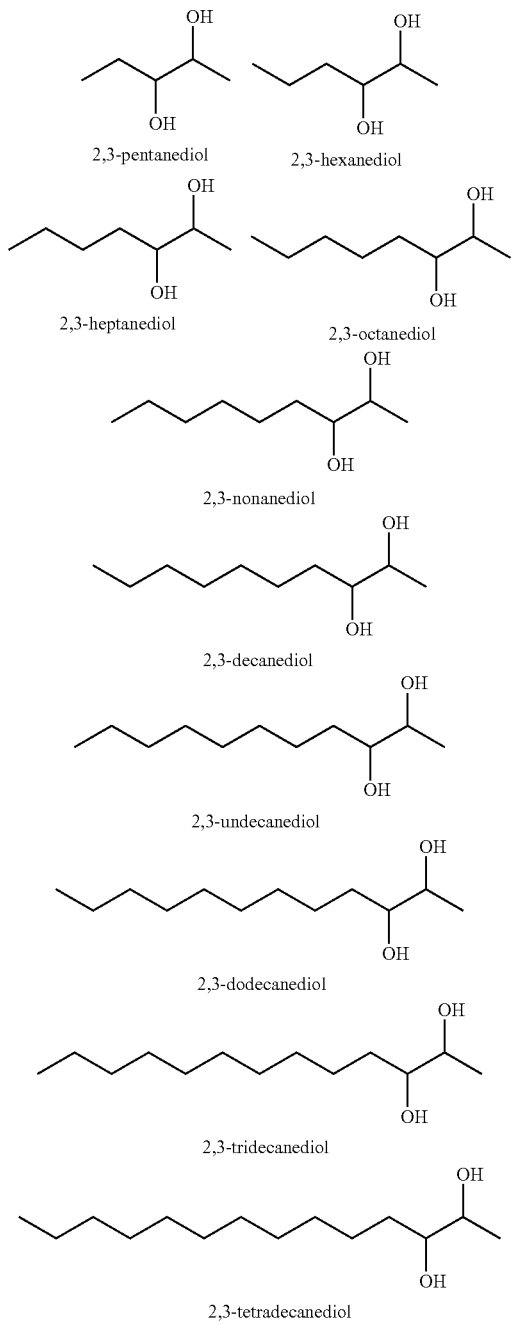

The 3,4-alkanediols of the linear alkanediol, preferably the first linear alkanediol having a carbon chain of 5 to 14 carbon atoms and/or the second linear alkanediol having a carbon chain of 5 to 14 carbon atoms, can preferably be those as represented by the following formulae:

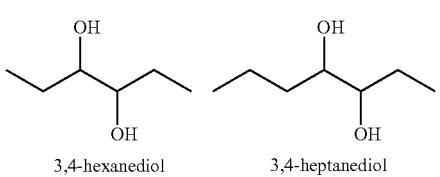

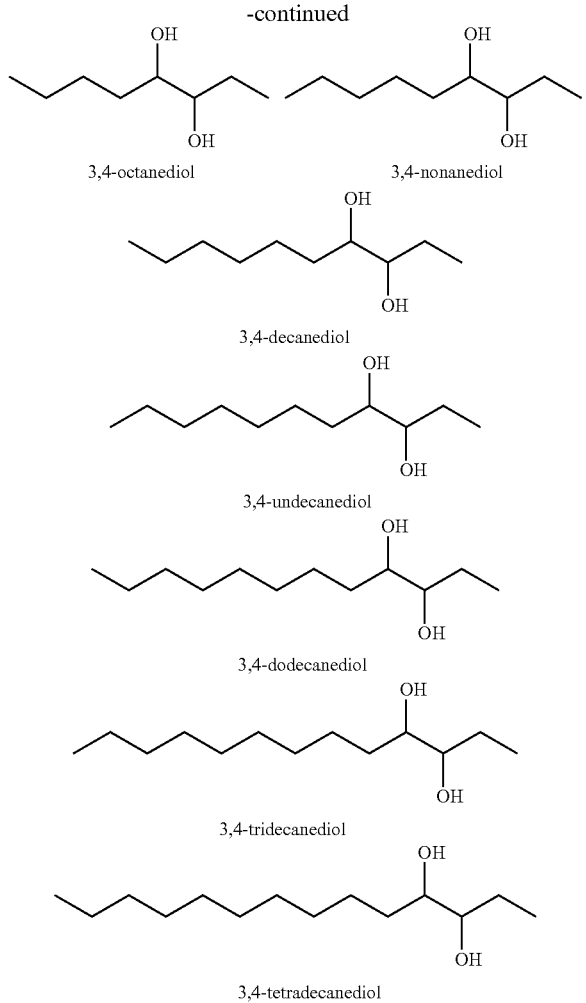

3,4-octanediol
3,4-nonanediol
3,4-decanediol
3,4-undecanediol
3,4-dodecanediol
3,4-tridecanediol
3,4-tetradecanediol In a preferred variant, the cosmetic or pharmaceutical composition according to the second aspect of the present invention comprises a mixture comprising at least one first linear alkanediol having a carbon chain of 5 to 14 carbon atoms and one or more second linear alkanediol having a carbon chain of 5 to 14 carbon atoms wherein the number of the carbon atoms of the first and the second alkanediol is either same or different.

If both, the first and the second alkanediol have the same number of carbon atoms, such an alkanediol combination is herein also referred to as "homo alkanediol mixture" or "homo combination". For example, the first linear alkanediol and the second linear alkanediol have a carbon chain of 7 carbon atoms, but the first linear alkanediol and the second linear alkanediol are different with regard to their constitutional isomerism or with regard to their stereoisomerism.

If the first and the second alkanediol have a different number of carbon atoms, such an alkanediol combination is herein also referred to as "hetero alkanediol mixture" or "hetero combination". For example, the first linear alkanediol has a carbon chain of 7 carbon atoms and the second linear alkanediol has a carbon chain of 8 carbon atoms. However, beyond that, the first linear alkanediol and the second linear alkanediol can be different with regard to their constitutional isomerism or with regard to their stereoisomerism.

In a preferred variant of the cosmetic or pharmaceutical composition or homecare product according to the second aspect of the present invention, the linear alkanediol or the first linear alkanediol is selected from the group consisting of: 1,2-pentanediol, 2,3-pentanediol, 3,4-pentanediol, 1,3-pentanediol, 1,2-hexanediol, 2,3-hexanediol, 3,4-hexanediol, 1,3-hexanediol, 1,2-heptanediol, 2,3-heptanediol, 3,4-heptanediol, 1,3-heptanediol, 1,2-octanediol, 2,3-octanediol, 3,4-octanediol, 1,3-octanediol, 1,2-nonanediol, 2,3-nonanediol, 3,4-nonanediol, 1,3-nonanediol, 1,2-decanediol, 2,3-decanediol, 3,4-decanediol, 1,3-decanediol, 1,2-undecanediol, 2,3-undecanediol, 3,4-undecanediol, 1,3-undecanediol, 1,2-dodecanediol, 2,3-dodecanediol, 3,4-dodecanediol, 1,3-dodecanediol, 1,2-tridecanediol, 2,3-tridecanediol, 3,4-tridecanediol, 1,3-tridecanediol, and mixtures thereof.

Of the aforesaid linear alkanediols or the first linear alkanediols, the following (x,x+1) constitutional isomers are preferred: 1,2-pentanediol, 2,3-pentanediol, 1,2-hexanediol, 2,3-hexanediol, 1,2-heptanediol, 2,3-heptanediol, 2,3-octanediol, 2,3-nonanediol, 2,3-decanediol, 2,3-undecanediol, 2,3-dodecanediol, 2,3-tridecanediol or mixtures thereof. Said alkanediols are liquid at a purity of 90 to 99%.

Of the aforesaid liquid alkanediols 1,2-pentanediol, 2,3-pentanediol, 1,2-hexanediol, 2,3-hexanediol, 1,2-heptanediol, 2,3-heptanediol, 2,3-octanediol, 2,3-nonanediol or mixtures of said liquid alkanediols are particularly preferred. Said alkanediols can be easier incorporated into semi-finished products or final products containing an antioxidant.

Of the aforesaid linear alkanediols or the first linear alkanediols, the following (x,x+2) constitutional isomers are preferred: 1,3-octanediol, 1,3-nonanediol, 1,3-decanediol, or 1,3-undecanediol, most preferred 1,3-nonanediol or 1,3-undecanediol.

In a more preferred variant, the at least one linear alkanediol or the at least one first linear alkanediol is selected from the group consisting of 1,2-alkanediols having an uneven number of carbon atoms of 5 to 13, i.e. 1,2-pentanediol, 1,2-heptanediol, 1,2-nonanediol, 1,2-undecanediol and 1,2-tridecanediol.

In a more preferred variant, the linear alkanediol or the first linear alkanediol is selected from the group consisting of 1,2-alkanediols having an uneven number of carbon atoms of 7, 9, 11 and 13, i.e. 1,2-heptanediol, 1,2-nonanediol, 1,2-undecanediol or 1,2-tridecanediol, or is selected from the group consisting of 1,2-alkanediols having an uneven number of carbon atoms of 9 and 11, i.e. 1,2-nonanediol and 1,2-undecanediol, or is selected from the group consisting of 1,2-alkanediols having an uneven number of carbon atoms of 9 and 13, i.e. 1,2-nonanediol and 1,2-tridecanediol, or is selected from the group consisting of 1,2-alkanediols having an uneven number of carbon atoms of 11 and 13, i.e. 1,2-undecanediol and 1,2-tridecanediol.

In a more preferred variant, the at least one linear alkanediol or the at least one first linear alkanediol is selected from the group consisting of 2,3-alkanediols having an uneven number of carbon atoms of 5 to 13, i.e. 2,3-pentanediol, 2,3-heptanediol, 2,3-nonanediol, 2,3-undecanediol and 2,3-tridecanediol.

In a still more preferred variant, the linear alkanediol or the first linear alkanediol is selected from the group consisting of 2,3-alkanediols having an uneven number of carbon atoms of 7, 9, 11 and 13, i.e. 2,3-heptanediol, 2,3-nonanediol, 2,3-undecanediol or 2,3-tridecanediol, or is selected from the group consisting of 2,3-alkanediols having an uneven number of carbon atoms of 9 and 11, i.e. 2,3-nonanediol and 2,3-undecanediol, or is selected from the group consisting of 2,3-alkanediols having an uneven number of carbon atoms of 9 and 13, i.e. 2,3-nonanediol and 2,3-tridecanediol, or is selected from the group consisting of 2,3-alkanediols having an uneven number of carbon atoms of 11 and 13, i.e. 2,3-undecanediol and 2,3-tridecanediol.

In a further preferred variant of the cosmetic or pharmaceutical composition or homecare product according to the second aspect of the present invention, the linear alkanediol or the first linear alkanediol is selected from the group consisting of: 1,2-pentanediol, 2,3-pentanediol, 3,4-pentanediol, 1,2-hexanediol, 2,3-hexanediol, 3,4-hexanediol 1,2-heptanediol, 2,3-heptanediol, 3,4-heptanediol, 1,2-octanediol, 2,3-octanediol, 3,4-octanediol, 1,2nonanediol, 2,3-nonanediol, 3,4-nonanediol, and mixtures thereof.

More preferred, in the cosmetic or pharmaceutical composition or homecare product according to the second aspect of the present invention, the linear alkanediol or the first linear alkanediol is selected from the group consisting of 1,2-pentanediol, 2,3-pentanediol and mixtures thereof or is selected from the group consisting of 1,2-heptanediol, 2,3-heptanediol, 3,4-heptanediol, and mixtures thereof. However, the linear alkanediol or the first linear alkanediol can also preferably be selected from the group consisting of 1,2-octanediol, 2,3-octanediol, 3,4-octanediol, and mixtures thereof.

Even more preferred, in the cosmetic or pharmaceutical composition or homecare product according to the second aspect of the present invention, the linear alkanediol or the first linear alkanediol is an alpha,beta or a beta,gamma diol as either 1,2-heptanediol, 2,3-heptanediol, or a mixture thereof. However, the linear alkanediol or the first linear alkanediol can also preferably be an alpha,beta or a beta,gamma 1,2-octanediol, 2,3-octanediol, or a mixture thereof. A mixture comprising 1,2-heptanediol and 2,3-octanediol or a mixture of 1,2-octanediol and 2,3-heptanediol is also possible.

Most preferred, the linear alkanediol or the first linear alkanediol is 1,2-heptanediol or 1,2-octanediol.

Likewise, in a further preferred variant of the cosmetic or pharmaceutical composition or homecare product according to the second aspect of the present invention, the linear alkanediol or the first linear alkanediol is selected from the group consisting of:
1,2-nonanediol, 2,3-nonanediol, 3,4-nonanediol,
1,2-decanediol, 2,3-decanediol, 3,4-decanediol,
1,2-undecanediol, 2,3-undecanediol, 3,4-undecanediol, and mixtures thereof.

More preferred, in the cosmetic or pharmaceutical composition or homecare product according to the second aspect of the present invention, the linear alkanediol or the first linear alkanediol is selected from the group consisting of 1,2-nonanediol, 2,3-nonanediol, 3,4-nonanediol, and mixtures thereof, or can also be preferably selected from the group consisting of 1,2-decanediol, 2,3-decanediol, 3,4-decanediol, and mixtures thereof, or can also be preferably selected from the group consisting of 1,2-undecanediol, 2,3-undecanediol, 3,4-undecanediol, and mixtures thereof.

Even more preferred, in the cosmetic or pharmaceutical composition or homecare product according to the second aspect of the present invention, the linear alkanediol or the first linear alkanediol is an alpha,beta or a beta,gamma diol as either 1,2-nonanediol, 2,3-nonanediol, or a mixture thereof. However, the linear alkanediol or the first linear alkanediol can also preferably be 1,2-decanediol, 2,3-decanediol, or a mixture thereof.

Additionally, the linear alkanediol or the first linear alkanediol can also preferably be 1,2-undecanediol, 2,3-undecanediol, or a mixture thereof. A mixture of 1,2-nonanediol and/or 2,3-decanediol and/or 2,3-undecanediol or a mixture of 1,2-decanediol and/or 2,3-nonanediol and/or 2,3-undecanediol or a mixture of 1,2-undecanediol and/or 2,3-nonanediol and 2,3-decanediol is also possible.

In a preferred variant of the cosmetic or pharmaceutical composition or homecareproduct according to the second aspect of the present invention, the second linear alkanediol is selected from the group consisting of:
1,2-pentanediol, 2,3-pentanediol, 3,4-pentanediol, 1,3-pentanediol,
1,2-hexanediol, 2,3-hexanediol, 3,4-hexanediol, 1,3-hexanediol,
1,2-heptanediol, 2,3-heptanediol, 3,4-heptanediol, 1,3-heptanediol,
1,2-octanediol, 2,3-octanediol, 3,4-octanediol, 1,3-octanediol,
1,2-nonanediol, 2,3-nonanediol, 3,4-nonanediol, 1,3-nonanediol,
1,2-decanediol, 2,3-decanediol, 3,4-decanediol, 1,3-decanediol,
1,2-undecanediol, 2,3-undecanediol, 3,4-undecanediol, 1,3-undecanediol,
1,2-dodecanediol, 2,3-dodecanediol, 3,4-dodecanediol, 1,3-dodecanediol,
1,2-tridecanediol, 2,3-tridecanediol, 3,4-tridecanediol, 1,3-tridecanediol, and mixtures thereof.

Of the aforesaid second linear alkanediols, the following (x,x+1) constitutional isomers are preferred: 1,2-pentanediol, 2,3-pentanediol, 1,2-hexanediol, 2,3-hexanediol, 1,2-heptanediol, 2,3-heptanediol, 2,3-octanediol, 2,3-nonanediol, 2,3-decanediol, 2,3-undecanediol, 2,3-dodedcanediol, or 2,3-tridecanediol. Said alkanediols are liquid at a purity of 90 to 99%.

Of the aforesaid liquid alkanediols 1,2-pentanediol, 2,3-pentanediol, 1,2-hexanediol, 2,3-hexanediol, 1,2-heptanediol, 2,3-heptanediol, 2,3-octanediol, 2,3-nonanediol or mixtures of said liquid alkanediols are particularly preferred. Said alkanediols can be easier incorporated into semi-finished products or final products containing an antioxidant.

Of the aforesaid linear alkanediols or the first linear alkanediols, the following (x,x+2) constitutional isomers are particularly preferred: 1,3-octanediol, 1,3-nonanediol, 1,3-decanediol, or 1,3-undecanediol, most preferred 1,3-nonanediol or 1,3-undecanediol.

In a more preferred variant, the second linear alkanediol is selected from the group consisting of 1,2-alkanediols having an uneven number of carbon atoms of 5 to 13, i.e. 1,2-pentanediol, 1,2-heptanediol, 1,2-nonanediol, 1,2-undecanediol and 1,2-tridecanediol.

In a more preferred variant, the second linear alkanediol is selected from the group consisting of 1,2-alkanediols having an uneven number of carbon atoms of 7, 9, 11 and 13, i.e. 1,2-heptanediol, 1,2-nonanediol, 1,2-undecanediol and 1,2-tridecanediol, or is selected from the group consisting of 1,2-alkanediols having an uneven number of carbon atoms of 9 and 11, i.e. 1,2-nonanediol and 1,2-undecanediol, or is selected from the group consisting of 1,2-alkanediols having an uneven number of carbon atoms of 9 and 13, i.e. 1,2-nonanediol and 1,2-tridecanediol, or is selected from the group consisting of 1,2-alkanediols having an uneven number of carbon atoms of 11 and 13, i.e. 1,2-undecanediol and 1,2-tridecanediol.

In a more preferred variant, the second linear alkanediol is selected from the group consisting of 2,3-alkanediols having an uneven number of carbon atoms of 5 to 13, i.e. 2,3-pentanediol, 2,3-heptanediol, 2,3-nonanediol, 2,3-undecanediol and 2,3-tridecanediol.

In a still more preferred variant, the second linear alkanediol is selected from the group consisting of 2,3-alkanediols having an uneven number of carbon atoms of 7, 9, 11 and 13, i.e. 2,3-heptanediol, 2,3-nonanediol, 2,3-undecanediol and 2,3-tridecanediol, or is selected from the group consisting of 2,3-alkanediols having an uneven number of carbon atoms of 9 and 11, i.e. 2,3-nonanediol and 2,3-undecanediol, or is selected from the group consisting of 2,3-alkanediols having an uneven number of carbon atoms of 9 and 13, i.e. 2,3-nonanediol and 2,3-tridecanediol, or is selected from the group consisting of 2,3-alkanediols having an uneven number of carbon atoms of 11 and 13, i.e. 2,3-undecanediol and 2,3-tridecanediol.

In a more preferred variant of the cosmetic or pharmaceutical composition or homecare product according to the second aspect of the present invention, the second linear alkanediol is selected from the group consisting of:
1,2-pentanediol, 2,3-pentanediol, 3,4-pentanediol,
1,2-hexanediol, 2,3-hexanediol, 3,4-hexanediol,
1,2-heptanediol, 2,3-heptanediol, 3,4-heptanediol,
1,2-octanediol, 2,3-octanediol, 3,4-octanediol,
1,2-nonanediol, 2,3-nonanediol, 3,4-nonanediol, and mixtures thereof.

More preferred, in the cosmetic or pharmaceutical composition or homecare product according to the second aspect of the present invention, the second linear alkanediol is selected from the group consisting of 1,2-pentanediol, 2,3-pentanediol, 3,4-pentanediol, and mixtures thereof. However, the second linear alkanediol can also preferably be selected from the group consisting of 1,2-hexanediol, 2,3-hexanediol, 3,4-hexanediol, and mixtures thereof or can also preferably be selected from the group consisting of 1,2-heptanediol, 2,3-heptanediol, 3,4-heptanediol, and mixtures thereof.

Even more preferred, in the cosmetic or pharmaceutical composition according to the second aspect of the present invention, the second linear alkanediol is an alpha,beta or a beta,gamma diol as either 1,2-pentanediol, 2,3-pentanediol or a mixture thereof. However, the second linear alkanediol can also preferably be 1,2-hexanediol or 2,3-hexanediol or a mixture thereof. A mixture comprising 1,2-pentanediol and 2,3-hexanediol or a mixture comprising 2,3-pentanediol and 1,2-hexanediol is also possible.

Most preferred, the second linear alkanediol is 1,2-pentanediol or 2,3-pentanediol or 1,2-hexanediol or 2,3-hexanediol or 1,2-heptanediol or 2,3-heptanediol or 2,3-octanediol or 2,3-nonanediol.

In a particularly preferred variant, the cosmetic or pharmaceutical composition or homecare product according to the second aspect of the present invention which comprises a mixture or a combination comprising at least one first linear alkanediol and one or more second linear alkanediol includes any one of the following mixtures/combinations:
a mixture comprising 1,2-pentanediol and 2,3-pentanediol;
a mixture comprising 1,2-hexanediol and 2,3-hexanediol;
a mixture comprising 1,2-heptanediol and 2,3-heptanediol;
a mixture comprising 1,2-octanediol and 2,3-octanediol;
a mixture comprising 1,2-nonanediol and 2,3-nonanediol;
a mixture comprising 1,2-decanediol and 2,3-decanediol;
a mixture comprising 1,2-undecanediol and 2,3-undecanediol;
a mixture comprising 1,2-dodecanediol and 2,3-dodecanediol; or
a mixture comprising 1,2-tridecanediol and 2,3-tridecanediol.

In said homo alkanediol mixtures the first linear alkanediol and the second linear alkanediol have the same number of carbon atoms.

Particularly favorable is a combination including 1,2-heptanediol in combination with 2,3-heptanediol and/or 3,4-heptanediol, or a combination including 1,2-octanediol in combination with 2,3-octanediol and/or 3,4-octanediol, or a combination including 1,2-nonanediol in combination with 2,3-nonanediol and/or 3,4-nonanediol.

The addition of an alkanediol mixture according to the second aspect of the present invention, comprising a 1,2-alkanediol and a 2,3-alkanediol and as specified above to a composition comprising an antioxidant result in considerably reduced ROS scores. In other words: the composition according to the first or second aspect of the present invention comprising an antioxidant plus a blend of 1,2-alkanediol and a 2,3-alkanediol has a significant increased antioxidative capacity and shows an improved ROS scavenging efficacy in comparison to the corresponding single 1,2-alkanediol or 2,3-alkanediol substances. The beneficial antioxidative properties are demonstrated by the following examples.

Said antioxidative effect is found for the homo mixture including 1,2-pentanediol and 2,3-pentanediol and leads to a better ROS score.

The same effect can also be observed for the homo mixture including 1,2-hexanediol and 2,3-hexanediol.

The homo mixture including 1,2-heptanediol and 2,3-heptanediol is also beneficial due to its improved ROS scavenging effect which results in a reduced ROS score.

The alkanediol mixture comprising 1,2-octanediol and 2,3-octanediol or an alkanediol mixture comprising 1,2-nonanediol and 2,3-nonanediol are particularly advantageous, since have also a remarkable ROS scavenging effect.

Also the alkanediol mixture comprising 1,2-decanediol and 2,3-decanediol or the alkanediol mixture comprising 1,2-undecanediol and 2,3-undecanediol show a significant antioxidative capacity.

An improved antioxidative effect is also true for an alkanediol mixture including 1,2-dodecanediol and 2,3-dodecanediol or an alkanediol mixture including 1,2-tridecanediol and 2,3-tridecanediol. The mixtures of said alkanediol mixture and an antioxidant result in a better ROS score.

The afore specified homo alkane diol mixtures including a 1,2-alkanediol and the corresponding 2,3-alkanediol display a significant antioxidative capacity when used with an antioxidant. This means that the composition is more stable against oxidative degradation.

Hence, a stable cosmetic or pharmaceutical formulation or homecare product can be obtained. With improvement of the storage stability the shelf life of the cosmetic or pharmaceutical preparation composition or homecare product can be considerably prolonged.

Additionally, with the admixture of the corresponding liquid 2,3-alkanediol, even in small amounts, to a solid 1,2-alkanediol, the solid 1,2-alkanedioles, such as 1,2-octanediol, 1,2-nonanediol etc., can be solved, resulting in a liquid alkanediol mixture. The 2,3-alkanediol serves as solvent for the solid 1,2-alkanediols. Such liquid mixtures have the benefit that firstly the availability of the solid 1,2-alkanediol in the mixture is improved and secondly the incorporation of the solid 1,2-alkanediol in semi-finished products or final products is facilitated. This effect is particularly favorably for emulsions, in which lipophilic 1,2-alkanediols having a carbon chain of 8 or more carbon atoms, when used alone, tend to migrate into the oil phase or tend to precipitate or recrystallize.

With the solution of the solid 1,2-octanediol in the liquid 2,3-octanediol or of the solid 1,2-nonanediol in the liquid 2,3-nonanediol, the availability of the 1,2-octanediol or 1,2-nonanediol can be likewise improved in the end use.

Thus, with the afore-mentioned properties of the specified alkanediol mixtures including a 1,2-alkanediol and the respective 2,3-alkanediol the processability in formulations can be improved.

Hence, a good compromise can be achieved when the alkanediol mixture is combined in such a way as to maintain the antioxidative effect, while improving processability in formulations. The above specified 1,2-alkanediol and corresponding 2,3-alkanediol combinations solve this balancing problem over the 1,2-alkanediol substances or 2,3-alkanediol substances alone. This is well achieved by combinations such as comprising 1,2-pentanediol and 2,3-pentanediol but also for 1,2-hexanediol and 2,3-hexandiol. Also, combinations such as comprising 1,2-heptanediol and 2,3-heptanediol, but also 1,2-octanediol and 2,3-octanediol show this effect. The same also counts for 1,2-nonanediol in combination with 2,3-nonanediol, but also for 1,2-decanediol in combination with 2,3-decanediol.

The afore specified homo alkanediol mixtures including a 1,2-alkanediol and the corresponding 2,3-alkanediol display a remarkably synergistic antioxidative efficacy and are clearly superior to the individually corresponding 1,2-alkanediols or 2,3-alkanediols and having the same concentration.

In a particularly preferred variant, the cosmetic or pharmaceutical composition according to the second aspect of the present invention which comprises a mixture or a combination comprising at least one first linear alkanediol and one or more second linear alkanediol thus includes any one of the following combinations:

1,2-pentanediol in combination with one of 1,2-hexanediol, 1,2-heptanediol, 1,2-octanediol, 1,2-nonanediol, 1,2-decanediol, 1,2-undecanediol, 1,2-doedecanediol, or 1,2-tridecanediol;

1,2-hexanediol in combination with one of 1,2-pentanediol, 1,2-heptanediol, 1,2-octanediol, 1,2-nonanediol, 1,2-decanediol, 1,2-undecanediol, 1,2-doedecanediol, or 1,2-tridecanediol;

1,2-heptanediol in combination with one of 1,2-pentanediol, 1,2-hexanediol, 1,2-octanediol, 1,2-nonanediol, 1,2-decanediol, 1,2-undecanediol, 1,2-doedecanediol, or 1,2-tridecanediol;

1,2-octanediol in combination with one of 1,2-pentanediol, 1,2-hexanediol, 1,2-heptanediol, 1,2-nonanediol, 1,2-decanediol, 1,2-undecanediol, 1,2-doedecanediol, or 1,2-tridecanediol;

1,2-nonanediol in combination with one of 1,2-pentanediol, 1,2-hexanediol, 1,2-heptanediol, 1,2-octanediol, 1,2-decanediol, 1,2-undecanediol, 1,2-doedecanediol, or 1,2-tridecanediol;

1,2-decanediol in combination with one of 1,2-pentanediol, 1,2-hexanediol, 1,2-heptanediol, 1,2-octanediol, 1,2-nonanediol, 1,2-undecanediol, 1,2-doedecanediol, or 1,2-tridecanediol;

1,2-undecanediol in combination with one of 1,2-pentanediol, 1,2-hexanediol, 1,2-heptanediol, 1,2-octanediol, 1,2-nonanediol, 1,2-decanediol, 1,2-dodecanediol, or 1,2-tridecanediol;

1,2-dodecanediol in combination with one of 1,2-pentanediol, 1,2-hexanediol, 1,2-heptanediol, 1,2-octanediol, 1,2-nonanediol, 1,2-decanediol, 1,2-undecanediol, or 1,2-tridecanediol;

1,2-tridecanediol in combination with one of 1,2-pentanediol, 1,2-hexanediol, 1,2-heptanediol, 1,2-octanediol, 1,2-nonanediol, 1,2-decanediol, 1,2-undecanediol, or 1,2-doedecanediol;

2,3-pentanediol in combination with one of 1,2-hexanediol, 1,2-heptanediol, 1,2-octanediol, 1,2-nonanediol, 1,2-decanediol, 1,2-undecanediol, 1,2-doedecanediol, or 1,2-tridecanediol;

2,3-hexanediol in combination with one of 1,2-pentanediol, 1,2-heptanediol, 1,2-octanediol, 1,2-nonanediol, 1,2-decanediol, 1,2-undecanediol, 1,2-doedecanediol, or 1,2-tridecanediol;

2,3-heptanediol in combination with one of 1,2-pentanediol, 1,2-hexanediol, 1,2-octanediol, 1,2-nonanediol, 1,2-decanediol, 1,2-undecanediol, 1,2-doedecanediol, or 1,2-tridecanediol;

2,3-octanediol in combination with one of 1,2-pentanediol, 1,2-hexanediol, 1,2-heptanediol, 1,2-nonanediol, 1,2-decanediol, 1,2-undecanediol, 1,2-doedecanediol, or 1,2-tridecanediol;

2,3-nonanediol in combination with one of 1,2-pentanediol, 1,2-hexanediol, 1,2-heptanediol, 1,2-octanediol, 1,2-decanediol, 1,2-undecanediol, 1,2-doedecanediol, or 1,2-tridecanediol;

2,3-decanediol in combination with one of 1,2-pentanediol, 1,2-hexanediol, 1,2-heptanediol, 1,2-octanediol, 1,2-nonanediol, 1,2-undecanediol, 1,2-doedecanediol, or 1,2-tridecanediol;

2,3-undecanediol in combination with one of 1,2-pentanediol, 1,2-hexanediol, 1,2-heptanediol, 1,2-octanediol, 1,2-nonanediol, 1,2-decanediol, 1,2-dodecanediol, or 1,2-tridecanediol;

2,3-dodecanediol in combination with one of 1,2-pentanediol, 1,2-hexanediol, 1,2-heptanediol, 1,2-octanediol, 1,2-nonanediol, 1,2-decanediol, 1,2-undecanediol, or 1,2-tridecanediol; or 2,3-tridecanediol in combination with one of 1,2-pentanediol, 1,2-hexanediol, 1,2-heptanediol, 1,2-octanediol, 1,2-nonanediol, 1,2-decanediol, 1,2-undecanediol, or 1,2-dodecanediol;

2,3-pentanediol in combination with one of 2,3-hexanediol, 2,3-heptanediol, 2,3-octanediol, 2,3-nonanediol, 2,3-decanediol, 2,3-undecanediol, 2,3-dodecanediol, or 2,3-tridecanediol;

2,3-hexanediol in combination with one of 2,3-pentanediol, 2,3-heptanediol, 2,3-octanediol, 2,3-nonanediol, 2,3-decanediol, 2,3-undecanediol, 2,3-dodecanediol, or 2,3-tridecanediol;

2,3-heptanediol in combination with one of 2,3-pentanediol, 2,3-hexanediol, 2,3-octanediol, 2,3-nonanediol, 2,3-decanediol, 2,3-undecanediol, 2,3-dodecanediol, or 2,3-tridecanediol;

2,3-octanediol in combination with one of 2,3-pentanediol, 2,3-hexanediol, 2,3-heptanediol, 2,3-nonanediol, 2,3-decanediol, 2,3-undecanediol, 2,3-dodecanediol, or 2,3-tridecanediol;

2,3-nonanediol in combination with one of 2,3-pentanediol, 2,3-hexanediol, 2,3-heptanediol, 2,3-octanediol, 2,3-decanediol, 2,3-undecanediol, 2,3-dodecanediol, or 2,3-tridecanediol;

2,3-decanediol in combination with one of 2,3-pentanediol, 2,3-hexanediol, 2,3-heptanediol, 2,3-octanediol, 2,3-nonanediol, 2,3-undecanediol, 2,3-dodecanediol, or 2,3-tridecanediol;

2,3-undecanediol in combination with one of 2,3-pentanediol, 2,3-hexanediol, 2,3-heptanediol, 2,3-octanediol, 2,3-nonanediol, 2,3-decanediol, 2,3-dodecanediol, or 2,3-tridecanediol;

2,3-dodecanediol in combination with one of 2,3-pentanediol, 2,3-hexanediol, 2,3-heptanediol, 2,3-octanediol, 2,3-nonanediol, 2,3-decanediol, 2,3-undecanediol, or 2,3-tridecanediol; or 2,3-tridecanediol in combination with one of 2,3-pentanediol, 2,3-hexanediol, 2,3-heptanediol, 2,3-octanediol, 2,3-nonanediol, 2,3-decanediol, 2,3-undecanediol, or 2,3-dodecanediol.

In a particular preferred variant, the cosmetic or pharmaceutical composition or homecare product according to the second aspect of the present invention which comprises a mixture or a combination comprising at least one first linear alkanediol and one or more second linear alkanediol thus may include any of the following mixtures/combinations:

a mixture comprising 1,2-heptanediol and 1,2-pentanediol;
a mixture comprising 1,2-heptanediol and 1,2-hexanediol;
a mixture comprising 1,2-heptanediol and 1,2-octanediol;
a mixture comprising 1,2-heptanediol and 1,2-nonanediol;
a mixture comprising 1,2-heptanediol and 1,2-decanediol;
a mixture comprising 1,2-heptanediol and 1,2-undecanediol;
a mixture comprising 1,2-heptanediol and 1,2-dodecanediol; or a mixture comprising 1,2-heptanediol and 1,2-tridecanediol.

In a particular preferred variant, the cosmetic or pharmaceutical composition or homecare product according to the second aspect of the present invention which comprises a mixture or a combination comprising at least one first linear alkanediol and one or more second linear alkanediol thus may include any of the following mixtures/combinations:

a mixture comprising 1,2-heptanediol and 2,3-pentanediol;
a mixture comprising 1,2-heptanediol and 2,3-hexanediol;
a mixture comprising 1,2-heptanediol and 2,3-octanediol;
a mixture comprising 1,2-heptanediol and 2,3-nonanediol;
a mixture comprising 1,2-heptanediol and 2,3-decanediol;
a mixture comprising 1,2-heptanediol and 2,3-undecanediol;
a mixture comprising 1,2-heptanediol and 2,3-dodecanediol; or a mixture comprising 1,2-heptanediol and 2,3-tridecanediol.

In a particular preferred variant, the cosmetic or pharmaceutical composition or homecare product according to the second aspect of the present invention which comprises a mixture or a combination comprising at least one first linear alkanediol and one or more second linear alkanediol thus may include any of the following mixtures/combinations:

1,2-pentanediol and 2,3-pentanediol;
1,2-pentanediol and 2,3-hexanediol;
1,2-pentanediol and 2,3-heptanediol;
1,2-pentanediol and 2,3-octanediol;
1,2-pentanediol and 2,3-nonanediol;
1,2-pentanediol and 2,3-decanediol;
1,2-pentanediol and 2,3-undecanediol;
1,2-pentanediol and 2,3-dodecanediol;
1,2-pentanediol and 2,3-tridecanediol;
1,2-hexanediol and 2,3-pentanediol;
1,2-hexanediol and 2,3-hexanediol;
1,2-hexanediol and 2,3-heptanediol;
1,2-hexanediol and 2,3-octanediol;
1,2-hexanediol and 2,3-nonanediol;
1,2-hexanediol and 2,3-decanediol;
1,2-hexanediol and 2,3-undecanediol;
1,2-hexanediol and 2,3-dodecanediol;
1,2-hexanediol and 2,3-tridecanediol;
1,2-heptanediol and 2,3-pentanediol;
1,2-heptanediol and 2,3-hexanediol;
1,2-heptanediol and 2,3-heptanediol;
1,2-heptanediol and 2,3-octanediol;
1,2-heptanediol and 2,3-nonanediol;
1,2-heptanediol and 2,3-decanediol;
1,2-heptanediol and 2,3-undecanediol;
1,2-heptanediol and 2,3-dodecanediol;
1,2-heptanediol and 2,3-tridecanediol;
1,2-octanediol and 2,3-pentanediol;
1,2-octanediol and 2,3-hexanediol;
1,2-octanediol and 2,3-heptanediol;
1,2-octanediol and 2,3-octanediol;
1,2-octanediol and 2,3-nonanediol;
1,2-octanediol and 2,3-decanediol;
1,2-octanediol and 2,3-undecanediol;
1,2-octanediol and 2,3-dodecanediol;
1,2-octanediol and 2,3-tridecanediol;
1,2-nonanediol and 2,3-pentanediol;
1,2-nonanediol and 2,3-hexanediol;
1,2-nonanediol and 2,3-heptanediol;
1,2-nonanediol and 2,3-octanediol;
1,2-nonanediol and 2,3-nonanediol;
1,2-nonanediol and 2,3-decanediol;
1,2-nonanediol and 2,3-undecanediol;
1,2-nonanediol and 2,3-dodecanediol;
1,2-nonanediol and 2,3-tridecanediol;
1,2-decanediol and 2,3-pentanediol;
1,2-decanediol and 2,3-hexanediol;
1,2-decanediol and 2,3-heptanediol;
1,2-decanediol and 2,3-octanediol;
1,2-decanediol and 2,3-nonanediol;
1,2-decanediol and 2,3-decanediol;
1,2-decanediol and 2,3-undecanediol;
1,2-decanediol and 2,3-dodecanediol;
1,2-decanediol and 2,3-tridecanediol;
1,2-undecanediol and 2,3-pentanediol;
1,2-undecanediol and 2,3-hexanediol;
1,2-undecanediol and 2,3-heptanediol;
1,2-undecanediol and 2,3-octanediol;
1,2-undecanediol and 2,3-nonanediol;
1,2-undecanediol and 2,3-decanediol;
1,2-undecanediol and 2,3-undecanediol;
1,2-undecanediol and 2,3-dodecanediol;
1,2-undecanediol and 2,3-tridecanediol; or
1,2-dodecanediol and 2,3-pentanediol;
1,2-dodecanediol and 2,3-hexanediol;
1,2-dodecanediol and 2,3-heptanediol;
1,2-dodecanediol and 2,3-octanediol;
1,2-dodecanediol and 2,3-nonanediol;
1,2-dodecanediol and 2,3-decanediol;
1,2-dodecanediol and 2,3-undecanediol;
1,2-dodecanediol and 2,3-dodecanediol;
1,2-dodecanediol and 2,3-tridecanediol.

In a particular preferred variant, the cosmetic or pharmaceutical composition or homecare product according to the second aspect of the present invention which comprises a mixture or a combination comprising at least one first linear alkanediol and one or more second linear alkanediol thus may include any of the following mixtures/combinations:

2,3-pentanediol and 2,3-hexanediol;
2,3-pentanediol and 2,3-heptanediol;

2,3-pentanediol and 2,3-octanediol;
2,3-pentanediol and 2,3-nonanediol;
2,3-pentanediol and 2,3-decanediol;
2,3-pentanediol and 2,3-undecanediol;
2,3-pentanediol and 2,3-dodecanediol;
2,3-pentanediol and 2,3-tridecanediol;
2,3-hexanediol and 2,3-pentanediol;
2,3-hexanediol and 2,3-heptanediol;
2,3-hexanediol and 2,3-octanediol;
2,3-hexanediol and 2,3-nonanediol;
2,3-hexanediol and 2,3-decanediol;
2,3-hexanediol and 2,3-undecanediol;
2,3-hexanediol and 2,3-dodecanediol;
2,3-hexanediol and 2,3-tridecanediol;
2,3-heptanediol and 2,3-pentanediol;
2,3-heptanediol and 2,3-hexanediol;
2,3-heptanediol and 2,3-octanediol;
2,3-heptanediol and 2,3-nonanediol;
2,3-heptanediol and 2,3-decanediol;
2,3-heptanediol and 2,3-undecanediol;
2,3-heptanediol and 2,3-dodecanediol;
2,3-heptanediol and 2,3-tridecanediol;
2,3-octanediol and 2,3-pentanediol;
2,3-octanediol and 2,3-hexanediol;
2,3-octanediol and 2,3-heptanediol;
2,3-octanediol and 2,3-nonanediol;
2,3-octanediol and 2,3-decanediol;
2,3-octanediol and 2,3-undecanediol;
2,3-octanediol and 2,3-dodecanediol;
2,3-octanediol and 2,3-tridecanediol;
2,3-nonaediol and 2,3-pentanediol;
2,3-nonaediol and 2,3-hexanediol;
2,3-nonaediol and 2,3-heptanediol;
2,3-nonaediol and 2,3-octanediol;
2,3-nonanediol and 2,3-decanediol;
2,3-nonanediol and 2,3-undecanediol;
2,3-nonanediol and 2,3-dodecanediol;
2,3-nonanediol and 2,3-tridecanediol;
2,3-decanediol and 2,3-pentanediol;
2,3-decanediol and 2,3-hexanediol;
2,3-decanediol and 2,3-heptanediol;
2,3-decanediol and 2,3-octanediol;
2,3-decanediol and 2,3-nonaediol;
2,3-decanediol and 2,3-decanediol;
2,3-decanediol and 2,3-undecanediol;
2,3-decanediol and 2,3-dodecanediol;
2,3-decanediol and 2,3-tridecanediol;
2,3-undecanediol and 2,3-pentanediol;
2,3-undecanediol and 2,3-hexanediol;
2,3-undecanediol and 2,3-heptanediol;
2,3-undecanediol and 2,3-octanediol;
2,3-undecanediol and 2,3-nonaediol;
2,3-undecanediol and 2,3-decanediol;
2,3-undecanediol and 2,3-dodecanediol;
2,3-undecanediol and 2,3-tridecanediol; or
2,3-dodecanediol and 2,3-tridecanediol.

Particularly favorable is a mixture or a combination including 2,3-hexanediol and 2,3-heptanediol or a mixture including 2,3-hexanediol and 2,3-octanediol or a mixture including 2,3-heptanediol and 2,3-octanediol.

In a very particularly preferred variant, the cosmetic or pharmaceutical composition or homecare product according to the second aspect of the present invention which comprises a mixture or a combination comprising at least one first linear alkanediol and one or more second linear alkanediol thus includes any one of the following mixtures/combinations:

1,3-octanediol in combination with 1,2-hexanediol and/or 2,3-hexanediol; or
1,3-octanediol in combination with 1,2-heptanediol and/or 2,3-heptanediol; or
1,3-octanediol in combination with 1,2-octanediol and/or 2,3-octanediol; or
1,3-nonanediol in combination with 1,2-hexanediol and/or 2,3-hexanediol; or
1,3-nonanediol in combination with 1,2-heptanediol and/or 2,3-heptanediol; or
1,3-nonanediol in combination with 1,2-octanediol and/or 2,3-octanediol; or
1,3-decanediol in combination with 1,2-hexanediol and/or 2,3-hexanediol; or
1,3-decanediol in combination with 1,2-heptanediol and/or 2,3-heptanediol; or
1,3-decanediol in combination with 1,2-octanediol and/or 2,3-octanediol; or
1,3-undecanediol in combination with 1,2-hexanediol and/or 2,3-hexanediol; or
1,3-undecanediol in combination with 1,2-heptanediol and/or 2,3-heptanediol; or
1,3-undecanediol in combination with 1,2-octanediol and/or 2,3-octanediol.

In the hetero alkanediol mixtures described before the first linear alkanediol and the second linear alkanediol have a different number of carbon atoms.

The above specified hetero alkanediol mixtures according to the second aspect of the present invention, comprising a first linear alkanediol and a second linear alkanediol are characterized in that they have a significant antioxidative capacity and a superior ROS scavenging activity. In other words: the composition according to the second aspect of the present invention comprising an antioxidant plus a blend of a first linear alkanediol and a second linear alkanediol has a significant antioxidative capacity and shows an improved ROS scavenging efficacy in comparison to the corresponding single alkanediol substances.

The use of a hetero alkanediol mixture comprising 1,2-hexanediol and 2,3-octanediol in combination with an antioxidant shows an improved ROS scavenging efficacy.

An antioxidative effect is found for the hetero alkanediol mixture comprising 1,2-octanediol and 2,3-hexanediol compared to the corresponding single first linear alkanediol and second linear alkanediol substances.

The hetero alkane mixture comprising 1,2-octanediol and 2,3-heptanediol is also beneficial since it has a particular antioxidation improving effect of antioxidants compared to the corresponding single first linear alkanediol and second linear alkanediol substances.

Furthermore, a distinct improvement in ROS score can be observed for the following specified alkanediol mixtures, namely a mixture of alkanediols including 1,2-pentanediol and 2,3-hexanediol; or a mixture including 1,2-pentanediol and 1,2-heptanediol; or a mixture including 1,2-pentanediol and 2,3-heptanediol; or a mixture including 1,2-pentanediol and 2,3-octanediol; or a mixture including 1,2-pentanediol and 1,2-nonanediol; or a mixture including 1,2-pentanediol and 2,3-nonanediol, compared to the corresponding single first linear alkanediol and second linear alkanediol substances. All of the afore specified hetero alkane diol mixtures including a first linear alkanediol and a second linear alkanediol display a remarkable ROS scavenging effect.

An improved ROS score can also be observed for a hetero alkanediol mixture comprising 1,2-pentanediol and 2,3-hexanediol when used with an antioxidant compared to the individual 1,2-alkanediol or 2,3-alkanediol.

Also, the alkanediol mixture comprising 1,2-pentanediol and 1,2-heptanediol show a significant improvement in antioxiative capacity.

An improved antioxidative effect is also observed for a combination of an antioxidant and a hetero alkanediol mixture comprising 1,2-pentanediol and 2,3-heptanediol compared to the corresponding single first linear alkanediol and second linear alkanediol substances.

An improvement or the ROS score can also be observed for the hetero alkanediol mixture comprising 1,2-pentanediol and 2,3-octanediol compared to the corresponding single first linear alkanediol and second linear alkanediol substances.

Said improvement of the antioxidative effect is also found for the alkanediol mixture comprising 1,2-pentanediol and 1,2-nonanediol compared to the corresponding single first linear alkanediol and second linear alkanediol substances.

Also, the hetero alkanediol mixture including 1,2-pentanediol and 2,3-nonanediol is effective in improving the antioxidative effect when used with an antioxidant.

Furthermore, a significant antioxidative capacity and improved ROS score can also be observed for mixtures comprising at least one first linear alkanediol and one or more second linear alkanediol according to the second aspect of the present invention, namely a mixture of alkanediols including 1,2-heptanediol and 1,2-octanediol or a mixture of alkanediols including 1,2-heptanediol and 2,3-octanediol or a mixture of alkanediols including 1,2-heptanediol and 1,2-nonanediol or a mixture of alkanediols including 1,2-heptanediol and 2,3-nonanediol compared to the corresponding single first linear alkanediol and second linear alkanediol substances of the alkanediol mixtures.

All of the afore specified hetero alkane diol mixtures including a first linear alkanediol and a second linear alkanediol in combination with an antioxidant leads to a better ROS score display an improved solubility towards solid UV filters.

Said antioxidative effect is found for the hetero alkanediol mixture including 1,2-heptanediol and 2,3-octanediol.

The improved antioxidative efficacy is well achieved by combinations with the hetero alkanediol mixture such as including 1,2-heptanediol and 2,3-nonanediol but also for 1,2-heptanediol and 1,2-nonanediol.

Hence, with the use of one hetero alkanediol mixtures as specified herein, a stable cosmetic or pharmaceutical formulation composition or homecare product can be achieved. With the improvement of the storage stability the shelf life of the cosmetic or pharmaceutical composition or homecare product can be considerable prolonged.

In a preferred variant according to the second aspect of the present invention in the cosmetic or pharmaceutical composition or the homecare product the linear alkanediol is selected from the group consisting of 2,3-pentanediol, 2,3-hexanediol, 2,3-heptanediol, 2,3-octanediol, 2,3-nonanediol, 2,3-decanediol, 2,3-undecanediol, 2,3-dodecanediol, 2,3-tridecanediol, and mixtures thereof.

In a more preferred variant of the cosmetic or pharmaceutical composition or the homecare product according to the second aspect of the present invention, the linear alkanediol is selected from the group consisting of 2,3-pentanediol, 2,3-hexanediol, 2,3-heptanediol, 2,3-octanediol, 2,3-nonanediol, and mixtures thereof.

Surprisingly, the addition of 2,3-pentanediol, 2,3-hexanediol, 2,3-heptanediol as well as other 2,3-alkanediols such as 2,3-octanediol, 2,3-nonanediol, 2,3-decanediol, 2,3-undecanediol, 2,3-dodecanediol and 2,3-tridecanediol to a cosmetic or pharmaceutical preparation or homecare product boosts the antioxidative effect of an antioxidant resulting in a better ROS score compared to the corresponding 1,2-alkanediols such as 1,2-pentanediol, 1,2-hexanediol, 1,2-heptanediol, 1,2-octanediol, 1,2-nonanediol etc.

With the improvement of the antioxidative effect the shelf life of the cosmetic or pharmaceutical preparation or homecare product can considerably be improved by using the 2,3-alkanediols as specified.

In addition, the 2,3-alkanediols as specified above have the benefit to be liquids, whereby their incorporation in semi-finished products or final products can be facilitated and their availability in said products can be increased. Additionally, in an emulsion the 2,3-alkanediols remain in the water phase and can develop their antimicrobial activity directly where contamination with microorganisms occurs and do not tend to migrate into the oil phase.

Hence, a good compromise can be achieved when the active mixture is combined in such a way as to maintain the antimicrobial effect, while improving processability in formulations. The above specified 2,3-alkanediols solve this balancing problem over the solid 1,2-alkanediol substances.

In a particularly advantageous variant according to the second aspect of the present invention, the linear alkanediol or the first linear alkanediol or the second linear alkanediol is a liquid alkanediol.

The term "liquid alkanediol" within the context of the present invention means an alkanediol component which is liquid at room or ambient temperature and under normal pressure, i.e., standard RTP conditions.

In a very preferred variant according to the second aspect of the present invention, the linear alkanediol or the first linear alkanediol or the second linear alkanediol is a liquid alkanediol selected from the group consisting of 1,2-pentanediol, 2,3-pentanediol, 1,2-hexanediol, 2,3-hexanediol, 1,2-heptanediol, 2,3-heptanediol, 2,3-octanediol, 2,3-nonanediol, 2,3-decanediol, 2,3-undecanediol, and mixtures thereof.

Of the aforesaid liquid alkanediols, 1,2-pentanediol, 2,3-pentanediol, 1,2-hexanediol, 2,3-hexanediol, 1,2-heptanediol, 2,3-heptanediol, 2,3-octanediol, 2,3-nonanediol or mixtures thereof are most preferred.

In a most particularly advantageous variant according to the second aspect of the present invention, the linear alkanediol or the first linear alkanediol or the second linear alkanediol are characterized by a maximum water solubility of less than or equal to 10% by weight. In a preferred variant, the maximum water solubility of the linear alkanediol or the first linear alkanediol or the second linear alkanediol is less than or equal to 10% by weight and more than or equal to 1.2% by weight. More preferred, the maximum water solubility of the linear alkanediol or the first linear alkanediol or the second linear alkanediol is less than or equal to 5% by weight and more than or equal to 1.4% by weight.

Preferably, the alkanediol with said water solubility is selected from the group consisting of 1,2-heptanediol, 2,3-heptanediol, 2,3-octanediol, and mixtures thereof.

The water solubility of a substance is the saturation mass concentration of the substance in water at a given temperature. The determination of the solubility in water relates to essentially pure substances which are stable in water and not volatile. The determination of the water solubility of the alkanediols is further described in the following Example 7.

The term "alkanediol" within the context of the present invention also includes its stereoisomers. Stereoisomers are molecules that have the same molecular formula and differ only in how their atoms are arranged in three-dimensional space. In accordance with said definition, the linear alkanediol of the invention and the first linear alkanediol having a carbon chain of 5 to 14 carbon atoms or the second linear alkanediol having a carbon chain of 5 to 14 carbon atoms as described above in detail encompass the following stereoisomers:

1,2-alkanediol stereoisomers:
(2S)-pentane-1,2-diol,
(2S)-hexane-1,2-diol,
(2S)-heptane-1,2-diol,
(2S)-octane-1,2-diol,
(2S)-nonane-1,2-diol,
(2S)-decane-1,2-diol,
(2S)-undecane-1,2-diol
(2S)-dodecane-1,2-diol,
(2S)-tridecane-1,2-diol,
(2S)-tetradecane-1,2-diol,
(2R)-pentane-1,2-diol,
(2R)-hexane-1,2-diol,
(2R)-heptane-1,2-diol,
(2R)-octane-1,2-diol,
(2R)-nonane-1,2-diol,
(2R)-decane-1,2-diol,
(2R)-undecane-1,2-diol,
(2R)-dodecane-1,2-diol,
(2R)-tridecane-1,2-diol,
(2R)-tetradecane-1,2-diol,
2,3-alkanediol stereoisomers:
(2S,3S)-pentane-2,3-diol,
(2S,3S)-hexane-2,3-diol,
(2S,3S)-heptane-2,3-diol,
(2S,3S)-octane-2,3-diol,
(2S,3S)-nonane-2,3-diol,
(2S,3S)-decane-2,3-diol,
(2S,3S)-undecane-2,3-diol
(2S,3S)-dodecane-2,3-diol,
(2S,3S)-tridecane-2,3-diol,
(2S,3S)-tetradecane-2,3-diol,
(2R,3R)-pentane-2,3-diol,
(2R,3R)-hexane-2,3-diol,
(2R,3R)-heptane-2,3-diol,
(2R,3R)-octane-2,3-diol,
(2R,3R)-nonane-2,3-diol,
(2R,3R)-decane-2,3-diol,
(2R,3R)-undecane-2,3-diol,
(2R,3R)-dodecane-2,3-diol,
(2R,3R)-tridecane-2,3-diol,
(2R,3R)-tetradecane-2,3-diol,
(2S,3R)-pentane-2,3-diol,
(2S,3R)-hexane-2,3-diol,
(2S,3R)-heptane-2,3-diol,
(2S,3R)-octane-2,3-diol,
(2S,3R)-nonane-2,3-diol,
(2S,3R)-decane-2,3-diol,
(2S,3R)-undecane-2,3-diol,
(2S,3R)-dodecane-2,3-diol,
(2S,3R)-tridecane-2,3-diol,
(2S,3R)-tetradecane-2,3-diol,
(2R,3S)-pentane-2,3-diol,
(2R,3S)-hexane-2,3-diol,
(2R,3S)-heptane-2,3-diol,
(2R,3S)-octane-2,3-diol,
(2R,3S)-nonane-2,3-diol,
(2R,3S)-decane-2,3-diol,
(2R,3S)-undecane-2,3-diol,
(2R,3S)-dodecane-2,3-diol,
(2R,3S)-tridecane-2,3-diol, and
(2R,3S)-tetradecane-2,3-diol.

3,4-alkanediol stereoisomers:
(3R,4R)-hexane-3,4-diol,
(3R,4R)-heptane-3,4-diol,
(3R,4R)-octane-3,4-diol,
(3R,4R)-nonane-3,4-diol,
(3R,4R)-decane-3,4-diol,
(3R,4R)-undecane-3,4-diol,
(3R,4R)-dodecane-3,4-diol,
(3R,4R)-tridecane-3,4-diol,
(3R,4R)-tetradecane-3,4-diol,
(3S,4S)-hexane-3,4-diol,
(3S,4S)-heptane-3,4-diol,
(3S,4S)-octane-3,4-diol,
(3S,4S)-nonane-3,4-diol,
(3S,4S)-decane-3,4-diol,
(3S,4S)-undecane-3,4-diol,
(3S,4S)-dodecane-3,4-diol,
(3S,4S)-tridecane-3,4-diol,
(3S,4S)-tetradecane-3,4-diol,
(3R,4S)-hexane-3,4-diol,
(3R,4S)-heptane-3,4-diol,
(3R,4S)-octane-3,4-diol,
(3R,4S)-nonane-3,4-diol,
(3R,4S)-decane-3,4-diol,
(3R,4S)-undecane-3,4-diol,
(3R,4S)-dodecane-3,4-diol,
(3R,4S)-tridecane-3,4-diol,
(3R,4S)-tetradecane-3,4-diol,
(3S,4R)-hexane-3,4-diol,
(3S,4R)-heptane-3,4-diol,
(3S,4R)-octane-3,4-diol,
(3S,4R)-nonane-3,4-diol,
(3S,4R)-decane-3,4-diol,
(3S,4R)-undecane-3,4-diol,
(3S,4R)-dodecane-3,4-diol,
(3S,4R)-tridecane-3,4-diol, and
(3S,4R)-tetradecane-3,4-diol.

In the context of the present text, the terms "1,2-diol" and "2,3-diol" or "3,4-diol" includes both the corresponding S-configured enantiomers and also the R-enantiomers as well as arbitrary mixtures of these S- and R-configured enantiomers, i.e. mixtures of racemates of the respective diols.

The alkanediol mixture of the cosmetic or pharmaceutical composition or homecare product according to the first aspect of the present invention according to the first aspect of the present invention comprises the 1,2-heptanediol and the 2,3-heptanediol in a ratio in a range of 50:50 to 99.9:0.1, preferably in a ratio in a range of 75:25 to 99:1, more preferred in a ratio in a range of 80:20 to 98:2, still more preferred in a ratio in a range of 90:10 to 95:5.

In the cosmetic or pharmaceutical composition according to the first aspect of the present invention, 1,2-heptanediol and 2,3-heptanediol are comprised in the mixture preferably in a ratio in a range of 98:2 to 99.9:0.1.

In the homecare products according to the first aspect of the present invention, 1,2-heptanediol and 2,3-heptanediol are comprised in the alkanediol mixture preferably in a ratio in a range of 95:5 to 99.9:0.1.

1,2-heptanediol and 2,3-heptanediol are comprised in the mixture of the cosmetic or pharmaceutical composition or homecare product according to the first aspect of the present invention preferred in a ratio of ≥95:≤5, more preferred in a ratio of ≥96:≤4; still more preferred in a ratio of ≥97:≤3, and most preferred in a ratio of ≥98—:≤2.

Most of all the mixture of the cosmetic or pharmaceutical composition or homecare product according to the first aspect of the present invention comprises 1,2-heptanediol and 2,3-heptanediol in a ratio of 95:≤5, including the ratios ≥95.5:≤4.5; ≥96:≤4; ≥96.5:≤3.5; ≥97≤3; ≥97.5:2,5 and ≥98.0:≤2.0.

Even more preferred the alkanediol mixture of the cosmetic or pharmaceutical composition or homecare product according to the first aspect of the present invention comprises 1,2-heptanediol and 2,3-heptanediol in a ratio of ≥98:≤2, including the ratios of ≥98.1:≤1.9; ≥98.2:≤0.8; ≥98.3:≤1.7; ≥98.4:≤1.6; ≥98.5:≤1.5; ≥98.6:≤1.4; ≥98.7:≤1.3; ≥98.8:≤1.2; ≥98.9:≤1.1; ≥99:≤1.0; ≥99.1:≤0.9; ≥99.2:≤0.8; ≥99.3:≤0.7; ≥99.4:≤0.6; ≥99.5:≤0.5; ≥99.6:≤0.4; ≥99.7≤0.3; ≥99.8:≤0.2 and ≥99.9:≤0.1.

The first linear alkanediol and the second linear alkanediol as defined in detail above are present in the alkanediol mixture according to the second aspect of the present invention in a ratio in a range of 50:50 to 99.9:0.1, preferably in a ratio in a range of 75:25 to 99:1, more preferred in a ratio in a range of 80:20 to 98:2, still more preferred in a ratio in a range of 90:10 to 95:5.

In the cosmetic or pharmaceutical preparation according to the second aspect of the present invention, the first linear alkanediol and the second linear alkanediol are comprised in the mixture preferably in a ratio in a range of 98:2 to 99.9:0.1.

In the homecare products according to second aspect of the present invention, the first linear alkanediol and the second linear alkanediol are comprised in the alkanediol mixture preferably in a ratio in a range of 95:5 to 99.9:0.1.

The first linear alkanediol and the second linear alkanediol are comprised in the mixture of the cosmetic or pharmaceutical composition or homecare product according to the second aspect of the present invention preferred in a ratio of ≥95:≤5, more preferred in a ratio of ≥96:≤4; still more preferred in a ratio of ≥97:≤3, and most preferred in a ratio of ≥98:≤2.

Most of all the alkanediol mixture of the cosmetic or pharmaceutical composition or homecare product according to the second aspect of the present invention comprises the first linear alkanediol and the second linear alkanediol in a ratio of ≥95:≤5, including the ratios ≥95.5:≤4.5; ≥96:≤4; ≥96.5:≤3.5; ≥97:≤3; ≥97.5:2,5 and ≥98.0:≤2.0.

Even more preferred, the alkanediol mixture of the cosmetic or pharmaceutical composition or homecare product according to the second aspect of the present invention comprises the first linear alkanediol and the second linear alkanediol in a ratio of ≥98:≤2, including the ratios of ≥98.1:≤1.9; ≥98.2:≤1.8; ≥98.3:≤1.7; ≥98.4:≤1.6; ≥98.5:≤1.5; ≥98.6≤1.4; ≥98.7:≤1.3; ≥98.8:≤1.2; ≥98.9:≤1.1; ≥99:≤1.0; ≥99.1:≤0.9; ≥99.2:≤0.8; ≥99.3:≤0.7; ≥99.4:≤0.6; 99.5:≤0.5; ≥99.6:≤0.4; ≥99.7:≤0.3; ≥99.8:≤0.2 and ≥99.9:≤0.1.

Alternatively, said ratio ranges for the first and second alkanediol are switched, such that the second alkanediol is the main component and the first alkanediol is the secondary component.

In an advantageous variant according to the second aspect of the present invention, the mixture comprises as first linear alkanediol an 1,2-alkanediol, such as 1,2-pentanediol, 1,2-hexanediol, 1,2-heptanediol, 1,2-octanediol, 1,2-nonanediol, 1,2-decanediol, 1,2-undecanediol, 1,2-dodecanediol, or 1,2-tridecanediol and as second linear alkanediol the corresponding 2,3-alkanediols, such as 2,3-pentanediol, 2,3-hexanediol, 2,3-heptanediol, 2,3-octanediol, 2,3-nonanediol, 2,3-decanediol, 2,3-undecanediol, 2,3-dodecanediol, or 2,3-tridecanediol in a ratio in a range of 50:50 to 99.9:0.1, preferably in a ratio in a range of 75:25 to 99:1, more preferred in a ratio in a range of 80:20 to 98:2, still more preferred in a ratio in a range of 90:10 to 95:5.

Likewise, for said specific mixtures, the further ratios or ranges of ratios as defined above in general for the first linear alkanediol:second linear alkanediol are also applicable.

In a still further variant, according to the second aspect of the present invention, the mixture comprises as first linear alkanediol an 2,3-alkanediol, such as 2,3-pentanediol, 2,3-hexanediol, 2,3-heptanediol, 2,3-octanediol, 2,3-nonanediol, 2,3-decanediol, 2,3-undecanediol, 2,3-dodecanediol, or 2,3-tridecanediol and as second linear alkanediol the corresponding 1,2-alkanediols, such as 1,2-pentanediol, 1,2-hexanediol, 1,2-heptanediol, 1,2-octanediol, 1,2-nonanediol, 1,2-decanediol, 1,2-undecanediol, 1,2-dodecanediol, or 1,2-tridecanediol in a ratio in a range of 50:50 to 99.9:0.1, preferably in a ratio in a range of 75:25 to 99:1, more preferred in a ratio in a range of 80:20 to 98:2, still more preferred in a ratio in a range of 90:10 to 95:5.

Likewise, for said specific mixtures, the further ratios or ranges of ratios as defined above in general for the first linear alkanediol:second linear alkanediol are also applicable.

In a more advantageous variant according to the second aspect of the present invention, in the mixtures comprising a combination of a 1,2-alkanediol as first linear alkandediol and the corresponding 2,3-alkanediol as second linear alkanediol, such as 1,2-pentanediol and 2,3-pentanediol, or
1,2-hexanediol and 2,3-hexanediol, or
1,2-heptanediol and 2,3-heptanediol, or
1,2-octanediol and 2,3-octanediol, or
1,2-nonanediol and 2,3-nonanediol, or
1,2-decanediol and 2,2-decanediol, or
1,2-undecanediol and 2,3-undecenaediol, or
1,2-dodecanediol and 2,3-dodecanediol, or
1,2-tridecanediol and 2,3-tridecanediol, the first linear alkanediol and the second linear alkanediol are present in a ratio in a range of 50:50 to 99.9:0.1, preferably in a ratio in a range of 75:25 to 99:1, more preferred in a ratio in a range of 80:20 to 98:2, still more preferred in ratio in a range of 90:10 to 95:5.

Likewise, for said mixtures, the ratios of first linear alkanediol:second linear alkanediol or ranges of ratios as described above are also applicable.

By these mixing ratios the afore mentioned mixtures show an improved ROS score when combined with an antioxidant in comparison to the corresponding single alkanediol substances as it is described and demonstrated in the experimental part.

In a more advantageous variant according to the second aspect of the present invention, in the mixtures comprising as first linear alkanediol a 2,3-alkanediol and as second linear alkanediol the corresponding 1,2-alkanediols, such as mixtures including 2,3-pentanediol and 1,2-pentanediol, or
2,3-hexanediol and 1,2-hexanediol, or
2,3-heptanediol and 1,2-heptanediol, or
2,3-octanediol and 1,2-octanediol, or
2,3-nonanediol and 1,2-nonanediol, or
2,3-decanediol and 1,2-decanediol, or
2,3-undecanediol and 1,2-undecenaediol, or
2,3-dodecanediol and 1,2-dodecanediol, or
2,3-tridecanediol and 1,2-tridecanediol, the first linear alkanediol and the second linear alkanediol are present in a ratio in a range of 50:50 to 99.9:0.1, preferably in a ratio in a range of 75:25 to 99:1, more preferred in a ratio in a range of 80:20 to 98:2 or still more preferred in a ratio in a range of 90:10 to 95:5.

Likewise for said specific mixtures, the further ratios or ranges of ratios as defined above in general for the first linear alkanediol:second linear alkanediol are also applicable.

By these mixing ratios the afore mentioned mixtures show an improved ROS score when combined with an antioxidant in comparison to the corresponding single alkanediol substances.

A preferred variant according to the second aspect the present invention also encompasses a mixture including as first linear alkanediol 1,2-hexanediol and as second linear alkanediol 2,3-octanediol or a mixture including as first linear alkanediol 1,2-octanediol and as second linear alkanediol 2,3-hexanediol or a mixture including as first linear alkanediol 1,2-octanediol and and as second linear alkanediol 2,3-heptandeiol either in a ratio in a range of 50:50 to 99.9:0.1, preferably in a ratio in a range of 75:25 to 99:1, more preferred in a ratio in a range of 80:20 to 98:2 or still more preferred in a ratio in a range of 90:10 to 95:5.

Likewise for said specific mixtures, the further ratios or ranges of ratios as defined above in general for the first linear alkanediol:second linear alkanediol are also applicable.

By these mixing ratios the afore mentioned mixtures show an improved ROS score when combined with an antioxidant in comparison to the corresponding single alkanediol substances.

In a further beneficial variant according to the second aspect of the present invention, the mixtures comprise a first linear alkanediol and a second linear alkanediol, such as mixtures including 1,2-pentanediol and 2,3-hexanediol; or
1,2-pentanediol and 1,2-heptanediol; or
1,2-pentanediol and 2,3-heptanediol; or
1,2-pentanediol and 2,3-octanediol; or
1,2-pentanediol and 1,2-nonanediol; or
1,2-pentanediol and 2,3-nonanediol, wherein the first linear alkanediol and the second linear alkanediol are present in a ratio in a range of 50:50 to 99.9:0.1, preferably in a ratio in a range of 75:25 to 99:1, more preferred in a ratio in a range of 80:20 to 98:2 or still more preferred in a ratio in a range of 90:10 to 95:5.

Likewise, for said specific mixtures, the further ratios or ranges of ratios as defined above in general for the first linear alkanediol:second linear alkanediol are also applicable.

By these mixing ratios the afore mentioned mixtures show an improved ROS score when combined with an antioxidant in comparison to the corresponding single alkanediol substances.

A particularly preferred variant according to the second aspect the present invention also encompasses a mixture including as first linear alkanediol 1,2-heptanediol and as second linear alkanediol 1,2-octanediol or a mixture including as first linear alkanediol 1,2-heptanediol and as second linear alkanediol 2,3-octanediol or a mixture including as first linear alkanediol 1,2-heptanediol and as second linear alkanediol 1,2-nonanediol or a mixture including as first linear alkanediol 1,2-heptanediol and as second linear alkanediol 2,3-nonanediol wherein the first linear alkanediol and the second linear alkanediol are present in a ratio in a range of 50:50 to 99.9:0.1, preferably in a ratio in a range of 75:25 to 99:1, more preferred in a ratio in a range of 80:20 to 98:2 or still more preferred in a ratio in a range of 90:10 to 95:5.

Likewise, for said specific mixtures, the further ratios or ranges of ratios as defined above in general for the first linear alkanediol:second linear alkanediol are also applicable.

By these mixing ratios the afore mentioned mixtures show an improved ROS score when combined with an antioxidant in comparison to the corresponding single alkanediol substances.

The alkanediols are obtained either by synthesis from petrochemical or other fossil fuel sources by known methods such as olefin bishydroxylation, hydrolysis from epoxide or various chemical transformations or from bioderived feedstock by fermentation or from bio-based natural and renewable feedstock such as biomass by catalytic synthesis as it is described in US 2019/0241491 A1 and US 2020/0189995 A1. The alkanediols used according to the present invention comprise either petrochemically derived and biobased natural and renewable feedstock derived alkanediols. Preferably, the alkanediols are from bio-based sources and are thus bio-alkanediols.

The compound (b) of the cosmetic or pharmaceutical composition or homecare product according to the first aspect or the second aspect of the present invention relates to an antioxidant.

The term "antioxidant" as used in this document refers to a substance or composition which significantly delays, prevents or even inhibits oxidation. Antioxidants react with free radicals, reducing them to stable, unreactive products. Oxidation is a chemical reaction that produces free radicals chain reactions which generate highly reactive peroxides and hydroperoxides. In turn, these peroxides and hydroperoxides react with substrates present in a cosmetic composition or in food which result in decomposition products such as carboxylic acids, aldehydes and ketones, among other, which alter the sensory properties of the productions and lead to degradation of the composition.

Antioxidants play an important physiological role as radical scavenger. In the organism antioxidants inactivate biologically important reactive free radicals or other reactive oxygen species (ROS) which excessively occurrence leads to oxidative stress. In a biological context, reactive oxygen species (ROS) are formed as a natural by-product of the normal metabolism of oxygen and have important roles in cell signalling and homeostasis. However, at times of environmental stress (for example UV or heat exposure), ROS levels can increase dramatically.

Oxidative stress occurs either when excess ROS are produced in cells, which could overwhelm the normal antioxidant capacity, or when antioxidant defence mechanisms are impaired. Reactive oxygen species (ROS) are chemically reactive species containing oxygen. Examples of ROS include superoxide anions ($O_2^{\cdot-}$, hydroxyl ($OH^{\cdot}$), peroxyl ($RO_2^{\cdot}$) alkoxyl ($RO^{\cdot}$) radicals, and non-radical compounds such as hydrogen peroxide ($H_2O_2$), hypochlorous acid (HOCl) and organic peroxides, which can be produced from either endogenous source (for example mitochondrial electron transport chain, cytochrome P450 monooxygenases, and NADPH oxidases) or exogenous sources (for example pollutants, drugs, xenobiotics and radiation). ROS toxicity affects major cellular components and contributes to significant protein, lipid and DNA damage, inflammation, cell and tissue injury, and apoptosis.

There is compelling evidence that oxidative stress plays a major role in the pathogenesis and progression of major human diseases, including inflammatory diseases, and that it is also implicated in aging. It not only directly damages the cellular structures of the skin but also enhances dermal inflammation and weakens the skin barrier function and enables infections by microbial pathogens. According to the free radical theory of aging, oxidative damage initiated by reactive oxygen species (ROS) is a major contributor to the functional decline that is characteristic of aging. Oxidative stress is a major underlying cause of neurodegenerative and neuroinflammatory disorders.

Interleukin 8 (IL-8) or CXCL8 is a chemokine produced by macrophages and other cell types such as epithelial cells, airway smooth muscle cells and endothelial cells. In humans, the interleukin-8 protein is encoded by the IL-8 gene. IL-8 is initially produced as a precursor peptide of 99 amino acids long which then undergoes cleavage to create several active IL-8 isoforms. In culture, a 72 amino acid peptide is the major form secreted by all kinds of cells. IL-8 is a key mediator associated with inflammation where it plays a key role in neutrophil recruitment and neutrophil degranulation. As an example, it has been cited as a pro-inflammatory mediator in gingivitis, psoriasis and other diseases.

Interleukin-8 secretion is increased by various kinds of stress including UV and oxidative stress, which thereby cause the recruitment of inflammatory cells and induces a further increase in oxidant stress mediators, making it a key parameter in localized inflammation.

UV irradiation induces increased synthesis and expression of matrix metalloproteinases (MMPs) in human skin, which is stimulated by the generation of excess reactive oxygen species (ROS), and plays a critical role in photoaging. Chronic or long-term exposure to UV radiation disrupts the normal skin structure leading to a host of skin issues including premature skin aging (photoaging) and skin cancer (photo carcinogenesis). MMPs are zinc-containing endopeptidases with a broad range of substrate specificities. Based on their structure and substrate specificity, they can be categorized into five main subgroups, namely (1) collagenases (MMP-1, MMP-8 and MMP-13); (2) gelatinases (MMP-2 and MMP-9); (3) stromelysins (MMP-3, MMP-10 and MMP-11); (4) matrilysins (MMP-7 and MMP-26); and (5) membrane-type (MT) MMPs (MMP-14, MMP-15, and MMP-16). They are secreted by keratinocytes and dermal fibroblasts in response to multiple stimuli such as oxidative stress, UV radiation, and cytokines. To date, MMPs have been identified that play important roles in various patho-physiological processes including photoaging, wound healing, skeletal growth and remodeling, arthritis, inflammation, angiogenesis, and cancer.

MMPs are responsible for degrading the extracellular matrix (ECM) proteins such as collagen, fibronectin, elastin, and proteoglycans, contributing to photoaging. Increased MMP activity is an important factor influencing the development of age-related changes in skin. Degradation of collagen is normally regulated by MMPs and by the activity of their natural inhibitors, tissue inhibitors of metalloproteinases. In the skin, epidermal keratinocytes and dermal fibroblasts mainly secrete MMP-1 (interstitial collagenase or collagenase 1), a collagenase that degrades collagens into specific fragments Other MMPs such as gelatinase further hydrolyse these fragments, ultimately impairing the function of the collagen-rich dermis. The alterations made to the ECM by MMPs contributes to skin wrinkling, a characteristic of premature skin aging.

With the use of an antioxidant, the above-described oxidation process in a product or the above described biochemically reactions caused by oxidative stress and excess reactive oxygen species (ROS) can be down regulated.

The cosmetic or pharmaceutical composition or homecare product according to the first or second aspect of the present invention encompasses at least one antioxidant selected from the group consisting of dimethylmethoxy chromanol, arbutin, amino acids (for example glycine, histidine, tyrosine, tryptophan) and their derivatives (for example acetyl-cysteine), tert-butylhydroquinone, caffeic acid, chlorogenic acid, imidazoles (for example urocanic acid) and their derivatives, cannabinoids, cannabidiol and its extracts (*Cannabis sativa* seed oil, *Cannabis sativa* extract), cannabinol, kojic acid, peptides such as D,L-carnosine, D-carnosine, L-carnosine and their derivatives (for example anserine), hydroxyphenyl propamidobenzoic acid (dihydroavenanthramide D), diethylhexyl syringylidene malonate, phenylethyl resorcinol, gallic acid and their derivatives, quercetin, hydroxyacetophenone, rosmarinic acid, carotenoids, carotenes (for example α-carotene, β-carotene, lycopene), phytoene, phytofluene and their derivatives, lipoic acid and its derivatives (for example dihydrolipoic acid), aurothioglucose, propylthiouracil and other thiols (for example thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, pentaerythrityl tetra-di-t-butyl hydroxyhydrocinnamate, distearyl thiodipropionate, thiodipropionic acid and their derivatives (esters, ethers, peptides, lipids, nucleotides, nucleosides and salts) as well as sulphoximine compounds (for example buthionine sulphoximines, *lactobacillus* (ferment, filtrate, lysate), homocysteine sulphoximines, buthionine sulphones, penta-, hexa-, hepta-thionine sulphoximine) in very low tolerated doses, and also (metal) chelating agents (for example α-hydroxy fatty acids, palmitic acid, phytic acid, lactoferrin, α-hydroxy acids (for example citric acid, lactic acid, malic acid), humic acid, bile acid, bile extracts, bilirubin, biliverdin, hinokitiol, EDTA, EGTA, Trisodium Dicarboxymethyl Alaninate, MGDA (methylglycinic diacetic acid), GLDA (Glutamic acid diacetic acid)) and their derivatives, unsaturated fatty acids and their derivatives (for example γ-linolenic acid, linoleic acid, oleic acid), folic acid and its derivatives, ubiquinone and ubiquinol and their derivatives, triethyl citrate, Vitamin C and its derivatives (for example ascorbyl palmitate, magnesium ascorbyl phosphate, ascorbyl acetate), tocopherols and their derivatives (for example α-tocopherol, ß-tocopherol, γ-tocopherol, δ-tocopherol, tocopheryl acetate), dexpanthenol, Vitamin A and its derivatives (for example Vitamin A palmitate, Hydroxypinacolone Retinoate) and also coniferyl benzoate of benzoin resin, rutinic acid and its derivatives, ferrulic acid and its derivatives, butylhydroxytoluene, butylhydroxyanisole, hydroxymethoxyphenyl decanone, nordihydroguaiacic acid, nordihydroguaiaretic acid, allantoin, tropolone, trihydroxybutyrophenone, uric acid and its derivatives, urea, mannose and its derivatives, hydroxy acetophenone (ortho/para), zinc and its derivatives (for example ZnO, $ZnSO_4$), beta-aspartyl arginine, selenium and its derivatives (such as selenium methionine), *Vitis Vinifera* (Grape) seed extract, oat extract, *Cichorium* intubybus (chicory) leaf extract, Leon-topodium *Alpinum* extract, green tea extract, Curcumin, *Zingiber Officinalis* (Ginger) Root Extract, Silymarin, stilbenes and their derivatives (such as stilbene oxide, trans-stilbene oxide) as well as the derivatives of said antioxidants, such as salts, esters, ethers, sugars, nucleotides, nucleosides, peptides and lipids, and mixtures of two or more of said antioxidants.

In a more preferred variant, the antioxidant of the cosmetic or pharmaceutical composition or homecare product of the present invention is selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *Zingiber Officinalis* (Ginger) root extract, tropolone, allantoin, and mixtures of two or more of said antioxidants.

In a particularly preferred variant, the antioxidant of the cosmetic or pharmaceutical composition of the present invention is tocopherol or tocopheryl acetate. Also preferred is dimethylmethoxy chromanol.

From the above antioxidants, the following antioxidants are in particular preferred for the use in anti-wrinkle or anti-aging compositions: tocopherol or a derivative thereof, and/or vitamin A or a derivative thereof, and/or vitamin C or a derivative thereof, carnosine or a derivative thereof, or *Zingiber Officinale* (Ginger) Root Extract.

Still more preferred from the above antioxidants are antioxidants selected from the group consisting of cannabinoids, cannabidiol and its extracts (*Cannabis sativa* seed oil, *Cannabis sativa* extract), cannabinol, hydroxyphenyl propamidobenzoic acid (dihydroavenanthramide D).

The aforesaid antioxidants can be used either as a single component or in combination with one or more further antioxidants as specified above.

In a preferred advantageously variant, the cosmetic or pharmaceutical composition or homecare product according to the first or second aspect of the present invention comprises one of the following combinations of components (a) and (b):

1,2-pentanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-hexanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-heptanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-octanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-nonanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-decanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabidiol and its extracts (*Cannabis sativa* seed oil, *Cannabis sativa* extract), green tea extract, *zingiber officinalis*(ginger) root extract, tropolone, allantoin, and mixtures of two or more of said antioxidants; or 1,2-undecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-dodecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-tridecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 2,3-pentanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 2,3-hexanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 2,3-heptanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 2,3-octanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 2,3-nonanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 2,3-decanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 2,3-undecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 2,3-dodecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 2,3-tridecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-heptanediol in combination with 2,3-heptanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-heptanediol in combination with one or more of 1,2-pentanediol, 1,2-hexanediol, 1,2-octanediol, 1,2-nonanediol, 1,2-decanediol, 1,2-undecanediol, 1,2-dodecanediol or 1,2-tridecanediol, plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-heptanediol in combination with one or more of 2,3-pentanediol, 2,3-hexanediol, 2,3-heptanediol, 2,3-octanediol, 2,3-nonanediol, 2,3-decanediol, 2,3-undecanediol, 2,3-dodecanediol, or 2,3-tridecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-pentanediol in combination with 2,3-pentanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-hexanediol in combination with 2,3-hexanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-octanediol in combination with 2,3-octanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-nonanediol in combination with 2,3-nonanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-decanediol in combination with 2,3-decanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-undecanediol in combination with 2,3-undecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-dodecanediol in combination with 2,3-dodecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-tridecanediol in combination with 2,3-tridecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,3-octanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,3-nonanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,3-decanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,3-dodecanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-hexanediol in combination with 2,3-octanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-octanediol in combination with 2,3-hexanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-octanediol in combination with 2,3-heptanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-pentanediol in combination with 2,3-hexanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-pentanediol in combination with 1,2-heptanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-pentanediol in combination with 2,3-heptanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-pentanediol in combination with 2,3-octanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-pentanediol in combination with 1,2-nonanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-pentanediol in combination with 2,3-nonanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-heptanediol in combination with 1,2-octanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-heptanediol in combination with 2,3-octanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-heptanediol in combination with 1,2-nonanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants; or 1,2-heptanediol in combination with 2,3-nonanediol plus one or more antioxidants selected from the group consisting of dimethylmethoxy chromanol, hydroxyacetophenone, acorbic acid and its salts, hydroxymethoxyphenyl decanone, beta-aspartyl arginine, uric acid, urea, hydroxypinacolone retinoate, vitamin A and vitamin A derivatives, butylhydroxytoluol (BHT), butylhydroxyanisol (BHA), hydroxyphenyl propamidobenzoic acid, ascorbyl palmitate, ascorbyl phosphate and salts thereof, carnosine, rutin, tocopherol, tocopheryl acetate, ubiquinone-10, dilauryl thiodipropionate, pentaerythrityl tetra-di-t-butyl hydroxyhydrocinnamate, triethyl citrate, diethylhexyl syringylidene malonate, *lactobacillus* (ferment, filtrate, lysate), cannabinoids, cannabidiol and its extracts (*Cannabis sativa* seed oil, *Cannabis sativa* extract), cannabinol, hydroxyphenyl propamidobenzoic acid (dihydroavenanthramide D), green tea extract, *zingiber officinalis* (ginger) root extract, tropolone, allantoin, and mixtures of two or more of said antioxidants.

More preferred combinations of component (a) and (b) in the cosmetic or pharmaceutical composition or homecare product according to the first or second aspect of the present invention, preferably in cosmetic or pharmaceutical compositions for anti-wrinkle or anti-aging prevention and/or treatment are:

1,2-pentanediol plus tocopherol or a derivative thereof, and/or vitamin A or a derivative thereof, and/or vitamin C or a derivate thereof, and/or carnosine or a derivative thereof and/or *Zingiber Officinale* (Ginger) Root Extract; or 1,2-hexanediol plus tocopherol or a derivative thereof, and/or vitamin A or a derivative thereof, and/or vitamin C or a derivate thereof, and/or carnosine or a derivative thereof and/or *Zingiber Officinale* (Ginger) Root Extract; or 1,2-heptanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-octanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-nonanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-decanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-undecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-dodecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-tridecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 2,3-pentanediol plus tocopherol or a derivative thereof, and/or vitamin A or a derivative thereof, and/or vitamin C or a derivate thereof, and/or carnosine or a derivative thereof and/or *Zingiber Officinale* (Ginger) Root Extract; or 2,3-hexanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 2,3-heptanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 2,3-octanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 2,3-nonanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 2,3-decanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 2,3-undecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 2,3-dodecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 2,3-tridecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-heptanediol in combination with 2,3-heptanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-heptanediol in combination with one or more of 1,2-pentanediol, 1,2-hexanediol, 1,2-octanediol, 1,2-nonanediol, 1,2-decanediol, 1,2-undecanediol, 1,2-dodecanediol or 1,2-tridecanediol, plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-heptanediol in combination with one or more of 2,3-pentanediol, 2,3-hexanediol, 2,3-heptanediol, 2,3-octanediol, 2,3-nonanediol, 2,3-decanediol, 2,3-undecanediol, 2,3-dodecanediol, or 2,3-tridecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-hexanediol in combination with 2,3-hexanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-octanediol in combination with 2,3-octanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or 1,2-nonanediol in combination with 2,3-nonanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-decanediol in combination with 2,3-decanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-undecanediol in combination with 2,3-undecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-dodecanediol in combination with 2,3-dodecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-tridecanediol in combination with 2,3-tridecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; ortocopherol and/or vitamin A and/or carnosine; or
1,3-octanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,3-nonanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,3-decanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,3-undecanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-hexanediol in combination with 2,3-octanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-octanediol in combination with 2,3-hexanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-octanediol in combination with 2,3-heptanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-pentanediol in combination with 2,3-hexanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-pentanediol in combination with 1,2-heptanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-pentanediol in combination with 2,3-heptanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-pentanediol in combination with 2,3-octanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-pentanediol in combination with 1,2-nonanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-pentanediol in combination with 2,3-nonanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-heptanediol in combination with 1,2-octanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-heptanediol in combination with 2,3-octanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-heptanediol in combination with 1,2-nonanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract; or
1,2-heptanediol in combination with 2,3-nonanediol plus tocopherol or a derivative thereof, and/or vitamin A or a derivative thereof, and/or vitamin C or a derivate thereof, and/or carnosine or a derivative thereof, and/or *Zingiber Officinale* (Ginger) Root Extract.

Alternatively, in the above combinations the b) component for the antioxidant can also be dimethylmethoxy chromanol.

Still more preferred combinations of component (a) and (b) in the cosmetic, pharmaceutical composition or home-care product according to the first or second aspect of the present invention are:

1,2-pentanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-hexanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-heptanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-octanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-nonanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-decanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-undecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-dodecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-tridecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
2,3-pentanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
2,3-hexanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
2,3-heptanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
2,3-octanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
2,3-nonanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
2,3-decanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
2,3-undecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
2,3-dodecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
2,3-tridecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-heptanediol in combination with 2,3-heptanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-heptanediol in combination with one or more of 1,2-pentanediol, 1,2-hexanediol, 1,2-octanediol, 1,2-nonanediol, 1,2-decanediol, 1,2-undecanediol, 1,2-dodecanediol or 1,2-tridecanediol, plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-heptanediol in combination with one or more of 2,3-pentanediol, 2,3-hexanediol, 2,3-heptanediol, 2,3-octanediol, 2,3-nonanediol, 2,3-decanediol, 2,3-undecanediol, 2,3-dodecanediol, or 2,3-tridecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-hexanediol in combination with 2,3-hexanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-octanediol in combination with 2,3-octanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-nonanediol in combination with 2,3-nonanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-decanediol in combination with 2,3-decanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-undecanediol in combination with 2,3-undecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-dodecanediol in combination with 2,3-dodecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,2-tridecanediol in combination with 2,3-tridecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or
1,3-octanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,3-nonanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,3-decanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,3-undecanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-hexanediol in combination with 2,3-octanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-octanediol in combination with 2,3-hexanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-octanediol in combination with 2,3-heptanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-pentanediol in combination with 2,3-hexanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-pentanediol in combination with 1,2-heptanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-pentanediol in combination with 2,3-heptanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-pentanediol in combination with 2,3-octanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-pentanediol in combination with 1,2-nonanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-pentanediol in combination with 2,3-nonanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-heptanediol in combination with 1,2-octanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-heptanediol in combination with 2,3-octanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-heptanediol in combination with 1,2-nonanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol; or 1,2-heptanediol in combination with 2,3-nonanediol plus hydroxyphenyl propamidobenzoic acid (dihydroavenanthramide D), and/or cannabinoids, and/or cannabidiol and its extracts (*Cannabis sativa* seed oil, *Cannabis sativa* extract), and/or cannabinol.

Alternatively, in the above combinations the b) component for the antioxidant can also be dimethylmethoxy chromanol.

In a most preferred variant, the cosmetic or pharmaceutical composition or homecare product according to the first or second aspect of the present invention comprises one of the following combinations of components (a) and (b):

1,2-hexanediol plus tocopherol or a derivative thereof; or
1,2-heptanediol plus tocopherol or a derivative thereof; or
1,2-octanediol plus tocopherol or a derivative thereof; or
1,2-nonanediol plus tocopherol or a derivative thereof; or
1,2-decanediol plus tocopherol or a derivative thereof; or
1,2-undecanediol plus tocopherol or a derivative thereof; or
1,2-dodecanediol plus tocopherol or a derivative thereof; or
1,2-tridecanediol plus tocopherol or a derivative thereof; or
2,3-hexanediol plus tocopherol or a derivative thereof; or
2,3-heptanediol plus tocopherol or a derivative thereof; or
2,3-octanediol plus tocopherol or a derivative thereof; or
2,3-nonanediol plus tocopherol or a derivative thereof; or
2,3-decanediol plus tocopherol or a derivative thereof; or
2,3-undecanediol plus tocopherol or a derivative thereof; or
2,3-dodecanediol plus tocopherol or a derivative thereof; or
2,3-tridecanediol plus tocopherol or a derivative thereof; or
1,2-heptanediol in combination with 2,3-heptanediol plus tocopherol or a derivative thereof; or
1,2-heptanediol in combination with one or more of 1,2-pentanediol, 1,2-hexanediol, 1,2-octanediol, 1,2-nonanediol, 1,2-decanediol, 1,2-undecanediol, 1,2-dodecanediol or 1,2-tridecanediol, plus tocopherol or a derivative thereof; or
1,2-heptanediol in combination with one or more of 2,3-pentanediol, 2,3-hexanediol, 2,3-heptanediol, 2,3-octanediol, 2,3-nonanediol, 2,3-decanediol, 2,3-undecanediol, 2,3-dodecanediol, or 2,3-tridecanediol plus tocopherol or a derivative thereof; or
1,2-hexanediol in combination with 2,3-hexanediol plus tocopherol or a derivative thereof; or
1,2-octanediol in combination with 2,3-octanediol plus tocopherol or a derivative thereof; or
1,2-nonanediol in combination with 2,3-nonanediol plus tocopherol or a derivative thereof; or
1,2-decanediol in combination with 2,3-decanediol plus tocopherol or a derivative thereof; or
1,2-undecanediol in combination with 2,3-undecanediol plus tocopherol or a derivative thereof; or 1,2-dodecanediol in combination with 2,3-dodecanediol plus tocopherol or a derivative thereof; or
1,2-tridecanediol in combination with 2,3-tridecanediol plus tocopherol or a derivative thereof; or
1,3-octanediol plus tocopherol or a derivative thereof; or
1,3-nonanediol plus tocopherol or a derivative thereof; or
1,3-decanediol plus tocopherol or a derivative thereof; or
1,3-undecanediol plus tocopherol or a derivative thereof; or
1,2-hexanediol in combination with 2,3-octanediol plus tocopherol or a derivative thereof; or
1,2-octanediol in combination with 2,3-hexanediol plus tocopherol or a derivative thereof; or
1,2-octanediol in combination with 2,3-heptanediol plus tocopherol or a derivative thereof; or
1,2-pentanediol in combination with 2,3-hexanediol plus tocopherol or a derivative thereof; or
1,2-pentanediol in combination with 1,2-heptanediol plus tocopherol or a derivative thereof; or
1,2-pentanediol in combination with 2,3-heptanediol plus tocopherol or a derivative thereof; or
1,2-pentanediol in combination with 2,3-octanediol plus tocopherol or a derivative thereof; or
1,2-pentanediol in combination with 1,2-nonanediol plus tocopherol or a derivative thereof; or
1,2-pentanediol in combination with 2,3-nonanediol plus tocopherol or a derivative thereof; or
1,2-heptanediol in combination with 1,2-octanediol plus tocopherol or a derivative thereof; or
1,2-heptanediol in combination with 2,3-octanediol plus tocopherol or a derivative thereof; or
1,2-heptanediol in combination with 1,2-nonanediol plus tocopherol or a derivative thereof; or
1,2-heptanediol in combination with 2,3-nonanediol plus tocopherol or a derivative thereof.

Alternatively, in the above combinations the b) component for the antioxidant can also be dimethylmethoxy chromanol.

Of the above combinations, the combinations with 1,2-heptanediol, 1,2-octanediol or 2,3-alkanediols, in particular 2,3-heptanediole or 2,3-octanediole, or mixtures comprising a 1,2-alkanediol and a 2,3-alkanediol, especially a mixture including 1,2-heptanediol and 2,3-heptanediol or a mixture including 1,2-octanediol and 2,3-octanediol result in distinguished antioxidant performance, as it is demonstrated by the following examples.

The above-defined specific combinations of components (a) and (b) can be combined again with one or more further component(s) as described later on.

The cosmetic or pharmaceutical, in particular dermatological, composition as defined herein, are preferably based on a carrier, which comprises at least one oil phase. However, preparations solely based on water or water/alcohol or water/glycol are likewise possible or even preferred.

The oil phase or oil component in the cosmetic or pharmaceutical, preferably dermatological, composition according to the present invention which may be suitable are for example plant oils, hydrocarbons, fatty alcohols, fatty acid esters, liquid UV filters, or mixtures of two or more of the aforesaid oil components.

The oil phase or oil component in the cosmetic or pharmaceutical, preferably dermatological, composition according to the present invention is preferably a plant oil and even more preferably a liquid plant oil. It can also advantageously be a mixture of two or more plant oils components, especially liquid plant oil mixtures.

Plant oils or vegetable oils are oils extracted from seeds, or less often, from other parts of fruits. Like animal fats, plant oils are mixtures of triglycerides. Soybean oil, rapeseed oil and cocoa butter are examples of plant oils from seeds. Olive oil, palm oil and rice bran oil are examples of oils from other parts of fruits. In common usage, plant oil or vegetable oil may refer exclusively to vegetable fats which are liquid at room temperature or at 35 to 37° C. skin temperature. Vegetable oils are usually edible.

The term "plant oils" also includes unsaturated plant oils. Unsaturated oils or vegetable oils can be transformed through partial or complete "hydrogenation" into oils of higher melting point. The hydrogenation process involves "sparging" the oil at high temperature and pressure with hydrogen in the presence of a catalyst, typically a powdered nickel compound. As each carbon-carbon double-bond is chemically reduced to a single bond, two hydrogen atoms each form single bonds with the two carbon atoms. The elimination of double bonds by adding hydrogen atoms is called saturation; as the degree of saturation increases, the oil progresses toward being fully hydrogenated. An oil may be hydrogenated to increase resistance to rancidity (oxidation) or to change its physical characteristics. As the degree of saturation increases, the oil's viscosity and melting point increase.

In a preferred variant, the plant oil is selected from the group consisting of *Persea gratissima* (Avocado Oil), *Abies alba* Seed Oil, *Acacia victoriae* Seed Oil, *Actinidia chinensis* (Kiwi) Seed Oil, *Amaranthus hypochondriacus* Seed Oil, *Arachis hypogaea* (Peanut) Oil, *Astrocaryum murumuru* Seed Butter, *Astrocaryum tucuma* Seed Butter, *Astrocaryum tucuma* Seed Oil, *Astrocaryum vulgare* Fruit Oil, *Astrocaryum vulgare* Kernel Oil, *Avena sativa* (Oat) Kernel Oil, *Brassica alba* Seed Oil, *Brassica campestris* (Rapeseed) Seed Oil, *Butyrospermum parkii* (Shea) Butter, *Butyrospermum parkii* (Shea) Oil, *Calendula officinalis* Seed Oil, *Calophyllum inophyllum* Seed Oil, *Calophyllum tacamahaca* Seed Oil, *Camellia oleifera* Seed Oil, *Camellia reticulata* Seed Oil, *Camellia sinensis* Seed Oil, *Cannabis sativa* Seed Oil, *Cannabis sativa* Seed/Stem Oil, Canola Oil, *Carthamus tinctorius* (Safflower) Seed Oil, *Chlorella vulgaris* Oil, *Citrullus lanatus* (Watermelon) Seed Oil, *Citrus aurantifolia* (Lime) Seed Oil, *Citrus aurantium dulcis* (Orange) Seed Oil, *Citrus grandis* (Grapefruit) Seed Oil, *Cocos nucifera* (Coconut) Oil, *Cocos nucifera* (Coconut) Seed Butter, *Coffea arabica* (Coffee) Seed Oil, *Chlorella* Oil (biotech), *Corylus americana* (Hazelnut) Seed Oil, *Corylus avellana* (Hazelnut) Seed Oil, *Cucumis melo* (Melon) Seed Oil, *Cucumis sativus* (Cucumber) Seed Oil, *Cucurbita pepo* (Pumpkin) Seed Oil, *Elaeis guineensis* (Palm) Oil, *Elaeis* (Palm) Fruit Oil, *Glycine soja* (Soybean) Oil, *Gossypium herbaceum* (Cotton) Seed Oil, *Gossypium Hirsutum* (Cotton) Seed Oil, *Helianthus annuus* (Sunflower) Seed Oil, *Macadamia integrifolia* Seed Oil, *Macadamia ternifolia* Seed Oil, *Mangifera indica* (Mango) Seed Butter, *Mangifera indica* (Mango) Seed Oil, *Melissa officinalis* Seed Oil, Microalgae Oil, *Moringa oleifera* Seed Oil, *Moringa peregrina* Seed Oil, *Oenothera biennis* (Evening Primrose) Oil, *Olea europaea* (Olive) Fruit Oil, Olus Oil, *Orbignya oleifera* Seed Oil, *Orbignya speciosa* Kernel Oil, *Oryza sativa* (Rice) Bran/Germ Oil, *Oryza sativa* (Rice) Bran Oil, *Oryza sativa* (Rice) Germ Oil, *Oryza sativa* (Rice) Lipids, *Oryza sativa* (Rice) Seed Oil, *Papaver somniferum* Seed Oil, *Passiflora edulis* Seed Oil, *Persea gratissima* (Avocado) Butter, *Persea gratissima* (Avocado) Oil, *Prunus amygdalus dulcis* (Sweet Almond) Oil, *Prunus armeniaca* (Apricot) Kernel Oil, *Prunus persica* (Peach) Kernel Oil, *Punica granatum* Seed Oil, *Pyrus malus* (Apple) Seed Oil, Ricinoleic/Caproic/Caprylic/Capric Triglyceride(s), *Ricinus communis* (Castor)

Seed Oil, *Rosa canina* Fruit Oil, *Rosa moschata* Seed Oil, *Rubus idaeus* (Raspberry) Seed Oil, *Sesamum indicum* (Sesame) Seed Butter, Soybean Glycerides, *Theobroma cacao* (Cocoa) Seed Butter, *Theobroma grandiflorum* Seed Butter, *Triticum vulgare* (Wheat) Bran Lipids, *Triticum vulgare* (Wheat) Germ Oil, *Vitis vinifera* (Grape) Seed Oil, *Zea mays* (Corn) Germ Oil, and *Zea mays* (Corn) Oil.

In a particular preferred variant, the cosmetic or pharmaceutical, preferably dermatological, composition according to the first aspect or the second aspect of the present invention comprises as oil component a plant oil, selected from the group consisting of Caprylic Capric Triglycerides, *Helianthus annuus* (Sunflower) Seed Oil, *Simmondsia chinensis* ((Jojoba) Seed Oil, *Olea europaea* (Olive) Fruit Oil, *Argania spinosa* kernel oil (Argan oil), *Prunus amygdalus dulcis* (Sweet Almond) Oil, *Persea gratissima* (Avocado Oil), *Butyrospermum parkii* (Shea) Butter, *Cocos nucifera* (Coconut) Oil, *Theobroma cacao* (Cocoa) Seed Butter, and mixtures of two or more of the aforesaid plant oils.

The plant oil can be used either as a single component or in mixture with one or more further different plant oil(s) as specified above.

Hydrocarbons (mineral oils) are in general organic compounds consisting entirely of hydrogen and carbon. As defined by IUPAC nomenclature or organic chemistry, the classifications for hydrocarbons are:

1. Saturated hydrocarbons are the simplest of the hydrocarbon species. They are composed entirely of single bonds and are saturated with hydrogen. The formula for acyclic saturated hydrocarbons (i.e., alkanes) is $C_nH_{2n+2}$. The most general form of saturated hydrocarbons is $C_nH_{2n+2(1-r)}$, where r is the number of rings. Those with exactly one ring are the cycloalkanes. Saturated hydrocarbons are the basis of petroleum fuels and are found as either linear or branched species.
2. Unsaturated hydrocarbons have one or more double or triple bonds between carbon atoms. Those with double bond are called alkenes. Those with one double bond have the formula $C_nH_{2n}$ (assuming non-cyclic structures). Those containing triple bonds are called alkynes. Those with one triple bond have the formula $C_nH_{2n-2}$.
3. Aromatic hydrocarbons, also known as arenes, are hydrocarbons that have at least one aromatic ring.

Hydrocarbons can be inter alia liquids (e.g. hexane and benzene), waxes or low melting solids (e.g. paraffin wax and naphthalene). The term 'aliphatic' refers to non-aromatic hydrocarbons. Saturated aliphatic hydrocarbons are sometimes referred to as "paraffins". Mineral oils and waxes are mixtures of predominantly saturated hydrocarbons consisting of straight-chain, branched and ring structures with carbon chain lengths greater than C14. Mineral oils and waxes are chemical substances prepared from naturally occurring crude petroleum oil. They mainly consist of mineral oil saturated hydrocarbons (MOSH) and mineral oil aromatic hydrocarbons (MOAN). Hydrocarbons have been used for many decades in skin and lip care cosmetic products due to their excellent skin tolerance as well as their high protecting and cleansing performance and broad viscosity options. In contrast to vegetable oils, mineral oils are non-allergenic since they are highly stable and not susceptible to oxidation or rancidity.

In a preferred variant, the hydrocarbon as the oil component of the cosmetic or pharmaceutical, preferably dermatological, composition of the present invention is selected from the group consisting of undecane, tridecane, mineral oil, petrolatum, squalane, isohexadecane, C7-C8 isoparaffin, C8-C9 isoparaffin, C9-C11 isoparaffin, C9-C12 isoparaffin, C9-C13 isoparaffin, C9-C14 isoparaffin, C9-C16 isoparaffin, C10-C11 isoparaffin, C10-C12 isoparaffin, C10-C13 isoparaffin, C11-C12 isoparaffin, C11-C13 isoparaffin, C11-C14 isoparaffin, C12-C14 isoparaffin, C12-C15 isoparaffin, C12-C20 isoparaffin, C13-C14 isoparaffin, C13-C16 isoparaffin, C14-C16 isoparaffin, C15-C19 isoparaffin, and C18-C70 isoparaffin.

In a particular preferred variant, the oil component of the cosmetic or pharmaceutical, preferably dermatological, composition of the present invention is a hydrocarbon selected from the group consisting of hydrocarbons, petrolatum, squalane, isohexadecane, C13-C14 isoparaffin, and mixtures of two or more of the aforesaid hydrocarbons.

The hydrocarbon can be used either as a single component or in mixture with one or more further different hydrocarbon(s) as specified above.

A fatty alcohol (or long-chain alcohol) is usually a high-molecular-weight, straight-chain primary alcohol, but can also range from as few as 4 to 6 carbons to as many as 22 to 26, derived from natural fats and oils. The precise chain length varies with the source. Some commercially important fatty alcohols are lauryl, stearyl and oleyl alcohols. They are colourless oily liquids (for smaller carbon numbers) or waxy solids, although impure samples may appear yellow. Fatty alcohols usually have an even number of carbon atoms and a single alcohol group (—OH) attached to the terminal carbon. Some are unsaturated and some are branched. Most fatty alcohols in nature are found as waxes which are esters with fatty acids and fatty alcohols. The traditional sources of fatty alcohols have largely been various vegetable oils and these remain a large-scale feedstock. The alcohols are obtained from the triglycerides (fatty acid triesters), which form the bulk of the oil. The process involves the transesterification of the triglycerides to give methyl esters which are then hydrogenated to give the fatty alcohols. Fatty alcohols are also prepared from petrochemical sources. In the Ziegler process, ethylene is oligomerized using triethylaluminium followed by air oxidation. Alternatively, ethylene can be oligomerized to give mixtures of alkenes, which are subjected to hydroformylation, this process affording odd-numbered aldehyde, which is subsequently hydrogenated. Fatty alcohols are mainly used in the production of detergents and surfactants. They are components also of cosmetic solvents. They find use as co-emulsifiers, emollients and thickeners in cosmetics.

In a preferred variant, the fatty alcohol as the oil component of the cosmetic or pharmaceutical, preferably dermatological, composition of the present invention is selected from the group consisting of phenyl propanol, dimethyl phenylbutanol, hexyldecanol, octyldodecanol, octyldecanol, tridecylalcohol, isostearyl alcohol, phenylisohexanol, phenylpropanol, trimethylbenzenepropanol, isoamylalcohol, isostearyl alcohol, and isotridecyl alcohol.

The fatty alcohol can be used either as a single component or in mixture with one or more further different fatty alcohol(s) as specified above.

A fatty acid ester is a type of ester that results from the combination of a fatty acid with an alcohol. When the alcohol component is glycerol, the fatty acid esters produced can be monoglycerides, diglycerides or triglycerides. Fatty acid esters have a conditioning effect of softening the skin to create a smoothing sensation. They are also added to cosmetics to dissolve high-polarity active ingredients and UV absorbers. Esters of straight-chain fatty acids and lower alcohols are effective for dissolving slightly soluble ingredients for oils with a light touch during application. Isostearic acids and other liquid oils with branched fatty acids and unsaturated fatty acids are commonly used as emollients. Higher fatty acid esters and esters of higher alcohols with relatively high melting points are added to skin creams to adjust the application touch.

In a preferred variant, the fatty acid ester as the oil component of the cosmetic or pharmaceutical, preferably dermatological, composition of the present invention is selected from the group consisting of C12-C15 Alkyl Benzoate, Capric/Lauric/Myristic/Oleic Triglyceride, Caprylic/Capric Triglyceride, Caprylic/Capric/Lauric Triglyceride, Caprylic/Capric/Linoleic Triglyceride, Caprylic/Capric/Myristic/Stearic Triglyceride, Caprylic/Capric/Palmitic/Stearic Triglyceride, Caprylic/Capric/Stearic Triglyceride, Caprylic/Capric/Succinic Triglyceride, Caprylyl Caprylate, Cetearyl Ethylhexanoate, Cetearyl Isononanoate, Cetearyl Nonanoate, Coco-Caprylate, Decyl Cocoate, Decyl Oleate, Dicaprylyl Carbonate, Diethyl Succinate, Diethylhexyl 2,6-Naphthalate, Diethylhexyl Carbonate, Dibutyl Adipate, Diisopropyl Adipate, Dipropylheptyl Carbonate, Ethyl Laurate, Ethylhexyl Isononanoate, Ethylhexyl Palmitate, Ethylhexyl Stearate, Glyceryl Caprylate Caprate, Glyceryl Caprylate, Glyceryl Laurate, Glyceryl Triacetyl Hydroxystearate, Glyceryl Triacetyl Ricinoleate, Hexyl Laurate, Isoamyl acetate, Isoamyl Cocoate, Isopropyl Palmitate, Isosorbide Dicaprylate, Isopropyl Myristate, Myristyl Myristate, Oleic/Linoleic Triglyceride, Oleic/Palmitic Triglyceride, Oleic/Palmitic/Lauric/Myristic/Linoleic Triglyceride, Propanediol Caprylate, Ricinoleic/Caproic/Caprylic/Capric Triglyceride, Oleostearine, Oleyl Erucate, Palmitic/Stearic Triglyceride, Propanediol Dicaprylate Caprate, Propylheptyl Caprylate, Stearyl Heptanoate/Stearyl Caprylate, Triheptanoin, Trihydroxystearin, Triisononanoin, Triisopalmitin, Triisostearin, Trilaurin, Trilinolein, Trilinolenin, Trimyristin, Triolein, Tripalmitin, Tripalmitolein, Tripelargonin, Triricinolein, and Tristearin.

In a particular preferred variant, the oil component of the cosmetic or pharmaceutical, preferably dermatological, composition of the present invention is a fatty acid ester selected from the group consisting of C12-C15 Alkyl Benzoate, Caprylic/Capric Triglyceride, Caprylyl Caprylate, Cetearyl Ethylhexanoate, Cetearyl Isononanoate, Cetearyl Nonanoate, Coco-Caprylate, Decyl Cocoate, Decyl Oleate, Dicaprylyl Carbonate, Diethylhexyl 2,6-Naphthalate, Dibutyl Adipate, Diisopropyl Adipate, Ethyl Laurate, Ethylhexyl Isononanoate, Ethylhexyl Palmitate, Ethylhexyl Stearate, Glyceryl Caprylate, Glyceryl Laurate, Hexyl Laurate, Isoamyl Cocoate, Isopropyl Palmitate, Isopropyl Myristate, Myristyl Myristate, Propanediol Caprylate, Oleyl Erucate, Palmitic/Stearic Triglyceride, Propanediol Dicaprylate Caprate, Trihydroxystearin, Triisostearin, Triisononanoin, Tristearin, and mixtures of two or more of the aforesaid fatty acid esters.

The fatty acid ester can be used either as a single component or in mixture with one or more further different fatty acid ester(s) as specified above.

An UV filter is a compound or a mixture of compounds that block or absorb ultraviolet (UV) light. Since excessive UV radiation can cause sunburn, photoaging, and skin cancer, care products such as sunscreen usually include a classification for the specific wavelengths they filter. UV classifications include UVA (320-400 nm), UVB (290-320 nm) and UVC (200-280 nm). UV-absorbing compounds are used not only in sunscreen, but also in other personal care products, such as lipstick, shampoo, hair spray, body wash, toilet soap, and insect repellent. Chemical filters protect against UV radiation by absorbing, reflecting, or scattering. Reflection and scattering are accomplished by inorganic physical UV filters, such as titanium dioxide ($TiO_2$) and zinc oxide (ZnO). Absorption, mainly of UVB, is done by organic UV filters, which are known as chemical UV filters.

In a preferred variant, the liquid UV filter as the oil component of the cosmetic or pharmaceutical, preferably dermatological, composition of the present invention is selected from the group consisting of Octocrylene, Ethylhexyl Salicylate, Homosalate, Ethylhexyl Methoxycinnamate, Isoamyl p-Methoxycinnamate, Camphor Benzalkonium Methosulfate, Polyarylamidomethyl Benzylidene Camphor, Isooctyl Methoxycionnamate, Ethylhexyl Triazone, Drometrizole Trisiloxane, Diethylhexyl Butamido Triazone, 3-Benzylidene Camphor, Octyl Salicylate, Ethylhexyl Dimethyl PABA, Bis-Ethylhexyloxyphenol Methoxyphenyl Triazine, Polysilicone-15, Diethylamino Hydroxybenzoyl Hexyl benzoate, N,N,N-Trimethyl-4-(2-oxoborn-3-ylidenemethyl) anilinium methyl sulfate, Benzoic acid-2-hydroxy-3,3,5-trimethylcyclohexyl ester/Homosalate, 2-Cyano-3,3-diphenyl acrylic acid, 2-Ethylhexyl ester/Octocrilene, 2-Ethylhexyl-4-m ethoxycinnamate/Octinoxate, Ethoxylated Ethyl-4-aminobenzoate, 2-Ethylhexyl salicylate/Octisalate, 2-Ethylhexyl-4-(dimethylamino)benzoate/Padimate O (USAN: BAN), 2,2'-Methylene-bis(6-(2H-benzotriazol-2-yl)-4-(1,1,3,3-tetramethyl-butyl)phenol)/Bisoctrizole, and Dimethicodiethylbenzalmalonate. The UV filter can be used either as a single component or in mixture with one or more further different UV filter (s) as specified above.

In a particular preferred variant the oil component of the cosmetic or pharmaceutical, preferably dermatological, composition of the present invention is a liquid UV filter selected from the group consisting of Octocrylene, Ethylhexyl Salicylate, Homosalate, Ethylhexyl Methoxycinnamate, Isoamyl p-Methoxycinnamate, N,N,N-Trimethyl-4-(2-oxoborn-3-ylidenemethyl) anilinium methyl sulfate, Benzoic acid-2-hydroxy-3,3,5-trimethylcyclohexyl ester/Homosalate, 2-Cyano-3,3-diphenyl acrylic acid, 2-Ethylhexyl ester/Octocrilene, 2-Ethylhexyl-4-methoxycinnamate/Octinoxate, Ethoxylated Ethyl-4-aminobenzoate, 2-Ethylhexyl salicylate/Octisalate, 2-Ethylhexyl-4-(dimethylamino)benzoate/Padimate 0 (USAN: BAN), 2,2'-Methylene-bis(6-(2H-benzotriazol-2-yl)-4-(1,1,3,3-tetramethyl-butyl)phenol)/Bisoctrizole, Dimethicodiethylbenzalmalonate, and mixtures of two or more of the aforesaid UV filters.

In addition to the oil phase or oil component as defined before, the cosmetic or pharmaceutical, preferably dermatological, composition according to the present invention preferably includes one or more further oil bodies. Suitable oil bodies, which form constituents of the O/W emulsions, are, for example, Guerbet alcohols based on fatty alcohols having 6 to 18, preferably 8 to 10, carbon atoms, esters of linear C5-C22 fatty acids with linear or branched C5-C22 fatty alcohols or esters of branched C1-C13 carboxylic acids with linear or branched C6-C22 fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear C6-C22 fatty acids with branched alcohols, in particular 2-ethylhexanol, esters of C18-C38 alkylhydroxy carboxylic acids with linear or branched C6-C22 fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on C6-C10 fatty acids, liquid mono-/di-/triglyceride mixtures based on C6-C18 fatty acids, esters of C6-C22 fatty alcohols and/or Guerbet alcohols with aromatic carboxylic acids, in particular benzoic acid, esters of C2-C12 dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched CC-C22 fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Within the context of the present invention, it is also possible and in some cases advantageous, to combine the cosmetic or pharmaceutical, in particular dermatological, composition according to the first or second aspect of the present invention with other active substances, adjuvants or additives. The cosmetically or pharmaceutically active agents and/or adjuvants and/or additives can in some instances provide one or more than one benefit or operate via more than one mode of action.

Thus, optionally, other conventional cosmetically and/or pharmaceutically active substances, adjuvants or additives, as further described below, may be added as component (c), i.e., in order to obtain a ready-for-use cosmetic or pharmaceutical, preferably dermatological, composition or formulation.

The cosmetic or pharmaceutical, preferably dermatological, composition according to the present invention can advantageously be combined with other cosmetically or pharmaceutically active agents and/or adjuvants and/or additives or auxiliaries, such as are customarily used in such compositions, such as for example abrasives, anti-acne agents, agents against ageing of the skin, anti-cellulitis agents, anti-dandruff agents, anti-inflammatory agents, anti-microbial agents, irritation-preventing agents, irritation-inhibiting agents, antioxidants, astringents, odor absorbers, perspiration-inhibiting agents, antiseptic agents, anti-statics, binders, buffers, carrier materials, chelating agents, cell stimulants, cleansing agents, depilatory agents, surface-active substances, deodorizing agents, antiperspirants, softeners, emulsifiers, enzymes, enzyme inhibitors, essential oils, fibers, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, dyes, friction-reducing agents, lubricants, moisturizing creams, ointments, opacifying agents, plasticizing agents, covering agents, polish, preservatives, gloss agents, green and synthetic polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, surfactants, UV-absorbing agents, UV filters, primary sun protection factors, secondary sun protection factors, detergents, fabric conditioning agents, suspending agents, skin-tanning agents, actives modulating skin or hair pigmentation, matrix metalloproteinase inhibitors, skin moisturizing agents, glycosaminoglycan stimulators, TRPV1 antagonists, desquamating agents, anti-cellulite agents or fat enhancing agents, hair growth activators or inhibitors, thickeners, rheology additives, vitamins, oils, waxes, pearlizing waxes, fats, phospholipids, saturated fatty acids, mono- or polyunsaturated fatty acids, α-hydroxy acids, polyhydroxy fatty acids, liquefiers, dyestuffs, colour-protecting agents, pigments, anti-corrosives, fragrances or perfume oils, aromas, flavouring substances, odoriferous substances, polyols, electrolytes, organic solvents, and mixtures of two or more of the aforementioned substances, as further described below.

Of the above cosmetically or pharmaceutically active agents and/or adjuvants and/or additives or auxiliary agents against ageing of the skin, anti-microbial agents, chelating agents, emulsifiers, surfactants, preservatives, green and synthetic polymers, skin-cooling agents, rheology additives, oils, fragrances or perfume oils, and polyols are particularly preferred in the preparation of cosmetic and pharmaceutical composition.

Since dermatological conditions or diseases are often associated with dry skin, scratched skin, skin lesions or even inflammation, the cosmetic or pharmaceutical, preferably dermatological, composition according to the present invention advantageously contains preferably anti-inflammatories, antibacterial or antimycotic substances, substances having a reddening-alleviating or itch-alleviating action, lenitive substances, moisturisers and/or cooling agents, osmolytes, keratolytic substances, nurturing substances, anti-inflammatory, antibacterial or antimycotic substances, substances having a reddening-alleviating or itch-alleviating action, lenitive substances, anti-dandruff substances, or other active compounds such as solvents, fragrances, antioxidants, preservatives, (metal) chelating agents, penetration enhancers, or mixtures of two or more of afore specified agents, as further described below.

Anti-ageing actives: The cosmetic or pharmaceutical, preferably dermatological, composition according to the present invention preferably contains one or more anti-ageing actives. In the context of the invention, anti-ageing or biogenic agents are, for example antioxidants, matrix metalloproteinase inhibitors (MMPI), skin moisturizing agents, glycosaminglycan stimulators, anti-inflammatory agents, TRPV1 antagonists and plant extracts.

Matrix Metalloproteinase Inhibitors (MMPI): A preferred cosmetic or pharmaceutical, preferably dermatological, composition according to the present invention comprises one or more matrix metalloproteinase inhibitors, especially those inhibiting matrix metalloproteinases enzymatically cleaving collagen, selected from the group consisting of ursolic acid, retinyl palmitate, propyl gallate, precocenes, 6-hydroxy-7-m ethoxy-2,2-dimethyl-1(2H)-benzopyran, 3,4-dihydro-6-hydroxy-7-m eth-oxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and *Lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf, as e.g. SymMatrix (company Symrise, INCI: Maltodextrin, *Rubus fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-moisturizing agents: A preferred cosmetic or pharmaceutical, preferably dermatological, composition according to the present invention comprises one or more skin-moisturizing agents. Preferred skin moisturizing agents are selected from the group consisting of alkane diols or alkane triols comprising 3 to 12 carbon atoms, preferably C3-C10-alkane diols and C3-C10-alkane triols. More preferably the skin moisturizing agents are selected from the group consisting of glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan stimulators: A preferred cosmetic or pharmaceutical, preferably dermatological, composition according to the present invention comprises one or more substances stimulating the synthesis of glycosaminoglycans which are selected from the group consisting of hyaluronic acid and derivatives or salts, Subliskin (Sederma, INCI: *Sinorhizobium meliloti* Ferment Filtrate, Cetyl Hydroxyethylcellulose, Lecithin), Hyalufix (BASF, INCI: Water, Butylene Glycol, Alpinia galanga leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, Alpinia galanga leaf extract and tetradecyl aminobutyroylvalylaminobutyric urea trifluoroacetate.

TRPV1 antagonists: A preferred cosmetic or pharmaceutical, preferably dermatological, composition according to the present invention comprises one or more TRPV1 antagonsits. Suitable compounds which reduce the hypersensitivity of skin nerves based on their action as TRPV1 antagonists, encompass e.g. trans-4-tert-butyl cyclohexanol, or indirect modulators of TRPV1 by an activation of the p-receptor, e.g. acetyl tetrapeptide-15, are preferred.

Plant extracts: A preferred cosmetic or pharmaceutical, preferably dermatological, composition according to the present invention comprises one or more plant extracts. Plant extracts, special highly active plant extract fractions and also highly pure active substances isolated from plant extracts can also be used in the cosmetic or pharmaceutical, preferably dermatological, composition according to the present invention. Extracts, fractions and active substances from camomile, aloe vera, *Commiphora* species, *Rubia* species, willows, willow-herb, ginger, marigold, *Arnica, Glycyrrhiza species, Echinacea species, Rubus* species and pure substances such as inter alia bisabolol, apigenin, apigenin-7-glucoside, gingerols such as [6]-gingerol, paradols such as [6]-paradol, boswellic acid, phytosterols, glycyrrhizine, glabridin or licochalcone A are particularly preferred.

Anti-inflammatory agents: The cosmetic or pharmaceutical, preferably dermatological, composition according to the present invention preferably also contains anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. More particularly:

(i) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone, (ii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone, (iii) natural or naturally occurring anti-inflammatory substances or substances that alleviate reddening and/or itching, in particular extracts or fractions from camomile, Aloe vera, *Commiphora* species, *Rubia* species, willow, willow-herb, oats, *Calendula, Arnica*, St John's wort, honeysuckle, rosemary, *Passiflora incarnata*, witch hazel, ginger or *Echinacea*, or single active compounds thereof, (iv) histamine receptor antagonists, serine protease inhibitors (e.g. of Soy extracts), TRPV1 antagonists (e.g. 4-t-Butylcyclohexanol), NK1 antagonists (e.g. Aprepitant, Hydroxyphenyl Propamidobenzoic Acid), cannabinoid receptor agonists (e.g. Palmitoyl Ethanolamine) and TRPV3 antagonists.

Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, *Calendula*, *Arnica*, St John's wort, honeysuckle, rosemary, *Passiflora incarnata*, witch hazel, ginger or *Echinacea*; preferably selected from the group consisting of extracts or fractions from camomile, Aloe vera, oats, *calendula*, *arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and ß-glucans, in particular 1,3→1,4-ß-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

Physiological cooling agents: The cosmetic or pharmaceutical, preferably dermatological, composition according to the present invention can be particularly advantageously combined with one or more physiological cooling agent(s). The use of cooling agents can alleviate itching. Preferred individual cooling agents for use within the framework of the present invention are listed below. The person skilled in the art can add many other cooling agents to this list; the cooling agents listed can also be used in combination with one another: which are preferably selected here from the following list: menthol and menthol derivatives (for example L-menthol, D-menthol, racemic menthol, isomenthol, neoisomenthol, neomenthol) menthylethers (for example (I-menthoxy)-1,2-propanediol, (1-menthoxy)-2-methyl-1,2-propanediol, I-menthyl-methylether), menthone glyceryl acetal, menthone glyceryl ketal or mixtures of both, menthylesters (for example menthylformiate, menthylacetate, menthylisobutyrate, menthyhydroxyisobutyrat, menthyllactates, L-menthyl-L-lactate, L-menthyl-D-lactate, menthyl-(2-m ethoxy)acetate, menthyl-(2-m ethoxyethoxy)-acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^{\alpha}$-(menthanecarbonyl)glycinethylester [WS5], menthanecarboxylic acid-N-(4-cyanophenyl)amide or menthanecarboxylic acid-N-(4-cyanomethylphenyl)amide, menthanecarboxylic acid-N-(alkoxyalkyl) amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(−)-isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrim idine-2-one (for example iciline or related compounds, as described in WO 2004/026840), further carboxamides (for example N-(2-(pyridin-2-yl) ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates and [(1R, 2S,5R)-2-isopropyl-5-methyl-cyclohexyl] 2-(ethylamino)-2-oxo-acetate (X Cool). Cooling agents which are preferred due to their particular synergistic effect are 1-menthol, d-menthol, racemic menthol, menthone glycerol acetal (trade name: Frescolat® MGA), menthyl lactate (preferably 1-menthyl lactate, in particular 1-menthyl 1-lactate (trade name: Frescolat® ML)), substituted menthyl-3-carboxamides (such as menthyl-3-carboxylic acid N-ethyl amide), 2-isopropyl-N-2,3-trimethyl butanamide, substituted cyclohexane carboxamides, 3-menthoxypropane-1,2-diol, 2-hydroxyethyl menthyl carbonate, 2-hydroxypropyl menthyl carbonate and isopulegol. Particularly preferred cooling agents are 1-menthol, racemic menthol, menthone glycerol acetal (trade name: Frescolat® MGA), menthyl lactate (preferably 1-menthyl lactate, in particular 1-menthyl 1-lactate (trade name: Frescolat® ML)), 3-menthoxypropane-1, 2-diol, 2-hydroxyethyl menthyl carbonate and 2-hydroxypropyl menthyl carbonate. Very particularly preferred cooling agents are 1-menthol, menthone glycerol acetal (trade name: Frescolat® MGA) and menthyl lactate (preferably 1-menthyl lactate, in particular 1-menthyl 1-lactate (trade name: Frescolat® ML).

Moisturising and/or moisture-retaining substances: Itching occurs with particular intensity when the skin is dry. The use of skin-moisturising and/or moisture-retaining substances can significantly alleviate itching. The cosmetic or pharmaceutical, preferably dermatological, composition according to the present invention can therefore advantageously also contain one or more of the following moisturising and/or moisture-retaining substances: sodium lactate, urea, urea derivatives, alcohols, glycerol, diols such as propylene glycol, hexylene glycol, collagen, elastin or hyaluronic acid, diacyl adipates, petrolatum, urocanic acid, lecithin, panthenol, phytantriol, lycopene, (pseudo-)ceramides, glycosphingolipids, cholesterol, phytosterols, chitosan, chondroitin sulphate, lanolin, lanolin esters, amino acids, alpha-hydroxy acids (such as citric acid, lactic acid, malic acid) and their derivatives, mono-, di- and oligosaccharides such as glucose, galactose, fructose, mannose, fructose and lactose, polysugars such as R-glucans, in particular 1,3-1,4-β-glucan from oats, alpha-hydroxy fatty acids, triterpene acids such as betulinic acid or ursolic acid, and algae extracts.

Lenitive substances: The cosmetic or pharmaceutical, preferably dermatological, composition according to the present invention can also contain advantageously one or more lenitive substances, wherein any lenitive substances can be used which are suitable or customary in cosmetic or pharmaceutical applications such as alpha-bisabolol, azulene, guaiazulene, 18-beta-glycyrrhetinic acid, allantoin, Aloe vera juice or gel, extracts of *Hamamelis virginiana* (witch hazel), *Echinacea* species, *Centella asiatica*, chamomile, *Arnica monatana, Glycyrrhiza* species, algae, seaweed and *Calendula officinalis*, and vegetable oils such as sweet almond oil, baobab oil, olive oil and panthenol, Laureth-9, Trideceth-9 and 4-t-butylcyclohexanol.

Antibacterial or antimycotic active substances: Antibacterial or antimycotic active substances can also particularly advantageously be used in the cosmetic or pharmaceutical, preferably dermatological, composition according to the present invention, wherein any antibacterial or antimycotic active substances can be used which are suitable or customary in cosmetic or pharmaceutical, in particular dermatological applications. In addition to the large group of conventional antibiotics, other products which are advantageous here include those relevant to cosmetics such as in particular triclosan, climbazole, octoxyglycerin, Octopirox® (1-hydroxy-4-methyl-6-(2,4,4-trimethylpentyl)-2(1H)-pyridone 2-aminoethanol salt), chitosan, farnesol, glycerol monolaurate or combinations of said substances, which are used inter alia against underarm odour, foot odour or dandruff.

Anti-microbial agents: The cosmetic or pharmaceutical, preferably dermatological, composition according to the present invention preferably contains one or more anti-microbioal agents. Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Desquamating agents: The cosmetic or pharmaceutical, preferably dermatological, composition according to the present invention preferably contains one or more desquamating agents. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; Trisodium Dicarboxymethyl Alaninate (tradename Neutrol MGDA), N-acyl-N,N',N'-ethylenediaminetriacetic acid; aminosulphonic compounds and in particular (N-2-hydroxyethylpiperazine-N-2-ethane) sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors.

Anti-dandruff substances: In addition, the cosmetic or pharmaceutical, preferably dermatological, composition according to the present invention can also advantageously be used in combination with one or more anti-dandruff substances, including triclosan, climbazole, octoxyglycerin, Octopirox® (1-hydroxy-4-methyl-6-(2,4,4-trimethylpentyl)-2(1H)-pyridone 2-aminoethanol salt), chitosan, farnesol, glycerol monolaurate, Propanediol Monocaprylate or combinations of said substances, which are used inter alia against dandruff.

Further suitable anti-dandruff agents are Pirocton Olam in (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

(Metal) chelating agents: A combination with one or more (metal) chelating agents can also be advantageous used in the cosmetic or pharmaceutical, preferably dermatological, composition according to the present invention, wherein any metal chelating agents can be used which are suitable or customary in cosmetic or pharmaceutical applications. Preferred (metal) chelating agents include α-hydroxy fatty acids, phytic acid, lactoferrin, α-hydroxy acids, such as inter alia gluconic acid, glyceric acid, glycolic acid, isocitric acid, citric acid, lactic acid, malic acid, mandelic acid, tartaric acid, as well as humic acids, bile acids, bile extracts, bilirubin, biliverdin or EDTA, EGTA, Trisodium Dicarboxymethyl Alaninate, and their derivatives. The use of one or more chelating agent(s) improves the stability of the composition according to the present invention.

Emulsifiers: In addition, the cosmetic or pharmaceutical, preferably dermatological, composition according to the present invention can also advantageously contain one or more emulsifiers, including for example:

products of the addition of 2 to 30 mol ethylene oxide and/or 0 to 5 mol propylene oxide onto linear C8-22 fatty alcohols, onto C12-22 fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides: Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters: Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters: Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Poly-glyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32), Polyglyceryl Polyricinoleate (Admul® WOL 1403), Polyglyceryl Dimerate Isostearate, and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers: Typical anionic emulsifiers are aliphatic C12 to C 22 fatty acids, such as palmitic acid, stearic acid or behenic acid for example, and C12 to C22 dicarboxylic acids, such as azelaic acid or sebacic acid for example.

Amphoteric emulsifiers: Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a C8/18 alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylam idopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Surfactants: The cosmetic or pharmaceutical, preferably dermatological, composition according to the present invention preferably includes one or more anionic and/or amphoteric or zwitterionic surfactants. Typical examples encompass: Almondamidopropylamine Oxide, Almondamidopropyl Betaine, Aminopropyl Laurylglutamine, Ammonium C12-15 Alkyl Sulfate, Ammonium C12-16 Alkyl Sulfate, Ammonium Capryleth Sulfate, Ammonium Cocomonoglyceride Sulfate, Ammonium Coco-Sulfate, Ammonium Cocoyl Isethionate, Ammonium Cocoyl Sarcosinate, Ammonium C12-15 Pareth Sulfate, Ammonium C9-10 Perfluoroalkylsulfonate, Ammonium Dinonyl Sulfosuccinate, Ammonium Dodecylbenzenesulfonate, Ammonium Isostearate, Ammonium Laureth-6 Carboxylate, Ammonium Laureth-8 Carboxylate, Ammonium Laureth Sulfate, Ammonium Laureth-5 Sulfate, Ammonium Laureth-7 Sulfate, Ammonium Laureth-9 Sulfate, Ammonium Laureth-12 Sulfate, Ammonium Lauroyl Sarcosinate, Ammonium Lauryl Sulfate, Ammonium Lauryl Sulfosuccinate, Ammonium Myreth Sulfate, Ammonium Myristyl Sulfate, Ammonium Nonoxynol-4 Sulfate, Ammonium Nonoxynol-30 Sulfate, Ammonium Oleate, Ammonium Palm Kernel Sulfate, Ammonium Stearate, Ammonium Tallate, AMPD-Isostearoyl Hydrolyzed Collagen, AMPD-Rosin Hydrolyzed Collagen, AMP-Isostearoyl Hydrolyzed Collagen, AMP-Isostearoyl Hydrolyzed Keratin, AMP-Isostearoyl Hydrolyzed Soy Protein, AMP-Isostearoyl Hydrolyzed Wheat Protein, Apricotamidopropyl Betaine, Arachidic Acid, Arginine Hexyldecyl Phosphate, Avocadamidopropyl Betaine, Avocado Oil Glycereth-8 Esters, Babassu Acid, Babassuamidopropylamine Oxide, Babassuamidopropyl Betaine, Beeswax Acid, Behenamidopropyl Betaine, Behenamine Oxide, Beheneth-25, Beheneth-30, Behenic Acid, Behenyl Betaine, Bis-Butyldimethicone Polyglyceryl-3, Butoxynol-5 Carboxylic Acid, Butoxynol-19 Carboxylic Acid, Butyldimoniumhydroxypropyl Butylglucosides Chloride, Butyldimoniumhydroxypropyl Laurylglucosides Chloride, Butyl Glucoside, Butylglucoside Caprate, Butylglucosides Hydroxypropyltrimonium Chloride, Butyloctanoic Acid, C18-36 Acid, C20-40 Acid, C30-50 Acid, C16-22 Acid Amide MEA, Calcium Dodecylbenzenesulfonate, Calcium Lauroyl Taurate, C9-16 Alkane/Cycloalkane, C10-14 Alkyl Benzenesulfonic Acid, C12-14 Alkyl Diaminoethylglycine HCL, C9-15 Alkyl Phosphate, *Candida bombicola*/Glucose/Methyl Rapeseedate Ferment, Canolamidopropyl Betaine, Capric Acid, Caproic Acid, Caproyl Ethyl Glucoside, Capryl/Capramidopropyl Betaine, Capryleth-4 Carboxylic Acid, Capryleth-6 Carboxylic Acid, Capryleth-9 Carboxylic Acid, Caprylic Acid, Capryloyl Collagen Amino Acids, Capryloyl Glycine, Capryloyl Hydrolyzed Collagen, Capryloyl Hydrolyzed Keratin, Capryloyl Keratin Amino Acids, Capryloyl Silk Amino Acids, Caprylyl/Capryl Glucoside, Caprylyl/Capryl Wheat Bran/Straw Glycosides, Caprylyl Glucoside, Caprylyl Glyceryl Ether, Caprylyl Pyrrolidone, Carnitine, Ceteareth-20, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Ceteareth-55, Ceteareth-60, Ceteareth-80, Ceteareth-100, Ceteareth-25 Carboxylic Acid, Ceteareth-2 Phosphate, Ceteareth-4 Phosphate, Ceteareth-5 Phosphate, Ceteareth-10 Phosphate, Ceteth-20, Ceteth-23, Ceteth-24, Ceteth-25, Ceteth-30, Ceteth-40, Ceteth-45, Ceteth-150, Ceteth-8 Phosphate, Ceteth-10 Phosphate, Ceteth-20 Phosphate, Cetoleth-22, Cetoleth-24, Cetoleth-25, Cetoleth-30, Cetyl Betaine, *Chrysanthemum sinense* Flower Extract, C12-14 Hydroxyalkyl Hydroxyethyl Beta-Alanine, C12-14 Hydroxyalkyl Hydroxyethyl Sarcosine, Cocamidoethyl Betaine, Cocamidopropylamine Oxide, Cocamidopropyl Betainamide MEA Chloride, Cocamidopropyl Betaine, Cocamidopropyl Hydroxysultaine, Cocamine Oxide, Cocaminobutyric Acid, Cocaminopropionic Acid, Coceth-7 Carboxylic Acid, Coceth-4 Glucoside, Cocoamphodipropionic Acid, Cocobetainamido Amphopropionate, Coco-Betaine, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Coco-Glucoside, Cocoglucosides Hydroxypropyltrimonium Chloride, Coco-Hydroxysultaine, Coco-Morpholine Oxide, Coconut Acid, Coconut Oil Glycereth-8 Esters, Coco/Oleamidopropyl Betaine, Coco-Sultaine, Coco/Sunfloweramidopropyl Betaine, Cocoylcholine Methosulfate, Cocoyl Glutamic Acid, Cocoyl Hydrolyzed Collagen, Cocoyl Hydrolyzed Keratin, Cocoyl Hydrolyzed Oat Protein, Cocoyl Hydrolyzed Rice Protein, Cocoyl Hydrolyzed Silk, Cocoyl Hydrolyzed Soy Protein, Cocoyl Hydrolyzed Wheat Protein, Cocoyl Sarcosine, Corn Acid, Cottonseed Acid, Cottonseed Oil Glycereth-8 Esters, C10-16 Pareth-1, C10-16 Pareth-2, C11-13 Pareth-6, C11-13 Pareth-9, C11-13 Pareth-10, C11-15 Pareth-30, C11-15 Pareth-40, C12-13 Pareth-1, C12-13 Pareth-23, C12-14 Pareth-5, C12-14 Pareth-9, C13-15 Pareth-21, C14-15 Pareth-8, C20-22 Pareth-30, C20-40 Pareth-40, C20-40 Pareth-95, C22-24 Pareth-33, C30-50 Pareth-40, C9-11 Pareth-6 Carboxylic Acid, C9-11 Pareth-8 Carboxylic Acid, C11-15 Pareth-7 Carboxylic Acid, C12-13 Pareth-5 Carboxylic Acid, C12-13 Pareth-7 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C12-15 Pareth-12 Carboxylic Acid, C14-15 Pareth-8 Carboxylic Acid, C6-10 Pareth-4 Phosphate, C12-13 Pareth-2 Phosphate, C12-13 Pareth-10 Phosphate, C12-15 Pareth-6 Phosphate, C12-15 Pareth-8 Phosphate, C12-15 Pareth-10 Phosphate, C12-16 Pareth-6 Phosphate, C4-18 Perfluoroalkylethyl Thiohydroxypropyltrimonium Chloride, Cupuassuamidopropyl Betaine, DEA-C12-13 Alkyl Sulfate, DEA-C12-15 Alkyl Sulfate, DEA-Ceteareth-2 Phosphate, DEA-Cetyl Sulfate, DEA-Cocoamphodipropionate, DEA-C12-13 Pareth-3 Sulfate, DEA-Cyclocarboxypropyloleate, DEA-Dodecylbenzenesulfonate, DEA-Isostearate, DEA- Laureth Sulfate, DEA-Lauryl Sulfate, DEA-Linoleate, DEA-Methyl Myristate Sulfonate, DEA-Myreth Sulfate, DEA-Myristate, DEA-Myristyl Sulfate, DEA-Oleth-5 Phosphate, DEA-Oleth-20 Phosphate, DEA PG-Oleate, Deceth-7 Carboxylic Acid, Deceth-7 Glucoside, Deceth-9 Phosphate, Decylamine Oxide, Decyl Betaine, Decyl Glucoside, Decyltetradeceth-30, Decyltetradecylamine Oxide, Diammonium Lauramido-MEA Sulfosuccinate, Diammonium Lauryl Sulfosuccinate, Diammonium Oleamido PEG-2 Sulfosuccinate, Dibutoxymethane, Di-CI 2-15 Pareth-2 Phosphate, Di-CI 2-15 Pareth-4 Phosphate, Di-CI 2-15 Pareth-6 Phosphate, Di-C12-15 Pareth-8 Phosphate, Di-CI 2-15 Pareth-10 Phosphate, Didodecyl Butanetetracarboxylate, Diethylamine Laureth Sulfate, Diethylhexyl Sodium Sulfosuccinate, Dihydroxyethyl C8-10 Alkoxypropylamine Oxide, Dihydroxyethyl C9-11 Alkoxypropylamine Oxide, Dihydroxyethyl C12-15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Dimethicone PEG-7 Phosphate, Dimethicone PEG-10 Phosphate, Dimethicone PEG/PPG-7/4 Phosphate, Dimethicone PEG/PPG-12/4 Phosphate, Dimethicone/Polyglycerin-3 Crosspolymer, Dimethicone Propyl PG-Betaine, Dimyristyl Phosphate, Dioleoylamidoethyl Hydroxyethylmonium Methosulfate, DIPA-Hydrogenated Cocoate, DIPA-Lanolate, DIPA-Myristate, Dipotassium Capryloyl Glutamate, Dipotassium Lauryl Sulfosuccinate, Dipotassium Undecylenoyl Glutamate, Disodium Babassuamido MEA-Sulfosuccinate, Disodium Caproamphodiacetate, Disodium Caproamphodipropionate, Disodium Capryloamphodiacetate, Disodium Capryloamphodipropionate, Disodium Capryloyl Glutamate, Disodium Cetearyl Sulfosuccinate, Disodium Cetyl Phenyl Ether Disulfonate, Disodium Cetyl Sulfosuccinate, Disodium Cocamido MEA-Sulfosuccinate, Disodium Cocamido MIPA PEG-4 Sulfosuccinate, Disodium Cocamido MIPA-Sulfosuccinate, Disodium Cocamido PEG-3 Sulfosuccinate, Disodium Coceth-3 Sulfosuccinate, Disodium Cocoamphocarboxyethylhydroxypropylsulfonate, Disodium Cocoamphodiacetate, Disodium Cocoamphodipropionate, Disodium Coco-Glucoside Sulfosuccinate, Disodium Coco-Sulfosuccinate, Disodium Cocoyl Butyl Gluceth-10 Sulfosuccinate, Disodium Cocoyl Glutamate, Disodium C12-14 Pareth-1 Sulfosuccinate, Disodium C12-14 Pareth-2 Sulfosuccinate, Disodium C12-15 Pareth Sulfosuccinate, Disodium C12-14 Sec-Pareth-3 Sulfosuccinate, Disodium C12-14 Sec-Pareth-5 Sulfosuccinate, Disodium C12-14 Sec-Pareth-7 Sulfosuccinate, Disodium C12-14 Sec-Pareth-9 Sulfosuccinate, Disodium C12-14 Sec-Pareth-12 Sulfosuccinate, Disodium Deceth-5 Sulfosuccinate, Disodium Deceth-6 Sulfosuccinate, Disodium Decyl Phenyl Ether Disulfonate, Disodium Dihydroxyethyl Sulfosuccinylundecylenate, Disodium Ethylene Dicocamide PEG-15 Disulfate, Disodium Hydrogenated Cottonseed Glyceride Sulfosuccinate, Disodium Hydrogenated Tallow Glutamate, Disodium Hydroxydecyl Sorbitol Citrate, Disodium Isodecyl Sulfosuccinate, Disodium Isostearamido MEA-Sulfosuccinate, Disodium Isostearamido MIPA-Sulfosuccinate, Disodium Isostearoamphodiacetate, Disodium Isostearoamphodipropionate, Disodium Isostearyl Sulfosuccinate, Disodium Laneth-5 Sulfosuccinate, Disodium Lauramido MEA-Sulfosuccinate, Disodium Lauramido MIPA Glycol Sulfosuccinate, Disodium Lauramido PEG-2 Sulfosuccinate, Disodium Lauramido PEG-5 Sulfosuccinate, Disodium Laureth-5 Carboxyamphacetate, Disodium Laureth-7 Citrate, Disodium Laureth Sulfosuccinate, Disodium Laureth-6 Sulfosuccinate, Disodium Laureth-9 Sulfosuccinate, Disodium Laureth-12 Sulfosuccinate, Disodium Lauriminobishydroxypropylsulfonate, Disodium Lauriminodiacetate, Disodium Lauriminodipropionate, Disodium Lauriminodipropionate Tocopheryl Phosphates, Disodium Lauroamphodiacetate, Disodium Lauroamphodipropionate, Disodium N-Lauroyl Aspartate, Disodium Lauroyl Glutamate, Disodium Lauryl Phenyl Ether Disulfonate, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleoamphodipropionate, Disodium Oleth-3 Sulfosuccinate, Disodium Oleyl Phosphate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-12 Dimethicone Sulfosuccinate, Disodium PEG-8 Palm Glycerides Sulfosuccinate, Disodium PPG-2-Isodeceth-7 Carboxyamphodiacetate, Disodium Ricinoleamido MEA-Sulfosuccinate, Disodium Sitostereth-14 Sulfosuccinate, Disodium Soyamphodiacetate, Disodium Stearamido MEA-Sulfosuccinate, Disodium Steariminodipropionate, Disodium Stearoamphodiacetate, Disodium Stearoyl Glutamate, Disodium Stearyl Sulfosuccinamate, Disodium Stearyl Sulfosuccinate, Disodium 2-Sulfolaurate, Disodium 2-Sulfopalmitate, Disodium Tallamido MEA-Sulfosuccinate, Disodium Tallowamido MEA-Sulfosuccinate, Disodium Tallowamphodiacetate, Disodium Tallowiminodipropionate, Disodium Tallow Sulfosuccinamate, Disodium Tridecylsulfosuccinate, Disodium Undecylenamido MEA-Sulfosuccinate, Disodium Undecylenamido PEG-2 Sulfosuccinate, Disodium Undecylenoyl Glutamate, Disodium Wheat Germamido MEA-Sulfosuccinate, Disodium Wheat Germamido PEG-2 Sulfosuccinate, Disodium Wheatgermamphodiacetate, Di-TEA-Cocamide Diacetate, Di-TEA-Oleamido PEG-2 Sulfosuccinate, Di-TEA-Palmitoyl Aspartate, Ditridecyl Sodium Sulfosuccinate, Dodecylbenzene Sulfonic Acid, Erucamidopropyl Hydroxysultaine, Ethylheketh-3 Carboxylic Acid, Ethyl PEG-15 Cocamine Sulfate, Glyceryl Capryl Ether, Hexyldecanoic Acid, Hydrogenated Coconut Acid, Hydrogenated Laneth-25, Hydrogenated Menhaden Acid, Hydrogenated Palm Acid, Hydrogenated Palm Kernel Amine Oxide, Hydrogenated Tallow Acid, Hydrogenated Tallowamine Oxide, Hydrogenated Tallow Betaine, Hydrogenated Talloweth-25, Hydrogenated Tallowoyl Glutamic Acid, Hydrolyzed *Candida Bombicola* Extract, Hydroxyceteth-60, Hydroxyethyl Acetomonium PG-Dimethicone, Hydroxyethylbutylamine Laureth Sulfate, Hydroxyethyl Carboxymethyl Cocamidopropylamine, Hydroxyethyl Hydroxypropyl C12-15 Alkoxypropylamine Oxide, Hydroxylauryl/Hydroxymyristyl Betaine, Hydroxystearic Acid, Hydroxysuccinim idyl C10-40 Isoalkyl Acidate, Hydroxysuccinim idyl C21-22 Isoalkyl Acidate, Hydroxysultaines, IPDI/PEG-15 Soyamine Oxide Copolymer, IPDI/PEG-15 Soyethonium Ethosulfate Copolymer, IPDI/PEG-15 Soy Glycinate Copolymer, Isoceteth-30, Isolaureth-4 Phosphate, Isopolyglyceryl-3 Dimethicone, Isopolyglyceryl-3 Dimethiconol, Isopropanolam ine Lanolate, Isopropylam ine Dodecylbenzenesulfonate, Isostearamidopropylamine Oxide, Isostearamidopropyl Betaine, Isostearamidopropyl Morpholine Oxide, Isosteareth-8, Isosteareth-16, Isosteareth-22, Isosteareth-25, Isosteareth-50, Isostearic Acid, Isostearoyl Hydrolyzed Collagen, Jojoba Oil PEG-150 Esters, Jojoba Wax PEG-80 Esters, Jojoba Wax PEG-120 Esters, Laneth-20, Laneth-25, Laneth-40, Laneth-50, Laneth-60, Laneth-75, Lanolin Acid, Lauramidopropylamine Oxide, Lauramidopropyl Betaine, Lauramidopropyl Hydroxysultaine, Lauramine Oxide, Lauraminopropionic Acid, Laurdimoniumhydroxypropyl Decylglucosides Chloride, Laurdimoniumhydroxypropyl Laurylglucosides Chloride, Laureth-16, Laureth-20, Laureth-21, Laureth-23, Laureth-25, Laureth-30, Laureth-38, Laureth-40, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, Laureth-6 Citrate, Laureth-7 Citrate, Laureth-1 Phosphate, Laureth-2 Phosphate, Laureth-3 Phosphate, Laureth-4 Phosphate, Laureth-7 Phosphate, Laureth-8 Phosphate, Laureth-7 Tartrate, Laurie Acid, Laurimino Bispropanediol, Lauriminodipropionic Acid, Lauroamphodipropionic Acid, Lauroyl Beta-Alanine, Lauroyl Collagen Amino Acids, Lauroyl Ethyltrimonium Methosulfate, Lauroyl Hydrolyzed Collagen, Lauroyl Hydrolyzed Elastin, Lauroyl Methyl Glucamide, Lauroyl Sarcosine, Lauroyl Silk Amino Acids, Lauryl Betaine, Lauryl Dimethicone/Polyglycerin-3 Crosspolymer, Lauryldimoniumhydroxypropyl Cocoglucosides Chloride, Lauryl Glucoside, Laurylglucosides Hydroxypropyltrimonium Chloride, Lauryl Glycol Hydroxypropyl Ether, Lauryl Hydroxysultaine, Lauryl Malamide, Lauryl Methylglucamide, Lauryl/Myristyl Glycol Hydroxypropyl Ether, Lauryl/Myristyl Wheat Bran/Straw Glycosides, Lauryl Polyglyceryl-3 Polydimethylsiloxyethyl Dimethicone, Lauryl Pyrrolidone, Lauryl Sultaine, Linoleic Acid, Linolenic Acid, Linseed Acid, Lysine Cocoate, *Macadamia* Seed Oil Glycereth-8 Esters, Magnesium Coceth Sulfate, Magnesium Coco-Sulfate, Magnesium Isododecylbenzenesulfonate, Magnesium Laureth-11 Carboxylate, Magnesium Laureth Sulfate, Magnesium Laureth-5 Sulfate, Magnesium Laureth-8 Sulfate, Magnesium Laureth-16 Sulfate, Magnesium Laureth-3 Sulfosuccinate, Magnesium Lauryl Hydroxypropyl Sulfonate, Magnesium Lauryl Sulfate, Magnesium Methyl Cocoyl Taurate, Magnesium Myreth Sulfate, Magnesium Oleth Sulfate, Magnesium/TEA-Coco-Sulfate, Manicouagan Clay, MEA-Cocoate, MEA-Laureth-6 Carboxylate, MEA-Laureth Sulfate, MEA-Lauryl Sulfate, MEA PPG-6 Laureth-7 Carboxylate, MEA-PPG-8-Steareth-7 Carboxylate, MEA-Undecylenate, Meroxapol 108, Meroxapol 174, Meroxapol 178, Meroxapol 254, Meroxapol 255, Meroxapol 258, Meroxapol 314, Methoxy PEG-450 Amidoglutaroyl Succinimide, Methoxy PEG-450 Amido Hydroxysuccinimidyl Succinamate, Methoxy PEG-450 Maleimide, Methyl Morpholine Oxide, Milkamidopropyl Amine Oxide, Milkamidopropyl Betaine, Minkamidopropylamine Oxide, Minkamidopropyl Betaine, MIPA C12-15 Pareth Sulfate, MIPA-Dodecylbenzenesulfonate, MIPA-Laureth Sulfate, MIPA-Lauryl Sulfate, Mixed Isopropanolamines Lanolate, Mixed Isopropanolamines Lauryl Sulfate, Mixed Isopropanolamines Myristate, Morpholine Oleate, Morpholine Stearate, Myreth-3 Carboxylic Acid, Myreth-5 Carboxylic Acid, Myristalkonium Chloride, Myristamidopropylamine Oxide, Myristamidopropyl Betaine, Myristamidopropyl Dimethylamine Phosphate, Myristamidopropyl Hydroxysultaine, Myristamidopropyl PG-Dimonium Chloride Phosphate, Myristamine Oxide, Myristaminopropionic Acid, Myristic Acid, Myristoyl Ethyltrimonium Methosulfate, Myristoyl Glutamic Acid, Myristoyl Hydrolyzed Collagen, Myristoyl Sarcosine, Myristyl Betaine, Myristyl/Cetyl Amine Oxide, Myristyldimoniumhydroxypropyl Cocoglucosides Chloride, Myristyl Glucoside, Myristyl Phosphate, Nonoxynol-20, Nonoxynol-23, Nonoxynol-25, Nonoxynol-30, Nonoxynol-35, Nonoxynol-40, Nonoxynol-44, Nonoxynol-50, Nonoxynol-100, Nonoxynol-120, Nonoxynol-5 Carboxylic Acid, Nonoxynol-8 Carboxylic Acid, Nonoxynol-10 Carboxylic Acid, Nonoxynol-3 Phosphate, Nonoxynol-4 Phosphate, Nonoxynol-6 Phosphate, Nonoxynol-9 Phosphate, Nonoxynol-10 Phosphate, Nonyl Nonoxynol-30, Nonyl Nonoxynol-49, Nonyl Nonoxynol-100, Nonyl Nonoxynol-150, Nonyl Nonoxynol-7 Phosphate, Nonyl Nonoxynol-8 Phosphate, Nonyl Nonoxynol-9 Phosphate, Nonyl Nonoxynol-10 Phosphate, Nonyl Nonoxynol-11 Phosphate, Nonyl Nonoxynol-15 Phosphate, Nonyl Nonoxynol-24 Phosphate, Oatamidopropyl Betaine, Octoxynol-16, Octoxynol-25, Octoxynol-30, Octoxynol-33, Octoxynol-40, Octoxynol-70, Octoxynol-20 Carboxylic Acid, Octyldodeceth-20, Octyldodeceth-25, Octyldodeceth-30, Oleamidopropylamine Oxide, Oleamidopropyl Betaine, Oleamidopropyl Hydroxysultaine, Oleamine Oxide, Oleic Acid, Oleoyl Hydrolyzed Collagen, Oleoyl Sarcosine, Oleth-20, Oleth-23, Oleth-24, Oleth-25, Oleth-30, Oleth-35, Oleth-40, Oleth-44, Oleth-50, Oleth-3 Carboxylic Acid, Oleth-6 Carboxylic Acid, Oleth-10 Carboxylic Acid, Oleyl Betaine, Olivamidopropylamine Oxide, Olivamidopropyl Betaine, Olive Acid, Olivoyl Hydrolyzed Wheat Protein, Ophiopogon Extract Stearate, Ozonized Oleth-10, Ozonized PEG-10 Oleate, Ozonized PEG-14 Oleate, Ozonized Polysorbate 80, Palm Acid, Palmamidopropyl Betaine, Palmeth-2 Phosphate, Palmitam idopropylam ine Oxide, Palmitam idopropyl Betaine, Palmitamine Oxide, Palmitic Acid, Palmitoyl Collagen Amino Acids, Palmitoyl Glycine, Palmitoyl Hydrolyzed Collagen, Palmitoyl Hydrolyzed Milk Protein, Palmitoyl Hydrolyzed Wheat Protein, Palmitoyl Keratin Amino Acids, Palmitoyl Oligopeptide, Palmitoyl Silk Amino Acids, Palm Kernel Acid, Palm Kernelamidopropyl Betaine, Peach Kernel Oil Glycereth-8 Esters, Peanut Acid, PEG-10 Castor Oil, PEG-40 Castor Oil, PEG-44 Castor Oil, PEG-50 Castor Oil, PEG-54 Castor Oil, PEG-55 Castor Oil, PEG-60 Castor Oil, PEG-80 Castor Oil, PEG-100 Castor Oil, PEG-200 Castor Oil, PEG-11 Cocamide, PEG-6 Cocamide Phosphate, PEG-4 Cocamine, PEG-8 Cocamine, PEG-12 Cocamine, PEG-150 Dibehenate, PEG-90 Diisostearate, PEG-75 Dilaurate, PEG-150 Dilaurate, PEG-75 Dioleate, PEG-150 Dioleate, PEG-75 Distearate, PEG-120 Distearate, PEG-150 Distearate, PEG-175 Distearate, PEG-190 Distearate, PEG-250 Distearate, PEG-30 Glyceryl Cocoate, PEG-40 Glyceryl Cocoate, PEG-78 Glyceryl Cocoate, PEG-80 Glyceryl Cocoate, PEG-30 Glyceryl Isostearate, PEG-40 Glyceryl Isostearate, PEG-50 Glyceryl Isostearate, PEG-60 Glyceryl Isostearate, PEG-90 Glyceryl Isostearate, PEG-23 Glyceryl Laurate, PEG-30 Glyceryl Laurate, PEG-25 Glyceryl Oleate, PEG-30 Glyceryl Oleate, PEG-30 Glyceryl Soyate, PEG-25 Glyceryl Stearate, PEG-30 Glyceryl Stearate, PEG-40 Glyceryl Stearate, PEG-120 Glyceryl Stearate, PEG-200 Glyceryl Stearate, PEG-28 Glyceryl Tallowate, PEG-80 Glyceryl Tallowate, PEG-82 Glyceryl Tallowate, PEG-130 Glyceryl Tallowate, PEG-200 Glyceryl Tallowate, PEG-45 Hydrogenated Castor Oil, PEG-50 Hydrogenated Castor Oil, PEG-54 Hydrogenated Castor Oil, PEG-55 Hydrogenated Castor Oil, PEG-60 Hydrogenated Castor Oil, PEG-80 Hydrogenated Castor Oil, PEG-100 Hydrogenated Castor Oil, PEG-200 Hydrogenated Castor Oil, PEG-30 Hydrogenated Lanolin, PEG-70 Hydrogenated Lanolin, PEG-50 Hydrogenated Palmamide, PEG-2 Isostearate, PEG-3 Isostearate, PEG-4 Isostearate, PEG-6 Isostearate, PEG-8 Isostearate, PEG-10 Isostearate, PEG-12 Isostearate, PEG-20 Isostearate, PEG-30 Isostearate, PEG-40 Isostearate, PEG-26 Jojoba Acid, PEG-40 Jojoba Acid, PEG-15 Jojoba Alcohol, PEG-26 Jojoba Alcohol, PEG-40 Jojoba Alcohol, PEG-35 Lanolin, PEG-40

Lanolin, PEG-50 Lanolin, PEG-55 Lanolin, PEG-60 Lanolin, PEG-70 Lanolin, PEG-75 Lanolin, PEG-85 Lanolin, PEG-100 Lanolin, PEG-150 Lanolin, PEG-75 Lanolin Oil, PEG-2 Lauramide, PEG-3 Lauramine Oxide, PEG-20 Laurate, PEG-32 Laurate, PEG-75 Laurate, PEG-150 Laurate, PEG-70 Mango Glycerides, PEG-20 Mannitan Laurate, PEG-8 Methyl Ether Dimethicone, PEG-120 Methyl Glucose Dioleate, PEG-80 Methyl Glucose Laurate, PEG-120 Methyl Glucose Trioleate, PEG-4 Montanate, PEG-30 Oleamine, PEG-20 Oleate, PEG-23 Oleate, PEG-32 Oleate, PEG-36 Oleate, PEG-75 Oleate, PEG-150 Oleate, PEG-20 Palmitate, PEG-150 Polyglyceryl-2 Tristearate, PEG/PPG-28/21 Acetate Dimethicone, PEG/PPG-24/18 Butyl Ether Dimethicone, PEG/PPG-3/17 Copolymer, PEG/PPG-5/35 Copolymer, PEG/PPG-8/55 Copolymer, PEG/PPG-10/30 Copolymer, PEG/PPG-10/65 Copolymer, PEG/PPG-12/35 Copolymer, PEG/PPG-16/17 Copolymer, PEG/PPG-20/9 Copolymer, PEG/PPG-20/20 Copolymer, PEG/PPG-20/60 Copolymer, PEG/PPG-20/65 Copolymer, PEG/PPG-22/25 Copolymer, PEG/PPG-28/30 Copolymer, PEG/PPG-30-35 Copolymer, PEG/PPG-30/55 Copolymer, PEG/PPG-35/40 Copolymer, PEG/PPG-50/40 Copolymer, PEG/PPG-150/35 Copolymer, PEG/PPG-160/30 Copolymer, PEG/PPG-190/60 Copolymer, PEG/PPG-200/40 Copolymer, PEG/PPG-300/55 Copolymer, PEG/PPG-20/22 Methyl Ether Dimethicone, PEG-26-PPG-30 Phosphate, PEG/PPG-4/2 Propylheptyl Ether, PEG/PPG-6/2 Propylheptyl Ether, PEG-7/PPG-2 Propylheptyl Ether, PEG/PPG-8/2 Propylheptyl Ether, PEG/PPG-10/2 Propylheptyl Ether, PEG/PPG-14/2 Propylheptyl Ether, PEG/PPG-40/2 Propylheptyl Ether, PEG/PPG-10/2 Ricinoleate, PEG/PPG-32/3 Ricinoleate, PEG-55 Propylene Glycol Oleate, PEG-25 Propylene Glycol Stearate, PEG-75 Propylene Glycol Stearate, PEG-120 Propylene Glycol Stearate, PEG-5 Rapeseed Sterol, PEG-10 Rapeseed Sterol, PEG-40 Ricinoleamide, PEG-75 Shea Butter Glycerides, PEG-75 Shorea Butter Glycerides, PEG-20 Sorbitan Cocoate, PEG-20 Sorbitan Isostearate, PEG-40 Sorbitan Lanolate, PEG-75 Sorbitan Lanolate, PEG-10 Sorbitan Laurate, PEG-40 Sorbitan Laurate, PEG-44 Sorbitan Laurate, PEG-75 Sorbitan Laurate, PEG-80 Sorbitan Laurate, PEG-20 Sorbitan Oleate, PEG-80 Sorbitan Palmitate, PEG-40 Sorbitan Stearate, PEG-60 Sorbitan Stearate, PEG-160 Sorbitan Triisostearate, PEG-40 Soy Sterol, PEG-2 Stearamide Carboxylic Acid, PEG-9 Stearamide Carboxylic Acid, PEG-20 Stearate, PEG-23 Stearate, PEG-25 Stearate, PEG-30 Stearate, PEG-32 Stearate, PEG-35 Stearate, PEG-36 Stearate, PEG-40 Stearate, PEG-45 Stearate, PEG-50 Stearate, PEG-55 Stearate, PEG-75 Stearate, PEG-90 Stearate, PEG-100 Stearate, PEG-120 Stearate, PEG-150 Stearate, PEG-45 Stearate Phosphate, PEG-20 Tallate, PEG-50 Tallow Amide, PEG-2 Tallowamide DEA, PEG-20 Tallowate, PEG-66 Trihydroxystearin, PEG-200 Trihydroxystearin, PEG-60 Tsubakiate Glycerides, Pelargonic Acid, Pentadoxynol-200, Pheneth-6 Phosphate, Poloxamer 105, Poloxamer 108, Poloxamer 182, Poloxamer 183, Poloxamer 184, Poloxamer 188, Poloxamer 217, Poloxamer 234, Poloxamer 235, Poloxamer 237, Poloxamer 238, Poloxamer 288, Poloxamer 334, Poloxamer 335, Poloxamer 338, Poloxamine 908, Poloxamine 1508, Polydimethylsiloxy PEG/PPG-24/19 Butyl Ether Silsesquioxane, Polydimethylsiloxy PPG-13 Butyl Ether Silsesquioxane, Polyglyceryl-6 Caprate, Polyglyceryl-10 Dilaurate, Polyglyceryl-20 Heptacaprylate, Polyglyceryl-20 Hexacaprylate, Polyglyceryl-2 Lauryl Ether, Polyglyceryl-10 Lauryl Ether, Polyglyceryl-20 Octaisononanoate, Polyglyceryl-6 Pentacaprylate, Polyglyceryl-10 Pentacaprylate, Polyglyceryl-3 Polydimethylsiloxyethyl Dimethicone, Polyglyceryl-6 Tetracaprylate, Polyglyceryl-10 Tetralaurate, Polyglyceryl-6 Tricaprylate, Polyglyceryl-10 Trilaurate, Polyquaternium-77, Polyquaternium-78, Polyquaternium-79, Polyquaternium-80, Polyquaternium-81, Polyquaternium-82, Pomaderris Kumerahou Flower/Leaf Extract, Poria *Cocos* Extract, Potassium Abietoyl Hydrolyzed Collagen, Potassium Babassuate, Potassium Behenate, Potassium C9-15 Alkyl Phosphate, Potassium C11-15 Alkyl Phosphate, Potassium C12-13 Alkyl Phosphate, Potassium C12-14 Alkyl Phosphate, Potassium Caprate, Potassium Capryloyl Glutamate, Potassium Capryloyl Hydrolyzed Rice Protein, Potassium Castorate, Potassium Cocoate, Potassium Cocoyl Glutamate, Potassium Cocoyl Glycinate, Potassium Cocoyl Hydrolyzed Casein, Potassium Cocoyl Hydrolyzed Collagen, Potassium Cocoyl Hydrolyzed Corn Protein, Potassium Cocoyl Hydrolyzed Keratin, Potassium Cocoyl Hydrolyzed Oat Protein, Potassium Cocoyl Hydrolyzed Potato Protein, Potassium Cocoyl Hydrolyzed Rice Bran Protein, Potassium Cocoyl Hydrolyzed Rice Protein, Potassium Cocoyl Hydrolyzed Silk, Potassium Cocoyl Hydrolyzed Soy Protein, Potassium Cocoyl Hydrolyzed Wheat Protein, Potassium Cocoyl Hydrolyzed Yeast Protein, Potassium Cocoyl PCA, Potassium Cocoyl Sarcosinate, Potassium Cocoyl Taurate, Potassium Cornate, Potassium Cyclocarboxypropyloleate, Potassium Dihydroxyethyl Cocamine Oxide Phosphate, Potassium Dimethicone PEG-7 Phosphate, Potassium Dodecylbenzenesulfonate, Potassium Hempseedate, Potassium Hydrogenated Cocoate, Potassium Hydrogenated Palmate, Potassium Hydrogenated Tallowate, Potassium Hydroxystearate, Potassium Isostearate, Potassium Lanolate, Potassium Laurate, Potassium Laureth-3 Carboxylate, Potassium Laureth-4 Carboxylate, Potassium Laureth-5 Carboxylate, Potassium Laureth-6 Carboxylate, Potassium Laureth-10 Carboxylate, Potassium Laureth Phosphate, Potassium Lauroyl Collagen Amino Acids, Potassium Lauroyl Glutamate, Potassium Lauroyl Hydrolyzed Collagen, Potassium Lauroyl Hydrolyzed Pea Protein, Potassium Lauroyl Hydrolyzed Soy Protein, Potassium Lauroyl PCA, Potassium Lauroyl Pea Amino Acids, Potassium Lauroyl Sarcosinate, Potassium Lauroyl Silk Amino Acids, Potassium Lauroyl Wheat Amino Acids, Potassium Lauryl Phosphate, Potassium Lauryl Sulfate, Potassium Linoleate, Potassium Metaphosphate, Potassium Methyl Cocoyl Taurate, Potassium Myristate, Potassium Myristoyl Glutamate, Potassium Myristoyl Hydrolyzed Collagen, Potassium Octoxynol-12 Phosphate, Potassium Oleate, Potassium Oleoyl Hydrolyzed Collagen, Potassium Olivate, Potassium Olivoyl Hydrolyzed Oat Protein, Potassium Olivoyl Hydrolyzed Wheat Protein, Potassium Olivoyl/Lauroyl Wheat Amino Acids, Potassium Olivoyl PCA, Potassium Palmate, Potassium Palmitate, Potassium Palmitoyl Hydrolyzed Corn Protein, Potassium Palmitoyl Hydrolyzed Oat Protein, Potassium Palmitoyl Hydrolyzed Rice Protein, Potassium Palmitoyl Hydrolyzed Sweet Almond Protein, Potassium Palmitoyl Hydrolyzed Wheat Protein, Potassium Palm Kernelate, Potassium Peanutate, Potassium Rapeseedate, Potassium Ricinoleate, Potassium Safflowerate, Potassium Soyate, Potassium Stearate, Potassium Stearoyl Hydrolyzed Collagen, Potassium Tallate, Potassium Tallowate, Potassium Taurate, Potassium Taurine Laurate, Potassium Trideceth-3 Carboxylate, Potassium Trideceth-4 Carboxylate, Potassium Trideceth-7 Carboxylate, Potassium Trideceth-15 Carboxylate, Potassium Trideceth-19 Carboxylate, Potassium Trideceth-6 Phosphate, Potassium Trideceth-7 Phosphate, Potassium Tsubakiate, Potassium Undecylenate, Potassium Undecylenoyl Hydrolyzed Collagen, Potassium Undecylenoyl Hydrolyzed Rice Protein, PPG-30-Buteth-30, PPG-36-

Buteth-36, PPG-38-Buteth-37, PPG-30-Capryleth-4 Phosphate, PPG-10 Cetyl Ether Phosphate, PPG-2 C9-11 Pareth-8, PPG-1-Deceth-5, PPG-3-Deceth-2 Carboxylic Acid, PPG-30 Ethylhexeth-4 Phosphate, PPG-20-Glycereth-30, PPG-2 Hydroxyethyl Coco/Isostearamide, PPG-2-Isodeceth-8, PPG-2-lsodeceth-10, PPG-2-lsodeceth-18, PPG-2-lsodeceth-25, PPG-4-lsodeceth-10, Propyltrimonium Hydrolyzed Collagen, Quaternium-24, Quaternium-52, Quaternium-87, Rapeseed Acid, Rice Bran Acid, Rice Oil Glycereth-8 Esters, Ricinoleamidopropyl Betaine, Ricinoleic Acid, Ricinoleth-40, Safflower Acid, Sapindus *Oahuensis* Fruit Extract, *Saponaria officinalis* Root Powder, Saponins, Sekken-K, Sekken-Na/K, Sekken Soji, Sekken Soji-K, Sesame Oil Glycereth-8 Esters, Sesamidopropylamine Oxide, Sesamidopropyl Betaine, Shea Butteramidopropyl Betaine, Shea Butter Glycereth-8 Esters, Sodium Arachidate, Sodium Arganampohoacetate, Sodium *Astrocaryum* Murumuruate, Sodium Avocadoate, Sodium Babassuamphoacetate, Sodium Babassuate, Sodium Babassu Sulfate, Sodium Behenate, Sodium Bisglycol Ricinosulfosuccinate, Sodium Bis-Hydroxyethylglycinate Coco-Glucosides Crosspolymer, Sodium Bis-Hydroxyethylglycinate LaurylGlucosides Crosspolymer, Sodium Borageamidopropyl PG-Dimonium Chloride Phosphate, Sodium Butoxynol-12 Sulfate, Sodium Butylglucosides Hydroxypropyl Phosphate, Sodium C13-17 Alkane Sulfonate, Sodium C14-18 Alkane Sulfonate, Sodium C12-15 Alkoxypropyl Iminodipropionate, Sodium C10-16 Alkyl Sulfate, Sodium C11-15 Alkyl Sulfate, Sodium C12-13 Alkyl Sulfate, Sodium C12-15 Alkyl Sulfate, Sodium C12-18 Alkyl Sulfate, Sodium C16-20 Alkyl Sulfate, Sodium C9-22 Alkyl Sec Sulfonate, Sodium C14-17 Alkyl Sec Sulfonate, Sodium Caprate, Sodium Caproamphoacetate, Sodium Caproamphohydroxypropylsulfonate, Sodium Caproamphopropionate, Sodium Caproyl Methyltaurate, Sodium Caprylate, Sodium Capryleth-2 Carboxylate, Sodium Capryleth-9 Carboxylate, Sodium Capryloamphoacetate, Sodium Capryloamphohydroxypropylsulfonate, Sodium Capryloamphopropionate, Sodium Capryloyl Glutamate, Sodium Capryloyl Hydrolyzed Wheat Protein, Sodium Caprylyl PG-Sulfonate, Sodium Caprylyl Sulfonate, Sodium Castorate, Sodium Ceteareth-13 Carboxylate, Sodium Cetearyl Sulfate, Sodium Ceteth-13 Carboxylate, Sodium Cetyl Sulfate, Sodium Cocamidopropyl PG-Dimonium Chloride Phosphate, Sodium Cocaminopropionate, Sodium Coceth Sulfate, Sodium Coceth-30 Sulfate, Sodium Cocoabutteramphoacetate, Sodium Cocoa Butterate, Sodium Cocoamphoacetate, Sodium Cocoamphohydroxypropylsulfonate, Sodium Cocoamphopropionate, Sodium Cocoate, Sodium Coco/Babassu/Andiroba Sulfate, Sodium Coco/Babassu Sulfate, Sodium Cocoglucosides Hydroxypropyl Phosphate, Sodium Cocoglucosides Hydroxypropylsulfonate, Sodium Coco-Glucoside Tartrate, Sodium Cocoglyceryl Ether Sulfonate, Sodium Coco/Hydrogenated Tallow Sulfate, Sodium Cocoiminodiacetate, Sodium Cocomonoglyceride Sulfate, Sodium Cocomonoglyceride Sulfonate, Sodium Coco PG-Dimonium Chloride Phosphate, Sodium Coco-Sulfate, Sodium Coco Sulfoacetate, Sodium Cocoyl Alaninate, Sodium Cocoyl Amino Acids, Sodium Cocoyl Collagen Amino Acids, Sodium Cocoyl Glutamate, Sodium Cocoyl Glutaminate, Sodium Cocoyl Glycinate, Sodium Cocoyl/Hydrogenated Tallow Glutamate, Sodium Cocoyl Hydrolyzed Collagen, Sodium Cocoyl Hydrolyzed Keratin, Sodium Cocoyl Hydrolyzed Rice Protein, Sodium Cocoyl Hydrolyzed Silk, Sodium Cocoyl Hydrolyzed Soy Protein, Sodium Cocoyl Hydrolyzed Sweet Almond Protein, Sodium Cocoyl Hydrolyzed Wheat Protein, Sodium Cocoyl Hydrolyzed Wheat Protein Glutamate, Sodium Cocoyl Isethionate, Sodium Cocoyl Methylaminopropionate, Sodium Cocoyl Oat Amino Acids, Sodium Cocoyl/Palmoyl/Sunfloweroyl Glutamate, Sodium Cocoyl Proline, Sodium Cocoyl Sarcosinate, Sodium Cocoyl Taurate, Sodium Cocoyl Threoninate, Sodium Cocoyl Wheat Amino Acids, Sodium C12-14 Olefin Sulfonate, Sodium C14-16 Olefin Sulfonate, Sodium C14-18 Olefin Sulfonate, Sodium C16-18 Olefin Sulfonate, Sodium Cornamphopropionate, Sodium Cottonseedamphoacetate, Sodium C13-15 Pareth-8 Butyl Phosphate, Sodium C9-11 Pareth-6 Carboxylate, Sodium C11-15 Pareth-7 Carboxylate, Sodium C12-13 Pareth-5 Carboxylate, Sodium C12-13 Pareth-8 Carboxylate, Sodium C12-13 Pareth-12 Carboxylate, Sodium C12-15 Pareth-6 Carboxylate, Sodium C12-15 Pareth-7 Carboxylate, Sodium C12-15 Pareth-8 Carboxylate, Sodium C14-15 Pareth-8 Carboxylate, Sodium C12-14 Sec-Pareth-8 Carboxylate, Sodium C14-15 Pareth-PG Sulfonate, Sodium C12-13 Pareth-2 Phosphate, Sodium C13-15 Pareth-8 Phosphate, Sodium C9-15 Pareth-3 Sulfate, Sodium C10-15 Pareth Sulfate, Sodium C10-16 Pareth-2 Sulfate, Sodium C12-13 Pareth Sulfate, Sodium C12-15 Pareth Sulfate, Sodium C12-15 Pareth-3 Sulfate, Sodium C13-15 Pareth-3 Sulfate, Sodium C12-14 Sec-Pareth-3 Sulfate, Sodium C12-15 Pareth-3 Sulfonate, Sodium C12-15 Pareth-7 Sulfonate, Sodium C12-15 Pareth-15 Sulfonate, Sodium Deceth-2 Carboxylate, Sodium Deceth Sulfate, Sodium Decylbenzenesulfonate, Sodium Decylglucosides Hydroxypropyl Phosphate, Sodium Decylglucosides Hydroxypropylsulfonate, Sodium Dilaureth-7 Citrate, Sodium Dilaureth-10 Phosphate, Sodium Dilinoleamidopropyl PG-Dimonium Chloride Phosphate, Sodium Dilinoleate, Sodium Dioleth-8 Phosphate, Sodium Dodecylbenzenesulfonate, Sodium Ethyl 2-Sulfolaurate, Sodium Glyceryl Oleate Phosphate, Sodium Grapeseedamidopropyl PG-Dimonium Chloride Phosphate, Sodium Grapeseedamphoacetate, Sodium Grapeseedate, Sodium Hempseedamphoacetate, Sodium Hexeth-4 Carboxylate, Sodium Hydrogenated Cocoate, Sodium Hydrogenated Cocoyl Methyl Isethionate, Sodium Hydrogenated Palmate, Sodium Hydrogenated Tallowate, Sodium Hydrogenated Tallowoyl Glutamate, Sodium Hydroxylauryldimonium Ethyl Phosphate, Sodium Hydroxypropyl Palm Kernelate Sulfonate, Sodium Hydroxypropylphosphate Decylglucoside Crosspolymer, Sodium Hydroxypropylphosphate Laurylglucoside Crosspolymer, Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer, Sodium Hydroxystearate, Sodium Isostearate, Sodium Isosteareth-6 Carboxylate, Sodium Isosteareth-11 Carboxylate, Sodium Isostearoamphoacetate, Sodium Isostearoamphopropionate, Sodium N-Isostearoyl Methyltaurate, Sodium Laneth Sulfate, Sodium Lanolate, Sodium Lardate, Sodium Lauramido Diacetate, Sodium Lauraminopropionate, Sodium Laurate, Sodium Laureth-3 Carboxylate, Sodium Laureth-4 Carboxylate, Sodium Laureth-5 Carboxylate, Sodium Laureth-6 Carboxylate, Sodium Laureth-8 Carboxylate, Sodium Laureth-11 Carboxylate, Sodium Laureth-12 Carboxylate, Sodium Laureth-13 Carboxylate, Sodium Laureth-14 Carboxylate, Sodium Laureth-16 Carboxylate, Sodium Laureth-17 Carboxylate, Sodium Laureth Sulfate, Sodium Laureth-5 Sulfate, Sodium Laureth-7 Sulfate, Sodium Laureth-8 Sulfate, Sodium Laureth-12 Sulfate, Sodium Laureth-40 Sulfate, Sodium Laureth-7 Tartrate, Sodium Laurim inodipropionate, Sodium Lauroamphoacetate, Sodium Lauroamphohydroxypropylsulfonate, Sodium Lauroampho PG-Acetate Phosphate, Sodium Lauroamphopropionate, Sodium Lauroyl Aspartate, Sodium Lauroyl Collagen Amino Acids, Sodium Lauroyl Glycine Propionate, Sodium Lauroyl Hydrolyzed Collagen, Sodium Lauroyl Hydrolyzed Silk, Sodium Lauroyl Hydroxypropyl Sulfonate, Sodium Lauroyl Isethionate, Sodium Lauroyl Methylaminopropionate, Sodium Lauroyl Methyl Isethionate, Sodium Lauroyl Millet Amino Acids, Sodium Lauroyl/Myristoyl Aspartate, Sodium Lauroyl Oat Amino Acids, Sodium Lauroyl Sarcosinate, Sodium Lauroyl Silk Amino Acids, Sodium Lauroyl Taurate, Sodium Lauroyl Wheat Amino Acids, Sodium Lauryl Diethylenediaminoglycinate, Sodium Lauryl Glucose Carboxylate, Sodium Laurylglucosides Hydroxypropyl Phosphate, Sodium Laurylglucosides Hydroxypropylsulfonate, Sodium Lauryl Glycol Carboxylate, Sodium Lauryl Hydroxyacetamide Sulfate, Sodium Lauryl Phosphate, Sodium Lauryl Sulfate, Sodium Lauryl Sulfoacetate, Sodium Linoleate, Sodium Macadamiaseedate, Sodium Mangoamphoacetate, Sodium Mangoseedate, Sodium/MEA Laureth-2 Sulfosuccinate, Sodium Methoxy PPG-2 Acetate, Sodium Methyl Cocoyl Taurate, Sodium Methyl Lauroyl Taurate, Sodium Methyl Myristoyl Taurate, Sodium Methyl Oleoyl Taurate, Sodium Methyl Palmitoyl Taurate, Sodium Methyl Stearoyl Taurate, Sodium Methyl 2-Sulfolaurate, Sodium Methyl 2-Sulfopalmitate, Sodium Methyltaurate Isopalmitamide, Sodium Methyltaurine Cocoyl Methyltaurate, Sodium Myreth Sulfate, Sodium Myristate, Sodium Myristoamphoacetate, Sodium Myristoyl Glutamate, Sodium Myristoyl Hydrolyzed Collagen, Sodium Myristoyl Isethionate, Sodium Myristoyl Sarcosinate, Sodium Myristyl Sulfate, Sodium Nonoxynol-6 Phosphate, Sodium Nonoxynol-9 Phosphate, Sodium Nonoxynol-1 Sulfate, Sodium Nonoxynol-3 Sulfate, Sodium Nonoxynol-4 Sulfate, Sodium Nonoxynol-6 Sulfate, Sodium Nonoxynol-8 Sulfate, Sodium Nonoxynol-10 Sulfate, Sodium Nonoxynol-25 Sulfate, Sodium Octoxynol-2 Ethane Sulfonate, Sodium Octoxynol-2 Sulfate, Sodium Octoxynol-6 Sulfate, Sodium Octoxynol-9 Sulfate, Sodium Oleate, Sodium Oleoamphoacetate, Sodium Oleoam phohydroxypropylsulfonate, Sodium Oleoamphopropionate, Sodium Oleoyl Hydrolyzed Collagen, Sodium Oleoyl Isethionate, Sodium Oleth Sulfate, Sodium Oleyl Methyl Isethionate, Sodium Oleyl Sulfate, Sodium Olivamphoacetate, Sodium Olivate, Sodium Olivoyl Glutamate, Sodium Palmamphoacetate, Sodium Palmate, Sodium Palm Glyceride Sulfonate, Sodium Palmitate, Sodium Palmitoyl Hydrolyzed Collagen, Sodium Palmitoyl Hydrolyzed Wheat Protein, Sodium Palmitoyl Sarcosinate, Sodium Palm Kernelate, Sodium Palm Kerneloyl Isethionate, Sodium Palmoyl Glutamate, Sodium *Passiflora edulis* Seedate, Sodium Peanutamphoacetate, Sodium Peanutate, Sodium PEG-6 Cocamide Carboxylate, Sodium PEG-8 Cocamide Carboxylate, Sodium PEG-4 Cocamide Sulfate, Sodium PEG-3 Lauramide Carboxylate, Sodium PEG-4 Lauramide Carboxylate, Sodium PEG-8 Palm Glycerides Carboxylate, Sodium Pentaerythrityl Hydroxypropyl Iminodiacetate Dendrimer, Sodium Propoxy PPG-2 Acetate, Sodium Rapeseedate, Sodium Ricebranamphoacetate, Sodium Ricinoleate, Sodium Ricinoleoamphoacetate, Sodium Rose Hipsamphoacetate, Sodium Rosinate, Sodium Safflowerate, Sodium Saffloweroyl Hydrolyzed Soy Protein, Sodium Sesameseedate, Sodium Sesamphoacetate, Sodium Sheabutteramphoacetate, Sodium Soyate, Sodium Soy Hydrolyzed Collagen, Sodium Stearate, Sodium Stearoamphoacetate, Sodium Stearoamphohydroxypropylsulfonate, Sodium Stearoamphopropionate, Sodium Stearoyl Casein, Sodium Stearoyl Glutamate, Sodium Stearoyl Hyaluronate, Sodium Stearoyl Hydrolyzed Collagen, Sodium Stearoyl Hydrolyzed Corn Protein, Sodium Stearoyl Hydrolyzed Silk, Sodium Stearoyl Hydrolyzed Soy Protein, Sodium Stearoyl Hydrolyzed Wheat Protein, Sodium Stearoyl Lactalbumin, Sodium Stearoyl Methyl Isethionate, Sodium Stearoyl Oat Protein, Sodium Stearoyl Pea Protein, Sodium Stearoyl Soy Protein, Sodium Stearyl Dimethyl Glycine, Sodium Stearyl Sulfate, Sodium Sunflowerseedamphoacetate, Sodium Surfactin, Sodium Sweetalmondamphoacetate, Sodium Sweet Almondate, Sodium Tallamphopropionate, Sodium Tallate, Sodium Tallowamphoacetate, Sodium Tallowate, Sodium Tallow Sulfate, Sodium Tamanuseedate, Sodium Taurate, Sodium Taurine Cocoyl Methyltaurate, Sodium Taurine Laurate, Sodium/TEA-Lauroyl Collagen Amino Acids, Sodium/TEA-Lauroyl Hydrolyzed Collagen, Sodium/TEA-Lauroyl Hydrolyzed Keratin, Sodium/TEA-Lauroyl Keratin Amino Acids, Sodium/TEA-Undecylenoyl Collagen Amino Acids, Sodium/TEA-Undecylenoyl Hydrolyzed Collagen, Sodium/TEA-Undecylenoyl Hydrolyzed Corn Protein, Sodium/TEA-Undecylenoyl Hydrolyzed Soy Protein, Sodium/TEA-Undecylenoyl Hydrolyzed Wheat Protein, Sodium *Theobroma grandiflorum* Seedate, Sodium Trideceth-3 Carboxylate, Sodium Trideceth-4 Carboxylate, Sodium Trideceth-6 Carboxylate, Sodium Trideceth-7 Carboxylate, Sodium Trideceth-8 Carboxylate, Sodium Trideceth-12 Carboxylate, Sodium Trideceth-15 Carboxylate, Sodium Trideceth-19 Carboxylate, Sodium Trideceth Sulfate, Sodium Tridecylbenzenesulfonate, Sodium Tridecyl Sulfate, Sodium Trimethylolpropane Hydroxypropyl Iminodiacetate Dendrimer, Sodium Undeceth-5 Carboxylate, Sodium Undecylenate, Sodium Undecylenoamphoacetate, Sodium Undecylenoamphopropionate, Sodium Undecylenoyl Glutamate, Sodium Wheat Germamphoacetate, Sorbeth-160 Tristearate, Soy Acid, Soyamidopropylamine Oxide, Soyamidopropyl Betaine, Soybean Oil Glycereth-8 Esters, Stearamidopropylamine Oxide, Stearamidopropyl Betaine, Stearamine Oxide, Steareth-15, Steareth-16, Steareth-20, Steareth-21, Steareth-25, Steareth-27, Steareth-30, Steareth-40, Steareth-50, Steareth-80, Steareth-100, Steareth-2 Phosphate, Steareth-3 Phosphate, Stearic Acid, Stearoxypropyltrimonium Chloride, Stearoyl Glutamic Acid, Stearoyl Sarcosine, Stearyl Betaine, Stearyldimoniumhydroxypropyl Butylglucosides Chloride, Stearyldimoniumhydroxy-propyl Decylglucosides Chloride, Stearyldimoniumhydroxypropyl Laurylglucosides Chloride, Sulfated Castor Oil, Sulfated Coconut Oil, Sulfated Glyceryl Oleate, Sulfated Olive Oil, Sulfated Peanut Oil, Sunfloweramide MEA, Sunflower Seed Acid, Sunflowerseedamidopropyl Hydroxyethyldimonium Chloride, Sunflower Seed Oil Glycereth-8 Esters, Tall Oil Acid, Tallow Acid, Tallowamidopropylamine Oxide, Tallowamidopropyl Betaine, Tallowamidopropyl Hydroxysultaine, Tallowamine Oxide, Tallow Betaine, Tallow Dihydroxyethyl Betaine, Tallowoyl Ethyl Glucoside, TEA-Abietoyl Hydrolyzed Collagen, TEA-C12-14 Alkyl Phosphate, TEA-C10-15 Alkyl Sulfate, TEA-C11-15 Alkyl Sulfate, TEA-C12-13 Alkyl Sulfate, TEA-C12-14 Alkyl Sulfate, TEA-C12-15 Alkyl Sulfate, TEA C14-17 Alkyl Sec Sulfonate, TEA-Canolate, TEA-Cocamide Diacetate, TEA-Cocoate, TEA-Coco-Sulfate, TEA-Cocoyl Alaninate, TEA-Cocoyl Glutamate, TEA-Cocoyl Glutaminate, TEA-Cocoyl Glycinate, TEA-Cocoyl Hydrolyzed Collagen, TEA-Cocoyl Hydrolyzed Soy Protein, TEA-Cocoyl Sarcosinate, TEA-Dimethicone PEG-7 Phosphate, TEA-Dodecylbenzenesulfonate, TEA-Hydrogenated Cocoate, TEA-Hydrogenated Tallowoyl Glutamate, TEA-Isostearate, TEA-Isostearoyl Hydrolyzed Collagen, TEA-Lauraminopropionate, TEA-Laurate, TEA-Laurate/Myristate, TEA-Laureth Sulfate, TEA-Lauroyl Collagen Amino Acids, TEA-Lauroyl Glutamate, TEA-Lauroyl Hydrolyzed Collagen, TEA-Lauroyl Keratin Amino Acids, TEA-Lauroyl Methylaminopropionate, TEA-Lauroyl/Myristoyl Aspartate, TEA-Lauroyl Sarcosinate, TEA-Lauryl Phosphate, TEA-Lauryl Sulfate, TEA-Myristaminopropionate, TEA-Myristate, TEA-Myristoyl Hydrolyzed Collagen, TEA-Oleate, TEA-Oleoyl Hydrolyzed Collagen, TEA-Oleoyl Sarcosinate, TEA-Oleyl Sulfate, TEA-Palmitate, TEA-Palm Kernel Sarcosinate, TEA-PEG-3 Cocamide Sulfate, TEA-Rosinate, TEA-Stearate, TEA-Tallate, TEA-Tridecylbenzenesulfonate, TEA-Undecylenate, TEA-Undecylenoyl Hydrolyzed Collagen, Tetramethyl Decynediol, Tetrasodium Dicarboxyethyl Stearyl Sulfosuccinamate, TIPA-Laureth Sulfate, TIPA-Lauryl Sulfate, TIPA-Myristate, TIPA-Stearate, Tocopheryl Phosphate, Trehalose Undecylenoate, TM-C12-15 Pareth-2 Phosphate, TM-C12-15 Pareth-6 Phosphate, TM-C12-15 Pareth-8 Phosphate, TM-C12-15 Pareth-10 Phosphate, Trideceth-20, Trideceth-50, Trideceth-3 Carboxylic Acid, Trideceth-4 Carboxylic Acid, Trideceth-7 Carboxylic Acid, Trideceth-8 Carboxylic Acid, Trideceth-15 Carboxylic Acid, Trideceth-19 Carboxylic Acid, Trideceth-10 Phosphate, Tridecylbenzenesulfonic Acid, Trilaureth-9 Citrate, Trimethylolpropane Hydroxypropyl Bis-Hydroxyethylamine Dendrimer, Trisodium Lauroampho PG-Acetate Chloride Phosphate, Undecanoic Acid, Undeceth-5 Carboxylic Acid, Undecylenamidopropylamine Oxide, Undecylenamidopropyl Betaine, Undecylenic Acid, Undecylenoyl Collagen Amino Acids, Undecylenoyl Glycine, Undecylenoyl Hydrolyzed Collagen, Undecylenoyl Wheat Amino Acids, Undecyl Glucoside, Wheat Germ Acid, Wheat Germamidopropylamine Oxide, Wheat Germamidopropyl Betaine, *Yucca schidigera* Leaf/Root/Stem Extract, *Yucca schidigera* Stem Extract, Zinc Coceth Sulfatea and Zinc Coco-Sulfate.

Preservatives: For preservative purposes, the cosmetic or pharmaceutical, preferably dermatological, composition according to the present invention preferably includes one or more preservatives which are suitable or customary in cosmetic or pharmaceutical, preferably dermatological, composition. Suitable and advantageously preservatives are, for example, phenoxyethanol, formaldehyde solution, parabens, pentanediol or sorbic acid.

Green and synthetic polymers: The cosmetic or pharmaceutical, preferably dermatological, composition according to the present invention preferably includes one or more green or synthetic polymers. Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, GrUnau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar® C-17, Jaguar® C-16 of Celanese, quaternized ammonium salt polymers such as, for example, Mirapol®A-15, Mirapol® AD-1, Mirapol® AZ-1 of Miranol and the various polyquaternium types (for example 5, 7, 32 or 37) which can be found in the market under the tradenames Rheocare® CC or Ultragel® 300. Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. In a preferred variant, the cosmetic or pharmaceutical, preferably dermatological, composition according to the present invention preferably includes an uncrosslinked or polyol-crosslinked polyacrylic acid as polymer component.

Thickening agents and/or rheology additives: The cosmetic or pharmaceutical, preferably dermatological, composition according to the present invention preferably includes one or more thickening agents and/or rheology additives. Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Perfume oils and/or fragrances: The cosmetic or pharmaceutical, preferably dermatological, composition according to the present invention preferably includes one or more perfume oils and/or fragrances. Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, *Angelica*, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (*Galbanum*, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert-butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, beta-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, *Galbanum* oil, *Ladanum* oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Anti-cellulite agent: The cosmetic or pharmaceutical, preferably dermatological, composition according to the present invention preferably includes one or more anti-cellulite agents. Anti-cellulite agents and lipolytic agents are preferably selected from the group consisting of beta-adrenergic receptor agonists such as synephrine and its derivatives, and cyclohexyl carbamates. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, ananas extract and conjugated linoleic acid.

Fat enhancing agents: The cosmetic or pharmaceutical, preferably dermatological, composition according to the present invention preferably includes one or more fat enhancing agents and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Superfatting agents and/or consistency factors: The cosmetic or pharmaceutical, preferably dermatological, composition according to the present invention preferably includes one or more superfatting agents and/or consistency factors. Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers. The consistency factors mainly used are fatty alcohols or hydroxy fatty alcohols containing 12 to 22 and preferably 16 to 18 carbon atoms and also partial glycerides, fatty acids or hydroxy fatty acids. A combination of these substances with alkyl oligoglucosides and/or fatty acid N-methyl glucamides of the same chain length and/or polyglycerol poly-12-hydroxystearates is preferably used.

Pearlizing waxes: The cosmetic or pharmaceutical, preferably dermatological, composition according to the present invention preferably includes one or more pearlizing waxes. Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups, and mixtures thereof.

Silicones: In order to impart a silky, spreadable, and luxurious texture and to make skin look and feel smoother, and additionally to improve processability (antifoaming) the cosmetic or pharmaceutical, preferably dermatological, composition according to the present invention preferably includes one or more silicone(s) or silicone derative(s). Suitable silicones can be chosen from the group consisting of Acefylline Methylsilanol Mannuronate, Acetylmethionyl Methylsilanol Elastinate Acrylates/Behenyl, Acrylate/Dimethicone Methacrylate Copolymer, Acrylates/Behenyl Methacrylate/Dimethicone Methacrylate Copolymer, Acrylates/Bis-Hydroxypropyl Dimethicone Crosspolymer, Acrylates/Dimethicone Copolymer, Acrylates/Dimethicone Methacrylate/Ethylhexyl Acrylate Copolymer, Acrylates/Dimethiconol Acrylate Copolymer, Acrylates/Ethylhexyl Acrylate/Dimethicone Methacrylate Copolymer, Acrylates/Octylacrylamide/Diphenyl Amodimethicone Copolymer, Acrylates/Polytrimethylsiloxymethacrylate Copolymer, Acrylates/Propyl Trimethicone Methacrylate Copolymer, Acrylates/Stearyl Acrylate/Dimethicone Methacrylate Copolymer, Acrylates/Tridecyl Acrylate/Triethoxysilylpropyl Methacrylate/Dimethicone Methacrylate Copolymer, Acrylates/Trifluoropropylm ethacrylate/Polytrim ethyl Siloxymethacrylate Copolymer, Amino Bispropyl Dimethicone, Aminoethylaminopropyl Dimethicone, Aminopropyl Dimethicone, Aminopropyl Phenyl Trimethicone, Aminopropyl Triethoxysilane, Ammonium Dimethicone PEG-7 Sulfate, Amodimethicone, Amodimethicone Hydroxystearate, Amodimethicone/Silsesquioxane Copolymer, Ascorbyl Carboxydecyl Trisiloxane, Ascorbyl Methylsilanol Pectinate, Behenoxy Dimethicone, Behentrimonium Dimethicone PEG-8 Phthalate, Behenyl Dimethicone, Bisamino PEG/PPG-41/3 Aminoethyl PG-Propyl Dimethicone, Bis-Aminopropyl/Ethoxy Aminopropyl Dimethicone, Bis (Butylbenzoate) Diaminotriazine Aminopropyltrisiloxane, Bis-Butyldimethicone Polyglyceryl-3, Bis-Butyloxyamodimethicone/PEG-60 Copolymer, Bis(C13-15 Alkoxy) Hydroxybutamidoamodimethicone, Bis(C13-15 Alkoxy) PG-Amodimethicone, Bis-(C1-8 Alkyl Lauroyl Lysine Decylcarboxamide) Dimethicone, Bis-Cetyl Cetyl Dimethicone, Bis-Cetyl/PEG-8 Cetyl PEG-8 Dimethicone, Bis-Diphenylethyl Disiloxane, Bis-Ethyl Ethyl Methicone, Bis-Gluconamidoethylaminopropyl Dimethicone, Bis-Hydrogen Dimethicone, Bis-Hydroxyethoxypropyl Dimethicone Bis-Hydroxylauryl, Dimethicone/IPDI Copolymer, Bis-Hydroxy/Methoxy Amodimethicone, Bis-Hydroxypropyl Dimethicone Behenate, Bis-Hydroxypropyl Dimethicone/SMDI Copolymer, Bis-Isobutyl PEG-14/Amodimethicone Copolymer, Bis-Isobutyl PEG-15/Amodimethicone Copolymer, Bis-Isobutyl PEG/PPG-20/35/ Amodimethicone Copolymer, Bis-Isobutyl PEG/PPG-10/7/ Dimethicone Copolymer, Bis-Isobutyl PEG-24/PPG-7/ Dimethicone Copolymer, Bis-PEG-1 Dimethicone, Bis- PEG-4 Dimethicone, Bis-PEG-8 Dimethicone, Bis-PEG-12 Dimethicone, Bis-PEG-20 Dimethicone, Bis-PEG-12 Dimethicone Beeswax, Bis-PEG-12 Dimethicone Candelillate, Bis-PEG-15 Dimethicone/IPDI Copolymer, Bis-PEG-15 Methyl Ether Dimethicone, Bis-PEG-18 Methyl Ether Dimethyl Silane, Bis-PEG/PPG-14/14 Dimethicone, Bis-PEG/PPG-15/5 Dimethicone, Bis-PEG/PPG-18/6 Dimethicone, Bis-PEG/PPG-20/20 Dimethicone, Bis-PEG/PPG-16/16 PEG/PPG-16/16 Dimethicone, Bis-PEG/PPG-20/5 PEG/PPG-20/5 Dimethicone, Bisphenylhexamethicone, Bis-Phenylpropyl Dimethicone, Bispolyethylene Dimethicone, Bis-(Polyglyceryl-3 Oxyphenylpropyl) Dimethicone, Bis-(Polyglyceryl-7 Oxyphenylpropyl) Dimethicone, Bis-PPG-15 Dimethicone/IPDI Copolymer, Bis(PPG-7 Undeceneth-21) Dimethicone, Bis-Stearyl Dimethicone, Bis-Trimethoxysilylethyl Tetramethyldisiloxyethyl Dimethicone, Bis-Vinyldimethicone, Bis-Vinyl Dimethicone/Dimethicone Copolymer, Borage Seed Oil PEG-7 Dimethicone Esters, Butyl Acrylate/C6-14 Perfluoroalkylethyl Acrylate/Mercaptopropyl Dimethicone Copolymer, Butyl Acrylate/Hydroxypropyl Dimethicone Acrylate Copolymer, Butyl Dimethicone Acrylate/Cyclohexylmethacrylate/Ethylhexyl Acrylate Copolymer, Butyldimethicone Methacrylate/Methyl Methacrylate Crosspolymer, t-Butyl Dimethyl Silyl Grape Seed Extract, Butyl Polydimethylsiloxyl Ethylene/Propylene/Vinylnorbornene Copolymer, C6-8 Alkyl C3-6 Alkyl Glucoside Dimethicone, C20-24 Alkyl Dimethicone, C24-28 Alkyl Dimethicone, C26-28 Alkyl Dimethicone, C30-45 Alkyl Dimethicone, C30-60 Alkyl Dimethicone, C32 Alkyl Dimethicone, C30-45 Alkyl Dimethicone/Polycyclohexene Oxide Crosspolymer, C26-28 Alkyldimethylsilyl Polypropylsilsesquioxane, C30-45 Alkyldimethylsilyl Polypropylsilsesquioxane, C20-24 Alkyl Methicone, C24-28 Alkyl Methicone, C26-28 Alkyl Methicone, C30-45 Alkyl Methicone, C20-28 Alkyl Perfluorodecylethoxy Dimethicone, C26-54 Alkyl Tetradecyl Dimethicone, Capryl Dimethicone, Caprylyl Dimethicone Ethoxy Glucoside, Caprylyl Methicone, Caprylyl Trimethicone, Carboxydecyl Trisiloxane, Castor Oil Bis-Hydroxypropyl Dimethicone Esters Cerotyl Dimethicone, Cetearyl Dimethicone Crosspolymer, Cetearyl Dimethicone/Vinyl Dimethicone Crosspolymer, Cetearyl Methicone, Cetrimonium Carboxydecyl PEG-8 Dimethicone, Cetrimonium Dimethicone PEG-7 Phthalate, Cetyl Behenyl Dimethicone, Cetyl Dimethicone, Cetyl Dimethicone/Bis-Vinyldimethicone Crosspolymer, Cetyl Hexacosyl Dimethicone, Cetyloxy Dimethicone, Cetyl PEG-8 Dimethicone, Cetyl PEG/PPG-15/15 Butyl Ether Dimethicone, Cetyl PEG/PPG-7/3 Dimethicone, Cetyl PEG/PPG-10/1 Dimethicone, Cetyl Triethylmonium Dimethicone PEG-8 Phthalate, Cetyl Triethylmonium Dimethicone PEG-8 Succinate, Copper Acetyl Tyrosinate Methylsilanol, Copper PCA Methylsilanol, C4-14 Perfluoroalkylethoxy Dimethicone, Cycloethoxymethicone, Cycloheptasiloxane, Cyclohexasiloxane, Cyclomethicone, Cyclopentasiloxane, Cyclophenylmethicone, Cyclotetrasiloxane,mCyclovinylmethicone, Cystine Bis-PG-Propyl Silanetriol, DEA PG-Propyl PEG/PPG-18/21 Dimethicone, Diisostearoyl Trimethylolpropane Siloxy Silicate, Dilauroyl Trimethylolpropane Siloxy Silicate, Dilinoleamidopropyl Dimethylamine Dimethicone PEG-7 Phosphate, Dimethicone, Dimethicone Crosspolymer, Dimethicone Crosspolymer-3, Dimethicone/Divinyldimethicone/Silsesquioxane Crosspolymer, Dimethicone Ethoxy Glucoside, Dimethicone Hydroxypropyl Trimonium Chloride, Dimethicone/Mercaptopropyl Methicone Copolymer, Dimethicone PEG-15 Acetate Dimethicone PEG-8 Adipate, Dimethicone PEG-7 Avocadoate, Dimethicone PEG-8 Avocadoate, Dimethicone PEG-8 Beeswax, Dimethicone PEG-8 Benzoate, Dimethicone PEG-8 Borageate, Dimethicone PEG-7 Cocoate, Dimethicone/PEG-10 Crosspolymer, Dimethicone/PEG-10/15 Crosspolymer, Dimethicone/PEG-15 Crosspolymer, Dimethicone PEG-7 Isostearate, Dimethicone PEG-8 Isostearate, Dimethicone PEG-7 Lactate, Dimethicone PEG-8 Lanolate, Dimethicone PEG-8 Laurate, Dimethicone PEG-8 Meadowfoamate, Dimethicone PEG-7 Octyldodecyl Citrate, Dimethicone PEG-7 Olivate, Dimethicone PEG-8 Olivate, Dimethicone PEG-7 Phosphate, Dimethicone PEG-8 Phosphate, Dimethicone PEG-10 Phosphate, Dimethicone PEG-7 Phthalate, Dimethicone PEG-8 Phthalate, Dimethicone PEG-8 Polyacrylate, Dimethicone PEG/PPG-20/23 Benzoate, Dimethicone PEG/PPG-7/4 Phosphate, Dimethicone PEG/PPG-12/4 Phosphate, Dimethicone PEG-7 Succinate, Dimethicone PEG-8 Succinate, Dimethicone PEG-7 Sulfate, Dimethicone PEG-7 Undecylenate, Dimethicone PG-Diethylmonium Chloride, Dimethicone/Phenyl Vinyl Dimethicone Crosspolymer, Dimethicone/Polyglycerin-3 Crosspolymer, Dimethicone/PPG-20 Crosspolymer, Dimethicone Propylethylenediamine Behenate, Dimethicone Propyl PG-Betaine, Dimethicone/Silsesquioxane Copolymer, Dimethicone Silylate, Dimethicone/Vinyl Dimethicone Crosspolymer, Dimethicone/Vinyltrimethylsiloxysilicate Crosspolymer, Dimethiconol, Dimethiconol Arginine, Dimethiconol Beeswax, Dimethiconol Behenate, Dimethiconol Borageate, Dimethiconol Candelillate, Dimethiconol Carnaubate, Dimethiconol Cysteine, Dimethiconol Dhupa Butterate, Dimethiconol Fluoroalcohol Dilinoleic Acid, Dimethiconol Hydroxystearate, Dimethiconol Illipe Butterate, Dimethiconol/IPDI Copolymer, Dimethiconol Isostearate, Dimethiconol Kokum Butterate, Dimethiconol Lactate, Dimethiconol Meadowfoamate, Dimethiconol Methionine, Dimethiconol/Methylsilanol/Silicate Crosspolymer, Dimethiconol Mohwa Butterate, Dimethiconol Panthenol, Dimethiconol Sal Butterate, Dimethiconol/Silica Crosspolymer, Dimethiconol/Silsesquioxane Copolymer, Dimethiconol Stearate, Dimethiconol/Stearyl, Methicone/Phenyl Trimethicone Copolymer, Dimethoxysilyl Ethylenediaminopropyl Dimethicone, Dimethylaminopropylamido PCA Dimethicone, Dimethyl Oxobenzo Dioxasilane, Dimethylsilanol Hyaluronate, Dioleyl Tocopheryl Methylsilanol, Diphenyl Amodimethicone, Diphenyl Dimethicone, Diphenyl Dimethicone Crosspolymer Diphenyl Dimethicone?/inyl Diphenyl Dimethicone/Silsesquioxane Crosspolymer, Diphenylethyl Benzyloxy Dilsiloxane, Diphenylisopropyl Dimethicone, Diphenylsiloxy Phenyl/Propyl Trimethicone, Diphenylsiloxy Phenyl Trimethicone Disiloxane, Disodium Amodimethicone Disuccinamide, Disodium PEG-12 Dimethicone Sulfosuccinate, Disodium PEG-8 Lauryl Dimethicone Sulfosuccinate, Divinyldimethicone/Dimethicone Copolymer, Divinyldimethicone/Dimethicone Crosspolymer, Drometrizole Trisiloxane, Ethylhexyl Acrylate/VP/Dimethicone Methacrylate Copolymer, Ethyl Methicone, Ethyl Trisiloxane, Fluoro C2-8 Alkyldimethicone, Gluconamidopropyl Aminopropyl Dimethicone, 4-(2-Beta-Glucopyranosiloxy) Propoxy-2-Hydroxybenzophenone, Glyceryl Undecyl Dimethicone, Glycidoxy Dimethicone, Hexadecyl Methicone, Hexyl Dimethicone, Hexyl Methicone, Hexyltrimethoxysilane, Hydrogen Dimethicone, Hydrogen Dimethicone/Octyl Silsesquioxane Copolymer, Hydrolyzed Collagen PG-Propyl Dimethiconol, Hydrolyzed Collagen PG-Propyl Methylsilanediol, Hydrolyzed Collagen PG-Propyl Silanetriol, Hydrolyzed Keratin PG-Propyl Methylsilanediol, Hydrolyzed Sesame Protein PG-Propyl Methylsilanediol, Hydrolyzed Silk PG-Propyl Methylsilanediol, Hydrolyzed Silk PG-Propyl Methylsilanediol Crosspolymer, Hydrolyzed Soy Protein/Dimethicone PEG-7 Acetate, Hydrolyzed Soy Protein PG-Propyl Methylsilanediol, Hydrolyzed Vegetable Protein PG-Propyl Silanetriol, Hydrolyzed Wheat Protein/Cystine Bis-PG-Propyl Silanetriol Copolymer, Hydrolyzed Wheat Protein/Dimethicone PEG-7 Acetate, Hydrolyzed Wheat Protein/Dimethicone PEG-7 Phosphate Copolymer, Hydrolyzed Wheat Protein PG-Propyl Methylsilanediol, Hydrolyzed Wheat Protein PG-Propyl Silanetriol, Hydroxyethyl Acetomonium PG-Dimethicone, Hydroxypropyldimethicone, Hydroxypropyl Dimethicone Behenate, Hydroxypropyl Dimethicone Isostearate, Hydroxypropyl Dimethicone Stearate, Isobutylmethacrylate/Bis-Hydroxypropyl Dimethicone Acrylate Copolymer, Isobutylmethacrylate/Trifluoroethylmethacrylate/Bis-Hydroxypropyl Dimethicone Acrylate Copolymer, Isopentyl Trimethoxycinnamate Trisiloxane, Isopolyglyceryl-3 Dimethicone, Isopolyglyceryl-3 Dimethiconol, Isopropyl Titanium Triisostearate/Triethoxysilylethyl, Polydimethylsiloxyethyl Dimethicone Crosspolymer, Isostearyl Carboxydecyl PEG-8 Dimethicone, Lactoyl Methylsilanol Elastinate, Lauryl Dimethicone, Lauryl Dimethicone PEG-15 Crosspolymer, Lauryl Dimethicone PEG-10 Phosphate, Lauryl Dimethicone/Polyglycerin-3 Crosspolymer, Lauryl Methicone, Lauryl PEG-8 Dimethicone, Lauryl PEG-10 Methyl Ether Dimethicone, Lauryl PEG-9 Polydimethylsiloxyethyl Dimethicone, Lauryl PEG/PPG-18/18 Methicone, Lauryl Phenylisopropyl Methicone, Lauryl Phenylpropyl Methicone, Lauryl Polydimethylsiloxyethyl Dimethicone/Bis-Vinyldimethicone Crosspolymer, Lauryl Polyglyceryl-3 Polydimethylsiloxyethyl Dimethicone, Lauryl Trimethicone, Linoleamidopropyl PG-Dimonium Chloride Phosphate Dimethicone, Methacryloyl Propyltrimethoxysilane, Methicone, Methoxy Amodimethicone/Silsesquioxane Copolymer, Methoxycinnamidopropyl Polysilsesquioxane, Methoxycinnamoylpropyl Silsesquioxane Silicate, Methoxy PEG-13 Ethyl Polysilsesquioxane, Methoxy PEG/PPG-7/3 Aminopropyl Dimethicone, Methoxy PEG/PPG-25/4 Dimethicone, Methoxy PEG-10 Propyltrimethoxysilane, Methyleugenyl PEG-8 Dimethicone, Methylpolysiloxane Emulsion, Methylsilanol Acetylmethionate, Methylsilanol Acetyltyrosine, Methylsilanol Ascorbate, Methylsilanol Carboxymethyl Theophylline, Methylsilanol Carboxymethyl Theophylline Alginate, Methylsilanol Elastinate, Methylsilanol Glycyrrhizinate, Methylsilanol Hydroxyproline, Methylsilanol Hydroxyproline Aspartate, Methylsilanol Mannuronate, Methylsilanol PCA, Methylsilanol PEG-7 Glyceryl Cocoate, Methylsilanol/Silicate Crosspolymer, Methylsilanol Spirulinate, Methylsilanol Tri-PEG-8 Glyceryl Cocoate, Methyl Trimethicone, Methyltrimethoxysilane, Myristylamidopropyl Dimethylamine Dimethicone PEG-7 Phosphate, Myristyl Methicone, Myristyl Trisiloxane, Nylon-611/Dimethicone Copolymer, PCA Dimethicone, PEG-7 Amodimethicone, PEG-8 Amodimethicone, PEG-8 Cetyl Dimethicone, PEG-3 Dimethicone, PEG-6 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG-10 Dimethicone Crosspolymer, PEG-12 Dimethicone Crosspolymer, PEG-8 Dimethicone Dimer Dilinoleate, PEG-8 Dimethicone/Dimer Dilinoleic Acid Copolymer, PEG-10 Dimethicone/Vinyl Dimethicone Crosspolymer, PEG-8 Distearmonium Chloride PG-Dimethicone, PEG-10/Lauryl Dimethicone Crosspolymer, PEG-15/Lauryl Dimethicone Crosspolymer, PEG-15/Lauryl Polydimethylsiloxyethyl Dimethicone Crosspolymer, PEG-8 Methicone, PEG-6 Methicone Acetate, PEG-6 Methyl Ether Dimethicone, PEG-7 Methyl Ether Dimethicone, PEG-8 Methyl Ether Dimethicone, PEG-9 Methyl Ether Dimethicone, PEG-10 Methyl Ether Dimethicone, PEG-11 Methyl Ether Dimethicone, PEG-32 Methyl Ether Dimethicone, PEG-8 Methyl Ether Triethoxysilane, PEG-10 Nonafluorohexyl Dimethicone Copolymer, PEG-4 PEG-12 Dimethicone, PEG-8 PG-Coco-Glucoside Dimethicone, PEG-9 Polydimethylsiloxyethyl Dimethicone, PEG/PPG-20/22 Butyl Ether Dimethicone, PEG/PPG-22/22 Butyl Ether Dimethicone, PEG/PPG-23/23 Butyl Ether Dimethicone, PEG/PPG-24/18 Butyl Ether Dimethicone, PEG/PPG-27/9 Butyl Ether Dimethicone, PEG/PPG-3/10 Dimethicone, PEG/PPG-4/12 Dimethicone, PEG/PPG-6/4 Dimethicone, PEG/PPG-6/11 Dimethicone, PEG/PPG-8/14 Dimethicone, PEG/PPG-8/26 Dimethicone, PEG/PPG-10/2 Dimethicone, PEG/PPG-12/16 Dimethicone, PEG/PPG-12/18 Dimethicone, PEG/PPG-14/4 Dimethicone, PEG/PPG-15/5 Dimethicone, PEG/PPG-15/15 Dimethicone, PEG/PPG-16/2 Dimethicone, PEG/PPG-16/8 Dimethicone, PEG/PPG-17/18 Dimethicone, PEG/PPG-18/6 Dimethicone, PEG/PPG-18/12 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, PEG/PPG-30/10 Dimethicone, PEG/PPG-25/25 Dimethicone/Acrylates Copolymer, PEG/PPG-20/22 Methyl Ether Dimethicone, PEG/PPG-24/24 Methyl Ether Glycidoxy Dimethicone, PEG/PPG-10/3 Oleyl Ether Dimethicone, PEG/PPG-5/3 Trisiloxane, PEG-4 Trifluoropropyl Dimethicone Copolymer, PEG-8 Trifluoropropyl Dimethicone Copolymer, PEG-10 Trifluoropropyl Dimethicone Copolymer, PEG-8 Trisiloxane, Perfluorocaprylyl riethoxysilylethyl Methicone, Perfluorononyl Dimethicone, Perfluorononyl Dimethicone/Methicone/Amodimethicone Crosspolymer, Perfluorononylethyl Carboxydecyl Behenyl Dimethicone, Perfluorononylethyl Carboxydecyl Hexacosyl Dimethicone, Perfluorononylethyl Carboxydecyl Lauryl/Behenyl Dimethicone, Perfluorononylethyl Carboxydecyl Lauryl Dimethicone, Perfluorononylethyl Carboxydecyl PEG-8 Dimethicone, Perfluorononylethyl Carboxydecyl PEG-10 Dimethicone, Perfluorononylethyl Dimethicone/Methicone Copolymer, Perfluorononylethyl PEG-8 Dimethicone, Perfluorononylethyl Stearyl Dimethicone, Perfluorooctylethyl/Diphenyl Dimethicone Copolymer, Perfluorooctylethyl Triethoxysilane, Perfluorooctylethyl Trimethoxysilane, Perfluorooctylethyl Trisiloxane, Perfluorooctyl Triethoxysilane, PG-Amodimethicone, Phenethyl Dimethicone, Phenethyl Disiloxane, Phenyl Dimethicone, Phenylisopropyl Dimethicone, Phenyl Methicone, Phenyl Methiconol, Phenylpropyldimethylsiloxysilicate, Phenylpropyl Ethyl Methicone, Phenyl Propyl Trimethicone, Phenyl Propyl Trimethicone/Diphenylmethicone, Phenyl Trimethicone, Platinum Divinyldisiloxane, Polyacrylate-6, Polydiethylsiloxane, Polydimethylsiloxyethyl Dimethicone/Bis-Vinyldimethicone Crosspolymer, Polydimethylsiloxyethyl Dimethicone/Methicone Copolymer, Polydimethylsiloxy PEG/PPG-24/19 Butyl Ether Silsesquioxane, Polydimethylsiloxy PPG-13 Butyl Ether Silsesquioxane, Polyglyceryl-3 Disiloxane Dimethicone, Polyglyceryl-3/Lauryl Polydimethylsiloxyethyl Dimethicone Crosspolymer, Polyglyceryl-3 Polydimethylsiloxyethyl Dimethicone, Poly(Glycol Adipate)/Bis-Hydroxyethoxypropyl Dimethicone Copolymer, Polymethylsilsesquioxane, Polymethylsilsesquioxane/Trimethylsiloxysilicate, Polyphenylsilsesquioxane, Polypropylsilsesquioxane, Polysilicone-1, Polysilicone-2, Polysilicone-3, Polysilicone-4, Polysilicone-5, Polysilicone-6, Polysilicone-7, Polysilicone-8, Polysilicone-9, Polysilicone-10, Polysilicone-11, Polysilicone-12, Polysilicone-13, Polysilicone-14, Polysilicone-15, Polysilicone-16, Polysilicone-17, Polysilicone-18, Polysilicone-19, Polysilicone-20, Polysilicone-21, Polysilicone-18 Cetyl Phosphate, Polysilicone-1 Crosspolymer, Polysilicone-18 Stearate, Polyurethane-10, Potassium Dimethicone PEG-7 Panthenyl Phosphate, Potassium Dimethicone PEG-7 Phosphate, PPG-12 Butyl Ether Dimethicone, PPG-2 Dimethicone, PPG-12 Dimethicone, PPG-27 Dimethicone, PPG-4 Oleth-10 Dimethicone, Propoxytetramethyl Piperidinyl Dimethicone, Propyl Trimethicone, Quaternium-80, Retinoxytrimethylsilane, Silanediol Salicylate, Silanetriol, Silanetriol Arginate, Silanetriol Glutamate, Silanetriol Lysinate, Silanetriol Melaninate, Silanetriol Trehalose Ether, Silica, Silica Dimethicone Silylate, Silica Dimethyl Silylate, Silica Silylate, Silicon Carbide, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, SiliconeQuaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Silicone Quaternium-22, Silicone Quaternium-24, Silicone Quaternium-25, Siloxanetriol Alginate, Siloxanetriol Phytate, Simethicone, Sodium Carboxydecyl PEG-8 Dimethicone, Sodium Dimethicone PEG-7 Acetyl Methyltaurate, Sodium Hyaluronate Dimethylsilanol, Sodium Lactate Methylsilanol, Sodium Mannuronate Methylsilanol, Sodium PCA Methylsilanol, Sodium PG-Propyldimethicone Thiosulfate Copolymer, Sodium PG-Propyl Thiosulfate Dimethicone, Sodium Propoxyhydroxypropyl Thiosulfate Silica, Sorbityl Silanediol, Soy Triethoxysilylpropyldimonium Chloride, Stearalkonium Dimethicone PEG-8 Phthalate, Stearamidopropyl Dimethicone, Steardimonium Hydroxypropyl Panthenyl PEG-7 Dimethicone Phosphate Chloride, Steardimonium Hydroxypropyl PEG-7 Dimethicone Phosphate Chloride, Stearoxy Dimethicone, Stearoxymethicone/Dimethicone Copolymer, Stearoxytrimethylsilane, Stearyl Aminopropyl Methicone, Stearyl Dimethicone, Stearyl/Lauryl Methacrylate Crosspolymer, Stearyl Methicone, Stearyl Triethoxysilanek, Stearyl Trimethicone, Styrene/Acrylates/Dimethicone Acrylate Crosspolymer, Styrene/Acrylates/Dimethicone Copolymer, TEA-Dimethicone PEG-7 Phosphate, Tetrabutoxypropyl Trisiloxane, Tetramethyl Hexaphenyl Tetrasiloxane, Tetramethyl Tetraphenyl Trisiloxane, Tocopheryloxypropyl Trisiloxane, Trideceth-9 PG-Amodimethicone, Triethoxycaprylylsilane, Triethoxysilylethyl Dimethicone/Methicone Copolymer, Triethoxysilylethyl Polydimethylsiloxyethyl Dimethicone, Triethoxysilylethyl Polydimethylsiloxyethyl Hexyl Dimethicone, Triethoxysilylpropylcarbamoyl Ethoxypropyl Butyl Dimethicone, Trifluoromethyl C1-4 Alkyl Dimethicone, Trifluoropropyl Cyclopentasiloxane, Trifluoropropyl Cyclotetrasiloxane, Trifluoropropyl Dimethicone, Trifluoropropyl Dimethicone/PEG-10 Crosspolymer, Trifluoropropyl Dimethicone/Trifluoropropyl Divinyldimethicone Crosspolymer, Trifluoropropyl Dimethicone/Vinyl Trifluoropropyl, Dimethicone/Silsesquioxane Crosspolymer, Trifluoropropyl Dimethiconol, Trifluoropropyldimethyl/trimethylsiloxysilicate, Trifluoropropyl Methicone, Trimethoxycaprylylsilane, Trimethoxysilyl Dimethicone, Trimethyl Pentaphenyl Trisiloxane, Trimethylsiloxyamodimethicone, Trimethylsiloxyphenyl Dimethicone, Trimethylsiloxysilicate, Trimethylsiloxysilicate/Dimethicone Crosspolymer, Trimethylsiloxysilicate/Dimethiconol Crosspolymer, Trimethylsiloxysilylcarbamoyl Pullulan, Trimethylsilyl Hydrolyzed Conchiolin Protein PG-Propyl Methylsilanediol Crosspolymer, Trimethylsilyl Hydrolyzed Silk PG-Propyl Methylsilanediol Crosspolymer, Trimethylsilyl Hydrolyzed Wheat Protein PG-Propyl Methylsilanediol Crosspolymer, Trimethylsilyl Pullulan, Trimethylsilyl Trimethylsiloxy Glycolate, Trimethylsilyl Trimethylsiloxy Lactate, Trimethylsilyl Trimethylsiloxy Salicylate, Triphenyl Trimethicone, Trisiloxane, Tris-Tributoxysiloxymethylsilane, Undecylcrylene Dimethicone, Vinyl Dimethicone, Vinyl Dimethicone/Lauryl Dimethicone Crosspolymer, Vinyl Dimethicone/Methicone Silsesquioxane Crosspolymer, Vinyldimethyl/Trimethylsiloxysilicate Stearyl Dimethicone Crosspolymer, VP/Dimethiconylacrylate/Polycarbamyl/Polyglycol Ester, Zinc Carboxydecyl Trisiloxane, Zinc Dimethicone PEG-8 Succinate, and mixtures thereof.

More preferably the silicones to be contained in the cosmetic or pharmaceutical, preferably dermatological, composition according to the invention are Dimethicone, Cyclomethicone, Cyclopentasiloxane, Cyclotetrasiloxane, Phenyl Trimethicone, and Cyclohexasiloxane.

Waxes and/or stabilizers: Besides natural oils used, one or more waxes may also be present in the cosmetic or pharmaceutical, preferably dermatological, composition according to the present invention, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Metal salts of fatty acids such as, for example, magnesium, aluminium and/or zinc stearate or ricinoleate may be used as stabilizers.

Apart from the abovementioned liquid UV filters, the cosmetic or pharmaceutical, preferably dermatological, composition as defined herein, is advantageously combined with at least one further primary sun protection factor and/or with at least one further secondary sun protection factor, in order to increase the SPF, i.e. to obtain a high SPF and to cover a broad UVA and UVB range.

Primary sun protection factors: Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The cosmetic or pharmaceutical, preferably dermatological, composition according to the invention advantageously contains at least one UV-A filter and/or at least one UV-B filter and/or a broadband filter and/or at least one inorganic pigment. Compositions according to the invention preferably contain at least one UV-B filter or a broadband filter, more particularly preferably at least one UV-A filter and at least one UV-B filter. Preferred cosmetic compositions, preferably topical compositions according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, a combination with active ingredients which penetrate into the skin and protect the skin cells from inside against sunlight-induced damage and reduce the level of cutaneous matrix metalloproteases is advantageously. Preferred respective ingredients are so called arylhydrocarbon receptor antagonists. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
- p-aminobenzoic acid
- p-aminobenzoic acid ethyl ester (25 mol) ethoxylated (INCI name: PEG-25 PABA)
- p-dimethylaminobenzoic acid-2-ethylhexyl ester
- p-aminobenzoic acid ethyl ester (2 mol) N-propoxylated
- p-aminobenzoic acid glycerol ester
- salicylic acid homomenthyl ester (homosalates) (Neo Heliopan®HMS)
- salicylic acid-2-ethylhexyl ester (Neo Heliopan® OS)
- triethanolamine salicylate
- 4-isopropyl benzyl salicylate
- anthranilic acid menthyl ester (Neo Heliopan®MA)
- diisopropyl cinnamic acid ethyl ester
- p-methoxycinnamic acid-2-ethylhexyl ester (Neo Heliopa®AV)
- diisopropyl cinnamic acid methyl ester
- p-methoxycinnamic acid isoamyl ester (Neo Heliopan®E 1000)
- p-methoxycinnamic acid diethanolamine salt
- p-methoxycinnamic acid isopropyl ester
- 2-phenylbenzimidazole sulfonic acid and salts (Neo Heliopan® Hydro)
- 3-(4'-trimethylammonium) benzylidene bornan-2-one methyl sulfate
- beta-imidazole-4(5)-acrylic acid (urocanic acid)
- 3-(4'-sulfo)benzylidene bornan-2-one and salts
- 3-(4'-methyl benzylidene)-D,L-camphor (Neo Heliopa®MBC)
- 3-benzylidene-D,L-camphor
- N-[(2 and 4)-[2-(oxoborn-3-ylidene) methyl]benzyl] acrylamide polymer
- 4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb®HEB)
- benzylidene malonate polysiloxane (Parsol®SLX)
- glyceryl ethylhexanoate dimethoxycinnamate
- dipropylene glycol salicylate
- tris(2-ethylhexyl)-4,4',4''-(1,3,5-triazine-2,4,6-triyl-triimino)tribenzoate (=2,4,6-trianilino-(p-carbo-2'-ethylhexyl-1'-oxy)-1,3,5-triazine) (Uvinul®T150).

In a preferred variant the cosmetic or pharmaceutical, preferably dermatological, composition according to the present invention comprises a combination with one or more broadband filters which are selected from the group consisting of
- 2-ethylhexyl-2-cyano-3,3-diphenyl acrylate (Neo Heliopan® 303)
- ethyl-2-cyano-3,3'-diphenyl acrylate
- 2-hydroxy-4-methoxybenzophenone (Neo Heliopan®BB)
- 2-hydroxy-4-methoxybenzophenone-5-sulfonic acid
- dihydroxy-4-methoxybenzophenone
- 2,4-dihydroxybenzophenone
- tetrahydroxybenzophenone
- 2,2'-dihydroxy-4,4'-dimethoxybenzophenone
- 2-hydroxy-4-n-octoxybenzophenone
- 2-hydroxy-4-methoxy-4'-methyl benzophenone
- sodium hydroxymethoxybenzophenone sulfonate
- disodium-2,2'-dihydroxy-4,4'-dimethoxy-5,5'-disulfobenzophenone
- phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl®XL)
- 2,2'-methylene bis-(6-(2H-benzotriazol-2-yl)-4-1,1,3,3-tetramethylbutyl) phenol) (Tinosorb® M)
- 2,4-bis-[4-(2-ethylhexyloxy)-2-hydroxyphenyl]-1,3,5-triazine
- 2,4-bis-[{(4-(2-ethylhexyloxy)-2-hydroxy}phenyl]-6-(4-methoxyphenyl)-1,3,5-triazine (Tinosorb® S)
- 2,4-bis-[{(4-(3-sulfonato)-2-hydroxypropyloxy)-2-hydroxy}phenyl]-6-(4-methoxyphenyl)-1,3,5-triazine sodium salt
- 2,4-bis-[{(3-(2-propyloxy)-2-hydroxypropyloxy)-2-hydroxy}phenyl]-6-(4-methoxyphenyl)-1,3,5-triazine
- 2,4-bis-[{4-(2-ethylhexyloxy)-2-hydroxy}phenyl]-6-[4-(2-methoxyethyl carbonyl) phenylamino]-1,3,5-triazine
- 2,4-bis-[{4-(3-(2-propyloxy)-2-hydroxypropyloxy)-2-hydroxy}phenyl]-6-[4-(2-ethylcarboxyl) phenylamino]-1,3,5-triazine
- 2,4-bis-[{4-(2-ethylhexyloxy)-2-hydroxy}phenyl]-6-(1-methylpyrrol-2-yl)-1,3,5-triazine
- 2,4-bis-[{4-tris-(trimethylsiloxysilylpropyloxy)-2-hydroxy}phenyl]-6-(4-methoxyphenyl)-1,3,5-triazine
- 2,4-bis-[{4-(2''-methylpropenyloxy)-2-hydroxy}phenyl]-6-(4-methoxyphenyl)-1,3,5-triazine
- 2,4-bis-[{4-(1',1',1',3',5',5',5'-heptamethylsiloxy-2''-methyl-propyloxy)-2-hydroxy}phenyl]-6-(4-methoxyphenyl)-1,3,5-triazine.

In a preferred variant the cosmetic or pharmaceutical, preferably dermatological, composition according to the present invention comprises a combination with one or more UV-A filters which are selected from the group consisting of
- 4-isopropyl dibenzoyl methane
- terephthalylidene dibornane sulfonic acid and salts (Mexoryl®SX)
- 4-t-butyl-4'-methoxydibenzoyl methane (avobenzone)/ (Neo Heliopan® 357)
- phenylene bis-benzimidazyl tetrasulfonic acid disodium salt (Neo Heliopan®AP)
- 2,2'-(1,4-phenylene)-bis-(1H-benzimidazole-4,6-disulfonic acid), monosodium salt
- 2-(4-diethylamino-2-hydroxybenzoyl) benzoic acid hexyl ester (Uvinul® A Plus)
- indanylidene compounds.

In a more preferred variant, the cosmetic or pharmaceutical, preferably dermatological, composition according to the present invention comprises a combination with one or more UV filters which are selected from the group consisting of:
- p-aminobenzoic acid
- 3-(4'-trimethylammonium) benzylidene bornan-2-one methyl sulfate salicylic acid homomenthyl ester (Neo Heliopan®CHMS)
2-hydroxy-4-methoxybenzophenone (Neo Heliopan®BB)
2-phenylbenzimidazole sulfonic acid (Neo Heliopan® Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan©303)
N-[(2 and 4)-[2-(oxoborn-3-ylidene) methyl]benzyl] acrylamide polymer
p-methoxycinnamic acid-2-ethylhexyl ester (Neo Heliopan®AV)
p-aminobenzoic acid ethyl ester (25 mol) ethoxylated (INCI name: PEG-25 PABA)
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl®XL)
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine (Tinosorb®S)
benzylidene malonate polysiloxane (Parsol®SLX)
menthyl anthranilate (Neo Heliopan®MA)
2-(4-diethylamino-2-hydroxybenzoyl) benzoic acid hexyl ester (Uvinul® A Plus)
indanylidene compounds.

In a further preferred variant, the cosmetic or pharmaceutical, preferably dermatological, composition according to the invention contains a total amount of sunscreen agents, i.e. in particular UV filters and/or inorganic pigments (UV filtering pigments) so that the composition according to the invention has a light protection factor of greater than or equal to 2 (preferably greater than or equal to 5). Such compositions according to the invention are particularly suitable for protecting the skin and hair.

Secondary sun protection factors: Besides the groups of primary sun protection factors mentioned above, secondary sun protection factors of the antioxidant type may also be advantageously used in the cosmetic or pharmaceutical, preferably dermatological, composition according to the present invention. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene), phytoene, phytofluene and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and heptathionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA, Trisodium Dicarboxymethyl Alaninate, and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$), and/or mixtures thereof.

Actives modulating skin and/or hair pigmentation: The cosmetic or pharmaceutical, preferably dermatological, composition according to the present invention may include active ingredients for skin and/or hair lightening. Preferred active ingredients for skin and/or hair lightening are selected from the group consisting of kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates, sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, *Papaya* extract, turmeric extract, mulberry extract, bengkoang extract, nutgrass extract, liquorice root extract or constituents concentrated or isolated therefrom, preferably glabridin or licochalcone A, *Artocarpus* extract, extract of *Rumex* and *Ramulus* species, extracts of pine species (*pinus*), extracts of *vitis* species or stilbene derivatives isolated or concentrated therefrom, saxifrage extract, scutelleria extract, grape extract and/or microalgae extract, in particular *Tetraselmis suecica* Extract.

Preferred skin lighteners are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, *Papaya* extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases"), tetrasubstituted cyclohexene derivatives, isoprenoids, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the *chrysanthemum* species, *sanguisorba* species, walnut extracts, urucum extracts, rhubarb extracts, microalgae extracts, in particular *Isochrysis galbana*, trehalose, erythrulose and dihydroxyacetone. Flavonoids which bring about skin and hair tinting or brown-ing (e.g. quercetin, rhamnetin, kaempferol, fisetin, genistein, daidzein, chrysin and apigenin, epicatechin, diosmin and diosmetin, morin, quercitrin, naringenin, hesperidin, phloridzin and phloretin) can also be used.

Hair growth activators or inhibitors: Cosmetic or pharmaceutical, preferably dermatological, compositions according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormones, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxacum*), *Orthosiphon*, *Vitex*, *Coffea*, *Paullinia*, *Theobroma*, *Asiasarum*, *Cucurbita* or *Styphnolobium*, *Serenoa repens* (saw palmetto), *Sophora flavescens*, *Pygeum africanum*, *Panicum miliaceum*, *Cimicifuga racemosa*, *Glycine max*, *Eugenia caryophyllata*, *Cotinus coggygria*, *Hibiscus rosa-sinensis*, *Camellia sinensis*, *Ilex paraguariensis*, *Isochrysis galbana*, licorice, grape, apple, barley or hops or/nd hydrolysates from rice or wheat.

Alternatively, the cosmetic or pharmaceutical, preferably dermatological, composition according to the present invention may include one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus*, *Gloiopeltis*, *Ceramium*, *Durvillea*, *Glycine max*, *Sanguisorba officinalis*, *Calendula officinalis*, *Hamamelis virginiana*, *Arnica montana*, *Salix alba*, *Hypericum perforatum* or *Gymnema sylvestre*.

Enzyme inhibitors: The cosmetic or pharmaceutical, preferably dermatological, composition according to the present invention may comprise one or more enzyme inhibitors. Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour absorbers and/or antiperspirant active agents: The cosmetic or pharmaceutical, preferably dermatological, composition according to the present invention may include one or more odour absorbers and/or antiperspirant active agents (antiperspirants). Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or *styrax* or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, *galbanum* oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film formers: The cosmetic or pharmaceutical, preferably dermatological, composition according to the present invention may include one or more film formers. Standard film formers are preferably chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Carriers and hydrotropes: The cosmetic or pharmaceutical, preferably dermatological, composition according to the present invention may comprise a carrier or a mixture of different carriers. Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water, and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of the cosmetic or pharmaceutical, preferably dermatological, composition according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin, inulin, and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Dyes: The cosmetic or pharmaceutical, preferably dermatological, composition according to the present invention may comprise one or more dyes. Suitable dyes are any of the substances suitable and approved for cosmetic purposes. Examples include cochineal red A (CI. 16255), patent blue V (CI. 42051), indigotin (CI. 73015), chlorophyllin (CI. 75810), quinoline yellow (CI. 47005), titanium dioxide (CI. 77891), indanthrene blue RS (CI. 69800) and madder lake (CI. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

In addition to the above-described substances, further ingredients commonly used in the cosmetic or pharmaceutical industry or the homecare product industry, which are suitable or customary in the compositions of the present invention, can be used.

The 1,2-heptanediol or the 2,3-heptanediol or the mixture comprising 1,2-heptanediol and 2,3-heptanediol is present in the cosmetic or pharmaceutical, preferably dermatological, composition or homecare product according to the first aspect of the present invention, in an amount of 0.001 to 15.0% by weight, based on the total weight of the composition or homecare product. In a preferred variant, the cosmetic or pharmaceutical, preferably dermatological, composition or homecare product comprises the 1,2-heptanediol or the 2,3-heptanediol or the mixture comprising 1,2-heptanediol and 2,3-heptanediol in an amount of 0.01 to 10.0% by weight, based on the total weight of the composition. In a more preferred variant, the 1,2-heptanediol or the 2,3-heptanediol or the mixture comprising 1,2-heptanediol and 2,3-heptanediol is advantageously used in the cosmetic or pharmaceutical, preferably dermatological, composition or homecare product in an amount of at 0.1 to 5.0% by weight, based on the total weight of the composition or homecare product. In a still more preferred variant, the 1,2-heptanediol or the 2,3-heptanediol or the mixture comprising 1,2-heptanediol and 2,3-heptanediol is advantageously used in the cosmetic or pharmaceutical, preferably dermatological, composition or homecare product in an amount of at 0.3 to 3.0% by weight, based on the total weight of the composition or homecare product. In a most preferred variant, the 1,2-heptanediol or 2,3-heptanediol or the mixture comprising 1,2-heptanediol and 2,3-heptanediol is advantageously used in the cosmetic or pharmaceutical composition or homecare product in an amount of 0.5 to 1.0% by weight, based on the total weight of the composition or homecare product.

For the heptanediol mixture, the above amounts relate to the total content of the 1,2-heptanediol and the 2,3-heptanediol in the mixture, i.e., the amount is the sum of the content of the 1,2-heptanediol and the content of the 2,3-heptanediol in the mixture.

The at least one linear alkanediol or the mixture comprising at least one first linear alkanediol and one or more second linear alkanediol according to the second aspect of the present invention is present in the cosmetic or pharmaceutical composition or homecare product in an amount of 0.001 to 15.0% by weight, based on the total weight of the composition or homecare product. In a preferred variant, the cosmetic or pharmaceutical composition or homecare product comprises the at least one linear alkanediol or the mixture comprising at least one first linear alkanediol and one or more second linear alkanediol in an amount of 0.01 to 10.0% by weight, based on the total weight of the composition or homecare product. In a more preferred variant, the at least one linear alkanediol or the mixture comprising at least one first linear alkanediol and one or more second linear alkanediol is advantageously used in the cosmetic or pharmaceutical composition or homecare product in an amount of at 0.1 to 5.0% by weight, based on the total weight of the composition. In a still more preferred variant, the at least one linear alkanediol or the mixture comprising at least one first linear alkanediol and one or more second linear alkanediol is advantageously used in the cosmetic or pharmaceutical composition or homecare product in an amount of at 0.3 to 3.0% by weight, based on the total weight of the composition. In a most preferred variant, the at least one linear alkanediol or the mixture comprising at least one first linear alkanediol and one or more second linear alkanediol is advantageously used in the cosmetic or pharmaceutical composition or homecare product in an amount of at 0.5 to 1.0% by weight, based on the total weight of the composition or homecare product.

For the alkane mixture, the above amounts relate to the total content of the first linear alkanediol and the second linear alkanediol in the mixture, i.e. the amount is the sum of the content of the first linear alkanediol and the second linear alkanediol in the mixture.

In a particular preferred variant according to the first aspect of the present invention, the cosmetic or pharmaceutical composition or the homecare product comprises the 2,3-heptanediol or the 2,3-heptanediol of the mixture comprising 1,2-heptanediol and 2,3-heptanediol in an amount of 0.001 to 15.0% by weight, preferred in an amount of 0.01 to 10.0% by weight, more preferred in an amount of 0.1 to 5.0% by weight, still more preferred in an amount of 0.3 to 3.0% by weight, and most preferred in an amount of 0.5 to 1.0% by weight, based on the total weight of the composition or homecare product.

Even more preferred, the cosmetic or pharmaceutical composition or the homecare product comprises the 2,3-heptanediol or the 2,3-heptanediol of the mixture comprising 1,2-heptanediol and 2,3-heptanediol in an amount of 0.001 to 0.5% weight, preferably in an amount of 0.005 to 0.1% by weight and most preferably in an amount of 0.01 to 0.075% by weight, based on the total weight of the composition or homecare product.

In a particular preferred variant according to the second aspect of the present invention, the cosmetic or pharmaceutical composition or the homecare product comprises the 2,3-alkandediol as linear alkanediol or of the mixture comprising at least one first linear alkanediol and one or more second linear alkanediol in an amount of 0.001 to 15.0% by weight, preferably in an amount of 0.01 to 10.0% by weight, more preferred in an amount of 0.1 to 5.0% by weight, still more preferred in an amount of 0.3 to 3.0% by weight, and most preferred in an amount of 0.5 to 1.0% by weight, based on the total weight of the composition or homecare product.

Even more preferred, the cosmetic or pharmaceutical composition or the homecare product comprises the 2,3-alkanediol as linear alkanediol or of the mixture comprising at least one first linear alkanediol and one or more second linear alkanediol in an amount of 0.001 to 0.5% weight of the composition or homecare product, preferably in an amount of 0.005 to 0.1% by weight and most preferably in an amount of 0.01 to 0.075% by weight, based on the total weight of the composition or homecare product.

The antioxidant is present in the cosmetic or pharmaceutical, preferably dermatological, composition or homecare product according to the present invention, in an amount of 0.0001% to 10.0 by weight, based on the total weight of the composition. In a preferred variant, the cosmetic or pharmaceutical, preferably dermatological, composition comprises the antioxidant in an amount of 0.005 to 8.0% by weight, based on the total weight of the composition. In a particular preferred variant, the antioxidant is advantageously used in the cosmetic or pharmaceutical, preferably dermatological, composition in an amount of at 0.001 to 5.0% by weight, based on the total weight of the composition.

The cosmetic or pharmaceutical, preferably dermatological, composition according to the first or second aspect of the present invention is intended for topical applications. The term "topical" is understood to mean external applications on a mammal's skin, which are in particular for the treatment, protection, care and cleansing of the skin, scalp, eyelashes, eyebrows, nails, mucous membranes and hair. The mammal is preferably a human.

For topical application, the cosmetic or pharmaceutical composition is either a rinse off or leave on preparation.

The cosmetic or pharmaceutical, in particular dermatological, composition according to the first or second aspect of the present invention can be present in different forms of, e.g., in the form of a dispersion, in the form of a water free formulation, in the form of a liquid surfactant formulation, in the form of a solid surfactant formulation or in the form of an aqueous or aqueous/alcoholic, particularly aqueous/ethanolic, or aqueous/glycolic based solution.

In a particular variant, the cosmetic or pharmaceutical, preferably dermatological, composition according to the present invention is a cold formulation, which can be prepared without a heating step.

The cosmetic or pharmaceutical, preferably dermatological, composition according to the first or second aspect of the present invention is preferably a dispersion. The term "dispersion" in the context of the present invention means, that the cosmetic or pharmaceutical composition is a disperse two-phase system consisting of colloidal particles (disperse phase) and a medium in which they are suspended (disperse medium). Both phases are not miscible with each other, only with an emulsifier. Such dispersions, for example emulsions, comprise the at least oil component preferably in an amount of 1% by weight, more preferably in an amount of 3% by weight.

If the cosmetic or pharmaceutical composition according to the present invention is a dispersion, preferably an emulsion, the oil component is present in the cosmetic or pharmaceutical composition in an amount of 0.01% to 50.0 by weight, based on the total weight of the composition. In a preferred variant, the cosmetic or pharmaceutical comprises the oil component in an amount of 1.0 to 40.0% by weight, based on the total weight of the composition. In a particular preferred variant, the oil component is advantageously used in the cosmetic or pharmaceutical composition in an amount of at 3.0 to 30% by weight, based on the total weight of the composition.

Preferably, the cosmetic or pharmaceutical composition according to the first or second aspect of the present invention takes various forms such as an emulsion, in particular a O/W emulsion, a W/O emulsion, a multiple emulsion, a hydro dispersion gel, a balm, a multiple emulsion of the water-in-oil type (W/0/WO) or of the oil-in-water type (O/W/O), PIT emulsion, Pickering emulsion, a micro-emulsion, a liquid, a lotion, a suspension, a milk, an ointment, a paste, a gel, a cream based, an oil based or a liposome based formulation.

In a further variant, the cosmetic or pharmaceutical, preferably dermatological, composition according to the first or second aspect of the present invention is a water free formulation, i.e., an oil formulation. The term water free formulation in the context of the present invention means that the at least one liquid lipophilic component is present in an amount of 60% by weight, preferably in an amount of 90% by weight.

Such water free formulations include e.g., oils, skin butters, powders, lip stick, antiperspirant/deo stick, and decorative cosmetics, etc.

In a further alternative, the cosmetic or pharmaceutical composition according to the present invention is a liquid surfactant formulation.

If the cosmetic or pharmaceutical composition according to the present invention is a liquid surfactant formulation, the surfactant component is present in the cosmetic or pharmaceutical, preferably dermatological, composition in an amount of 1 to 40% by weight, preferably in an amount of 3 to 30% by weight, more preferably in an amount of 5 to 25% by weight, based on the total weight of the composition.

Such liquid surfactant formulations include for example shampoo, shower gel, micellar water, liquid soap, cleansing preparations.

In a further alternative, the cosmetic or pharmaceutical composition according to the present invention is a solid surfactant formulation.

Such solid surfactant formulations include for example solid shampoos, solid body wash, bar soaps, etc.

Alternatively, the cosmetic or pharmaceutical composition as disclosed herein is an aqueous or aqueous/alcoholic or aqueous/glycolic based solution. The aqueous/alcoholic or aqueous/glycolic based solution comprises an aliphatic alcohol or a glycol in an amount of 0.1 to ≤50% by weight, based on the total weight of the solution. The aliphatic alcohol is preferably selected from the group consisting of ethanol, isopropanol, n-propanol. The glycol is preferably selected from the group consisting of glycerin, propylene glycol, butylene glycol or dipropylene glycol. Preferably, the overall water content in the final composition of such compositions can be ≥60%, more preferably ≥70%, even more preferably ≥80%, and even more preferably ≥90%. New applications such as those including solutions for water wipes have high water content. In a particular variant, the inventive compositions can be used for such wet wipe applications. They may then most preferably contain ≥95% water, or even ≥98% water.

Such aqueous or aqueous/alcoholic or aqueous/glycolic based solutions include for example deo/antiperspirant preparations, after shave, cleansing preparations, anti-acne preparations, or wet wipe solutions.

In one preferred variant, the cosmetic or pharmaceutical, preferably dermatological, composition according to the present invention is in the form of an emulsion as defined herein, advantageously in the form of an oil-in-water (O/W) emulsion comprising an oily phase dispersed in an aqueous phase in the presence of an O/W emulsifier.

In an alternative preferred variant, the cosmetic or pharmaceutical composition according to the present invention is in the form of an aqueous or aqueous/alcoholic, preferably aqueous/ethanolic, or aqueous/glycolic based solution. Typically, this could be glycerin in water compositions.

These cosmetic or pharmaceutical ready-to-use compositions or formulations are prepared according to usual and known methods.

Surprisingly, it turns out that the composition according to the first or second aspect of the present invention has a significant antioxidative capacity, has a superior ROS scavenging activity, has superior performance in suppressing interleukin 8 (IL-8) expression and/or in suppressing matrix metalloproteinases expression.

Surprisingly, it was found, as described in more detail in the following Example 1, oxidative degradation of a composition according to the present invention can considerably be reduced or minimized with an antioxidant in the presence of a 1,2-alkanediol, in particular 1,2-heptanediol, 1,2-octanediol, 1,2-nonanediol, or 1,2-decanediol. The same effect was achieved with a 2,3-alkanediol, in particular 2,3-octanediol. A superior antioxidative effect was achieved with a homo alkanediol mixture comprising a 1,2-alkanediol and a 2,3-alkanediols as defined herein. Advantageous antioxidative effects were also achieved with hetero alkanediol mixtures comprising a first linear alkanediol and a second linear alkanediol as defined herein.

This means that the composition is more stable against oxidative degradation. This comes along with a lower acid value, which is a measure of decomposition of triglycerides, and a less rancid odor. By contrast, 1,2-alkanediol alone do not show any antioxidant performance.

Moreover, the use of a 1,2-heptanediol and/or 2,3-heptanediol or a linear alkanediol or a mixture of a first linear alkanediol with a second linear alkanediol allows for the use of less antioxidant.

Surprisingly, it was found, as described in more detail in the following Example 3, the addition of 1,2-alkanediols, in particular 1,2-pentanediol, 1,2-hexanediol, 1,2-heptanediol, 1,2-octanediol, 1,2-nonanediol or 1,2-undecanediol to a composition according to the present invention including an antioxidant leads to an improved ROS scavenging effect, i.e., to a better ROS score. The same effect was achieved with 2,3-alkanediol, in particular 2,3-heptanediol, 2,3-octanediol or 2,3-undecanediol.

Surprisingly, with the synergistic combination of an antioxidant and 1,2-heptanediol or 2,3-heptanediol or a mixture comprising 1,2-heptanediol and 2,3-heptanediol or a linear alkanediol, preferably a 2,3-alkanediol, or a homo alkanediol mixture or a hetero alkanediol mixture comprising at least one first linear alkanediol and one or more second linear alkanediol as defined herein, the interleukin 8 (IL-8) expression can be significantly reduced as it is demonstrated by Example 5.

Surprisingly, with the synergistic combination of an antioxidant and 1,2-heptanediol or 2,3-heptanediol or a mixture comprising 1,2-heptanediol and 2,3-heptanediol or a linear alkanediol, preferably a 2,3-alkanediol, or a homo alkanediol mixture or a hetero alkanediol mixture comprising at lest one first linear alkanediol and one or more second linear alkanediol as defined herein, it is achieved that the matrix metalloproteinases expression is significantly suppressed.

Due to its beneficial antioxidative properties and its advantageously influence on ROS scavenging, interleukin 8 expression and/or matrix metalloproteinases expression, the present invention pertains in a further aspect to the cosmetic and/or non-therapeutic use of the composition according to the present invention for personal care, skin protection, skin care, scalp protection, scalp care, hair care, nail care, in particular for the prevention and/or treatment of skin conditions, intolerant or sensitive skin, skin irritation, skin reddening, wheals, pruritus (itching), skin aging, wrinkle formation, loss of skin volume, loss of skin elasticity, pigment spots, pigment abnormalities, skin dryness, flaking, greasiness, hypopigmentation and/or hyperpigmentation of the skin; or for animal care.

Advantageously, the cosmetic composition according to the present invention is used as anti-wrinkle or anti-aging formulation.

Examples of personal care are preferably anti-ageing preparations, skin care emulsions, body oils, body lotions, cleansing lotions, face or body balms, after shave balms, after sun balms, deo emulsions, cationic emulsions, body gels, treatment creams, skin protection ointments, moisturizing gels, face and/or body moisturizers, light protective preparations (sunscreens), micellar water, hair spray, colour protection hair care products, skin lightening product, anti-dark spot preparations, etc.

Alternatively, the composition according to the present invention is a preparation for medical use.

The pharmaceutical, in particular dermatological, composition according to the present invention is a preparation for the prevention and treatment of a condition of the skin or mucosa or of inflammatory diseases which come along with excess intracellular reactive oxygen species.

Preferably, the pharmaceutical composition according to the first or second aspect of the present invention is used in the prevention and/or treatment of dysfunctions of human hair, skin and/or nails, in particular dermatological or keratological diseases, wherein the dermatological or keratological diseases are selected from the group consisting of atopic dermatitis (neurodermitis), psoriasis, acneiform exanthema, sebostasis, xerosis, eczema, hyper seborrhea and hypo seborrhea, dermatitis, rosacea, wheals, erythema, pruritus (itching), inflammation, irritation, fibrosis, lichen planus, *pityriasis rosea, pityriasis versicolor*, autoimmune bullous diseases, urticaria, angioedema, allergic skin reactions, wound healing, tissue regeneration, or inflammatory diseases.

In order to be used, the cosmetic or pharmaceutical, in particular dermatological, composition according to the first or second aspect of the present invention is applied to the skin, hair, scalp and/or nails in an adequate amount in such manner as is customary with cosmetics and dermatological products.

Surprisingly, the use of 1,2-heptanediol or 2,3-heptanediol or a mixture comprising 1,2-heptanediol and 2,3-heptanediol or of at least one linear alkanediol, preferably a 2,3-alkanediol, or of a homo alkanediol mixture or a hetero alkanediol mixture comprising at least one first linear alkanediol and one or more second linear alkanediol as defined herein considerably improves the antioxidative performance of an antioxidant as described above.

Due to the improved antioxidant performance, with the use of 1,2-heptanediol or 2,3-heptanediol or a mixture comprising 1,2-heptanediol and 2,3-heptanediol or of at least one linear alkanediol, preferably 2,3-alkandeiol, or of a homo alkanediol mixture or a heteroalakanediol mixture comprising at least one first linear alkanediol and one or more second linear alkanediol in an antioxidant containing cosmetic or pharmaceutical, preferably dermatological, composition or homecare product, a higher antioxidative performance can be achieved with the same amounts of antioxidant or, vice versa, the same performance can be achieved with less amounts antioxidant.

In particular, the enhanced antioxidative effect has a beneficial effect on ROS scavenging performance of an antioxidant; and/or interleukin 8 (IL-8) secretion; and/or matrix metal proteinases expression.

Thus, the present invention relates in a final aspect to the use of 1,2-heptanediol or 2,3-heptanediol or a mixture comprising 1,2-heptanediol and 2,3-heptanediol or of at least one linear alkanediol, preferably a 2,3-alkanediol, or of a homo alkanediol mixture or a hetero alkane mixture comprising at least one first linear alkanediol and one or more second linear alkanediol
- for enhancing the antioxidative effect of an antioxidant in a cosmetic or pharmaceutical composition or homecare product; and/or
- for enhancing the antioxidative effect of an antioxidant upon application, for example on the skin; and/or
- for enhancing the ROS scavenging performance of an antioxidant; and/or
- for enhancing the inhibition of the interleukin 8 (IL-8) secretion by an antioxidant; and/or
- for enhancing the inhibition of the matrix metal proteinases expression by an antioxidant.

The present invention shall now be described in detail with reference to the following examples, which are merely illustrative of the present invention, such that the content of the present invention is not limited by or to the following examples.

EXAMPLES

To evaluate the influence of 1,2-alkanediols or of 2,3-alkanediols on the antioxidative capacity of antioxidants, two different tests were performed:
(1) Oxipres treatment to simulate product protection; and
(2) Evaluation of reactive oxygen species (ROS) for skin protection.

The following tests were performed with sunflower oil +/− antioxidant and +/− alkanediols. Sunflower oil was used because it is primarily composed of less stable polyunsaturated and monounsaturated fatty acids. Treating it with heat and oxygen triggers and accelerates oxidation easily.

Example 1: Oxipres Test to Simulate Product Protection

An Oxipres test was performed in order to evaluate the antioxidative capacity of different test samples as described below.
Test samples:
Sample 1: Sunflower oil without additives
Sample 2: Sunflower oil plus 0.1% tocopherol
Sample 3: Sunflower oil plus 0.1% tocopherol plus 0.5% 1,2-heptanediol
Sample 4: Sunflower oil plus 0.1% tocopherol plus 0.5% of an alkanediol blend of 95% 1,2-heptanediol plus 0.5% 2,3 heptanediol
Sample 5: Sunflower oil plus 0.5% 1,2-heptanediol
Sample 6: Sunflower oil plus 0.5% 2,3-heptanediol
Sample 7: Sunflower oil plus 0.5% 1,2-nonanediol
Sample 8: Sunflower oil plus 0.1% tocopherol plus 0.5% 1,2-nonanediol
Sample 9: Sunflower oil plus 0.1% 1,2-decanediol
Sample 10: Sunflower oil plus 0.1% tocopherol plus 0.1% 1,2-decanediol
Sample 11: Sunflower oil plus 0.5% 2,3-octanediol
Sample 12: Sunflower oil plus 0.1% tocopherol plus 0.5% 2,3-octanediol
Sample 13: Sunflower oil without additives
Sample 14: Sunflower oil plus 0.1% tocopherol
Sample 15: Sunflower oil plus 0.1% tocopherol plus 0.5% 1,2-heptanediol
Sample 16: Sunflower oil plus 0.1% tocopherol plus 0.5% 2,3-heptanediol
Sample 17: Sunflower oil plus 0.1% tocopherol plus 0.5% blend of 1,2-heptanediol and 2,3-heptanediol; ratio 98:2
Sample 18: Sunflower oil plus 0.1% tocopherol plus 0.5% blend of 1,2-heptanediol and 2,3-heptanediol; ratio 99:1
Sample 19: Sunflower oil without additives
Sample 20: Sunflower oil plus 0.1% tocopherol
Sample 21: Sunflower oil plus 0.1% tocopherol plus 0.5% 1,2-hexanediol
Sample 22: Sunflower oil plus 0.1% tocopherol plus 0.5% 2,3-hexanediol
Sample 23: Sunflower oil plus 0.1% tocopherol plus 0.5% blend of 1,2-hexanediol and 2,3-hexanediol; ratio 95:5
Sample 24: Sunflower oil plus 0.1% tocopherol plus 0.5% blend of 1,2-hexanediol and 2,3-hexanediol; ratio 50:50
Sample 25: Sunflower oil plus 0.1% tocopherol plus 0.5% 1,2-octanediol
Sample 26: Sunflower oil plus 0.1% tocopherol plus 0.5% 2,3-octanediol
Sample 27: Sunflower oil plus 0.1% tocopherol plus 0.5% blend of 1,2-octanediol and 2,3-octanediol; ratio 50:50
Sample 28: Sunflower oil plus 0.1% tocopherol plus 0.5% 1,2-decanediol
Sample 29: Sunflower oil plus 0.1% tocopherol plus 0.5% 2,3-decanediol
Sample 30: Sunflower oil plus 0.1% tocopherol plus 0.5% blend of 1,2-decanediol and 2,3-decanediol; ratio 95:5
Sample 31: Sunflower oil plus 0.1% tocopherol plus 0.5% blend of 1,2-decanediol and 2,3-decanediol; ratio 50:50
Sample 32: Sunflower oil without additives
Sample 33: Sunflower oil plus 0.1% tocopherol
Sample 34: Sunflower oil plus 0.1% tocopherol plus 0.5% 1,2-heptanediol
Sample 35: Sunflower oil plus 0.1% tocopherol plus 0.5% 2,3-hexanediol
Sample 36: Sunflower oil plus 0.1% tocopherol plus 0.5% blend of 1,2-heptanediol and 2,3-hexanediol; ratio 50:50
Sample 37: Sunflower oil plus 0.1% tocopherol plus 0.5% 2,3-octanediol
Sample 38: Sunflower oil plus 0.1% tocopherol plus 0.5% blend of 1,2-heptanediol and 2,3-octanediol; ratio 95:5
Sample 39: Sunflower oil without additives
Sample 40: Sunflower oil plus 0.1% tocopherol
Sample 41: Sunflower oil plus 0.1% tocopherol plus 0.5% 1,2-nonanediol
Sample 42: Sunflower oil plus 0.1% tocopherol plus 0.5% 2,3-nonanediol
Sample 43: Sunflower oil plus 0.1% tocopherol plus 0.5% blend of 1,2-nonanediol and 2,3-nonanediol; ratio 50:50
Sample 44: Sunflower oil without additives
Sample 45: Sunflower oil plus 2.0% Symdecanox HA*
*INCI Symdecanox HA:

Sample 46: Sunflower oil plus 2.0% Symdecanox HA plus 0.5% 1,2-heptanediol
Sample 47: Sunflower oil plus 2.0% Symdecanox HA plus 0.5% 1,2-heptanediol
Sample 48: Sunflower oil plus 2.0% Symdecanox HA plus 0.5% blend of 1,2-heptanediol and 2,3-heptanediol; ratio 95:5
Sample 49: Sunflower oil plus 2.0% Symdecanox HA plus 0.5% 1,2-octanediol
Sample 50: Sunflower oil plus 2.0% Symdecanox HA plus 0.5% 2,3-octanediol
Sample 51: Sunflower oil plus 2.0% Symdecanox HA plus 0.5% blend of 1,2-octanediol and 2,3-octanediol; ratio 95:5
Sample 52: Sunflower oil without additives
Sample 53: Sunflower oil plus 0.1% Pentaerythrityl Tetra-di-t-butyl Hydroxyhydrocinnamate (Tinogard Sample TT)
Sample 54: Sunflower oil plus 0.1% Pentaerythrityl Tetra-di-t-butyl Hydroxyhydrocinnamate (Tinogard TT) plus 0.5% 1,2-heptandiol
Sample 55: Sunflower oil plus 0.1% Pentaerythrityl Tetra-di-t-butyl Hydroxyhydrocinnamate (Tinogard TT) plus 0.5% 2,3-heptanediol
Sample 56: Sunflower oil plus 0.1% Pentaerythrityl Tetra-di-t-butyl Hydroxyhydrocinnamate (Tinogard TT) plus 0.5% blend of 1,2-octanediol and 2,3-octanediol; ratio 95:5
Sample 57: Sunflower oil without additives
Sample 58: Sunflower oil plus 0.5% Hydroxyacetophenone
Sample 59: Sunflower oil plus 0.5% Hydroxyacetophenone plus 0.5% 1,2-heptanediol
Sample 60: Sunflower oil plus 0.5% Hydroxyacetophenone plus 0.5% 2,3-heptanediol
Sample 61: Sunflower oil without additives
Sample 62: Sunflower oil plus 0.05% Ascorbyl Palmitate
Sample 63: Sunflower oil plus 0.05% Ascorbyl Palmitate plus 0.5% 1,2-heptanediol
Sample 64: Sunflower oil plus 0.05% Ascorbyl Palmitate plus 0.5% 2,3-heptanediol
Caprylic Capric Triglyceride, Hydroxymethoxyphenyl Decanonenone Test procedure: For the evaluation of the antioxidative capacity of the above-described samples, an Oxipres test was conducted. The Oxipres method is bases on oxygen consumption at high temperatures and pressures and allows the determination of oxidative resistance (shelf life) of e.g. oils. The test runs under elevated pressure and temperature, where the process is accelerated. In the Oxipres test the sample is placed inside a hermetically closed iron vessel that is subjected to high oxygen pressures and temperatures of 90 to 120° C. The above-described samples were treated in Oxipres device for 48 hours at 80° C. and 5 bar pressure and determination of induction period. The consumption of oxygen results in a pressure drop in the vessel during the test. Higher decrease of pressure indicates more consumption of oxygen and higher oxidation of the test product. Oils with a high degree of unsaturation are most susceptible to autoxidation.

The induction period is the period during which a fat or oil shows stability against oxidation because of its content of antioxidants, either naturally or added. In the test, the antioxidants are oxidized preferentially before the oxidizable fat or oil is oxidized. Thus, the antioxidants protect the fat or oil against oxidation. After this there is a sudden and large consumption of oxygen and the fat becomes rancid. This can be defined by the induction period (IP) in hours. A lower IP correlates with a faster oxidation.

Equipment: The tests were performed with an Oxipres device ex Mikrolab. The instrument is a modification of the bomb method (ASTM D941), which is based on oxidation with oxygen.

Before and after Oxipres treatment additionally an odor evaluation of the samples was performed and the acid value of the samples before and after Oxipres treatment was determined. The principle of acid value determination: Neutralization of the free acids by titration with ethanolic or aqueous solution of potassium hydroxide. It shows the number of milligram (mg) KOH required in order to neutralize the free acids in 1 g test substance. The titration according to the IFU respectively § 64 LFGB (formerly § 35 LMBG) is carried out potentiometrically with potassium hydroxide solution to a pH value of 8.1.

The following Table 1 gives an overview of the samples, the antioxidants, the alkanediols and the resulting induction period (IP) value.

TABLE 1

Overview Antioxidants, alkanediol and Induction Period (IP)

| Sample No. | Antioxidant | Alkanediol | IP |
|---|---|---|---|
| 1 | No | no | 22.6 |
| 2 | 0.1% tocopherol | no | 29.5 |
| 3 | 0.1% tocopherol | 0.5% 1,2-heptanediol | 31.2 |
| 4 | 0.1% tocopherol | 0.5% (blend of 1,2-heptanediol and 2,3-heptanediol; ratio 95:5) | 31.7 |
| 5 | No | 0.5% 1,2-heptanediol | 23.6 |
| 6 | No | 0.5% 2,3-heptanediol | 24.3 |
| 7 | No | 0.5% 1,2-nonanediol | 22.7 |
| 8 | 0.1% tocopherol | 0.5% 1,2-nonanediol | 32.4 |
| 9 | No | 0.5% 1,2-decanediol | 25 |
| 10 | 0.1% tocopherol | 0.1% 1,2-decanediol | 30 |
| 11 | No | 0.5% 2,3-decanediol | 19.8 |
| 12 | 0.1% tocopherol | 0.5% 2,3-octanediol | 32.3 |
| 13 | no | no | 25.4 |
| 14 | 0.1% tocopherol | no | 31.6 |
| 15 | 0.1% tocopherol | 0.5% 1,2-heptanediol | 31.0 |
| 16 | 0.1% tocopherol | 0.5% 2,3-heptanediol | 30.9 |
| 17 | 0.1% tocopherol | 0.5% (blend of 1,2-heptanediol and 2,3-heptanediol; ratio 98:2) | 32.0 |
| 18 | 0.1% tocopherol | 0.5% (blend of 1,2-heptanediol and 2,3-heptanediol; ratio 99:1) | 32.0 |
| 19 | no | no | 24.5 |
| 20 | 0.1% tocopherol | no | 31.2 |
| 21 | 0.1% tocopherol | 0.5% 1,2-hexanediol | 30.3 |
| 22 | 0.1% tocopherol | 0.5% 2,3-hexanediol | 31.6 |
| 23 | 0,1% tocopherol | 0.5% (blend of 1,2-hexanediol and 2,3-hexanediol; ratio 95:5) | 31.2 |
| 24 | 0.1% tocopherol | 0.5% (blend of 1,2-hexanediol and 2,3-hexanediol; ratio 50:50) | 32.8 |
| 25 | 0.1% tocopherol | 0.5% 1,2-octanediol | 32.2 |
| 26 | 0.1% tocopherol | 0.5% 2,3-octanediol | 31.7 |
| 27 | 0.1% tocopherol | 0.5% (blend of 1,2-octanediol and 2,3-octanediol; ratio 50:50) | 32.9 |
| 28 | 0.1% tocopherol | 0.5% 1,2-decanediol | 31.7 |
| 29 | 0.1% tocopherol | 0.5% 2,3-decanediol | 31.8 |
| 30 | 0.1% tocopherol | 0.5% (blend of 1,2-decanediol and 2,3-decanediol; ratio 95:5) | 31.9 |
| 31 | 0.1% tocopherol | 0.5% (blend of 1,2-decanediol and 2,3-decanediol; ratio 50:50) | 32.4 |
| 32 | no | no | 25.9 |
| 33 | 0.1% tocopherol | no | 31.6 |
| 34 | 0.1% tocopherol | 0.5% 1,2-heptanediol | 32.3 |
| 35 | 0.1% tocopherol | 0.5% 2,3-hexanediol | 32.9 |
| 36 | 0.1% tocopherol | 0.5% (blend of 1,2-heptanediol and 2,3-hexanediol; ratio 50:50) | 33.2 |
| 37 | 0.1% tocopherol | 0.5% 2,3-octanediol | 31.2 |
| 38 | 0.1% tocopherol | 0.5% (blend of 1,2-heptanediol and 2,3-octanediol; ratio 95:5) | 32.2 |
| 39 | no | no | 16.2 |

TABLE 1-continued

Overview Antioxidants, alkanediol and Induction Period (IP)

| Sample No. | Antioxidant | Alkanediol | IP |
|---|---|---|---|
| 40 | 0.1% tocopherol | no | 23.5 |
| 41 | 0.1% tocopherol | 0.5% 1,2-nonanediol | 24.1 |
| 42 | 0.1% tocopherol | 0.5% 2,3-nonanediol | 25.4 |
| 43 | 0.1% tocopherol | 0.5% (blend of 1,2-nonanediol and 2,3-nonanediol; ratio 50:50) | 25.7 |
| 44 | no | no | 23.1 |
| 45 | 2% Symdecanox HA | no | 24.4 |
| 46 | 2% Symdecanox HA | 0.5% 1,2-heptanediol | 24.4 |
| 47 | 2% Symdecanox HA | 0.5% 1,2-heptanediol | 24.7 |
| 48 | 2% Symdecanox HA | 0.5% (blend of 1,2-heptanediol and 2,3-heptanediol; ratio 95:5) | 25.3 |
| 49 | 2% Symdecanox HA | 0.5% 1,2-octanediol | 23.9 |
| 50 | 2% Symdecanox HA | 0.5% 2,3-octanediol | 24.0 |
| 51 | 2% Symdecanox HA | 0.5% (blend of 1,2-octanediol and 2,3-octanediol; ratio 95:5) | 25.1 |
| 52 | no | no | 21.9 |
| 53 | 0.01% Pentaerythrityl Tetra-di-t-butyl Hydroxyhydrocinnamate (Tinogard TT) | no | 25.8 |
| 54 | 0.01% Pentaerythrityl Tetra-di-t-butyl Hydroxyhydrocinnamate (Tinogard TT) | 0.5% 1,2-heptandiol | 27.7 |
| 55 | 0.01% Pentaerythrityl Tetra-di-t-butyl Hydroxyhydrocinnamate (Tinogard TT) | 0.5%2,3-heptanediol | 27.6 |
| 56 | 0.01% Pentaerythrityl Tetra-di-t-butyl Hydroxyhydrocinnamate (Tinogard TT) | 0.5% (blend of 1,2-octanediol and 2,3-octanediol; ratio 95:5) | 28.1 |
| 57 | no | no | 22.9 |
| 58 | 0.5% Hydroxyacetophenone | no | 23.2 |
| 59 | 0.5 % Hydroxyacetophenone | 0.5% 1,2-heptanediol | 24.4 |
| 60 | 0.5 % Hydroxyacetophenone | 0.5% 2,3-heptanediol | 24.3 |
| 61 | no | no | 23.5 |
| 62 | 0.05% Ascorbyl Palmitate | no | 25.5 |
| 63 | 0.05% Ascorbyl Palmitate | 0.5% 1,2-heptanediol | 26.7 |
| 64 | 0.05% Ascorbyl Palmitate | 0.5% 2,3-heptanediol | 26.6 |

TABLE 2

Results of induction period (IP) and acid value after Oxipres treatment (for samples 1 to 12)

| Sample No. | Induction period (h) | Acid value (mg KOH/g) start | Acid value (mg KOH/g) after treatment |
|---|---|---|---|
| 1 | 22.6 | 0.2 | 8.5 |
| 2 | 29.5 | 0.2 | 6.1 |
| 3 | 31.2 | 0.1 | 5.1 |
| 4 | 31.7 | 0.1 | 5.2 |
| 5 | 23.6 | 0.2 | 8.2 |
| 6 | 24.3 | 0.1 | 8.7 |
| 7 | 22.7 | 0 | 7.5 |
| 8 | 32.4 | 0 | 5.6 |
| 9 | 25.0 | 0 | 8.6 |
| 10 | 30.0 | 0 | 6.6 |
| 11 | 19.8 | 0 | 8.0 |
| 12 | 32.3 | 0 | 3.9 |

The results in Table 1 clearly show that sample 3 (sunflower oil plus 0.1% tocopherol plus 0.5% 1,2-heptanediol), sample 4 (sunflower oil plus 0.1% tocopherol plus 0.5% of an alkanediol blend of 95% 1,2-heptanediol and 0.5% 2,3 heptanediol), sample 8 (sunflower oil plus 0.1% tocopherol plus 0.5% 1,2-nonanediol), sample 10 (sunflower oil plus 0.1% tocopherol plus 0.1% 1,2-decanediol) and sample 12 (sunflower oil plus 0.1% tocopherol plus 0.5% 2,3-octanediol), i.e., samples containing an antioxidant in combination with an 1,2-alkanediol and/or an 2,3-alkanediol or a mixture thereof have prolonged induction periods (indicating longer shelf life). This means that the samples are more stable against oxidative degradation than the comparative samples. The samples with 1,2-alkanediol or 2,3-alkanediol alone have no antioxidative effect.

The above advantageous results are confirmed by a lower acid value. The acid value is defined as the number of milligrams of potassium hydroxide required to neutralize the free fatty acids present in one gram of fat. It is a relative measure of rancidity as free fatty acids are normally formed during decomposition of triglycerides. Hence, the acid value correlates with the rancidity degree in an oil. In comparison, comparative sample 1 (sunflower oil without antioxidant or alkanediol, comparative sample 2 (sunflower oil with tocopherol) and comparative samples 5 and 6 (sunflower oil with alkanediols without tocopherol) had a shorter induction period (IP) (indicating shorter shelf life), which means that oxidation degradation starts earlier in comparison to the samples containing an antioxidant plus an alkanediol. The comparative samples showed also higher acid vales.

In addition, for the above samples delta values of IP points were calculated versus the corresponding IP points of sunflower oil without additives as indicated in Table 1. The results of the ROS tests are summarized in the following tables:

TABLE 3

| Sample No. | Heptanediol | IP value (h) | delta IP versus sunflower oil without additive |
|---|---|---|---|
| 1 | sunflower oil without additive | 22.6 | |
| 2 | plus 0.1% tocopherol | 29.5 | 6.9 |
| 3 | plus 0.1% tocopherol + 0.5% 1,2-heptanediol | 31.2 | 8.6 |
| 4 | plus 0.1% tocopherol plus 0.5% blend of 1,2-heptanediol and 2,3-heptanediol (ratio 95:5) | 31.7 | 9.1 |

Figure 13:
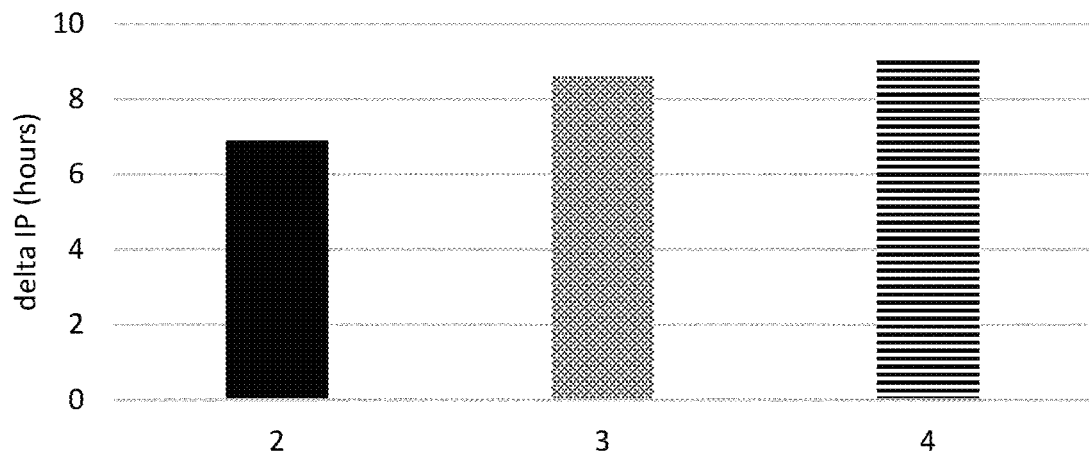
FIG. 13 is a diagram showing the delta IP values of tocopherol, tocopherol and 1,2-heptanediol and tocopherol and a blend of 1,2-heptanediol and 2,3-heptanediol (95:5).

The results are shown in FIG. 13. As can be seen from FIG. 13, both sample 3 and sample 4 have prolonged induction periods (indicating longer shelf life). This means that these samples are more stable against oxidative degradation than the comparative samples.

TABLE 4

| Sample No. | Heptanediol | IP value (h) | delta IP vs sunflower oil wo additive |
|---|---|---|---|
| 13 | sunflower oil without additive | 25.4 | |
| 14 | plus 0.1% tocopherol | 31.6 | 6.2 |
| 15 | plus 0.1% tocopherol plus 0.5% 1,2-heptanediol | 31 | 5.6 |
| 16 | plus 0.1% tocopherol plus 0.5% 2,3-heptanediol | 30.9 | 5.5 |
| 17 | plus 0.1% tocopherol plus 0.5% blend of 1,2- and 2,3-heptanediol (ratio 98:2) | 32 | 6.6 |

Figure 14:
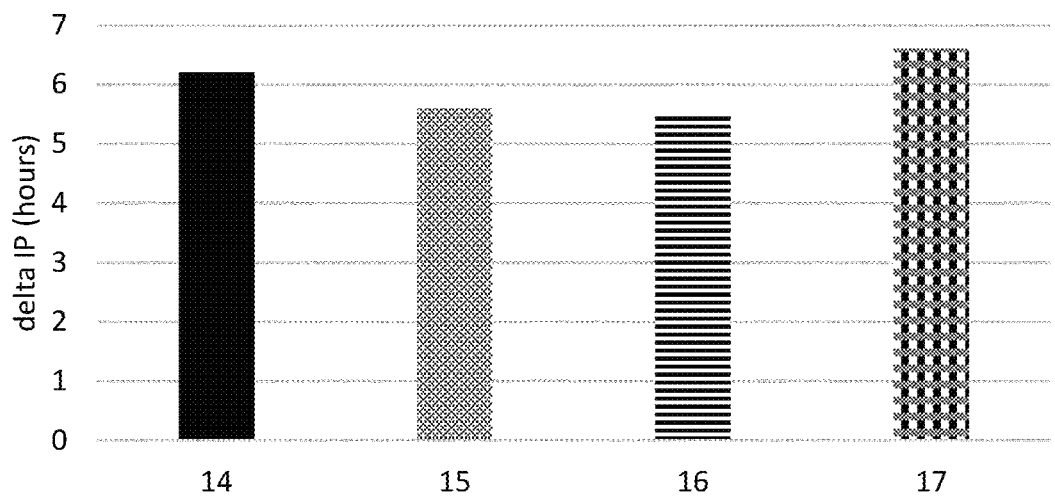
FIG. 14 is a diagram showing the delta IP values of tocopherol and 1,2-heptanediol, tocopherol and 2,3-heptanediol and tocopherol and a blend of 1,2-heptanediol and 2,3-heptanediol (98:2).

The results are shown in FIG. 14. As can be seen from FIG. 14, a blend of 1,2-heptanediol and 2,3-heptanediol (98:2) results in prolonged induction periods (indicating longer shelf life). This means that the sample is more stable against oxidative degradation than the comparative samples.

TABLE 5

| Sample No. | Heptanediol | IP value (h) | delta IP versus sunflower oil without additive |
|---|---|---|---|
| 13 | sunflower oil without additive | 25.4 | |
| 14 | plus 0.1% tocopherol | 31.6 | 6.2 |
| 15 | plus 0.1% tocopherol plus 0.5% 1,2-heptanediol | 31 | 5.6 |
| 16 | plus 0.1% tocopherol plus 0.5% 2,3-heptanediol | 30.9 | 5.5 |
| 18 | plus 0.1% tocopherol plus 0.5% blend of 1,2- and 2,3-heptanediol (ratio 99:1) | 32 | 6.6 |

Figure 15:
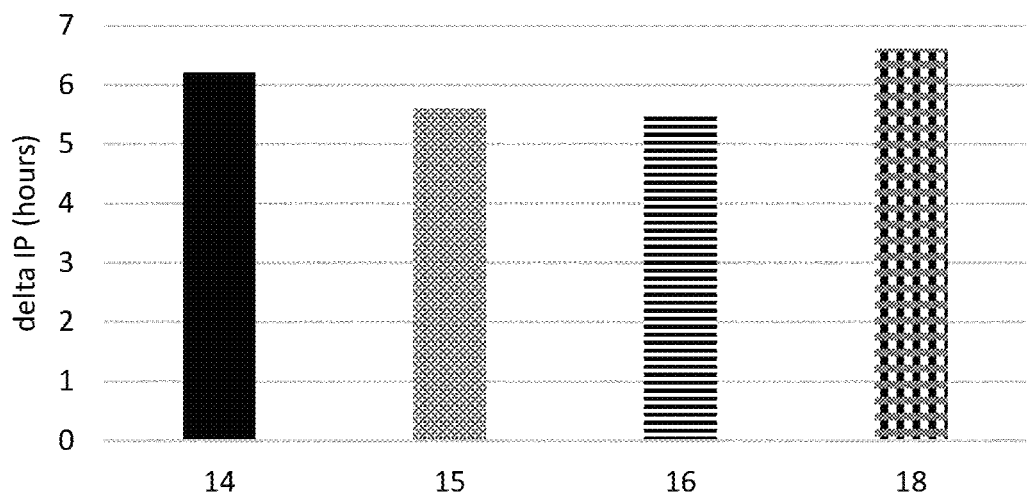
FIG. 15 is a diagram showing the delta IP values of tocopherol and 1,2-heptanediol, tocopherol and 2,3-heptanediol and tocopherol and a blend of 1,2-heptanediol and 2,3-heptanediol (99:1).

The results are shown in FIG. 15. As can be seen from FIG. 15, a blend of 1,2-heptanediol and 2,3-heptanediol (99:1) results in prolonged induction periods (indicating longer shelf life). This means that the sample is more stable against oxidative degradation than the comparative samples.

TABLE 6

| Sample No. | Hexanediol | IP value (h) | delta IP versus sunflower oil without additive |
|---|---|---|---|
| 19 | sunflower oil without additive | 24.5 | |
| 20 | plus 0.1% tocopherol | 31.2 | 6.7 |
| 21 | plus 0.1% tocopherol plus 0.5% 1,2-hexanediol | 30.3 | 5.8 |
| 22 | plus 0.1% tocopherol plus 0.5% 2,3-hexanediol | 31.6 | 7.1 |
| 23 | plus 0.1% tocopherol plus 0.5% blend of 1,2- and 2,3-hexanediol (ratio 95:5) | 31.2 | 6.7 |

Figure 16:
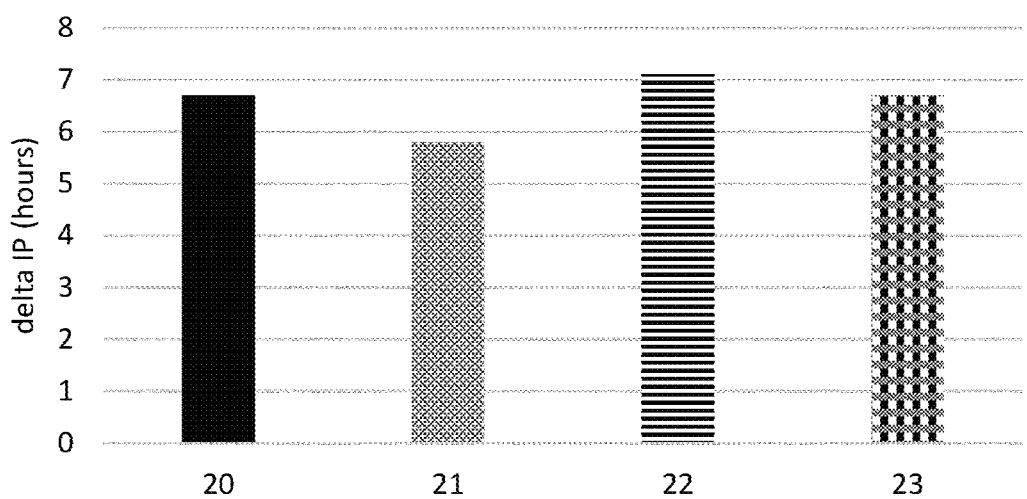
FIG. 16 is a diagram showing the delta IP values of tocopherol and 1,2-hexanediol, tocopherol and 2,3-hexanediol and tocopherol and a blend of 1,2-hexanediol and 2,3-hexanediol (95:5).

The results are shown in FIG. 16. As can be seen from FIG. 16, 2,3-hexanediol results in prolonged induction periods (indicating longer shelf life). This means that the sample is more stable against oxidative degradation than the comparative sample.

TABLE 7

| Sample No. | Hexanediol | IP value (h) | delta IP versus sunflower oil without additive |
|---|---|---|---|
| 19 | sunflower oil without additive | 24.5 | |
| 20 | plus 0.1% tocopherol | 31.2 | 6.7 |
| 21 | plus 0.1% tocopherol plus 0.5% 1,2-hexanediol | 30.3 | 5.8 |
| 22 | plus 0.1% tocopherol plus 0.5% 2,3-hexanediol | 31.6 | 7.1 |
| 24 | plus 0.1% tocopherol plus 0.5% blend of 1,2- and 2,3-hexanediol (ratio 50:50) | 32.8 | 8.3 |

Figure 17:
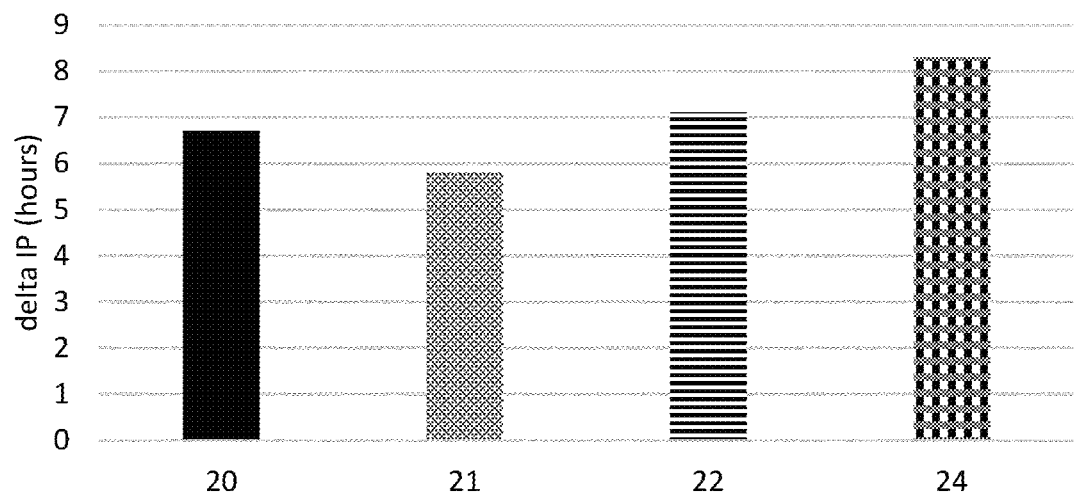
FIG. 17 is a diagram showing the delta IP values of tocopherol and 1,2-hexanediol, tocopherol and 2,3-hexanediol and tocopherol and a blend of 1,2-hexanediol and 2,3-hexanediol (50:50).

The results are shown in FIG. 17. As can be seen from FIG. 17, both sample 22 and sample 24 results in prolonged induction periods (indicating longer shelf life). This means that the sample is more stable against oxidative degradation than the comparative samples.

TABLE 8

| Sample No. | Octanediol | IP value (h) | delta IP versus sunflower oil without additive |
|---|---|---|---|
| 19 | sunflower oil without additive | 24.5 | |
| 20 | plus 0.1% tocopherol | 31.2 | 6.7 |
| 25 | plus 0.1% tocopherol plus 0.5% 1,2-octanediol | 32.2 | 7.7 |
| 26 | plus 0.1% tocopherol plus 0.5% 2,3-octanediol | 31.7 | 7.2 |
| 27 | plus 0.1% tocopherol plus 0.5% blend of 1,2-octanediol and 2,3-octanediol (ratio 50:50) | 32.9 | 8.4 |

Figure 18:
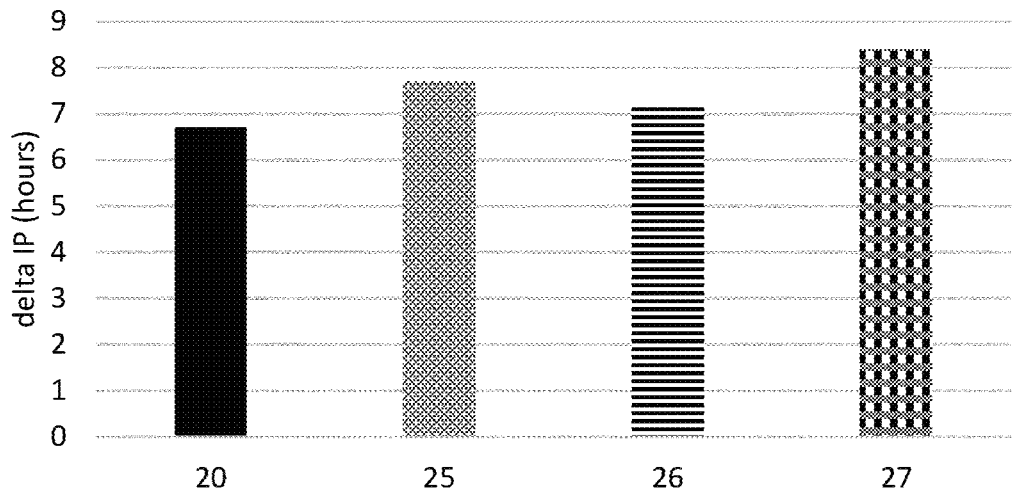
FIG. 18 is a diagram showing the delta IP values of tocopherol and 1,2-octanediol, tocopherol and 2,3-octanediol and tocopherol and a blend of 1,2-octanediol and 2,3-octanediol (50:50).

The results are shown in FIG. 18. As can be seen from FIG. 18, a blend of 1,2-octanediol and 2,3-octanediol (50:50) results in prolonged induction periods (indicating longer shelf life). This means that the sample is more stable against oxidative degradation than the comparative samples.

TABLE 9

| Sample No. | Decanediol | IP value (h) | delta IP versus sunflower oil without additive |
|---|---|---|---|
| 19 | sunflower oil without additive | 24.5 | |
| 20 | plus 0.1% tocopherol | 31.2 | 6.7 |
| 28 | plus 0.1% tocopherol plus 0.5% 1,2-decanediol | 31.7 | 7.2 |
| 29 | plus 0.1% tocopherol plus 0.5% 2,3-decanediol | 31.8 | 7.3 |
| 30 | plus 0.1% tocopherol plus 0.5% blend of 1,2-decanediol and 2,3-decanediol (ratio 95:5) | 31.9 | 7.4 |

Figure 19:
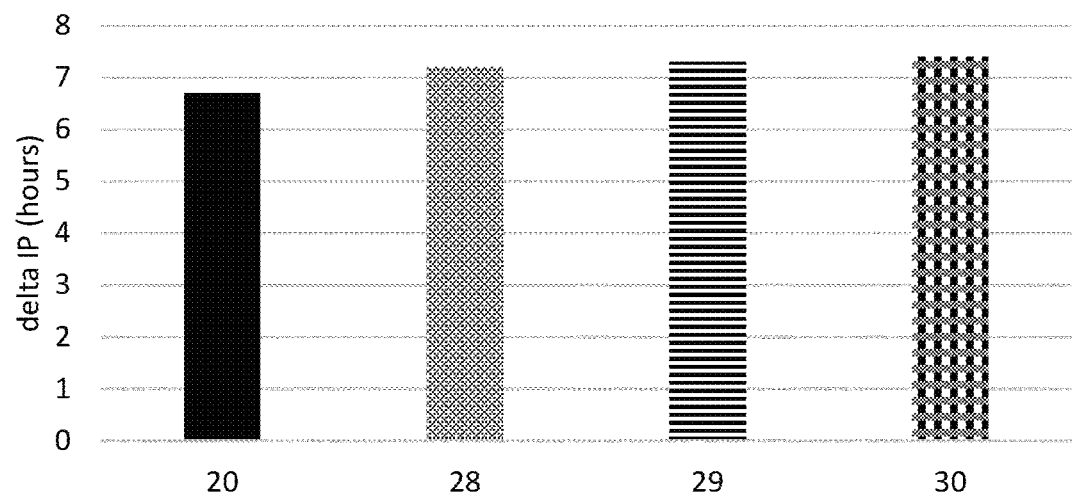
FIG. 19 is a diagram showing the delta IP values of tocopherol and 1,2-decanediol, tocopherol and 2,3-decanediol and tocopherol and a blend of 1,2-decanediol and 2,3-decanediol (95:5).

The results are shown in FIG. 19. As can be seen from FIG. 19, a blend of 1,2-decanediol and 2,3-decanediol (95:5) results in prolonged induction periods (indicating longer shelf life). This means that the sample is more stable against oxidative degradation than the comparative samples.

TABLE 10

| Sample No. | Decanediol | IP value (h) | delta IP versus sunflower oil without additive |
|---|---|---|---|
| 19 | sunflower oil without additive | 24.5 | |
| 20 | plus 0.1% tocopherol | 31.2 | 6.7 |
| 28 | plus 0.1% tocopherol plus 0.5% 1,2-decanediol | 31.7 | 7.2 |
| 29 | plus 0.1% tocopherol plus 0.5% 2,3-decanediol | 31.8 | 7.3 |
| 31 | plus 0.1% tocopherol plus 0.5% blend of 1,2-decanediol and 2,3-decanediol (ratio 50:50) | 32.4 | 7.9 |

Figure 20:
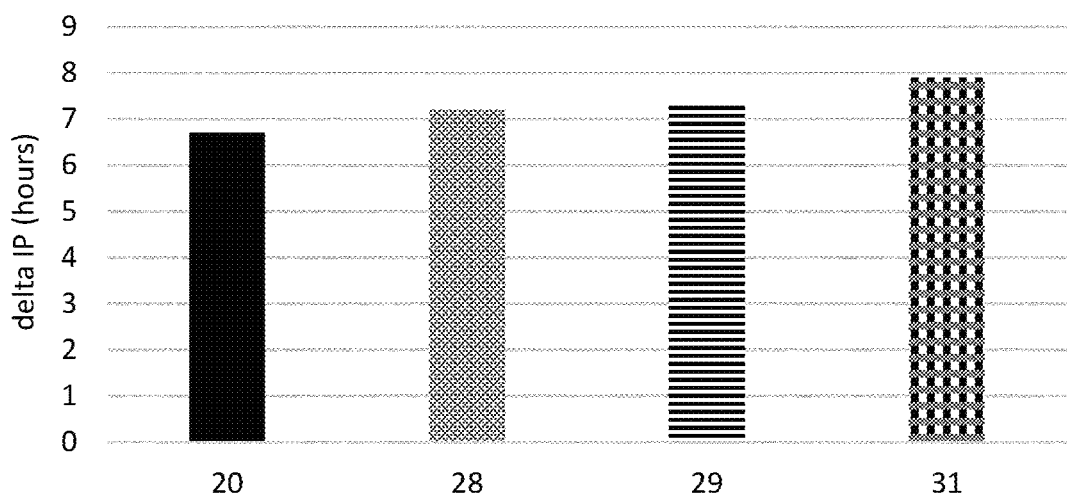
FIG. 20 is a diagram showing the delta IP values of tocopherol and 1,2-decanediol, tocopherol and 2,3-decanediol and tocopherol and a blend of 1,2-decanediol and 2,3-decanediol (50:50).

The results are shown in FIG. 20. As can be seen from FIG. 20, a blend of 1,2-decanediol and 2,3-decanediol (50:50) results in prolonged induction periods (indicating longer shelf life). This means that the sample is more stable against oxidative degradation than the comparative samples. The induction period is even higher compared to a blend of 1,2-decanediol and 2,3-decanediol (95:5).

TABLE 11

| Sample No. | Heptanediol/Hexanediol | IP value (h) | delta IP versus sunflower oil without additive |
|---|---|---|---|
| 32 | sunflower oil without additive | 25.9 | |
| 33 | plus 0.1% tocopherol | 31.6 | 5.7 |
| 34 | plus 0.1% tocopherol + 0.5% 1,2-heptanediol | 32.3 | 6.9 |
| 35 | plus 0.1% tocopherol plus 0.5% 2,3-hexanediol | 32.9 | 7.5 |
| 36 | plus 0.1% tocopherol plus 0.5% blend of 1,2-heptanediol and 2,3-hexanediol (ratio 50:50) | 33.2 | 7.8 |

Figure 21:
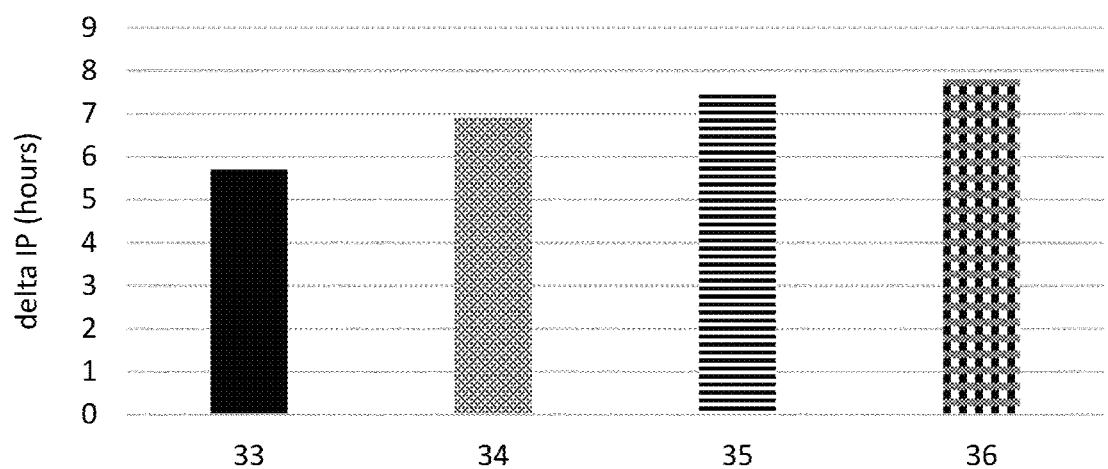
FIG. 21 is a diagram showing the delta IP values of tocopherol and 1,2-heptanediol, tocopherol and 2,3-hexanediol and tocopherol and a blend of 1,2-heptanediol and 2,3-hexanediol (50:50).

The results are shown in FIG. 21. As can be seen from FIG. 21, a blend of 1,2-heptanediol and 2,3-hexanediol (50:50) results in prolonged induction periods (indicating longer shelf life). This means that the sample is more stable against oxidative degradation than the comparative samples.

TABLE 12

| Sample No. | Heptanediol/Octanediol | IP value (h) | delta IP versus sunflower oil without additive |
|---|---|---|---|
| 32 | sunflower oil without additive | 25.9 | |
| 33 | plus 0.1% tocopherol | 31.2 | 5.3 |
| 34 | plus 0.1% tocopherol plus 0.5% 1,2-heptanediol | 32.3 | 6.4 |
| 37 | plus 0.1% tocopherol plus 0.5% 2,3-octanediol | 31.2 | 5.3 |
| 38 | plus 0.1% tocopherol plus 0.5% blend of 1,2-heptanediol and 2,3-octanediol (ratio 95:5) | 32.2 | 6.3 |

Figure 22:
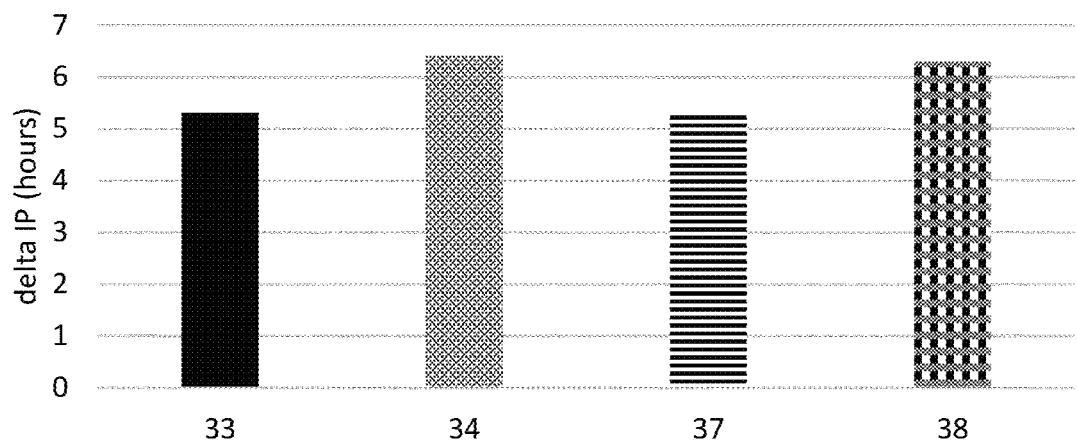
FIG. 22 is a diagram showing the delta IP values of tocopherol and 1,2-heptanediol, tocopherol and 2,3-octanediol and tocopherol and a blend of 1,2-heptanediol and 2,3-otanediol (95:5).

The results are shown in FIG. 22. As can be seen from FIG. 22, a slightly improvement of he ROS score was obtained with a blend of 1,2-heptanediol asn 2,3-octanediol in a ratio of 95:5.

TABLE 13

| Sample No. | Nonanediol | IP value (h) | delta IP versus sunflower oil without additive |
|---|---|---|---|
| 39 | sunflower oil without additive | 16.2 | |
| 40 | plus 0.1% tocopherol | 23.5 | 7.3 |
| 41 | plus 0.1% tocopherol + 0.5% 1,2-nonanediol | 24.1 | 7.9 |
| 42 | plus 0.1% tocopherol + 0.5% 2,3-nonanediol | 25.4 | 9.2 |
| 43 | plus 0.1% tocopherol plus 0.5% blend of 1,2-nonanediol and 2,3-nonanediol (ratio 50:50) | 25.7 | 9.5 |

Figure 23:
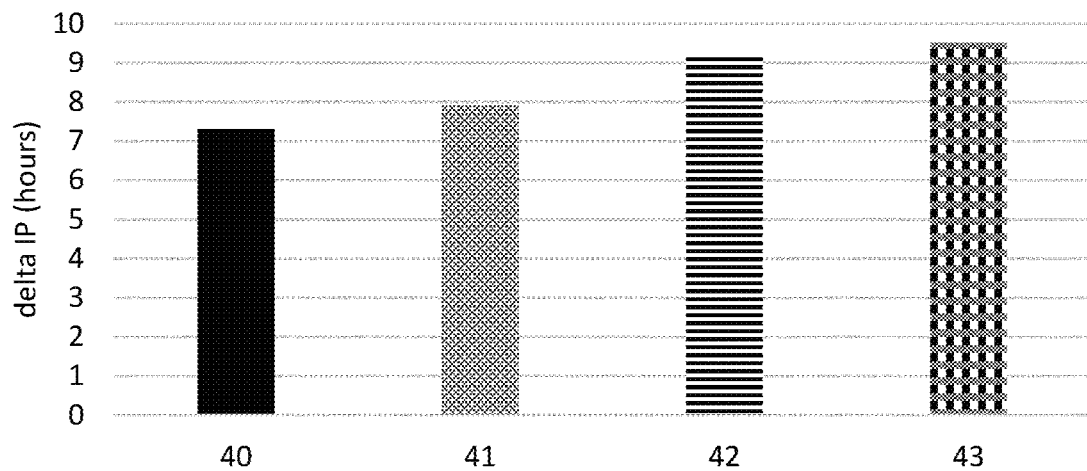
FIG. 23 is a diagram showing the delta IP values of tocopherol and 1,2-nonanediol, tocopherol and 2,3-nonanediol and tocopherol and a blend of 1,2-nonanediol and 2,3-nonanediol (50:50).

The results are shown in FIG. 23. As can be seen from FIG. 23, sample 41 and sample results in prolonged induction periods (indicating longer shelf life). However, a blend of 1,2-nonanediol and 2,3-nonanediol considerably prolonged the induction period. This means that the samples are more stable against oxidative degradation than the comparative samples.

TABLE 14

| Sample No. | Heptanediol | IP value (h) | delta IP versus sunflower oil without additive |
|---|---|---|---|
| 44 | sunflower oil without additive | 23.1 | |
| 45 | plus 2.0% Symdecanox HA | 24.4 | 1.3 |
| 46 | plus 2.0% Symdecanox HA plus 0.5% 1,2-heptanediol | 24.4 | 1.3 |
| 47 | plus 2.0% Symdecanox HA plus 0.5% 2,3-heptanediol | 24.7 | 1.6 |
| 48 | plus 2.0% Symdecanox HA plus 0.5% blend of 1,2-heptanediol and 2,3-heptanediol (ratio 95:5) | 25.3 | 2.2 |

Figure 24:
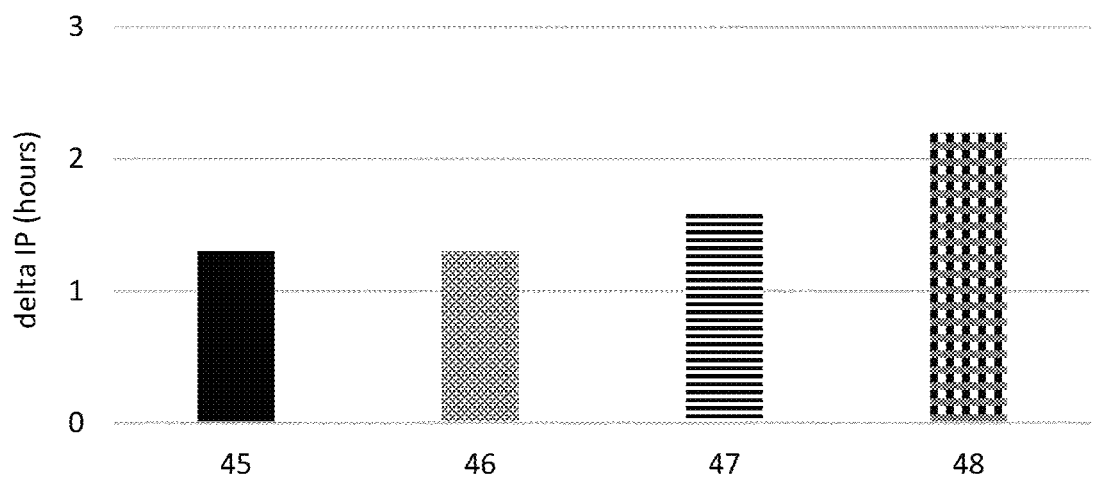
FIG. 24 is a diagram showing the delta IP values of Symdecanox HA and 1,2-heptanediol, Symdecanox HA and 2,3-heptanediol and Symdexanox HA and a blend of 1,2-heptanediol and 2,3-heptanediol (95:5).

The results are shown in FIG. 24. As can be seen from FIG. 24, sample 47 results in prolonged induction periods (indicating longer shelf life). However, a blend of 1,2-heptanediol and 2,3-heptanediol (95:5) considerably prolonged the induction period. This means that the samples are more stable against oxidative degradation than the comparative samples.

TABLE 15

| Sample No. | Octanediol | IP value (h) | delta IP versus sunflower oil without additive |
|---|---|---|---|
| 44 | sunflower oil without additive | 23.1 | |
| 45 | plus 2.0% Symdecanox HA | 24.4 | 1.3 |
| 49 | plus 2.0% Symdecanox HA plus 0.5% 1,2-octanediol | 23.9 | 0.8 |
| 50 | plus 2.0% Symdecanox HA plus 0.5% 2,3-octanediol | 24 | 0.9 |
| 51 | plus 2.0% Symdecanox HA plus 0.5% blend of 1,2-octanediol and 2,3-octanediol (ratio 95:5) | 25.1 | 2 |

Figure 25:
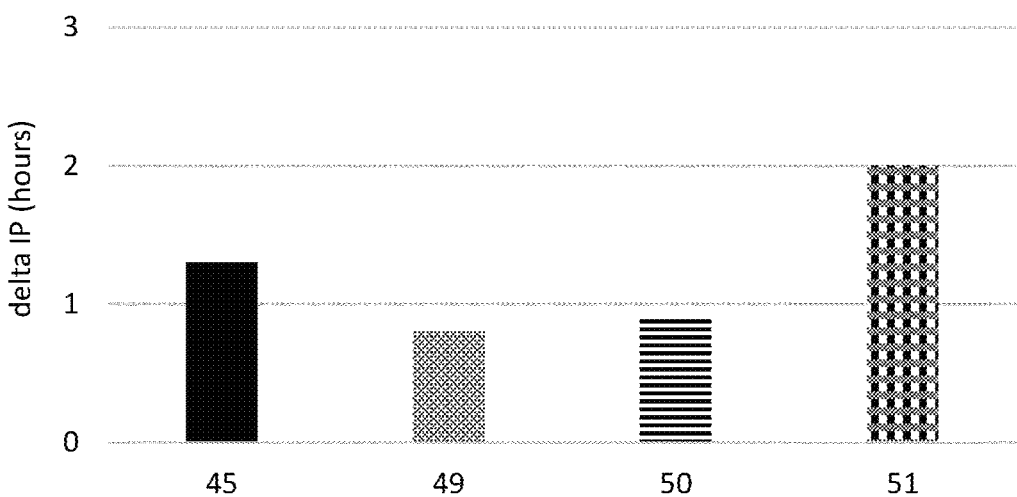
FIG. 25 is a diagram showing the delta IP values of Symdecanox HA and 1,2-octanediol, Symdecanox HA and 2,3-octanediol and Symdexanox HA and a blend of 1,2-octanediol and 2,3-octanediol (95:5).

INCI Symdecanox HA: Caprylic/Capric Triglyceride, Hydroxymethyoxyphenyl decanone The results are shown in FIG. 25. As can be seen from FIG. 25, sample 51 results in prolonged induction periods (indicating longer shelf life). This means that the samples are more stable against oxidative degradation than the comparative samples.

TABLE 16

| Sample No. | Heptanediol | IP value (h) | delta IP versus sunflower oil without additive |
|---|---|---|---|
| 52 | sunflower oil without additive | 21.9 | |
| 53 | plus 0.01% Pentaerythrityl Tetra-di-t-butyl Hydroxyhydrocinnamate | 25.8 | 3.9 |
| 54 | plus 0.01% Pentaerythrityl Tetra-di-t-butyl Hydroxyhydrocinnamate plus 0.5% 1,2-heptanediol | 27.7 | 5.8 |
| 55 | plus 0.01% Pentaerythrityl Tetra-di-t-butyl Hydroxyhydrocinnamate plus 0.5% 2,3-heptanediol | 27.6 | 5.7 |

TABLE 16-continued

| Sample No. | Heptanediol | IP value (h) | delta IP versus sunflower oil without additive |
|---|---|---|---|
| 56 | plus 0.01% Pentaerythrityl Tetra-di-t-butyl Hydroxyhydrocinnamate plus 0.5% blend of 1,2-heptanediol and 2,3-heptanediol (ratio 95:5) | 28.1 | 6.2 |

Figure 26:
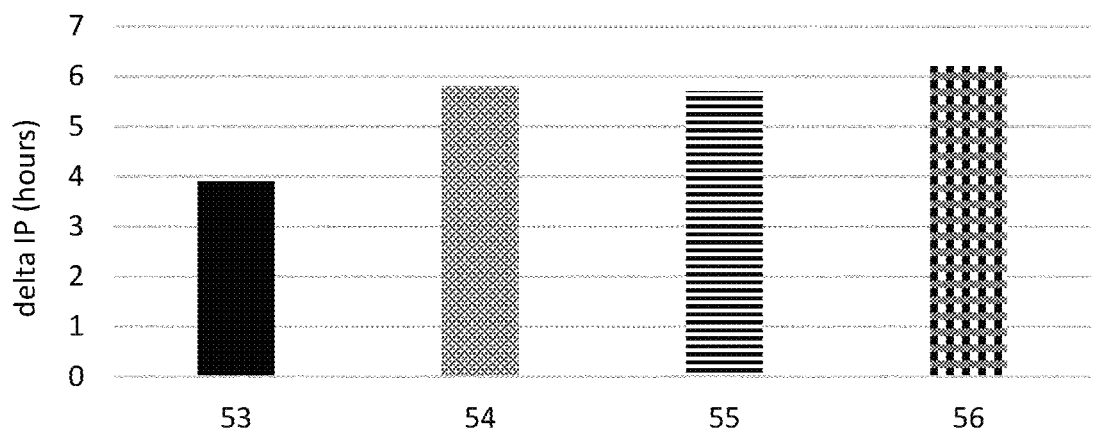
FIG. 26 is a diagram showing the delta IP values of Pentaerythrityl Tetra-di-t-butyl Hydroxyhydrocinnamate and 1,2-heptanediol, Pentaerythrityl Tetra-di-t-butyl Hydroxyhydrocinnamate and 2,3-heptanediol and Pentaerythrityl Tetra-di-t-butyl Hydroxyhydrocinnamate and a blend of 1,2-heptanediol and 2,3-heptanediol (95:5).

The results are shown in FIG. 26. As can be seen from FIG. 26, both sample 54 and sample 55 results in prolonged induction periods (indicating longer shelf life). However, a blend of 1,2-heptanediol and 2,3-heptanediol (95:5) considerably prolonged the induction period. This means that the samples are more stable against oxidative degradation than the comparative samples.

TABLE 17

| Sample No. | Heptanediol | IP value (h) | delta IP versus sunflower oil without additive |
|---|---|---|---|
| 57 | sunflower oil without additive | 22.9 | |
| 58 | plus 0.5% Hydroxyacetophenone | 23.2 | 0.3 |
| 59 | plus 0.5% Hydroxyacetophenone plus 0.5% 1,2-heptanediol | 24.4 | 1.5 |
| 60 | plus 0.5% Hydroxyacetophenone plus 0.5% 2,3-heptanediol | 24.3 | 1.4 |

Figure 27:
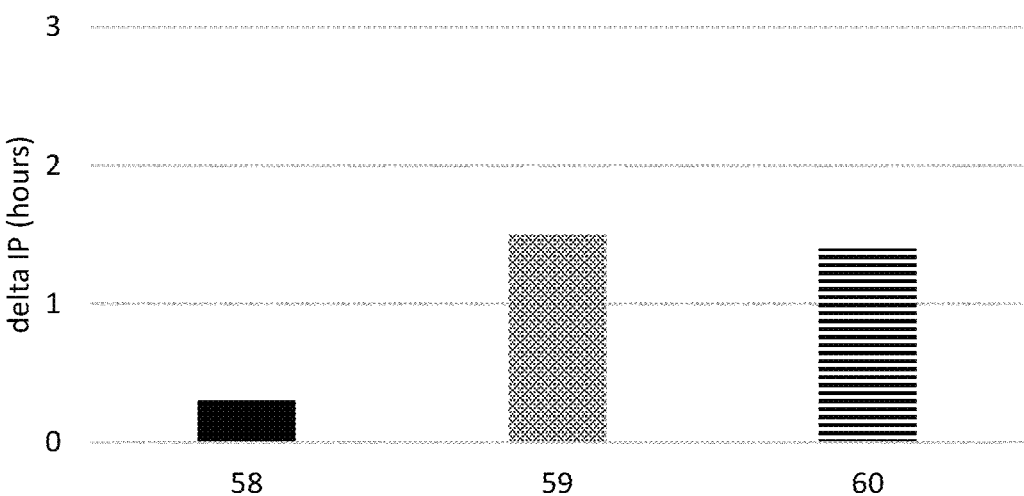
FIG. 27 is a diagram showing the delta IP values of Hydroxyacetophenone and 1,2-heptanediol and Hydroxyacetophenone and 2,3-heptanediol.

The results are shown in FIG. 27. As can be seen from FIG. 27, both 1,2-heptanediol and 2,3-heptanediol in combination with Hydroxyacetophenone result in remarkably prolonged induction periods (indicating longer shelf life). This means that the samples are more stable against oxidative degradation than the comparative samples.

TABLE 18

| Sample No. | Heptanediol | IP value (h) | delta IP versus sunflower oil without additive |
|---|---|---|---|
| 61 | sunflower oil without additive | 23.5 | |
| 62 | plus 0.05% Ascorbyl Palmitate | 25.5 | 2.0 |
| 63 | plus 0.05% Ascorbyl Palmitate plus 0.5% 1,2-heptanediol | 26.7 | 3.2 |
| 64 | plus 0.05% Ascorbyl Palmitate plus 0.5% 2,3-heptanediol | 26.6 | 3.1 |

Figure 28:
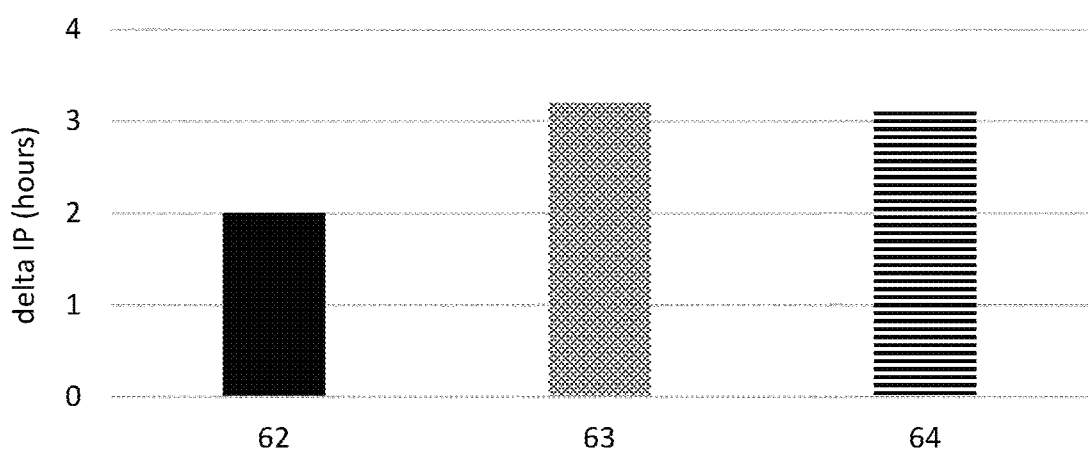
FIG. 28 is a diagram showing the delta IP values of Ascorbyl Palmitate and 1,2-heptanediol and Ascorbyl Palmitate and 2,3-heptanediol.

The results are shown in FIG. 28. As can be seen from FIG. 28, both 1,2-heptanediol and 2,3-heptanediol in combination with Ascorbyl Palmitate result in remarkably prolonged induction periods (indicating longer shelf life). This means that the samples are more stable against oxidative degradation than the comparative samples.

As it is demonstrated by the above example, the induction period of the samples can be extended with an antioxidant (tocopherol) and can be even more, i.e., synergistically, improved with a combination of an antioxidant in combination with an alkanediol. Hence, the oxidation process of sample including an oil can be decelerated with the concurrent use of an antioxidant and an alkanediol.

Example 2: Odor Evaluation of the Samples 1 to 12 of Example 1

A sensory evaluation of the samples of Example 1 after Oxipres treatment was performed with 12 untrained panelists. The panelists evaluated the rancid odor of each sample on a scale from 1 to 5 (5=strong rancid odor; 1=no rancid odor).

Test samples:
Sample 1: Sunflower oil without additives
Sample 2: Sunflower oil plus 0.1% tocopherol
Sample 3: Sunflower oil plus 0.1% tocopherol and 0.5% 1,2-heptanediol
Sample 4: Sunflower oil plus 0.1% tocopherol and 0.5% of an alkanediol blend of 95% 1,2-heptanediol and 0.5% 2,3-heptanediol
Sample 5: Sunflower oil plus 0.5% 1,2-heptanediol
Sample 6: Sunflower oil plus 0.5% 2,3-heptanediol
Sample 7: Sunflower oil plus 0.5% 1,2-nonanediol
Sample 8: Sunflower oil plus 0.1% tocopherol and 0.5% 1,2-nonanediol
Sample 9: Sunflower oil plus 0.1% 1,2-decanediol
Sample 10: Sunflower oil plus 0.1% tocopherol and 0.1% 1,2-decanediol
Sample 11: Sunflower oil plus 0.5% 2,3-octanediol
Sample 12: Sunflower oil plus 0.1% tocopherol and 0.5% 2,3-octanediol The results of the sensory evaluation are summarized in Table 19.

TABLE 19

| | Results of sensory evaluation | | | | | | | | | | | |
|---|---|---|---|---|---|---|---|---|---|---|---|---|
| Panelists | Sample 1 | Sample 2 | Sample 3 | Sample 4 | Sample 5 | Sample 6 | Sample 7 | Sample 8 | Sample 9 | Sample 10 | Sample 11 | Sample 12 |
| A | 5 | 4 | 3 | 2 | 5 | 5 | 5 | 3 | 5 | 2 | 5 | 2 |
| B | 5 | 4 | 2 | 3 | 4 | 4 | 4 | 4 | 4 | 3 | 4 | 2 |
| C | 5 | 4 | 2 | 2 | 4 | 5 | 3 | 3 | 3 | 2 | 3 | 1 |
| D | 4 | 2 | 2 | 2 | 5 | 5 | 4 | 2 | 4 | 3 | 4 | 3 |
| E | 5 | 4 | 4 | 3 | 4 | 4 | 5 | 4 | 3 | 3 | 4 | 3 |
| mean value | 4.8 | 3.6 | 2.6 | 2.4 | 4.4 | 4.6 | 4.2 | 3.2 | 3.8 | 2.6 | 4.0 | 2.2 |

The values in Table 19 clearly show that sample 3 (sunflower oil plus 0.1% tocopherol plus 0.5% 1,2-heptanediol), sample 4 (sunflower oil plus 0.1% tocopherol plus 0.5% of an alkanediol blend of 95% 1,2-heptanediol and 0.5% 2,3 heptanediol), sample 8 (sunflower oil plus 0.1% tocopherol plus 0.5% 1,2-nonanediol), sample 10 (sunflower oil plus 0.1% tocopherol plus 0.1% 1,2-decanediol) and sample 12 (sunflower oil plus 0.1% tocopherol plus 0.5% 2,3-octanediol), i.e. samples containing an antioxidant in combination with 1,2-heptanediol and/or 2,3-heptanediol have a better odor, i.e. the samples showed less rancid odor than the comparative examples. Comparative sample 1 (sunflower oil without antioxidant or alkanediol, comparative sample 2 (sunflower oil with tocopherol) and comparative samples 5 and 6 (sunflower oil with alkanediols without tocopherol) had a stronger rancid odor.

As it is demonstrated by the above tests, oxidative degradation can be reduced or minimized with an antioxidant (tocopherol) and can be even more reduced, i.e., boosted, with the addition of and antioxidant in combination with an alkanediol.

A distinguished efficacy for antioxidative boosting (prolonged induction time, less rancidity and reduced acid value) could be shown for 1,2-heptanediol as well as for 1,2-nonediol, 1,2-decanediol and 2,3-octanediol.

The above results allow the conclusion that the samples comprising an antioxidant in combination with an alkanediol have an antioxidative effect which is clearly above the one provided with an antioxidant alone.

Example 3: Antioxidant Potential on Ex Vivo Skin Biopsies (Lipophilic or Aqueous/Alcoholic (Ethanolic) Test Samples)

A dichlorofluorescein test (DCF) assay was performed in order to determine the amount of reactive oxygen species (ROS) on ex vivo skin treated with different test samples in a lipophilic or an aqueous/alcoholic system as described below.

DCF assay—assay principle: Ex vivo skin was incubated with 2',7'-dichlorodihydrofluorescein diacetate at 37° C., 5% $CO_2$. After PBS washing, samples were exposed or not to cumene hydroperoxide. Immediately after exposure, ex vivo skin samples were frozen in liquid nitrogen and 5 µm cryostat sections were made and fixed with acetone to allow the visualisation of fluorescence generated by ROS in cells of the reconstructed skins. The resulting fluorescence was measured at EX/EM 504/524 nm. Green fluorescence was quantified in ex vivo skin using ImageJ software. The depth of immunostaining was measured as follows: green DCFH-DE positive cells were automatically detected using Histolab software and the distance between dermal epidermal junction and the deepest positive cells were measured in each condition. Means were compared using a student's test. Two means were considered statistically different when p<0.005.

The image acquisition was performed by using Olympus BX51 microscope and Olympus DP70 camera. For each skin sample two skin sections have been taken and the related fluorescent images acquired and analyzed. Thus, for each test condition, 12 images have been acquired and analyzed (i.e. 12 data). The analysis of fluorescence has been performed within the dermis area. For each image the upper dermis has been analyzed by evaluating the fluorescence through modified Image-J application (NIH, USA). The analyzed area is selected from the upper part by following the perimeter of the basal lamina, to the deep dermis, by carefully avoiding the risk of including irregularities and agglomerates, such as blood vessels, sebaceous glands, hair follicles. The obtained value has been normalized upon the dimension of the selected area.

In addition, as positive control an AOX mix is always co-tested, i.e., as bench mark for the ROS analysis. The AOX mix is a mixture of the following antioxidants: 15% vitamin C, 1% vitamin E, 0.5% ferulic acid in a $EtOH/H_2O$ (50:50) mixture.

ROS score method description: The pigmentation score is based on the following process steps:
(1) Analysis of the image based on pixel grey intensities;
(2) Selection of an informative area excluding the pixel area not covered from tissue;
(3) Transformation of pixel grey intensities in degrees of L*;
(4) Normalization of the obtained values on the ratio between the selected area and the area of the slide.

An increased level of ROS (reactive oxygen species) led to an increased amount of fluorescence.

The chemical principle of the dichlorofluorescein (DCF) assay is depicted below:

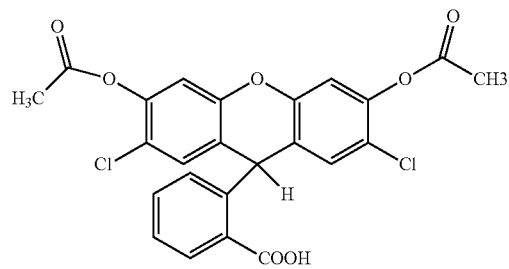

2'7'-Dichlorodihydrofluorescein-diacetate
(H2DCF-DA, non-fluorescent)

↙ Deacetylation by cellular esterases

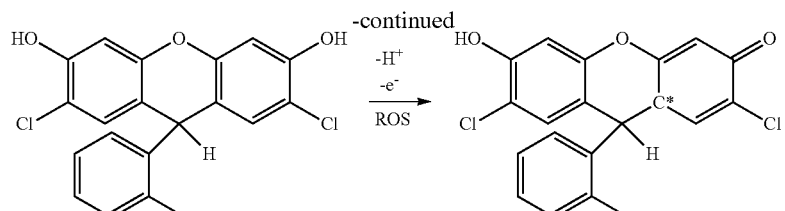

2'7'-Dichlorodihydrofluorescein
(H2DCF, non-fluorescent)

2'7'-Dichlorodihydrofluorescein
(H2DCF, non-fluorescent)

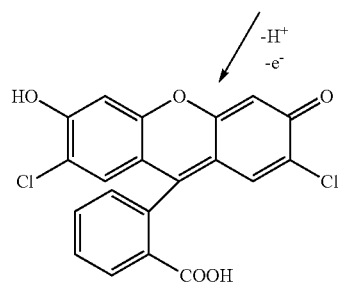

2'7'-Dichlorodihydrofluorescein
(DCF, fluorescent
(ex-em 485 nm/530 nm)

The chemical equation illustrates the conversion of 2',7'-dichlorodihydrofluorescein diacetate (H2DCFDA) by esterases in the intracellular environment and its subsequent two-step-oxidation in the presence of radical species (mainly ROS).

Example 3.1: DCF-Assay in Biopsy Antioxidation Test: 1,2-alkanediols or 2,3-alkanediols Plus/Minus Tocopherol for Lipophilic Test Samples The dichlorofluorescein test (DCF) as described before was performed with different test samples in a lipophilic test system as described below:

Test Samples:
Sample A: Vehicle: sunflower oil without additives
Sample B: Sunflower oil plus 0.1% tocopherol
Sample C: Sunflower oil plus 0.1% tocopherol plus 0.3% 1,2-pentanediol
Sample D: Sunflower oil plus 0.1% tocopherol plus 0.3% 1,2-hexanediol
Sample E: Sunflower oil plus 0.1% tocopherol plus 0.3% 1,2-heptanediol
Sample F: Sunflower oil plus 0.1% tocopherol plus 0.3% 2,3-heptanediol
Sample K: Sunflower oil plus 0.5% 1,2-pentanediol
Sample L: Sunflower oil plus 0.5% 1,2-hexanediol
Sample M: Sunflower oil plus 0.5% 1,2-heptanediol
Sample O: Sunflower oil plus 0.5% 2,3-heptanediol
Sample P: Sunflower oil plus 0.5% 1,2-nonanediol The ROS scores of the above specified samples are summarized in Table 20.

TABLE 20

Results ROS score

| Test | No cumene Untreated | Untreated cumene | AOX mix | A sunflower oil | B | C | D | E | F |
|---|---|---|---|---|---|---|---|---|---|
| | | | | Cumene hydroperoxide 0.5M | | | | | |
| 1 | 0.000 | 4.438 | 0.001 | 0.001 | 1.320 | 0.008 | 0.001 | 0.000 | 0.003 |
| 2 | 0.001 | 5.004 | 0.283 | 1.319 | 0.871 | 0.862 | 0.001 | 0.003 | 0.001 |
| 3 | 0.004 | 2.456 | 0.002 | 0.967 | 0.814 | 0.331 | 0.002 | 0.081 | 0.000 |
| 4 | 0.013 | 4.701 | 0.055 | 2.109 | 1.206 | 0.505 | 0.001 | 0.106 | 0.099 |
| 5 | 0.001 | 2.241 | 0.002 | 1.969 | 1.336 | 0.035 | 0.437 | 0.006 | 0.593 |
| 6 | 0.007 | 2.039 | 0.459 | 2.570 | 0.417 | 0.500 | 0.001 | 1.159 | 0.167 |
| 7 | 0.002 | 1.926 | 0.002 | 1.481 | 0.896 | 0.002 | 0.008 | 0.616 | 0.019 |
| 8 | 0.000 | 0.926 | 0.010 | 2.020 | 0.433 | 0.911 | 0.130 | 0.019 | 0.046 |
| 9 | 0.001 | 3.068 | 0.003 | 2.027 | 1.522 | 0.130 | 0.001 | 0.295 | 0.001 |
| 10 | 0.000 | 2.644 | 0.001 | 1.233 | 0.823 | 0.062 | 0.002 | 0.000 | 0.013 |

TABLE 20-continued

| Results ROS score | | | | | | | | |
|---|---|---|---|---|---|---|---|---|
| 11 | 0.001 | 3.488 | 0.175 | 1.624 | 0.395 | 0.582 | 0.006 | 0.113 | 0.000 |
| 12 | 0.253 | 1.708 | 0.000 | 2.497 | 0.783 | 0.001 | 0.002 | 0.003 | 0.003 |
| Mean Score | 0.02 | 2.89 | 0.08 | 1.65 | 0.90 | 0.33 | 0.05 | 0.20 | 0.08 |
| St. Dev | 0.07 | 1.28 | 0.15 | 0.72 | 0.38 | 0.34 | 0.13 | 0.35 | 0.17 |
| D percent vs untreated cumene | | −97% | −43% | −69% | −89% | −98% | −93% | −97% |
| D percent vs sample A cumene (sunflower oil) | | | −45% | −80% | −97% | −88% | −95% |
| D percent vs sample B cumene (sunflower oil plus plus 0.1% tocopherol) | | | | −64% | −95% | −78% | −91% |

| | Cumene hydroperoxide 0.5M | | | | | | | |
|---|---|---|---|---|---|---|---|---|
| Test | No cumene Untreated | Untreated cumene | AOX mix | A sunflower oil | K | L | M | O | P |
| 1 | 0.000 | 0.302 | 0.001 | 0.301 | 0.560 | 0.033 | 0.533 | 0.306 | 0.695 |
| 2 | 0.000 | 0.342 | 0.000 | 0.141 | 0.071 | 0.001 | 0.314 | 0.204 | 0.895 |
| 3 | 0.035 | 0.056 | 0.001 | 0.451 | 1.173 | 0.272 | 0.401 | 0.112 | 1.079 |
| 4 | 0.003 | 0.005 | 0.001 | 0.119 | 0.426 | 0.336 | 0.185 | 0.038 | 0.802 |
| 5 | 0.005 | 0.930 | 0.000 | 0.589 | 0.085 | 0.091 | 0.747 | 0.001 | 0.271 |
| 6 | 0.000 | 0.772 | 0.000 | 0.495 | 0.112 | 0.008 | 0.515 | 0.111 | 0.972 |
| 7 | 0.005 | 0.134 | 0.001 | 0.256 | 0.323 | 0.161 | 0.225 | 0.103 | 1.171 |
| 8 | 0.003 | 0.000 | 0.001 | 0.034 | 0.182 | 0.261 | 0.013 | 0.443 | 0.728 |
| 9 | 0.002 | 0.039 | 0.000 | 0.579 | 0.308 | 0.485 | 0.335 | 0.399 | 1.220 |
| 10 | 0.001 | 0.001 | 0.001 | 0.477 | 0.193 | 0.281 | 0.872 | 0.395 | 0.523 |
| 11 | 0.005 | 0.003 | 0.000 | 0.014 | 0.382 | 0.143 | 0.002 | 0.047 | 0.532 |
| 12 | 0.000 | 0.001 | 0.000 | 0.656 | 0.579 | 0.200 | 0.001 | 0.593 | 0.153 |
| Mean Score | 0.00 | 0.22 | 0.00 | 0.34 | 0.37 | 0.19 | 0.35 | 0.23 | 0.75 |
| St. Dev | 0.01 | 0.32 | 0.00 | 0.23 | 0.31 | 0.15 | 0.29 | 0.19 | 0.34 |
| SEM | 0.00 | 0.09 | 0.00 | 0.07 | 0.09 | 0.04 | 0.08 | 0.06 | 0.10 |
| D percent vs untreated cumene | | −100% | 59% | 70% | −12% | 60% | 6% | 250% |
| D percent vs A cumene | | | | 7% | −45% | 1% | −33% | 120% |

Figure 1B:
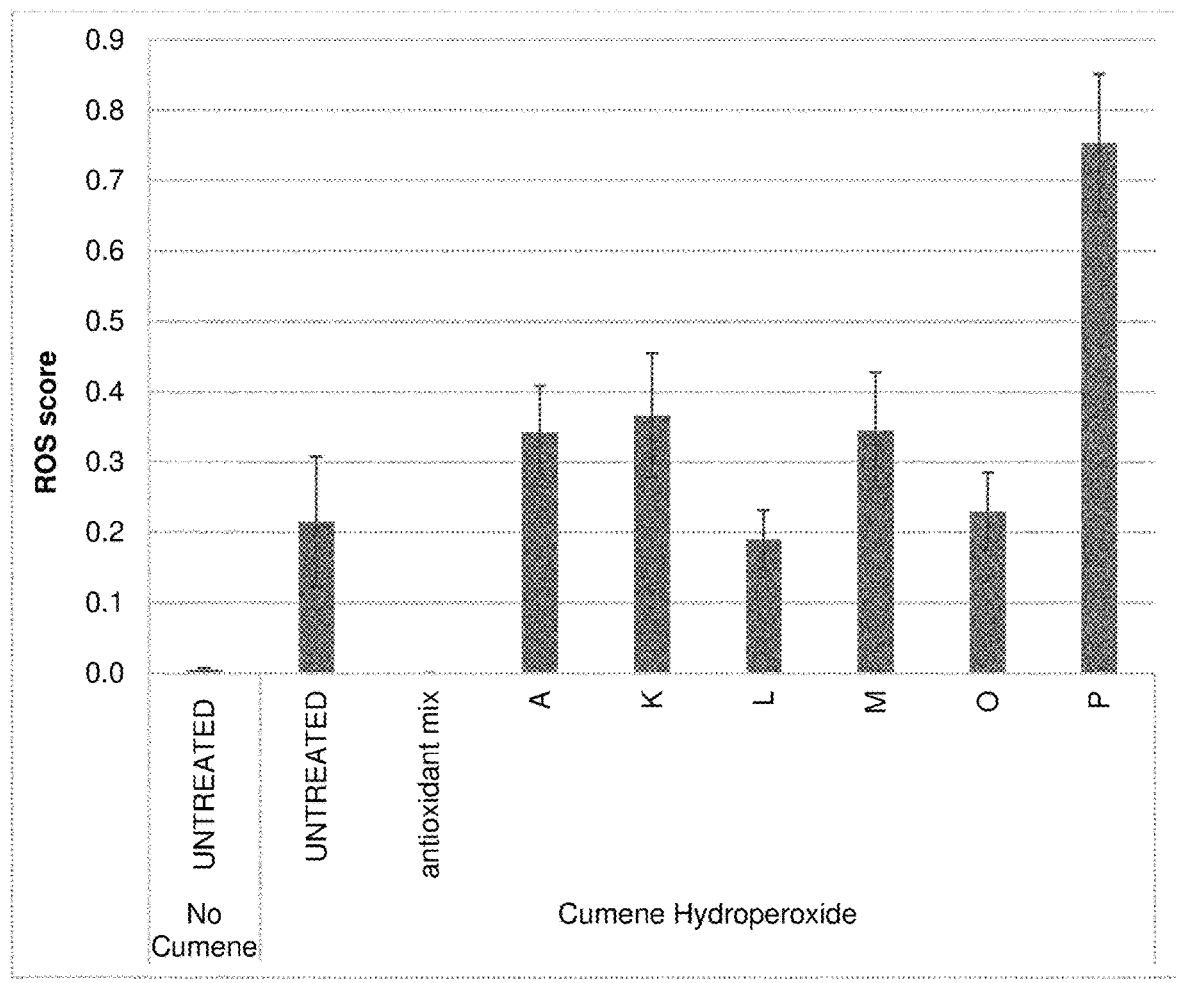

The ROS score results from Table 20 are visualized in FIGS. 1a and 1b.

The results in Table 20 and FIGS. 1a and 1b clearly demonstrate that the addition of 1,2-alkanediols or 2,3-alkanediols to a sample (C, D, E or F) including sunflower oil plus an antioxidant (tocopherol) leads to more than 60% reduced ROS scores versus a sample of sunflower oil with only tocopherol and without the addition of a 1,2 alkanediol or a 2,3-alkanediol. The samples K, L, M, O and P including only a 1,2-alkanediol or a 2,3-alkanediol without an antioxidant do not have an antioxidative efficacy.

From the above it can be concluded, that the addition of an 1,2-alkanediol or an 2,3-alkanediol to a composition comprising an antioxidant results in a considerably reduced ROS scores. In other words: the combination of an antioxidant plus 1,2-alkanediol and/or 2,3-alkanediol shows an improved ROS scavenging efficacy.

Example 3.2: DCF-Assay in Biopsy Antioxidation Test: 1,2-alkanediols or 2,3-alkanediols Plus/Minus Tocopherol for Aqueous/Alcoholic Test Samples The dichlorofluorescein test (DCF) as described before was performed with different test samples in an aqueous/alcoholic (ethanolic) test system as described below:

Test samples:
Sample 1: Vehicle (EtOH/H$_2$O)
Sample 2: Vehicle plus 0.1% tocopherol
Sample 3: Vehicle plus 0.1% tocopherol plus 0.5% 1,2-heptanediol
Sample 4: Vehicle plus 0.1% tocopherol plus 0.5% 2,3-heptanediol
Sample 5: Vehicle plus 0.1% tocopherol plus alkanediol blend (0.5% 1,2-heptanediol and 0.5% 2,3-heptanediol)
Sample 6: Vehicle plus 0.1% tocopherol plus 0.5% 1,2-octanediol
Sample 7: Vehicle plus 0.1% tocopherol plus 0.5% 2,3-octanediol
Sample 8: Vehicle plus 0.1% tocopherol plus alkanediol blend (0.5% 1,2-octanediol and 0.5% 2,3-octanediol)
Sample 10: Vehicle plus 0.1% tocopherol plus 0.5% 1,2-nonanediol
Sample 11: Vehicle plus 0.1% tocopherol plus 0.5% 1,2-undecanediol
Sample 12: Vehicle plus 0.1% tocopherol plus 0.5% 2,3-undecanediol
Sample 13: Vehicle plus 0.5% 1,2-heptanediol
Sample 14: Vehicle plus 0.5% 2,3-heptanediol
Sample 15: Vehicle plus 0.5% 1,2-octanediol
Sample 16: Vehicle plus 0.5% 2,3-octanediol
Sample 17: Vehicle plus 0.5% 1,2-nonanediol
Sample 18: Vehicle plus 0.5% 1,2-undecanediol
Sample 19: Vehicle plus 0.5% 2,3-undecanediol
The ROS scores are summarized in Table 21.

TABLE 21

| | | | | Results ROS score | | | | | | | | | | |
|---|---|---|---|---|---|---|---|---|---|---|---|---|---|---|
| | No | | | Cumene Hydroperoxide 0.5M | | | | | | | | | | |
| Test | cumene Untreated | Untreated cumene | AOX mix | 1 | 2 | 3 | 4 | 5 | 6 | 7 | 8 | 10 | 11 | 12 |
| 1 | 0.003 | 0.356 | 0.001 | 0.552 | 0.001 | 0.001 | 0.001 | 0.001 | 0.000 | 0.000 | 0.035 | 0.000 | 0.001 | 0.004 |
| 2 | 0.001 | 0.617 | 0.017 | 0.795 | 0.000 | 0.001 | 0.022 | 0.000 | 0.001 | 0.000 | 0.001 | 0.022 | 0.012 | 0.029 |
| 3 | 0.001 | 0.421 | 0.002 | 0.196 | 0.001 | 0.001 | 0.002 | 0.002 | 0.000 | 0.003 | 0.038 | 0.001 | 0.000 | 0.000 |
| 4 | 0.080 | 0.769 | 0.003 | 0.880 | 0.038 | 0.029 | 0.000 | 0.000 | 0.074 | 0.014 | 0.001 | 0.000 | 0.000 | 0.001 |
| 5 | 0.001 | 0.999 | 0.000 | 0.528 | 0.180 | 0.001 | 0.001 | 0.001 | 0.000 | 0.001 | 0.000 | 0.001 | 0.001 | 0.002 |
| 6 | 0.000 | 0.584 | 0.149 | 0.067 | 0.679 | 0.001 | 0.009 | 0.001 | 0.001 | 0.000 | 0.002 | 0.001 | 0.109 | 0.000 |
| 7 | 0.370 | 1.005 | 0.036 | 0.288 | 0.001 | 0.002 | 0.000 | 0.001 | 0.016 | 0.010 | 0.002 | 0.001 | 0.000 | 0.043 |
| 8 | 0.009 | 0.642 | 0.001 | 0.441 | 0.018 | 0.000 | 0.001 | 0.001 | 0.001 | 0.001 | 0.001 | 0.002 | 0.015 | 0.008 |
| 9 | 0.000 | 0.417 | 0.001 | 0.546 | 0.011 | 0.000 | 0.001 | 0.001 | 0.000 | 0.001 | 0.028 | 0.093 | 0.000 | 0.002 |
| 10 | 0.003 | 0.861 | 0.001 | 0.623 | 0.192 | 0.001 | 0.006 | 0.000 | 0.001 | 0.018 | 0.025 | 0.001 | 0.000 | 0.054 |
| 11 | 0.018 | 0.349 | 0.001 | 0.547 | 0.437 | 0.001 | 0.000 | 0.001 | 0.019 | 0.001 | 0.130 | 0.001 | 0.000 | 0.000 |
| 12 | 0.000 | 1.327 | 0.001 | 0.043 | 0.170 | 0.000 | 0.001 | 0.002 | 0.001 | 0.007 | 0.002 | 0.000 | 0.002 | 0.051 |
| Mean Score | 0.04 | 0.70 | 0.02 | 0.46 | 0.14 | 0.00 | 0.00 | 0.00 | 0.01 | 0.00 | 0.02 | 0.01 | 0.01 | 0.02 |
| St. Dev | 0.11 | 0.31 | 0.04 | 0.26 | 0.21 | 0.01 | 0.01 | 0.00 | 0.02 | 0.01 | 0.04 | 0.03 | 0.03 | 0.02 |
| SEM | 0.03 | 0.09 | 0.01 | 0.08 | 0.06 | 0.00 | 0.00 | 0.00 | 0.01 | 0.00 | 0.01 | 0.01 | 0.01 | 0.01 |
| D percent vs untreated Cumene | | | -97% | -34% | -79% | -100% | -99% | -100% | -99% | -99% | -97% | -99% | -98% | -98% |
| D percent vs 1 cumene (vehicle (EtOH/H$_2$O)) | | | | -69% | -99% | -99% | -100% | -98% | -99% | -95% | -98% | -97% | -96% | |
| D percent vs 2 cumene (vehicle plus 0.1% tocopherol) | | | | | -98% | -97% | -99% | -93% | -97% | -85% | -93% | -92% | -89% | |

| | No | | | Cumene Hydroperoxide 0.5M | | | | | | | | |
|---|---|---|---|---|---|---|---|---|---|---|---|---|
| Test | cumene Untreated | Untreated cumene | AOX mix | 1 | 2 | 13 | 14 | 15 | 16 | 17 | 18 | 19 |
| 1 | 0.003 | 0.356 | 0.001 | 0.552 | 0.001 | 0.779 | 0.645 | 0.595 | 0.438 | 1.160 | 0.186 | 0.655 |
| 2 | 0.001 | 0.617 | 0.017 | 0.795 | 0.000 | 0.319 | 0.646 | 1.058 | 0.432 | 0.284 | 0.043 | 0.447 |
| 3 | 0.001 | 0.421 | 0.002 | 0.196 | 0.001 | 0.479 | 0.469 | 0.461 | 0.270 | 0.287 | 0.169 | 0.394 |
| 4 | 0.080 | 0.769 | 0.003 | 0.880 | 0.038 | 0.042 | 0.313 | 0.410 | 0.502 | 0.431 | 0.756 | 0.365 |
| 5 | 0.001 | 0.999 | 0.000 | 0.528 | 0.180 | 0.438 | 0.992 | 0.334 | 0.326 | 0.539 | 0.720 | 0.876 |
| 6 | 0.000 | 0.584 | 0.149 | 0.067 | 0.679 | 0.089 | 0.574 | 0.664 | 0.323 | 0.429 | 0.724 | 1.300 |
| 7 | 0.370 | 1.005 | 0.036 | 0.288 | 0.001 | 0.379 | 0.521 | 0.454 | 0.157 | 0.364 | 0.292 | 0.290 |
| 8 | 0.009 | 0.642 | 0.001 | 0.441 | 0.018 | 0.527 | 0.238 | 0.816 | 0.379 | 0.412 | 0.001 | 0.775 |
| 9 | 0.000 | 0.417 | 0.001 | 0.546 | 0.011 | 0.086 | 0.211 | 0.627 | 0.442 | 0.145 | 0.842 | 1.268 |
| 10 | 0.003 | 0.861 | 0.001 | 0.623 | 0.192 | 0.663 | 0.158 | 0.551 | 0.245 | 0.022 | 0.001 | 0.529 |
| 11 | 0.018 | 0.349 | 0.001 | 0.547 | 0.437 | 0.444 | 0.513 | 0.217 | 0.175 | 0.523 | 0.558 | 0.435 |
| 12 | 0.000 | 1.327 | 0.001 | 0.043 | 0.170 | 1.199 | 0.195 | 0.365 | 0.357 | 0.121 | 0.402 | 0.205 |
| Mean Score | 0.04 | 0.70 | 0.02 | 0.46 | 0.14 | 0.45 | 0.46 | 0.55 | 0.34 | 0.39 | 0.39 | 0.63 |
| St. Dev | 0.11 | 0.31 | 0.04 | 0.26 | 0.21 | 0.33 | 0.25 | 0.23 | 0.11 | 0.29 | 0.32 | 0.36 |
| SEM | 0.03 | 0.09 | 0.01 | 0.08 | 0.06 | 0.09 | 0.07 | 0.07 | 0.03 | 0.08 | 0.09 | 0.10 |
| D percent vs untreated cumene | | | -97% | -34% | -79% | -35% | -34% | -21% | -52% | -43% | -44% | -10% |
| D percent vs 1 cumene (vehicle (EtOH/H$_2$O)) | | | | -69% | -1% | -1% | 19% | -26% | -14% | -15% | 37% | |
| D percent vs 2 cumene (vehicle plus 0.1% tocopherol) | | | | | 215% | 217% | 279% | 134% | 173% | 172% | 336% | |

Figure 2A:
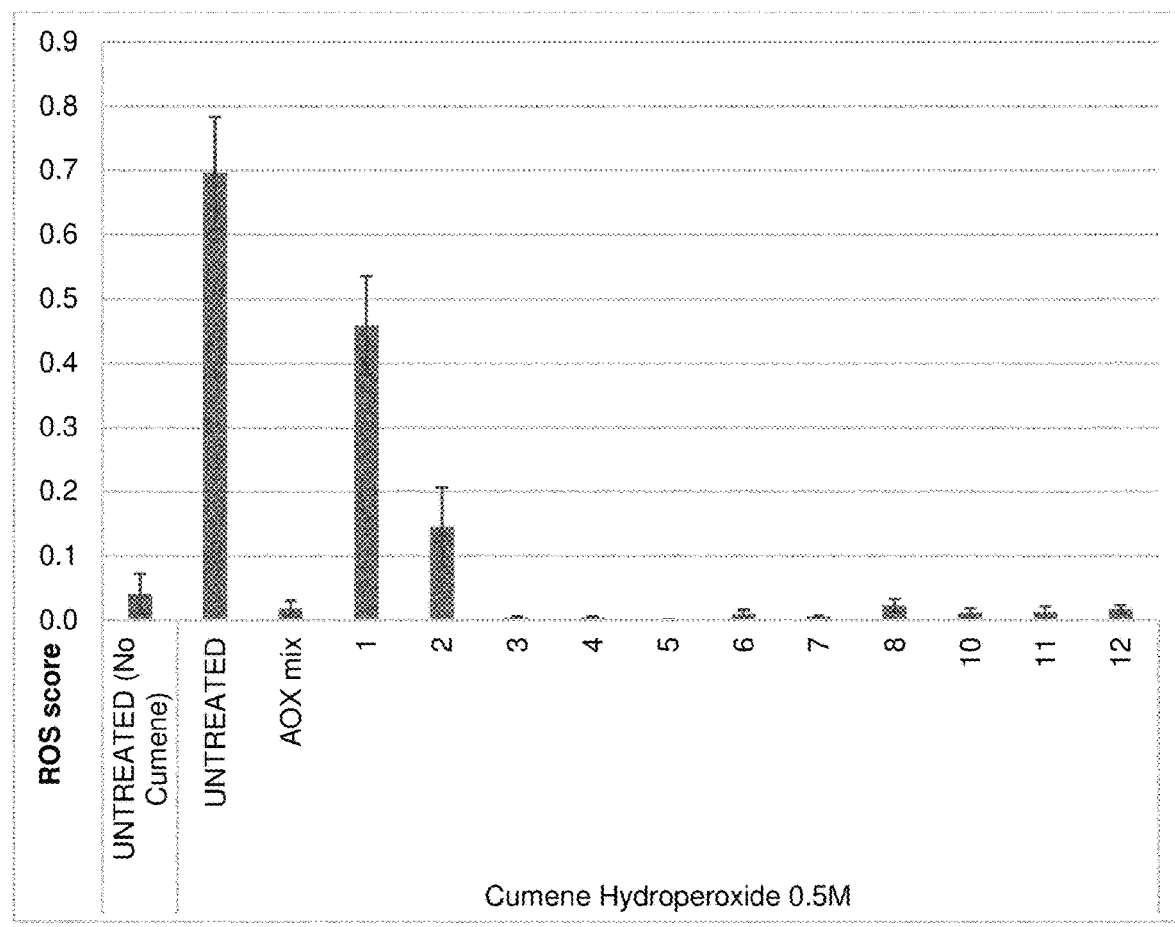
FIGS. 2a and 2b are diagrams showing the ROS scores of different compositions comprising tocopherol and/or a 1,2-alkanediol or a 2,3-alkanediol according to the present invention in an aqueous/alcoholic test system.
Figure 2B:
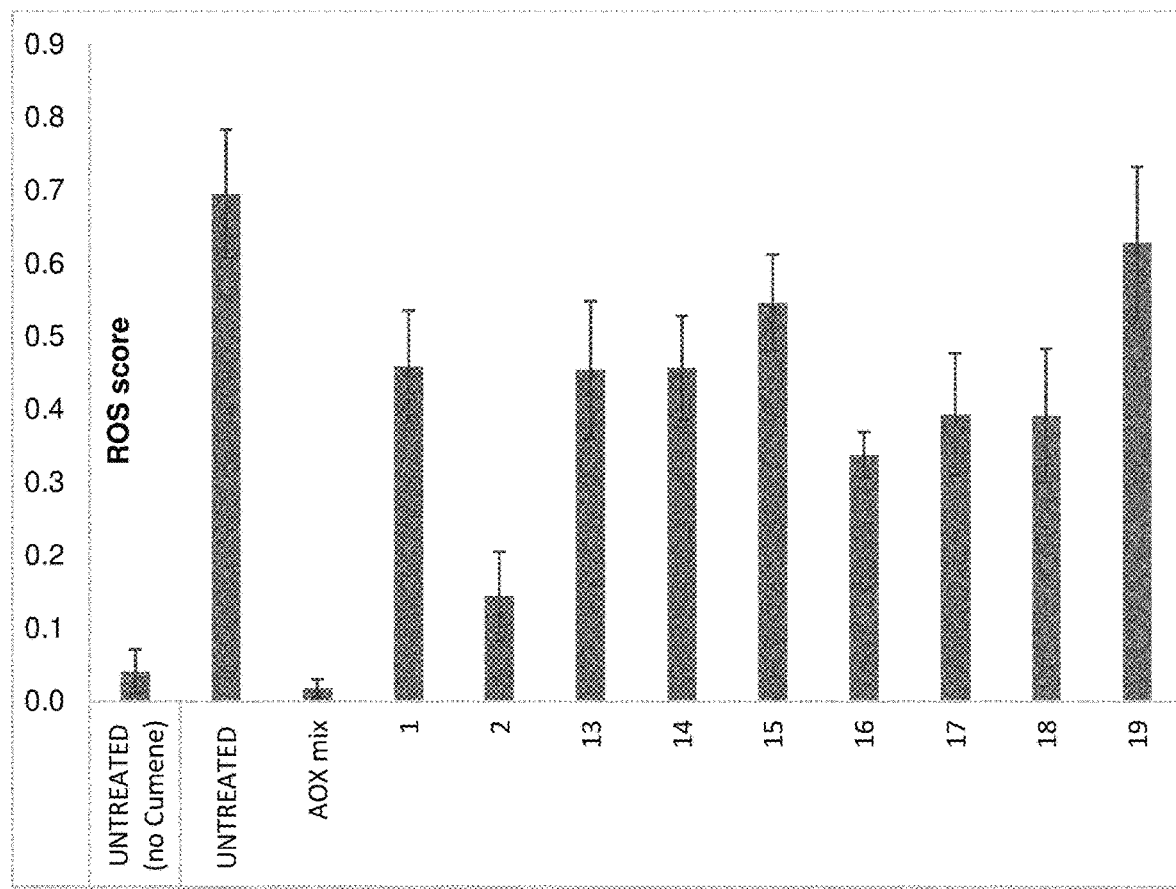

The ROS score results from Table 21 are visualized in FIGS. 2a and 2b.

The results in Table 21 and FIGS. 2a and 2b clearly demonstrate that the addition of 1,2-alkanediols or 2,3-alkanediols to a sample including an aqueous alcoholic vehicle plus an antioxidant (tocopherol) leads to more than 80% reduced ROS scores versus a sample of an aqueous/alcoholic vehicle with only tocopherol and without the addition of a 1,2 alkanediol or a 2,3-alkanediol. The samples including only the vehicle and a 1,2-alkanediol or a 2,3-alkanediol do not have an antioxidative efficacy.

From the above it can be concluded, that the addition of an 1,2-alkanediol or an 2,3-alkanediol to a composition comprising an antioxidant results in a considerably reduced ROS scores. In other words: the combination of an antioxidant plus 1,2-alkanediol and/or 2,3-alkanediol shows an improved ROS scavenging efficacy.

Example 3.3: DCF-Assay in Biopsy Antioxidation Test: 1,2-alkanediols or 2,3-alkanediols Plus/Minus Dihydroavenanthramide D for Aqueous/Alcoholic Test Samples The dichlorofluorescein test (DCF) as described before was performed with different test samples in an aqueous/alcoholic (ethanolic) test system as described below:
Test Samples:
Sample 1: Vehicle (EtOH/H$_2$O)
Sample 2: Vehicle plus 50 ppm Dihydroavenanthramide D
Sample 3: Vehicle plus 50 ppm Dihydroavenanthramide D plus 0.5% 1,2-heptanediol
Sample 4: Vehicle plus 50 ppm Dihydroavenanthramide D plus 0.5% 2,3-heptanediol
Sample 5: Vehicle plus 50 ppm Dihydroavenanthramid D plus 0.5% alkanediol blend of 1,2-heptanediol and 2,3-heptanediol (ratio 95:5)

The ROS scores are summarized in Table 22.

Figure 29:
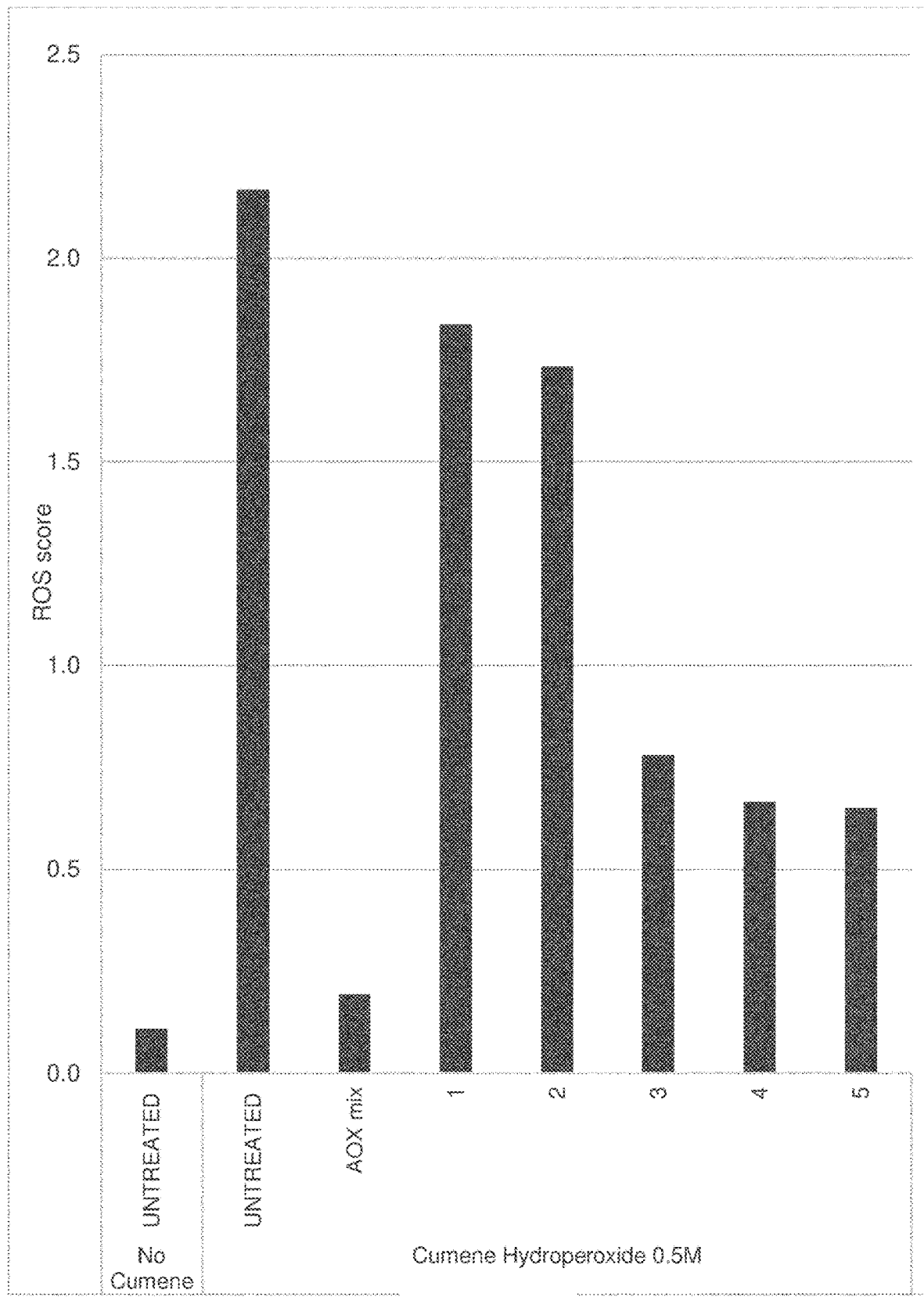
FIG. 29 is a diagram showing the ROS scores of different compositions comprising Dihydroavenanthramide D and 1,2-heptanediol or 2,3-heptanediol or blend of 1,2-heptanediol and 2,3-heptanediol according to the present invention in an aqueous/alcoholic test system.

The ROS score results from Table 22 are visualized in FIG. 29.

The results in Table 22 and FIG. 29 clearly demonstrate that the addition of 1,2-heptanediol or 2,3-heptanediol or an alkanediol mixture including 1,2-heptanediol and 2,3-heptanediol to a sample including an aqueous alcoholic vehicle plus an antioxidant (Dihydroavenanthramide D) leads to more than 60% reduced ROS scores versus a sample of an aqueous/alcoholic vehicle with only Dihydroavenanthramide and without the addition of 1,2-heptanediol or 2,3-heptanediol. The samples including only the vehicle and 1,2-heptanediol or 2,3-heptanediol do not have an antioxidative efficacy.

From the above it can be concluded, that the addition of an 1,2-alkanediol or an 2,3-alkanediol to a composition comprising an antioxidant results in a considerably reduced ROS scores. In other words: the combination of an antioxidant plus 1,2-alkanediol and/or 2,3-alkanediol shows an improved ROS scavenging efficacy.

Example 3.4: DCF-Assay in Biopsy Antioxidation Test: 1,2-alkanediols or 2,3-alkanediols Plus/Minus Cannabidiol for Aqueous/Alcoholic Test Samples The dichlorofluorescein test (DCF) as described before was performed with different test samples in an aqueous/alcoholic (ethanolic) test system as described below:
Test samples:
Sample 1: Vehicle (EtOH/H$_2$O)
Sample 2: Vehicle plus 5 ppm Cannabidiol
Sample 3: Vehicle plus 5 ppm Cannabidiol plus 0.5% 1,2-heptanediol
Sample 4 Vehicle plus 5 ppm Cannabidiol plus 0.5% 2,3-heptanediol
Sample 5: Vehicle plus 5 ppm Cannabidiol plus 0.5% alkanediol blend of 1,2-heptanediol and 2,3-heptanediol (ratio 95:5)

The ROS scores are summarized in Table 23.

TABLE 22

Results ROS score

| | | | Cumene Hydroperoxide 0.5M | | | | | |
|---|---|---|---|---|---|---|---|---|
| | No Cumene UNTREATED | UNTREATED | AOX mix | 1 | 2 | 3 | 4 | 5 |
| 1 | | 2.397 | | 0.894 | 1.552 | 0.748 | 0.116 | 0.694 |
| 2 | 0.132 | 3.447 | 0.021 | 3.201 | 2.083 | 0.709 | 0.414 | 0.322 |
| 3 | 0.120 | 2.359 | 0.305 | 2.012 | 1.367 | 0.288 | 0.919 | 0.289 |
| 4 | 0.163 | 2.648 | 0.067 | 1.044 | 2.338 | 0.874 | 0.552 | 0.802 |
| 5 | 0.061 | 4.630 | 0.167 | 2.820 | 1.245 | 0.071 | 0.274 | 0.409 |
| 6 | 0.110 | 0.680 | 0.263 | 3.397 | 1.929 | 0.079 | 1.685 | 0.230 |
| 7 | 0.008 | 2.754 | 0.227 | 2.535 | outlier | 1.060 | 1.009 | outlier |
| 8 | 0.186 | 1.355 | 0.330 | 0.931 | 1.230 | 0.718 | 0.230 | 0.921 |
| 9 | 0.088 | 0.994 | 0.212 | 0.828 | 2.420 | 1.073 | 0.344 | 1.693 |
| 10 | 0.159 | 1.161 | 0.314 | 1.230 | 1.706 | 1.580 | 0.414 | 0.661 |
| 11 | 0.057 | 1.431 | 0.021 | 1.316 | 1.466 | 1.375 | 1.357 | 0.481 |
| Mean Score | 0.11 | 2.17 | 0.19 | 1.84 | 1.73 | 0.78 | 0.66 | 0.65 |
| St. Dev | 0.06 | 1.19 | 0.12 | 0.99 | 0.44 | 0.49 | 0.51 | 0.43 |
| SEM | 0.02 | 0.36 | 0.04 | 0.30 | 0.14 | 0.15 | 0.15 | 0.14 |
| D percent vs Untr No Cumene | | 1900% | 78% | 1594% | 1499% | 619% | 513% | 500% |
| D percent vs Untr Cumene | | | -91% | -15% | -20% | -64% | -69% | -70% |
| D percent vs −A Cumene | | | | | -6% | -58% | -64% | -65% |

TABLE 23

| Results | | | Cumene Hydroperoxide 0.5M | | | | | |
|---|---|---|---|---|---|---|---|---|
| ROS score | No Cumene UNTREATED | UNTREATED | AOX mix | A | B | C | D | E |
| 1 | 0.003 | 1.800 | 0.069 | 1.602 | 0.560 | 0.002 | 0.003 | 0.047 |
| 2 | 0.006 | 3.127 | 0.498 | 2.370 | 0.362 | 0.054 | 0.410 | 0.017 |
| 3 | 0.104 | 0.903 | 0.008 | 3.935 | 0.621 | 0.016 | 0.075 | 0.147 |
| 4 | 0.028 | 1.980 | 0.001 | 1.927 | 0.200 | 0.114 | 0.082 | 0.018 |
| 5 | 0.111 | 1.903 | 0.402 | 2.072 | 1.230 | 0.673 | outlier | 0.028 |
| 6 | 0.030 | 0.719 | 0.007 | 2.770 | 1.096 | 0.182 | 0.027 | 0.414 |
| 7 | 0.005 | 1.705 | 0.007 | 1.016 | 0.010 | 0.587 | 0.006 | 0.028 |
| 8 | outlier | 3.104 | 0.157 | 2.499 | 1.025 | 0.127 | 0.188 | 0.164 |
| 9 | 0.060 | 1.330 | 0.196 | 0.932 | 0.304 | 0.080 | 0.350 | 0.065 |
| 10 | 0.007 | 2.331 | 0.234 | 0.952 | 0.005 | 0.586 | 0.313 | 0.484 |
| 11 | 0.144 | 2.578 | 0.011 | 2.034 | 0.014 | 0.098 | 0.562 | 0.016 |
| Mean Score | 0.05 | 1.95 | 0.14 | 2.01 | 0.49 | 0.23 | 0.20 | 0.13 |
| St. Dev | 0.05 | 0.80 | 0.17 | 0.90 | 0.45 | 0.25 | 0.20 | 0.17 |
| SEM | 0.02 | 0.24 | 0.05 | 0.27 | 0.14 | 0.08 | 0.06 | 0.05 |
| D percent vs Untr No Cumene | | 3810% | 190% | 3924% | 887% | 359% | 304% | 160% |
| D percent vs Untr Cumene | | | −93% | 3% | −75% | −88% | −90% | −93% |
| D percent vs −1 Cumene | | | | | −75% | −89% | −90% | −94% |

Figure 30:
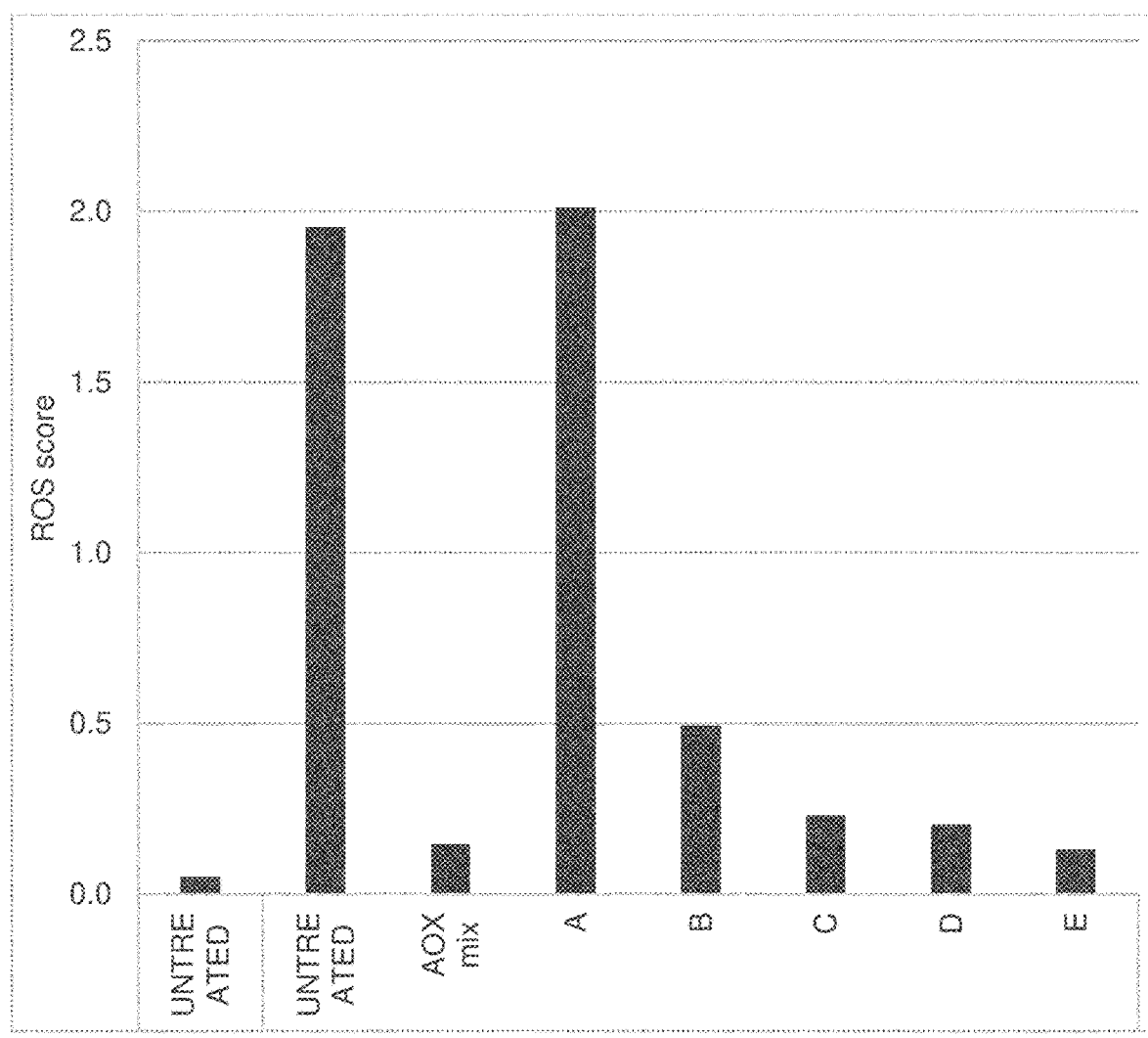
FIG. 30 is a diagram showing the ROS scores of different compositions comprising Cannabidiol and 1,2-heptanediol or 2,3-heptanediol or a blend of 1,2-heptanediol and 2,3-heptanediol according to the present invention in an aqueous/alcoholic test system.

The ROS score results from Table 23 are visualized in FIG. 30.

The results in Table 23 and FIG. 30 clearly demonstrate that the addition of 1,2-heptanediol or 2,3-heptanediol or an alkanediol mixture including 1,2-heptanediol and 2,3-heptanediol to a sample including an aqueous alcoholic vehicle plus an antioxidant (Cannabidiol) leads to more than 70% reduced ROS scores versus a sample of an aqueous/alcoholic vehicle with only Cannabidiol and without the addition of 1,2-heptanediol or 2,3-heptanediol. The samples including only the vehicle and 1,2-heptanediol or 2,3-heptanediol do not have an antioxidative efficacy.

From the above it can be concluded, that the addition of an 1,2-alkanediol or an 2,3-alkanediol to a composition comprising an antioxidant results in a considerably reduced ROS scores. In other words: the combination of an antioxidant plus 1,2-alkanediol and/or 2,3-alkanediol shows an improved ROS scavenging efficacy.

Example 4: Antioxidant Potential on Monolayer Cells

A dichlorofluorescein test (DCF) assay was performed in order to determine the amount of reactive oxygen species (ROS) on monolayer cells with different test samples as described below.

DCF assay—assay principle (2D): One procedure to quantify intracellular radicals in a cell model is by using the dichlorofluorescein (DCF) assay. The cell-permeant 2′,7′-dichlorodihydrofluorescein diacetate ($H_2$DCF-DA) is a chemically reduced form of fluorescein used as an indicator-dye for reactive oxygen species (ROS) in cells. By intracellular esterases and oxidation, the nonfluorescent $H_2$DCFDA is converted to the highly fluorescent 2′,7′-dichlorofluorescein (DCF). The nonfluorescent fluorescein (2′,7′-dichlorofluorescein diacetate (DCFH-DA)) passes the cell membranes. In the cytoplasm, it is cleaved by intracellular esterases and cannot leave the cell in this form. The oxidation by intracellularly existing ROS (reactive oxygen species) modifies the molecule so that will become DCF and emits fluorescence. ROS stimulation is done by exposure to 300 µM $H_2O_2$ for 1 h.

The determination of the anti-oxidative capacity is performed in 96-well microplates from Nunc (Wiesbaden, Germany) and with the microplate reader "Spark" from Tecan (Crailsheim, Germany). Cells are seeded in a black 96 well microplate with transparent bottom and incubated at 37° C. After 24 h the supernatant is decanted and fresh media with 0.1% FBS is added. Further 24 hours later the supernatant is decanted again and the test samples are added and incubated for 24 h. As a positive control Trolox is always co-tested. 300 µM $H_2O_2$ is used as ROS source (1 h exposure) The emitted fluorescence is measured from bottom of well at EX/EM 485/528 nm.

The antioxidative capacity is expressed as relative reduction of the stimulated control, which can be determined by rule of proportion in combination with the control.

Example 4.1: Tocopherol Plus 1,2-heptanediol

TABLE 24

| Compound | Concentration | Mean, ROS concentration (%) |
|---|---|---|
| Untreated | | 100 |
| 1,2-heptanediol | 500 µM | 112 |
| alpha-Tocopherol | 100 µM | 58 |
| alpha-Tocopherol + 1,2-heptanediol | 100 µM + 500 µM | 44 |
| alpha-Tocopherol | 50 µM | 45 |
| alpha-Tocopherol + 1,2-heptanediol | 50 µM + 500 µM | 40 |

Figure 3:
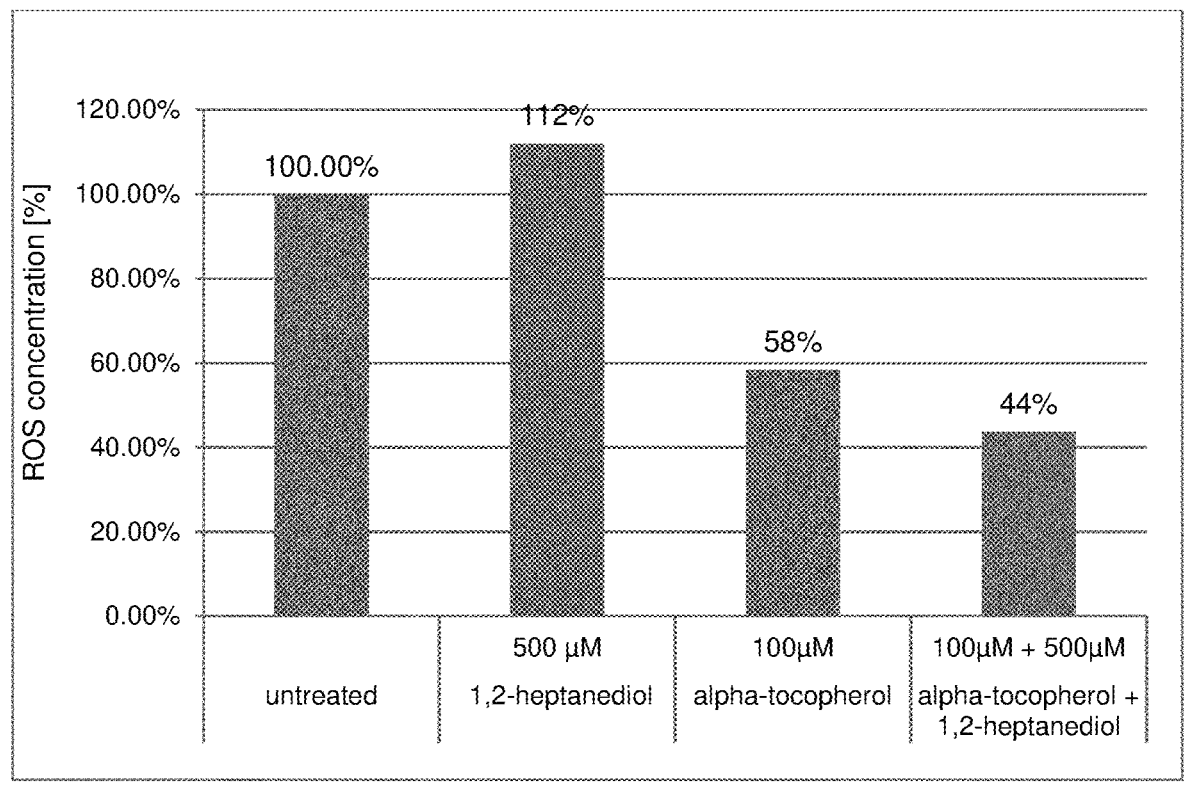
FIG. 3 is a diagram showing the ROS reducing capacity of tocopherol, 1,2-heptanediol, and a mixture thereof.

The ROS concentration results from Table 24 are visualized in FIG. 3.

1,2-heptanediol alone does not show a ROS reducing capacity, as the ROS value is with 112% not reduced. In contrast, it enhances the tocopherol activity in a concentration of 100 µM by 12%, as the ROS concentration is reduced from 58% to 44%, when 1,2-heptanediol is added. An enhanced tocopherol activity can also be achieved in combination with 1,2-heptanediol, even when the concentration of tocopherol is reduced half.

Example 4.2: Carnosine Plus 1,2-heptanediol

TABLE 25

| Compound | Concentration | Mean, ROS concentration (%) |
| --- | --- | --- |
| Untreated | | 100 |
| 1,2-heptanediol | 500 µM | 112 |
| Carnosine | 10 mM | 96 |
| Carnosine + 1,2-heptanediol | 10 mM + 500 µM | 91 |

Figure 4:
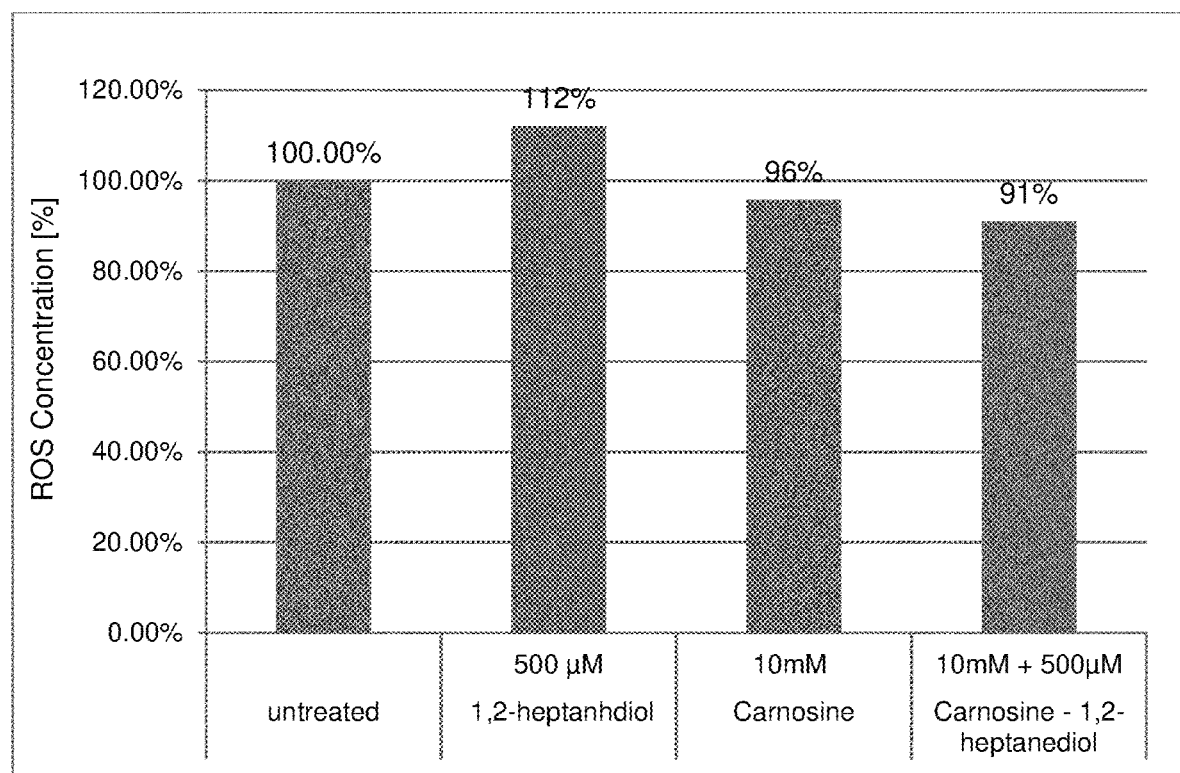
FIG. 4 is a diagram showing the ROS reducing capacity of Carnosine (Dragosine®), 1,2-heptanediol, and a mixture thereof.

The ROS concentration results from Table 25 are visualized in FIG. 4.

1,2-heptanediol alone does not show a ROS reducing capacity, as the ROS value is with 112% not reduced. In contrast, it enhances the Carnosine activity in a concentration of 10 mM by 5%, as the ROS concentration is reduced from 96% to 91%, when 1,2-heptanediol is added.

Example 4.3: Retinol Plus 1,2-heptanediol

TABLE 26

| Compound | Concentration | Mean, ROS concentration (%) |
| --- | --- | --- |
| Untreated | | 100 |
| 1,2-heptanediol | 500 µM | 112 |
| all trans-Retinol | 50 µM | 100 |
| all trans-Retinol + 1,2-heptanediol | 50 µM + 500 µM | 75 |

Figure 5:
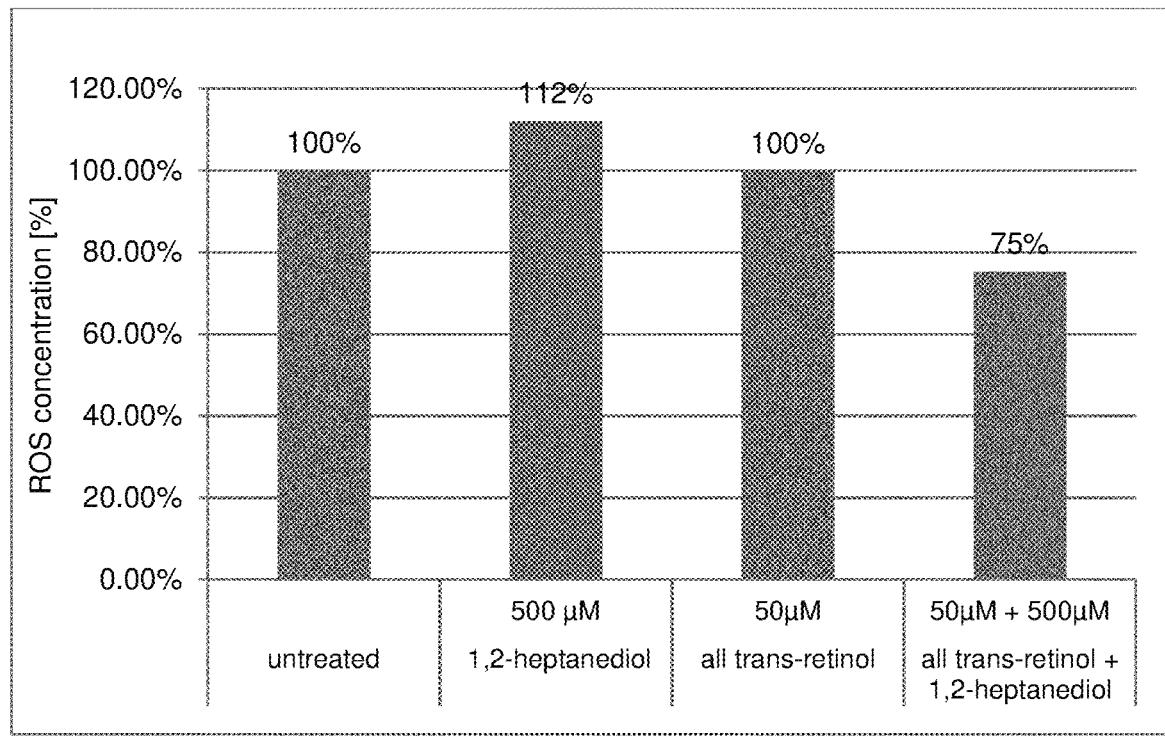
FIG. 5 is a diagram showing the ROS reducing capacity of Retinol, 1,2-heptanediol, and a mixture thereof.

The ROS concentration results from Table 26 are visualized in FIG. 5.

1,2-heptanediol alone does not show a ROS reducing capacity, as the ROS value is with 112% not reduced. In contrast, it enhances the Retinol activity in a concentration of 50 µM by 25%, as the ROS concentration is reduced from 100% to 75%, when 1,2-heptanediol is added.

Example 4.4: Green Tea Extract Plus 1,2-heptanediol

TABLE 27

| Compound | Concentration | Mean, ROS concentration (%) |
| --- | --- | --- |
| Untreated | | 100 |
| 1,2-heptanediol | 500 µM | 112 |
| Green Tea Extract | 0.002% | 94 |
| Green Tea Extract + 1,2-heptanediol | 0.002% + 500 µM | 75 |
| Green Tea Extract | 0.001% | 79 |
| Green Tea Extract + 1,2-heptanediol | 0.001% + 500 µM | 76 |

Figure 6:
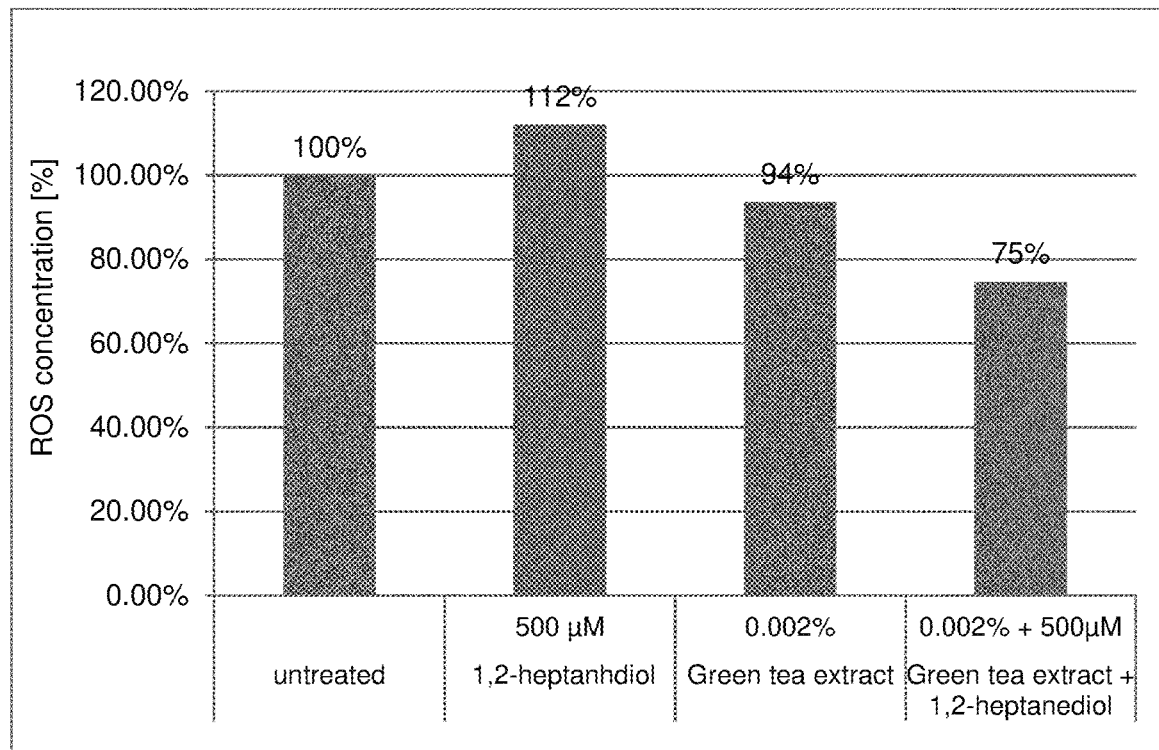
FIG. 6 is a diagram showing the ROS reducing capacity of Green Tea Extract, 1,2-heptanediol, and a mixture thereof.

The ROS concentration results from Table 27 are visualized in FIG. 6.

1,2-heptanediol alone does not show a ROS reducing capacity, as the ROS value is with 112% not reduced. In contrast, it enhances the Green Tea Extract activity by 19%, as the ROS concentration is reduced from 94% to 75%, when 1,2-heptanediol is added. An enhanced Green Tea Extract activity can also be achieved in combination with 1,2-heptanediol, even when the concentration of green tea extract is reduced half.

Example 4.5: *Zingiber Officinale* (Ginger) Root Extract (SymVital AgeRepair 3040) plus 1,2-heptanediol

TABLE 28

| Compound | Concentration | Mean, ROS concentration (%) |
| --- | --- | --- |
| Untreated | | 100 |
| 1,2-heptanediol | 500 µM | 112 |
| SymVital AgeRepair 3040 | 0.0003% | 26 |
| SymVital AgeRepair 3040 + 1,2-heptanediol | 0.0003% + 500 µM | 12 |

Figure 7:
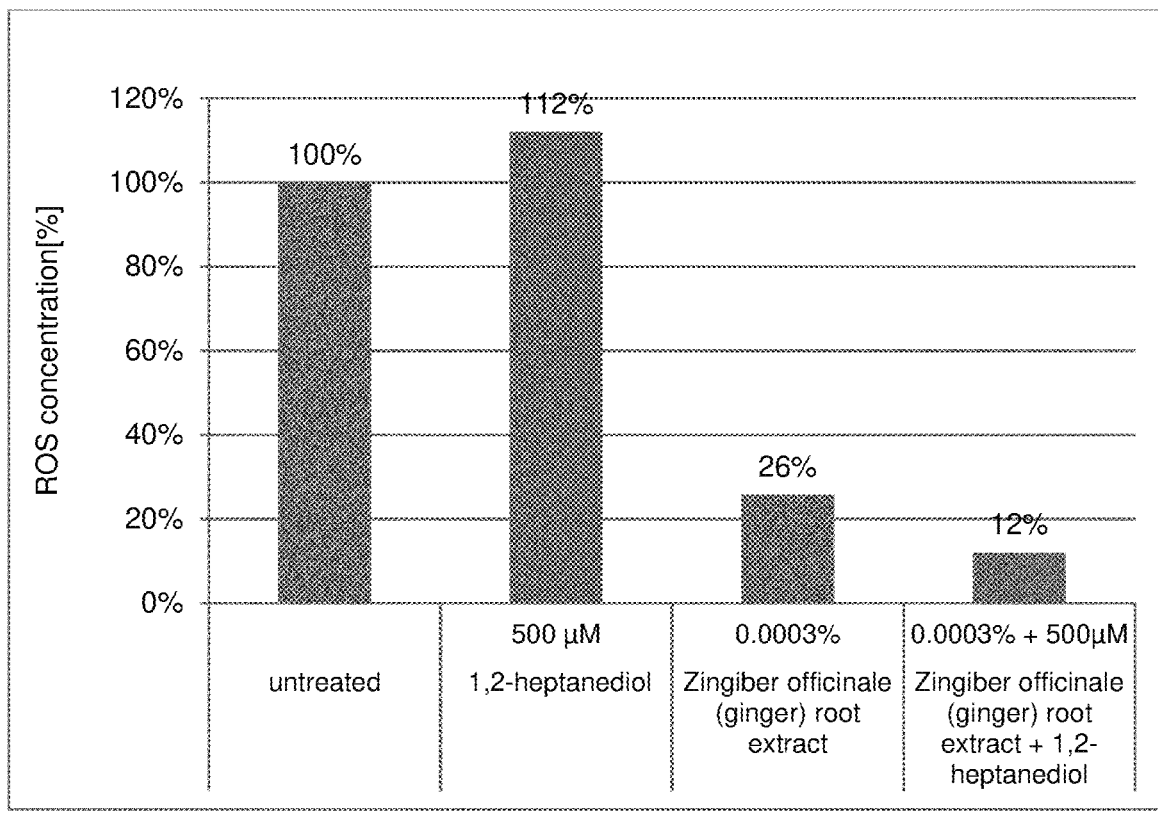
FIG. 7 is a diagram showing the ROS reducing capacity of *Zingiber Officinale* (Ginger) Root Extract, 1,2-heptanediol, and a mixture thereof.

The ROS concentration results from Table 28 are visualized in FIG. 7.

1,2-heptanediol alone does not show a ROS reducing capacity, as the ROS value is with 112% not reduced. In contrast, it enhances the SymVital AgeRepair 3040 activity by 14%, as the ROS concentration is reduced from 26% to 12%, when 1,2-heptanediol is added.

Example 4.6: Hydroxypinacolone Retinoate Plus 1,2-heptanediol

TABLE 29

| Compound | Concentration | Mean, ROS concentration (%) |
| --- | --- | --- |
| Untreated | | 100 |
| 1,2-heptanediol | 500 µM | 112 |
| Hydroxypinacolone Retinoate | 5 µM + 500 µM | 53 |
| Hydroxypinacolone Retinoate + 1,2-heptanediol | 5 µM + 500 µM | 18 |

Figure 8:
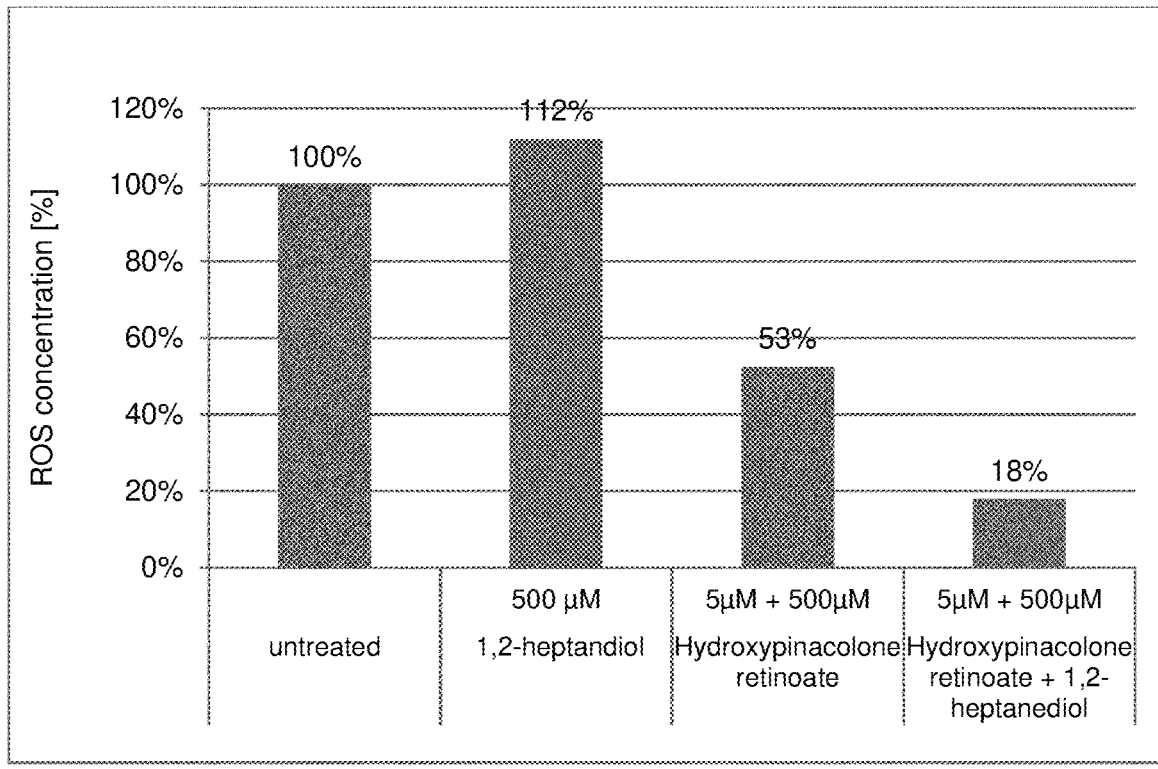
FIG. 8 is a diagram showing the ROS reducing capacity of Hydroxypinacolone Retinoate, 1,2-heptanediol, and a mixture thereof.

The ROS concentration results from Table 29 are visualized in FIG. 8.

1,2-heptanediol alone does not show a ROS reducing capacity, as the ROS value is with 112% not reduced. In contrast, it enhances the Hydroxypinacolone Retinoate activity by 35%, as the ROS concentration is reduced from 53% to 18%, when 1,2-heptanediol is added.

Example 4.7: beta-aspartyl Arginine (SymReserve) Plus 1,2-heptanediol

TABLE 30

| Compound | Concentration | Mean, ROS concentration (%) |
| --- | --- | --- |
| Untreated | | 100 |
| 1,2-heptanediol | 500 µM | 112 |
| beta-aspartyl arginine | 10000 µM | 103 |
| beta-aspartyl arginine + 1,2-heptanediol | 10000 µM + 500 µM | 93 |

Figure 9:
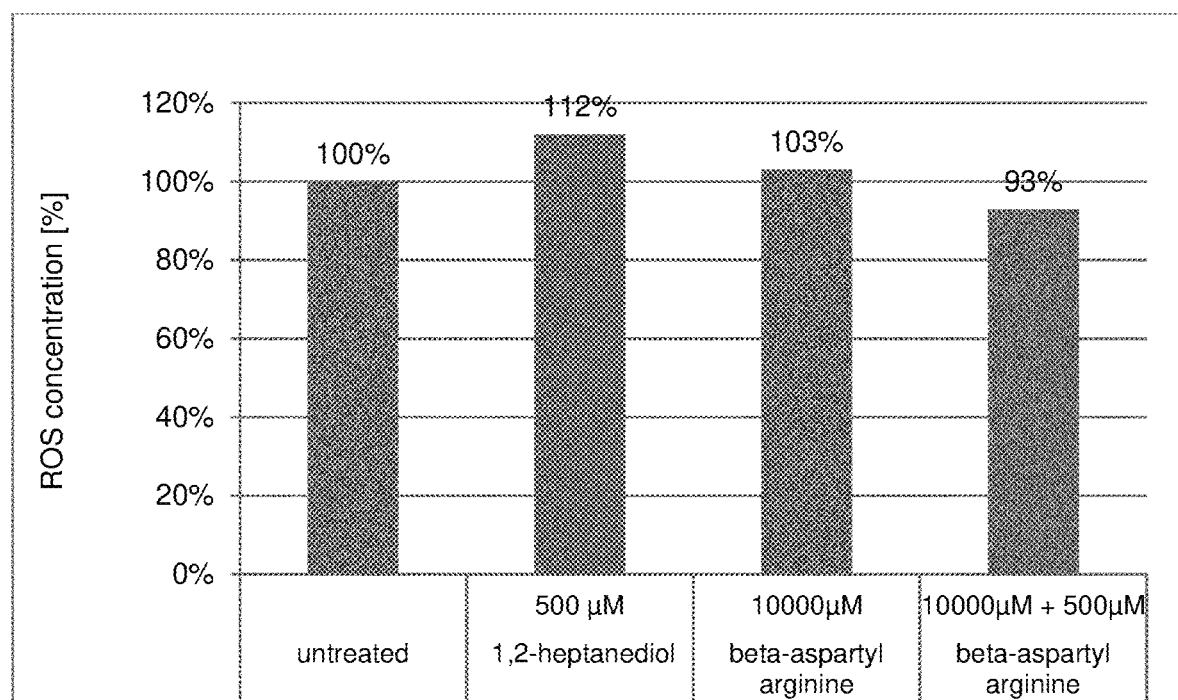
FIG. 9 is a diagram showing the ROS reducing capacity of beta-aspartyl arginine, 1,2-heptanediol, and a mixture thereof.

The ROS concentration results from Table 30 are visualized in FIG. 9.

1,2-heptanediol alone does not show a ROS reducing capacity, as the ROS value is with 112% not reduced. In contrast, it enhances the beta-aspartyl arginine (SymReserve) activity by 10%, as the ROS concentration is reduced from 103% to 93%, when 1,2-heptanediol is added.

Example 4.8: *Zingiber Officinale* (Ginger) Root (SymVital AgeRepair 3040) Plus 2,3-octanediol or 1,2-octancediol Plus 2,3-octanediol

TABLE 31

| Compound | Concentration μM | Mean, ROS concentration (%) |
|---|---|---|
| 2,3-octanediol | 500 μM | 98 |
| Zingiber Officinale (Ginger) Root Extract | 0.0003% | 37 |
| 2,3-octanediol + Zingiber Officinale (Ginger) Root Extract | 500 μM + 0.0003% | 26 |
| 1,2-octanediol:2,3-octanediol (95:5) | 500 μM | 100 |
| Zingiber Officinale (Ginger) Root Extract | 0.0003% | 24 |
| 1,2-octanediol:2,3-octanediol (95:5) + Zingiber Officinale (Ginger) Root Extract | 500 μM + 0.0003% | 20 |

Figure 10:
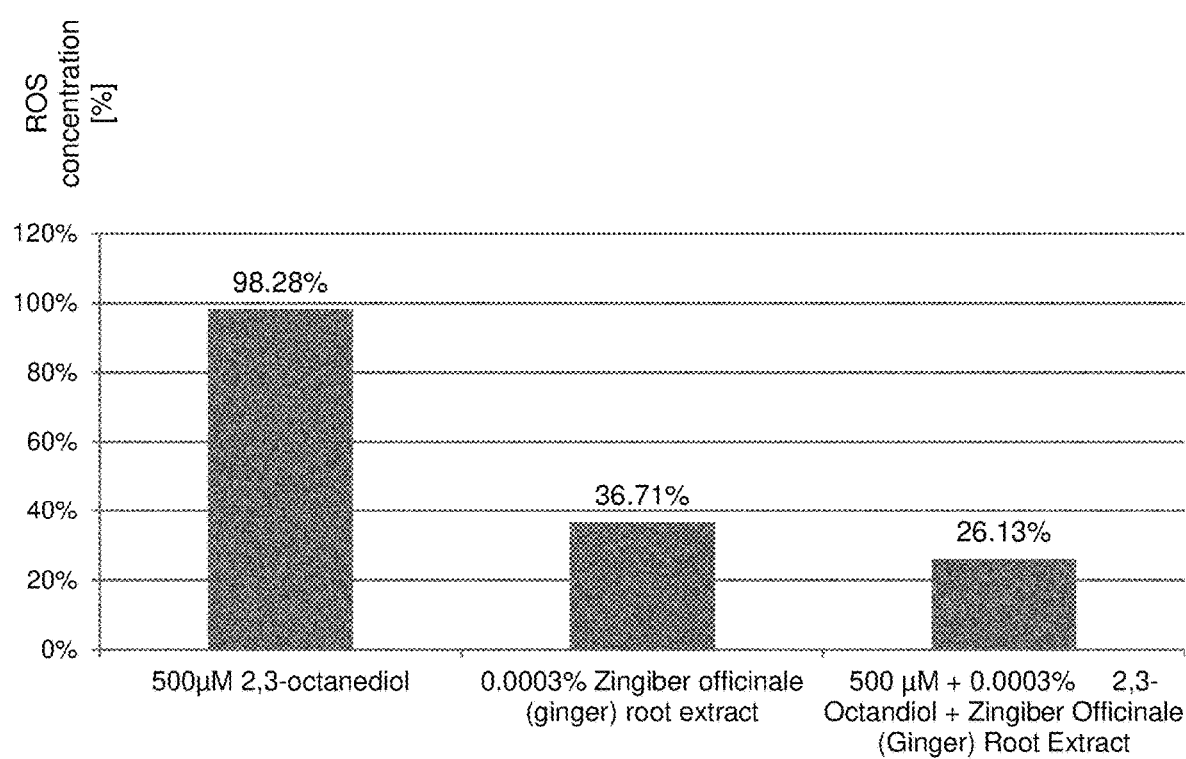
FIG. 10 is a diagram showing the ROS reducing capacity of *Zingiber Officinale* (Ginger) Root Extract, 2,3-octancediol, and a mixture thereof.
Figure 11:
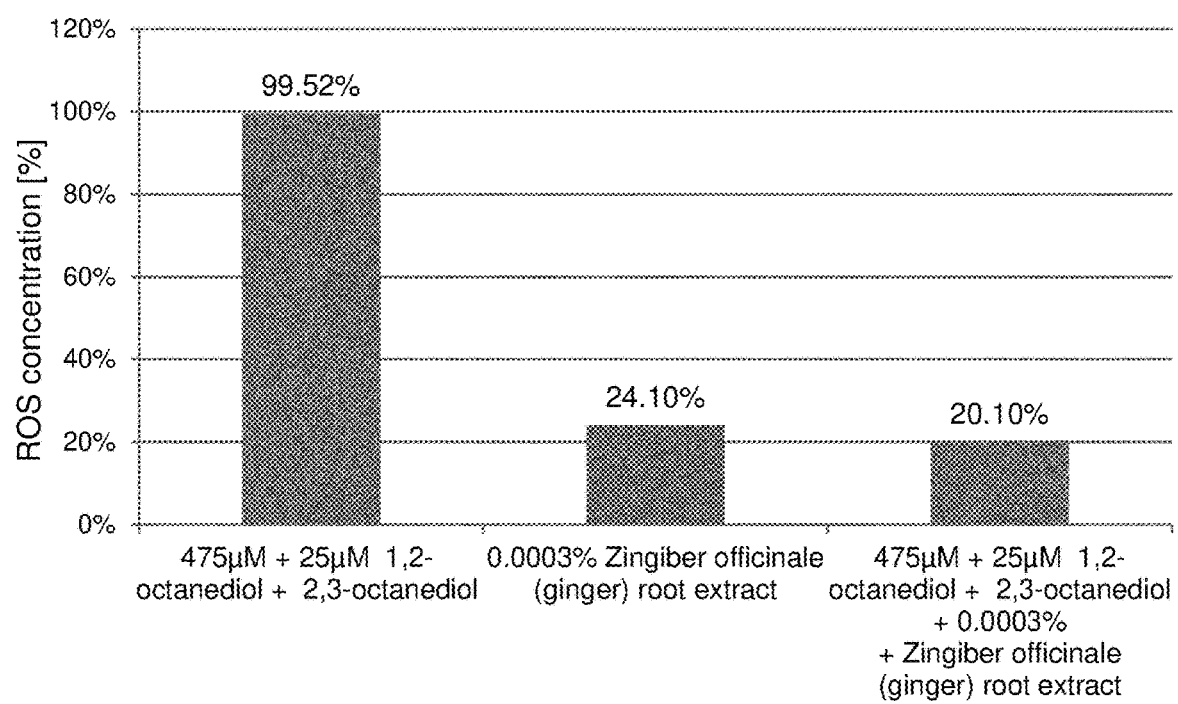
FIG. 11 is a diagram showing the ROS reducing capacity of *Zingiber Officinale* (Ginger) Root Extract, 1,2-octanediol plus 2,3-octancediol, and a mixture thereof.

The ROS concentration results from Table 31 are visualized in FIGS. 10 and 11.

2,3-Octanediol alone does not show a ROS reducing capacity, as the ROS value is with 98% not reduced. In contrast, it enhances the *Zingiber Officinale* (Ginger) Root (SymVital AgeRepair 3040) activity by 11%, as the ROS concentration is reduced from 37% to 26%, when 2,3-octanediol is added.

A similar effect is achieved, when a mixture of 1,2-octanediol and 2,3-octanediol is added to the *Zingiber Officinale* (Ginger) Root Extract.

Example 5: Interleukin 8 (IL-8) ELISA

Interleukin 8 (IL-8) is increased by various kinds of stress including UV and oxidant stress, which thereby cause the recruitment of inflammatory cells and induces further increase in oxidant stress mediators, making it a key parameter in localized inflammation.

An IL-8 ELISA (enzyme lined immunosorbance assay) was performed in order to determine IL-8 produced and secreted by cells from the cell supernatant utilizing antibodies detecting the IL-8.

Experimental procedure: HaCaT cells (spontaneously transformed aneuploid immortal keratinocyte cell line from adult human skin) were seeded in a black 96 well microplate with transparent bottom and incubated at 37° C. After 24 hours the supernatant is decanted and the test samples (100 μl/well) are added and incubated for 24 hours at 37° C. Then IL 1-alpha (1 ng/ml per 100 μl/well) was added as stimulant. Then the medium was changed (100 μl/well) and incubated at 37° C. After 4 h a 70 μl sample was recovered from the cell supernatant. Thereafter, an IL-8 ELISA is carried out with the cell supernatant sample.

The lower the IL-8 concentration the better the proinflammatory effect of the antioxidant of the sample.

Example 5.1: Retinol Plus 1,2-heptanediol

TABLE 32

| Compound | Concentration | IL-8 concentration (pg/ml) |
|---|---|---|
| 1,2-heptanediol | 500 μM | 959.85 |
| Retinol | 50 μM | 670.84 |
| Retinol + 1,2-heptanediol | 50 μM 500 μM | 608.62 |
| Stimulated control | | 876.58 |
| Unstimulated control | | 95.15 |

Figure 12:
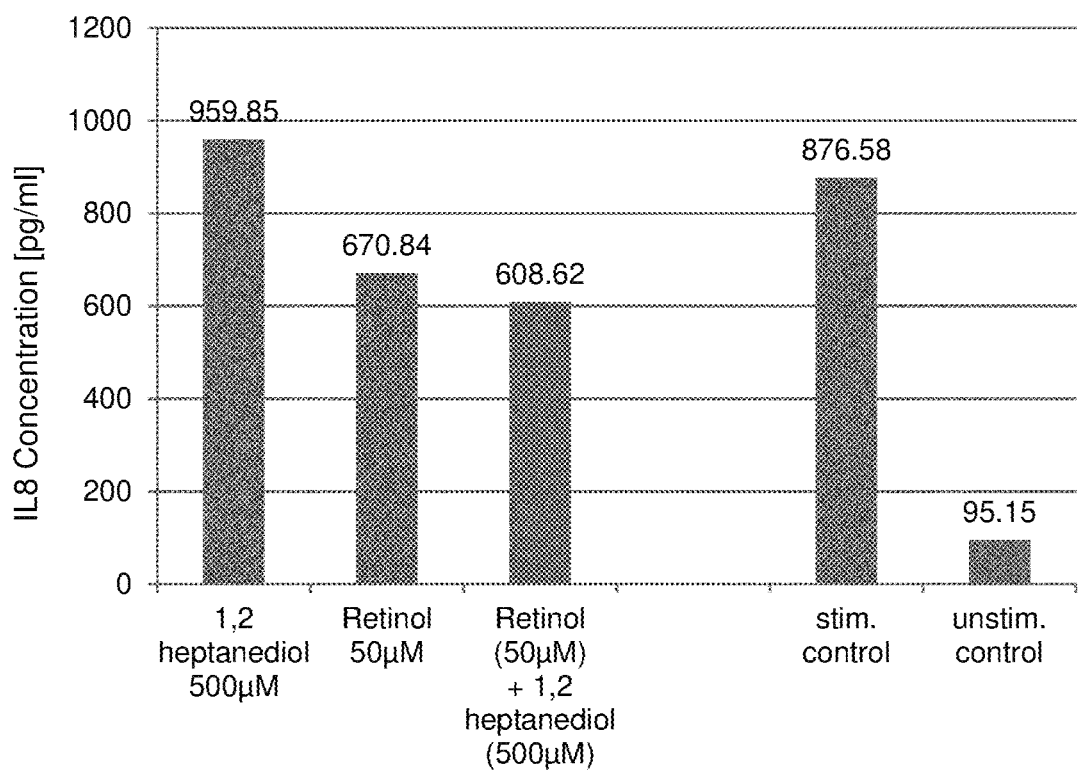
FIG. 12 is a diagram showing the IL-8 reducing capacity of 1,2-heptanediol, Retinol, and a mixture thereof.

The IL8 concentration results from Table 32 are visualized in FIG. 12.

1,2-heptanediol alone does not show a IL-8 reducing capacity, as the IL-8 concentration is with 959.8 not reduced in comparison to the stimulated control. In contrast, Retinol inhibits IL-8 secrection; 1,2-heptanediol enhances the Retinol activity by 9.25%, as the IL-8 value is reduced from 670.8 to 608.6.

Example 6: Solubility of Alkanediols in Water

For the determination of the maximum water solubility of an alkanediol. water and different concentrations of the respective alkanediol were blended by stirring. The assessment of solubility was carried out at ambient temperature after 24 h storage at 5° C. The determination of whether the alkanediol has dissolved in water is based entirely on visual observation. An alkanediol compound has dissolved if the mixture is clear and shows no signs of cloudiness or precipitation.

TABLE 33

| Tradename/ Chemical name | INCI | Maximum solubility in water (% by weight) |
|---|---|---|
| Hydrolite ® 5 green | Pentylene Glycol | 50 |
| Hydrolite ® 6 | Hexanediol | 50 |
| 1,2-heptanediol | Heptanediol | 2.5 |
| Hydrolite ® 8 | Caprylyl Glycol | 0.5 |
| SymDiol ® 68 | Hexanediol. Caprylyl Glycol | 1.0 |
| 1,2-nonanediol | Nonanediol | 0.1 |
| Sym Clariol ® | Decylene Glycol | — |
| 1,2-undecanediol | Undecanediol | — |
| 2,3-heptanediol | — | 3.6 |
| 2,3-octanediol | — | 1.5 |
| 2,3-nonanediol | — | 0.3 |
| 2,3-undecanediol | — | — |

Example 7: Formulation Examples

The following formulations according to the present invention were prepared:
  Skin Renewing Cream
  Anti-Aging Hand and Body cream
  Daily Anti-Wrinkle Face Cream; SPF 20
  Night Repair Cream WIG
  Body Lotion
  Body Lotion (sprayable)
  Aseptic wound cream
  Anti-Acne Balm
  Barrier Repair & Anti-Aging Cream
  Skin Soothing Lotion Baby Nappy Rash Cream (w/o)
Skin Lightening Day Cream (o/w)
After Shave Tonic
Antidandruff Hair Conditioner
Hair Conditioner, Leave On
Deodorant Stick
Antiperspirant Stick
Sunscreen Lotion (ow; broadband protection)
Sun Protection Soft Cream (w/o; SPF 40)
After Sun Lotion
Syndet Antimicrobial Soap Bar
Syndet Soap Bar
Antimicrobial Toilet Soap Bar
Shaving Foam
Skin Oil
Body, Face and Hair Care Oil
Beard Care
Solid Skin Care Concentrate
Solid Shampoo
Fresh Hair Shampoo
Hair Refresher Mist
Sensi-SCALP (Green Solid Shampoo)
Shampoo Sulfate Free In the following formulation examples the following five perfume oils PFO1 PFO2, PFO3, PFO4 or PFO5 were each used as fragrance.

TABLE 34

Composition of perfume oil 1; PO1 (amounts in % by weight)

| Ingredients | Amount |
|---|---|
| ALDEHYDE C14 SO-CALLED | 2 |
| ALLYL AMYL GLYCOLATE 10% DPG | 5 |
| ANISIC ALDEHYDE PURE | 5 |
| APPLE OLIFFAC TYPE | 10 |
| Benzylacetate | 50 |
| BERGAMOT IDENTOIL ® COLOURLESS | 15 |
| CANTHOXAL | 5 |
| CETALOX 10% IPM | 3 |
| CITRONELLOL 950 | 40 |
| DAMASCENONE TOTAL 1% DPG | 5 |
| DAMASCONE ALPHA 10% DPG | 5 |
| DAMASCONE DELTA 10% DPG | 2 |
| DIMETHYL BENZYL CARBINYL BUTYRATE | 2 |
| DIPROPYLENE GLYCOL | 178 |
| EBANOL | 2 |
| ETHYL DECADIENOATE TRANS CIS-2.4 10% IPM | 2 |
| FLOROSA | 5 |
| FRAMBINON ® 10% DPG | 7 |
| GALAXOLIDE 50% IN IPM | 100 |
| GALBEX TYPE BASE | 1 |
| GERANYL ACETATE PURE | 2 |
| HEDIONE | 30 |
| HELIOTROPIN | 10 |
| HEXENYL ACETATE CIS-3 10% DPG | 1 |
| HEXENYL SALICYLATE CIS-3 | 5 |
| HEXYL CINNAMIC ALDEHYDE ALPHA | 70 |
| HEXYL SALICYLATE | 50 |
| HYDROXY CITRONELLAL | 10 |
| ISO E SUPER | 15 |
| ISORALDEINE 70 | 20 |
| LEAFOVERT ® | 1 |
| LILIAL | 60 |
| LINALOOL | 60 |
| LINALYL ACETATE | 20 |
| LYRAL | 7 |
| MANZANATE | 2 |
| PHENOXANOL | 7 |
| PHENYLETHYL ALCOHOL | 120 |
| SANDAL MYSORE CORE | 2 |
| SANDRANOL ® | 7 |
| STYRALYL ACETATE | 3 |
| TAGETES RCO 10% TEC | 2 |

TABLE 34-continued

Composition of perfume oil 1; PO1 (amounts in % by weight)

| Ingredients | Amount |
|---|---|
| TERPINEOL PURE | 20 |
| TETRAHYDROGERANIOL 10% DPG | 5 |
| TONALIDE | 7 |
| VERTOCITRAL 10% DPG | 5 |
| VERTOFIX | 15 |
| Total: | 1000 |

TABLE 35

Composition of perfume oil 2; PO2 (amounts in % by weight)

| Ingredients | Amount |
|---|---|
| Acetophenone, 10% in DPG | 10 |
| n-Undecanal | 5 |
| Aldehyde C14 (peach aldehyde) | 15 |
| Allylamyl glycolate, 10% in DPG | 20 |
| Amyl salicylate | 25 |
| Benzyl acetate | 60 |
| Citronellol | 80 |
| d-Limonene | 50 |
| Decenol trans-9 | 15 |
| Dihydromyrcenol | 50 |
| Dimethylbenzylcarbinyl acetate | 30 |
| Diphenyloxide | 5 |
| Eucalyptol | 10 |
| Geraniol | 40 |
| Nerol | 20 |
| Geranium oil | 15 |
| Hexenol cis-3. 10% in DPG | 5 |
| Hexenyl salicylate cis-3 | 20 |
| Indole. 10% in DPG | 10 |
| Alpha-ionone | 15 |
| Beta-ionone | 5 |
| Lilial ® (2-methyl-3-(4-tert-butyl-phenyl)propanal) | 60 |
| Linalool | 40 |
| Methylphenyl acetate | 10 |
| Phenylethyl alcohol | 275 |
| Styrolyl acetate | 20 |
| Terpineol | 30 |
| Tetrahydrolinalool | 50 |
| Cinnamyl alcohol | 10 |
| Total: | 1000 |

TABLE 36

Composition of perfume oil 3; PO3 (amounts in % by weight)

| Ingredients | Amount |
|---|---|
| Benzyl acetate | 60 |
| Citronellyl acetate | 60 |
| Cyclamenaldehyde (2-methyl-3-(4-isopropyl-phenyl)propanal | 20 |
| Dipropylene glycol (DPG) | 60 |
| Ethyllinalool | 40 |
| Florol (2-isobutyl-4-methyltetrahydro-2H-pyran-4-ol) | 30 |
| Globanone ® [(E/Z)-8-cyclohexadecen-1-one] | 180 |
| Hedione ® (methyldihydrojasmonate) | 140 |
| Hexenyl salicylate. cis-3 | 10 |
| Vertocitral (2.4-dimethyl-3-cyclohexenecarboxaldehyde) | 5 |
| Hydratropaldehyde. 10% in DPG | 5 |
| Isodamascone (1-(2.4.4-trimethyl-2-cyclohexen-1-yl)-2-buten-1-one. 10% in DPG | 5 |
| Isomuscone (cyclohexadecanone) | 40 |
| Jacinthaflor (2-methyl-4-phenyl-1.3-dioxolane) | 10 |
| Cis-jasmone. 10% in DPG | 20 |
| Linalool | 50 |
| Linalyl acetate | 30 |

TABLE 36-continued

Composition of perfume oil 3; PO3 (amounts in % by weight)

| Ingredients | Amount |
|---|---|
| Methyl benzoate. 10% in DPG | 25 |
| para-Methyl cresol. 10% in DPG | 10 |
| Nerol | 20 |
| Phenylpropylaldehyde | 5 |
| 2-Phenylethyl alcohol | 82 |
| Tetrahydrogeraniol | 13 |
| 2.2-Dimethyl-3-cyclohexyl-1-propanol | 80 |
| Total: | 1000 |

TABLE 37

Composition of perfume oil 4; PO4 (amounts in % by weight)

| Ingredients | Amount |
|---|---|
| AMBRETTOLIDE (MACRO) | 10 |
| AMBROXIDE 10% in IPM | 10 |
| BENZYL ACETATE | 20 |
| BENZYL SALICYLATE | 15 |
| BERGAMOT OIL. bergapten-free | 60 |
| CALONE ® 1951 10% in DPG | 15 |
| COUMARIN | 5 |
| CYCLOGALBANATER 10% in DPG | 10 |
| ALPHA -DAMASCONE 1% in DPG | 20 |
| DIHYDROMYRCENOL | 10 |
| ETHYL LINALOOL | 75 |
| ETHYL LINALYLACETATE | 50 |
| ETHYL MALTOL 1% in DEP | 10 |
| ETHYLENE BRASSYLATE (MACRO) | 80 |
| FLOROSA | 40 |
| GERANYLACETATE | 10 |
| HEDIONE ® HC/30 | 35 |
| HEDIONE ® | 210 |
| HELIONAL ® | 15 |
| HELVETOLIDE ® (ALICYC) | 30 |
| HEXENYLSALICYLATE CIS-3 | 20 |
| ISO E SUPER ® | 40 |
| LEAFOVERT ® 10% in DEP | 10 |
| LILIAL ® | 80 |
| LYRAL ® | 20 |
| MANDARIN OIL | 10 |
| STYRALYL ACETATE | 5 |
| SYMROSE ® | 15 |
| VANILLIN 10% in DEP | 20 |
| DIPROPYLENE GLYCOL (DPG) | 50 |
| TOTAL: | 1000 |

TABLE 38

Composition of perfume oil 5; PO5 (amounts in % by weight)

| Ingredients | Amount |
|---|---|
| AMAROCITE ® | 10 |
| AMBROCENIDE ® 10% in DPG | 5 |
| AMBROXIDE | 15 |
| AURELIONE ® (7/8-Cyclohexadecenone) (MACRO) | 70 |
| BERGAMOT OIL. bergapten-free | 90 |
| CALONE ® 1951 10% in DPG | 20 |
| CARAWAY OIL | 10 |
| CITRAL | 20 |
| COUMARIN | 10 |
| ALPHA-DAMASCONE 1% in DPG | 15 |
| DIHYDROMYRCENOL | 70 |
| ESTRAGON OIL | 10 |
| ETHYL LINALOOL | 100 |
| ETHYL LINALYLACETATE | 90 |
| EUGENOL | 10 |
| EVERNYL ® | 5 |

TABLE 38-continued

Composition of perfume oil 5; PO5 (amounts in % by weight)

| Ingredients | Amount |
|---|---|
| FRUCTATE ® | 5 |
| GERANIUM OIL | 5 |
| HEDIONE ® HC/30 | 100 |
| HELIONAL ® | 10 |
| INDOLE 10% in DPG | 5 |
| ISO E SUPER ® | 100 |
| KEPHALIS ® | 5 |
| LAVENDER OIL | 40 |
| CITRUS OIL | 80 |
| LILIAL ® | 30 |
| MANDARIN OIL | 20 |
| MUSCENONE (MACRO) | 5 |
| SANDRANOL ® | 10 |
| VANILLIN 10% in DPG | 5 |
| DIPROPYLENE GLYCOL | 30 |
| TOTAL: | 1000 |

The above perfume oils PO1, PO2, PO3, PO4, or PO5 were incorporated into the formulations presented below.

Cosmetic formulations (compositions); amounts are indicated as % by weight for all formulations.

TABLE 39

Skin Renewing Cream

| Ingredients | INCI | Amount |
|---|---|---|
| Dracorin ® CE | Glyceryl Stearate Citrate | 1.0 |
| Lanette ® O | Cetearyl Alcohol | 2.0 |
| Cutina ® GMS-V | Glyceryl Stearate | 1.0 |
| Sodium Ascorbyl Phosphate | Sodium Ascorbyl Phosphate | 0.5 |
| Hydroxypinacolone Retinoate | Hydroxypinacolone Retinoate | 0.1 |
| Vitamin A | Retinol | 0.1 |
| SymRelief | Bisabolol, Zingiber Officinale (Ginger) Root Extract | 0.2 |
| Tegosoft ® MM | Myristyl Myristate | 1.0 |
| Tocopherol | Tocopherol | 0.5 |
| Hydrolite-6 | Hexanediol | 1.0 |
| Xiameter ® UMX-0246. Cyclosiloxane | Cyclohexasiloxane (and) Cyclopentasiloxane | 0.5 |
| Dragoxat ® 89 | Ethylhexyl Isononanoate | 2.0 |
| PCL-Liquid 100 | Cetearyl Ethylhexanoate | 4.0 |
| Neutral Oil | Caprylic/Capric Triglyceride | 4.0 |
| Carbopol ® Ultrez 21 | Acrylates/C10-30 Alkyl Acrylate Crosspolymer | 0.2 |
| Keltrol ® CG-T | Xanthan Gum | 0.1 |
| Water | Water (Aqua) | ad 100 |
| Dragosine | Carnosine | 0-1 |
| Glycerol 99.5 P. | Glycerol | 3.0 |
| 1.2-Propylene Glycol 99 P GC | Propylene Glycol | 2.0 |
| Sodium Benzoate | Sodium Benzoate | 0.1 |
| Sodium Hydroxide 10% solution | Sodium Hydroxide | 0.5 |
| Perfume oil PO1, PO2, PO3, PO4, or PO5 | Perfume | 0.3 |
| SymSave ® H | Hydroxyacetophenone | 0.5 |
| 1,2-heptanediol | 1,2-heptanediol | 1.0 |
| 2,3-heptanediol | 2,3-heptanediol | 0.02 |
| 1,2-octanediol | Caprylyl Glycol | 0.3 |
| 2,3-octanediol | 1,2-octanediol/2,3-octanediol | 0.05 |

TABLE 40

Anti Aging Hand and Body cream

| Ingredients | INCI | Amount |
|---|---|---|
| Dracorin ® GOC | Glyceryl Oleate Citrate, Caprylic/Capric Triglyceride | 2.0 |
| PCL-Solid | Stearyl Heptanoate, Stearyl Caprylate | 2.5 |
| Lanette ® O | Cetearyl Alcohol | 1.5 |
| Tocopherol | Tocopherol Acetate | 0.3 |
| SymVital ® AR 3040 | Zingiber Officinale (Ginger) Root Extract | 0.1 |
| Cutina ® GMS-V | Glyceryl Stearate | 1.0 |
| Dragoxat ® 89 | Ethylhexyl Isononanoate | 3.0 |
| PCL-Liquid 100 | Cetearyl Ethylhexanoate | 7.0 |
| Isodragol ® | Triisononanoin | 4.0 |
| Xiameter ® UMX-0345 Cyclosiloxane | Cyclopentasiloxane (and) Cyclohexasiloxane | 0.5 |
| Water | Water (Aqua) | ad 100 |
| Carbopol ® Ultrez 21 | Acrylates/C10-30 Alkyl Acrylate Crosspolymer | 0.2 |
| Keltrol ® CG-RD | Xanthan Gum | 0.1 |
| Glycerol 85 P. | Glycerol | 3.0 |
| DragoBetaGlucan | Water (Aqua). Butylene Glycol. Glycerol. Avena Sativa (Oat) Kernel Extract | 1.5 |
| Dragosine | Carnosine | 0.2 |
| Potassium Sorbate | Potassium Sorbate | 0.1 |
| Sodium Hydroxide 10% solution | Sodium Hydroxide | 0.5 |
| Perfume oil PO1, PO2, PO3, PO4, or PO5 | Perfume | 0.2 |
| Sym Save ® H | Hydroxyacetophenone | 0.3 |
| 1,2-heptanediol | 1,2-heptanediol | 1.0 |
| 2,3-heptanediol | 2,3-heptanediol | 1.0 |

TABLE 41

Daily Anti Wrinkle Face Cream (SPF 20)

| Ingredients | Amount |
|---|---|
| SymOcide PH | |
| Phenoxyethanol, Hydroxyacetophenone, Caprylyl Glycol, Water (Aqua) | 1 |
| Ascorbyl Palmitate | |
| Ascorbyl Palmitate | 0.1 |
| Biotive L-Arginine | |
| Arginine | 0.2 |
| Buriti oil | |
| Mauritia Flexuosa Fruit Oil | 1 |
| Cocoa butter | |
| Theobroma Cacao (Cocoa) Seed Butter | 2 |
| Dimethicone | |
| Dimethicone | 0.5 |
| Disodium EDTA | |
| Disodium EDTA | 0.1 |
| Dragosantol 100 | |
| Bisabolol | 0.1 |
| Dragoxat 89 | |
| Ethylhexyl Isononanoate | 5 |
| Emulsiphos | |
| Potassium Cetyl Phosphate, Hydrogenated Palm Glycerides | 2 |
| Extrapone Corail | |
| Glycerin, Aqua, Hydrolyzed Corallina Officinalis | 1 |
| Glycerin | |
| Glycerin | 3 |
| Isoadipate | |
| Diisopropyl Adipate | 5 |
| Jojoba Wax Flakes | |
| Hydrogenated Jojoba Oil | 1 |
| Keltrol CG-T | |
| Xanthan Gum | 0.1 |
| Lanette O | |
| Cetearyl Alcohol | 5 |
| Vitamin E | |
| Tocopherol | 0.2 |
| Lanette 16 | |
| Cetyl Alcohol | 1 |
| Lanette 22 | |
| Behenyl Alcohol | 1 |
| Neo Heliopan 357 | |
| Butyl Methoxydibenzoylmethane | 3 |
| Neo Heliopan HMS | |
| Homosalate | 10 |
| Neo Heliopan Hydro | |
| used as a 25% aq. Solution neutralized by arginine Phenylbenzimidazole Sulfonic Acid | 8 |
| Neo Heliopan OS | |
| Ethylhexyl Salicylate | 5 |
| Orgasol Caresse | |
| Polyamide-5 | 1 |
| Perfume oil PO1, PO2, PO3, PO4, or PO5 | 0.1 |
| Shea butter | |
| Butyrospermum Parkii (Shea) Butter | 3 |
| Simugel EG | |
| Sodium Acrylate/Sodium Acryloyldimethyl Taurate Copolymer, Isohexadecane, Polysorbate 80 | 1 |
| SymFinity 1298 | |
| Echinacea Purpurea Extract | 0.1 |
| SymMatrix | |
| Maltodextrin. Rubus Fructicosus (Blackberry) Leaf Extract | 0.1 |
| SymSitive 1609 | |
| Pentylene Glycol, 4-t-Butylcyclohexanol | 1 |
| Tegosoft TN | |
| C12-15 Alkyl Benzoate | 4 |
| Hydrolite-8 (Caprylyl Glycol) | 0.5 |
| 1,2-heptanediol/2,3-heptanediol blend (95:5 w/w %) | 1.0 |
| Water | |
| Aqua | ad 100 |

TABLE 42

Night Repair Cream m W/O

| Ingredients | INCI | Amount |
|---|---|---|
| 1,2-heptanediol | 1,2-heptanediol | 3.0 |
| 2,3-heptanediol | 2,3-heptanediol | 0.1 |
| 2,3-octanediol | 2,3-octanediol | 0.5 |
| Aloe Vera Gel Concentrate 10/1 * | Water (Aqua), Aloe Barbadensis Leaf Juice | 3.0 |
| Alugel 34 TH | Aluminium Stearate | 1.0 |
| Dragosan W/O P* | Sorbitan Isostearate, Hydrogenated Castor Oil, Ceresin, Beeswax (Cera Alba) | 6.0 |
| Dragosantol ® 100* | Bisabolol | 0.2 |
| Extrapone ® Witch Hazel Distillate colourless | Propylene Glycol, Hamamelis Virginiana (Witch Hazel) Water, Water (Aqua), Hamamelis Virginiana (Witch Hazel) Extract | 1.0 |
| Perfume oil PO1, PO2, PO3, PO4, or PO5 | Perfume | 0.4 |
| Glycerol 85 % | Glycerin | 2.0 |
| Karion F | Sorbitol | 2.0 |
| Magnesium Chloride | Magnesium Chloride | 0.7 |
| Isoadipate | Diisoadipate | 2.0 |
| PCL Liquid 100 | Cetearyl Ethylhexoate | 12.0 |
| Retinyl Palmitate in Oil | Retinyl Palmitate | 0.05 |
| Hydroxypinacolone Retinoate | Hydroxypinacolone Retinoate | 0.05 |
| Sun Flower Oil | Helianthus Annuus (Sunflower) Seed Oil | 5.0 |
| Sweet Almond Oil | Prunus dulcis | 5.0 |
| SymMatrix ® | Maltodextrin, Rubus Fruticosus (Blackberry) Leaf Extract | 1.0 |
| SymOcide PS | Phenoxyethanol, Decylene glycol, 1,2-Hexanediol | 1.0 |
| SymVital ® AgeRepair | Zingiber Officinale (Ginger) Root Extract | 0.1 |
| Vitamin E | Tocopherol | 3.0 |
| Water (demineralized) | Water (Aqua) | ad 100 |

TABLE 43

Moisturizing Body lotion

| Ingredients | Amount |
|---|---|
| Cetearyl Alcohol | 2.0 |
| Ethylhexyl Isononanoate | 5.0 |
| Tocopherylacetate | 0.3 |
| Cetearyl Ethylhexanoate, Isopropyl Myristate | 3.0 |
| Glyceryl Oleate Citrate, Caprylic/Capric Triglyceride | 4.0 |
| Water (Aqua) | ad 100 |
| Carbomer | 0.3 |
| Sodium Benzoate | 0.1 |
| Urea | 3.0 |
| Propylene Glycol | 5.0 |
| Sodium Hydroxide 30% aqueous solution | 0.3 |
| Perfume oil PO1, PO2, PO3, PO4, or PO5 | 0.3 |
| SymSave H (Hydroxyacetophenone) | 0.3 |
| 1,2-heptanediol | 0.2 |
| 2,3-octanediol | 0.2 |

TABLE 44

Calming Body lotion (sprayable)

| Ingredients | INCI | Amount |
|---|---|---|
| 1,2-heptanediol/ 2,3-heptanediol blend (95:5 w/w %) | 1,2-heptanediol/ 2,3-heptanediol blend (95:5 w/w %) | 1.5 |
| Potassium Sorbate | Potassium Sorbate | 0.2 |
| Dow Corning 345 Fluid | Cyclomethicone | 0.5 |
| Dracorin ® GOC | Glyceryl Oleate Citrate, Caprylic/Capric Triglyceride | 2.0 |
| Drago-Calm | Water, Glycerin, Avena Sativa (Oat) Kernel Extract | 1.0 |
| Dragosantol ® 100* | Bisabolol | 0.1 |
| Perfume oil PO1, PO2, PO3, PO4, or PO5 | Perfume | 0.3 |
| Hydrolite ®-5 | Pentylene Glycol | 5.0 |
| Neutral Oil | Caprylic/Capric Triglyceride | 4.0 |
| Paraffin Oil | Mineral Oil | 4.0 |
| PCL Liquid 100 | Cetearyl Ethylhexoate | 7.0 |
| Pemulen TR-2 | Acrylates/C10-30 Alkyl Acrylate Crosspolymer | 0.2 |
| Sodium Hydroxide (10% sol.) | Sodium Hydroxide | 0.4 |
| SymDeo ® MPP | Dimethyl Phenylbutanol | 0.5 |
| SymCalmin ® | Butylene Glycol, Pentylene Glycol, Hydroxyphenyl Propamidobenzoic acid | 2.0 |
| SymRelief ® 100 | Bisabolol, Zingiber Officinale (Ginger) Root Extract | 0.1 |
| Water (demineralized) | Water (Aqua) | ad 100 |

TABLE 45

Aseptic wound cream

| Ingredients | Amount |
|---|---|
| Sorbitan Isostearate, Hydrogenated Castor Oil, Ceresin, Beeswax (Cera Alba) | 6.0 |
| Petrolatum | 21.0 |
| Bisabolol | 0.2 |
| Cera Alba | 5.0 |
| Cetearyl Alcohol | 7.0 |
| Cocos Nucifera (Coconut) Oil | 7.0 |
| Lanolin | 5.0 |
| Paraffinum Liquidum | 12.0 |
| Perfume oil PO1, PO2, PO3, PO4, or PO5 | 0.3 |
| Water (Aqua) | ad 100 |
| Panthenol | 7.0 |
| Magnesium Sulfate | 0.7 |
| Pentylene Glycol | 1.0 |
| Tocopheryl Acetate | 1.0 |
| Octenidine dihydrochloride | 0.1 |
| Phenoxyethanol | 0.5 |
| 1,2-heptanediol | 0.4 |
| 2,3-heptanediol | 0.01 |

TABLE 46

Anti Acne Balm

| Ingredients | INCI | Amount |
|---|---|---|
| 1,2-heptanediol/ 1,2-octanediol blend (1:1 w/w %) | 1,2-heptanediol/ 1,2-octanediol blend (1:1 w/w %) | 3.0 |
| SymClariol | Decylene Glycol | 0.2 |
| Vitamin E | Tocopherol | |
| Abil 350 | Dimethicone | 1.0 |
| Allantoin | Allantoin | 0.1 |
| Aloe Vera Gel Concentrate 10/1 * | Water (Aqua), Aloe Barbadensis Leaf Juice | 3.0 |
| Azelaic Acid | Azelaic Acid | 5.0 |
| Cetiol OE | Dicaprylyl Ether | 4.0 |
| Cetiol SB 45 | Butyrospermum Parkii (Shea Butter) | 1.0 |

TABLE 46-continued

Anti Acne Balm

| Ingredients | INCI | Amount |
|---|---|---|
| D-Panthenol | Panthenol | 1.0 |
| Emulsiphos ® | Potassium Cetyl Phosphate. Hydrogenated Palm Glycerides | 2.0 |
| Perfume oil PO1, PO2, PO3, PO4, or PO5 | Perfume | 0.2 |
| Frescolat ®ML cryst. | Menthyl Lactate | 0.8 |
| Glycerol 85% | Glycerin | 4.0 |
| Hydroviton ® PLUS | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium hyaluronate, Glucose | 1.0 |
| Lara Care A-200 | Galactoarabinan | 0.3 |
| Pemulen TR-2 | Acrylates/C10-30 Alkyl Acrylate Crosspolymer | 0.2 |
| Sodium Hydroxide (10% sol.) | Sodium Hydroxide | 0.4 |
| SymOcide PH | Hydroxyacetophenone, Phenoxyethanol, Caprylyl glycol, Aqua | 1.0 |
| Tegosoft TN | C12-15 Alkyl Benzoate | 5.0 |
| Tocopherol Acetate | Tocopheryl Acetate | 0.5 |
| Water (demineralized) | Water (Aqua) | ad 100 |

TABLE 47

Barrier Repair & Anti Aging Cream

| Ingredients | INCI | Amount |
|---|---|---|
| 2,3-octanediol | 2,3-octanediol | 0.5 |
| 1,2-heptanediol/ 2,3-heptanediol blend (95:5 w/w %) | 1,2-heptanediol/ 2,3-heptanediol blend (95:5 w/w %) | 0.5 |
| Abil 350 | Dimethicone | 0.5 |
| Allantoin | Allantoin | 0.25 |
| Dracorin ® CE | Glyceryl Stearate Citrate | 1.5 |
| Dragoxat ® 89 | Ethylhexylisononanoate | 2.0 |
| Emulsiphos ® | Potassium Cetyl Phosphate, Hydrogenated Palm Glycerides | 2.0 |
| Extrapone ® Rosemary GW | Glycerin, Water (Aqua), Rosmarinus officinalis (Rosemary) Leaf Extract | 0.5 |
| Perfume oil PO1, PO2, PO3, PO4, or PO5 | Perfume | 0.1 |
| Glycerol 85% | Glycerin | 3.0 |
| Dragosine | Carnosine | |
| Glyceryl Stearate | Glyceryl Stearate | 2.0 |
| Hydroviton ® 24 | Water, Glycerin, Sodium Lactate, TEA Lactate, Serine, Lactic Acid, Urea, Sorbitol, Sodium Chloride, Lauryl Diethylenediaminoglycine, Lauryl Aminopropylglycine. Allantoin | 1.0 |
| Isodragol ® | Triisononanoin | 3.0 |
| Lanette O | Cetearyl Alcohol | 2.0 |
| NaOH 10% sol. | Sodium Hydroxide | 0.3 |
| Neutral Oil | Caprylic/Capric Triglyceride | 10.0 |
| SymCalmin ® | Pentylene Glycol, Butylene Glycol, Hydroxyphenyl Propamidobenzoic Acid | 1.0 |
| SymRepair ® 100 | Hexyldecanol, Bisabolol, Cetylhydroxyproline Palmitamide, Stearic Acid, Brassica Campestris (Rapeseed) Sterols | 2.0 |
| Vitamin E | Tocopherol | 0.3 |
| Sym Triol | Caprylyl glycol, 1,2-Hexanediol, Methylbenzyl alcohol | 1.0 |

TABLE 47-continued

Barrier Repair & Anti Aging Cream

| Ingredients | INCI | Amount |
|---|---|---|
| Tegosoft PC 31 | Polyglyceryl 3-Caprate | 0.3 |
| Tocopherol Acetate | Tocopheryl Acetate | 0.3 |
| Water (demineralized) | Water (Aqua) | ad 100 |

TABLE 48

Skin Soothing Lotion

| Ingredients | INCI | Amount |
|---|---|---|
| 2,3-heptanediol | 2,3-heptanediol | 0.5 |
| 2,3-octanediol | 2,3-octanediol | 0.5 |
| Abil 350 | Dimethicone | 2.0 |
| Allantoin | Allantoin | 0.2 |
| Carbopol Ultrez-10 | Carbomer | 0.1 |
| Ceramide BIO* | Cetylhydroxyproline Palmitamide | 0.1 |
| Citric Acid 10% sol. | Citric Acid | 0.4 |
| Emulsiphos ® | Potassium Cetyl Phosphate, Hydrogenated Palm Glycerides | 2.0 |
| Extrapone ® Green Tea GW | Glycerin, Water (Aqua), Camellia Sinensis Leaf Extract | 0.2 |
| Extrapone ® Rosemary GW | Glycerin, Water (Aqua), Rosmarinus officinalis (Rosemary) Leaf Extract | 0.3 |
| Perfume oil PO1, PO2, PO3, PO4, or PO5 | Perfume | 0.3 |
| Glycerol 85 % | Glycerin | 2.0 |
| Glyceryl Stearate | Glyceryl Stearate | 2.0 |
| Isodragol ® | Triisononanoin | 2.0 |
| Keltrol RD | Xanthan Gum | 0.1 |
| Lanette O | Cetearyl Alcohol | 3.0 |
| Neo PCL wssl. N | Trideceth-9. PEG-5 Ethylhexanoate. Water | 1.0 |
| PCL Liquid 100 | Cetearyl Ethylhexanoate | 5.0 |
| Vitamin E | Tocopherol | 0.3 |
| PCL Solid | Stearyl Heptanoate. Stearyl Caprylate | 2.0 |
| Propylene Glycol | Propylene Glycol | 5.0 |
| Sodium Hydroxide (10% sol.) | Sodium Hydroxide | 0.3 |
| SymCalmin ® | Pentylene Glycol, Butylene Glycol, Hydroxyphenyl Propamidobenzoic Acid | 2.0 |
| SymMatrix ® | Maltodextrin, Rubus Fruticosus (Blackberry) Leaf Extract | 0.1 |
| SymSave H | Hydroxyacetophenone | 0.4 |
| 2-Phenoxyethyl Alcohol | Phenoxyethanol | 0.4 |
| SymSitive ®1609 | Pentylene Glycol, 4-t-Butylcyclohexanol | 1.5 |
| Water (demineralized) | Water (Aqua) | ad 100 |

TABLE 49

Baby nappy rash cream W/O

| Ingredients | Amount |
|---|---|
| SymOcide PH | |
| Phenoxyethanol, Hydroxyacetophenone, Caprylyl Glycol, Water (Aqua) | 1 |
| Cupuaçu butter | |
| Theobroma Grandiflorum Seed Butter | 1 |
| Cutina HR Powder | |
| Hydrogenated Castor Oil | 1.5 |
| Dehymuls PGPH | |
| Polyglyceryl-2 Dipolyhydroxystearate | 5 |

TABLE 49-continued

Baby nappy rash cream W/O

| Ingredients | Amount |
|---|---|
| Glycerin | |
| Glycerin | 5 |
| Jojoba oil | |
| Simmondsia Chinensis (Jojoba) Seed Oil | 5 |
| Magnesium Sulfate Hepta Hydrate | |
| Magnesium Sulfate | 0.5 |
| Monomuls 90-O18 | |
| Glyceryl Oleate | 1 |
| Neutral oil | |
| Caprylic/capric triglyceride | 8 |
| Vitamin E | |
| Tocopherol | 0.5 |
| SymDecanox HA | |
| Caprylic/Capric Triglyceride, Hydroxymethoxyphenyl Decanone | 2 |
| PCL Liquid 100 | |
| Cetearyl Ethylhexanoate | 5 |
| SymCalmin | |
| Butylene Glycol. Pentylene Glycol. Hydroxyphenyl Propamidobenzoic Acid | 1 |
| Tamanu oil | |
| Calophyllum Inophyllum Seed Oil | 0.2 |
| Tetrasodium EDTA | |
| Tetrasodium EDTA | 0.1 |
| Titan dioxide | |
| Titan dioxide | 4 |
| Water | |
| Aqua | ad 100 |
| Wheat germ oil | |
| Triticum Vulgare (Wheat) Germ Oil | 2 |
| Zinc oxide | |
| Zinc oxide | 10 |
| 1,2-heptanediol | 1.0 |

TABLE 50

Skin Lightening Day Cream O/W

| Ingredients | INCI | Amount |
|---|---|---|
| 1,2-heptanediol/2,3-heptanediol blend (95:5 w/w %) | 1,2-heptanediol/2,3-heptanediol blend (95:5 w/w %) | 3.0 |
| Abil 350 | Dimethicone | 0.5 |
| Dracorin ® CE | Glyceryl Stearate Citrate | 2.5 |
| Dracorin ® GOC | Glyceryl Oleate Citrate, Caprylic/Capric Triglyceride | 0.5 |
| Drago-Beta-Glucan | Water (Aqua), Butylene Glycol, Glycerin, Avena Sativa (Oat), Kernel Extract | 0.3 |
| Dragosantol ® 100* | Bisabolol | 0.2 |
| Hydroxypinacolone Retinoate | Hydroxypinacolone Retinoate | 0.1 |
| Perfume oil PO1, PO2, PO3, PO4, or PO5 | Perfume | 0.1 |
| Frescolat ®MGA | Menthone Glycerol Acetal | 0.5 |
| Glycerol 85% | Glycerin | 3.0 |
| Isopropyl Palmitate | Isopropyl Palmitate | 4.0 |
| Keltrol RD | Xanthan Gum | 0.2 |
| Lanette 16 | Cetyl Alcohol | 1.0 |
| Neo Heliopan ® AV | Ethylhexyl Methoxycinnamate | 5.0 |
| Vitamin E | Tocopherol | 0.3 |
| Neutral Oil | Caprylic/Capric Triglyceride | 6.0 |
| Isoadipate | Diisopropyl Adipate | 3.0 |
| PCL Liquid 100 | Cetearyl Ethylhexoate | 3.0 |
| Sodium Benzoate | Sodium Benzoate | 0.1 |
| Symdiol ®68T | 1,2-Hexanediol, Caprylyl-glycol, Tropolone | 0.5 |
| SymVital ® AgeRepair | Zingiber Officinale (Ginger) Root Extract | 0.1 |
| SymWhite ®377 | Phenylethylresorcinol | 0.5 |
| Water (demineralized) | Water (Aqua) | ad 100 |

TABLE 51

After Shave Tonic

| Ingredients | INCI | Amount |
|---|---|---|
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, SodiumOleate. Sodium Sulfate | 3.0 |
| SymSitive ® 1609 | Pentylene Glycol, 4-t-Butylcyclohexanol | 1.0 |
| SymRelief 100 | Bisabolol, Zingiber Officinalis (Ginger) Root Extract | 0.3 |
| Glycerol 99.5 P. | Glycerol | 5.0 |
| Water | Water (Aqua) | ad 100 |
| Extrapone ® Glacier Water GW | Glycerol, Water (Aqua) | 1.0 |
| Sym Calmin ® | Butylene Glycol, Pentylene Glycol, Hydroxyphenyl Propamidobenzoic Acid | 0.5 |
| Dragosine ® | Carnosine | 0.1 |
| Hydrolite ® 5 | Pentylene Glycol | 5.0 |
| Ethanol 96% | Alcohol | 5.0 |
| Colour Pigment | Colour Pigment | 0.05 |
| Perfume oil PO1, PO2, PO3, PO4, or PO5 | Perfume | 0.15 |
| 1,2-octanediol/2,3-octanediol blend (99:1) | 1,2-octanediol/2,3-octanediol blend (99:1) | 0.5 |

TABLE 52

Anti-dandruff Hair Conditioner

| Ingredients | INCI | Amount |
|---|---|---|
| Lanette ® O | Cetearyl Alcohol | 4.0 |
| Dragoxat 89 | Ethylhexyl Isononanoate | 2.0 |
| Genamin ® KDM-P | Behentrimonium Chloride | 1.0 |
| SF 1550 | Phenyl Trimethicone | 0.1 |
| Neo Heliopan ® BB | Benzophenone-3 | 0.1 |
| Crinipan ® AD | Climbazole | 0.4 |
| Crinipan ® PMC Green | Propanediol Caprylate | 1.0 |
| Glycerol 99.5 P. | Glycerol | 6.0 |
| Sym Control Scalp | Water (Aqua), Glycerin, Mannitol, Tetraselmis Suecica Extract | 1.0 |
| Water | Water (Aqua) | ad 100 |
| Extrapone ® Bamboo P | Propylene Glycol, Water (Aqua), Butylene Glycol, Bambusa Vulgaris Shoot Extract | 0.5 |

TABLE 52-continued

Anti-dandruff Hair Conditioner

| Ingredients | INCI | Amount |
|---|---|---|
| Sodium Hydroxide 10% solution | Sodium Hydroxide | 0.4 |
| Colour I | Colour | 0.6 |
| Colour II | Colour | 0.3 |
| Perfume oil PO1, PO2, PO3, PO4, or PO5 | Perfume | 0.4 |
| Preservative | Methylparaben | 0.3 |
| 2,3-heptanediol | 2,3-heptanediol | 0.3 |
| 2,3-octanediol | 2,3-octanediol | 0.3 |

TABLE 53

Hair Conditioner, Leave on

| Ingredients | INCI | Amount |
|---|---|---|
| 1,2-heptanediol/2,3-heptanediol blend (95:5 w/w %) | 1,2-heptanediol/2,3-heptanediol blend (95:5 w/w %) | 1.0 |
| Dehyquart A CA | Cetrimonium Chloride | 0.2 |
| Dehyquart SP | Quaternium-52 | 2.0 |
| Dracorin ® CE | Glyceryl Stearate Citrate | 1.0 |
| Drago-Calm | Water, Glycerin, Avena Sativa (Oat) Kernel Extract | 2.0 |
| Farnesol | Farnesol | |
| Perfume oil PO1, PO2, PO3, PO4, or PO5 | Perfume | 0.5 |
| Lara Care A-200 | Galactoarabinan | 0.1 |
| Polymer JR 400 | Polyquaternium-10 | 0.1 |
| Propylene Glycol | Propylene Glycol | 0.8 |
| Neo Actipone Organic Green Tea | Maltodextrin, Camellia Sinensis Leaf Extract | 1.0 |
| SymMollient ® WS | Trideceth-9, PEG-5 Isononanoate, Water | 1.0 |
| SymSol ®PF3 * | Water, Pentylene Glycol, Sodium Lauryl Sulfoacetate, Sodium Oleoyl Sarcosinate, Sodium Chloride, Disodium Sulfoacetate, Sodium Oleate, Sodium Sulfate | 1.5 |
| SymSave ® H | Hydroxyacetophenone | 0.2 |
| Sym Triol ® | Caprylyl Glycol, 1,2-Hexanediol, Methylbenzyl Alcohol | 1.0 |
| Water (demineralized) | Water (Aqua) | ad 100 |

TABLE 54

Deodorant Stick

| Ingredients | Amount |
|---|---|
| Sodium stearate | 8.0 |
| PPG-3 Myristyl ether | 70.0 |
| 1,2-propylene glycol | 10.0 |
| 1,1-dimethyl-3-phenylpropanol | 0.2 |
| 2-butyloctanoic acid | 0.2 |
| Perfume oil PO1, PO2, PO3, PO4, or PO5 | 0.6 |
| Magnesium Ascorbyl Phosphate | 0.5 |
| Water | ad 100 |
| SymDeo Plus (Jasmol (2-benzlheptanol), 1-Dodecanol (Lauryl Alcohol), 1.2-Decanediol (Decylene Glycol), 2-Phenoxyethyl Alcohol (Phenoxyethanol)) | 0.5 |
| 2,3-heptanediol | 0.1 |
| 2,3-octanediol | 0.1 |

TABLE 55

Antiperspirant Stick

| Ingredients | INCI | Amount |
|---|---|---|
| PCL Liquid 100 | Cetearyl ethylhexanonate | ad 100 |
| Silicone Fluid 345 | Cyclomethicone | 10.0 |
| CRODACOL C90 | Cetyl Alcohol | 8.0 |
| SYNCROWAX HGLC | C18-36 Triglyceride | 8.0 |
| CRODAMOL PTC | Pentaerythritol Tetracaprylate/Caprate | 5.0 |
| SYNCROWAX HRC | Tribehenin | 4.0 |
| VOLPO N5 | Oleth-5 | 1.0 |
| Vitamin E | Tocopherol | 0.3 |
| Titanium Dioxide | Titanium Dioxide | 1.0 |
| Rezal 36GP | Aluminium Tetrachlorohydrex GLY | 20.0 |
| Dry Flo C | Aluminium Starch Octenyl Succinate | 22.5 |
| Preservative | Phenoxyethanol | 0.8 |
| Perfume oil PO1, PO2, PO3, PO4, or PO5 | Perfume | 0.6 |
| 1,2-heptanediol/2,3-heptanediol blend (95:5 w/w %) | 1,2-heptanediol/2,3-heptanediol blend (95:5 w/w %) | 1.5 |

TABLE 56

Sunscreen Lotion (ow; broadband protection)

| Ingredients | INCI | Amount |
|---|---|---|
| 1,2-heptanediol | 1,2-heptanediol | 0.15 |
| 1,2-octanediol/2,3-octanediol blend (95:5 w/w %) | 1,2-octanediol/2,3-octanediol blend (95:5 w/w %) | 0.5 |
| Carbopol Ultrez-10 | Carbomer | 0.2 |
| Dow Corning 246 Fluid | Cyclohexasiloxane and Cyclopentasiloxane | 2.0 |
| Dragosantol ® 100* | Bisabolol | 0.3 |
| EDETA BD | Disodium EDTA | 0.1 |
| Emulsiphos | Potassium Cetyl Phosphate, Hydrogenated Palm Glycerides | 1.5 |
| Perfume oil PO1, PO2, PO3, PO4, or PO5 | Perfume | 0.4 |
| Frescolat ®MGA | Menthone Glycerol Acetal | 0.3 |
| Glycerol 85% | Glycerin | 4.7 |
| Dragosine | Carnosine | 0.2 |
| Keltrol RD | Xanthan Gum | 0.2 |
| Lanette O | Cetearyl Alcohol | 1.0 |
| Neo Heliopan ® 357 | Butyl Methoxy-dibenzoyl-methane | 1.0 |
| Neo Heliopan ® AP (10% as sodium salt) | Disodium Phenyl Dibenzimidazole Tetrasulfonate | 10.0 |
| Neo Heliopan ® AV | Ethylhexyl Methoxy-cinnamate | 3.0 |
| Neo Heliopan ® Hydro (15% as sodium salt) | Phenylbenz-imidazole Sulfonic Acid | 6.7 |
| Neo Heliopan ® MBC | 4-Methylbenzyl-idene Camphor | 1.5 |
| Neo Heliopan ® OS | Ethylhexyl Salicylate | 5.0 |
| Neutral Oil | Caprylic/Capric Triglyceride | 2.0 |
| SymMatrix ® | Maltodextrin. Rubus Fruticosus (Blackberry) Leaf Extract | 0.3 |
| SymOcide ® BHO | Hydroxyacetophenone. Benzyl alcohol. Caprylyl glycol. Aqua | |
| Tegosoft TN | C12-15 Alkyl Benzoate | 5.0 |
| Tocopherol Acetate | Tocopheryl Acetate | 0.5 |
| Triethanolamine. 99% | Triethanolamine | 0.5 |
| Water (demineralized) | Water (Aqua) | ad 100 |

TABLE 57

Sun Protection Soft Cream W/O; SPF 40

| Ingredients | INCI | Amount |
|---|---|---|
| Dehymuls PGPH | Polyglyceryl-2 dipolyhydroxystearate | 5.0 |
| Copherol 1250 | Tocopheryl acetate | 0.5 |
| Permulgin 3220 | Ozocerite | 0.5 |
| Zinc stearate | Zinc stearate | 0.5 |
| Tegosoft TN | C12-15 Alkyl benzoate | 10.0 |
| Neo Heliopan ® E1000 | Isoamyl-p-methoxycinnamate | 2.0 |
| Ubiquinone 10 | Ubiquinone-10 | 0,1 |
| Neo Heliopan ® 303 | Octocrylene | 5.0 |
| Neo Heliopan ® MBC | 4-Methylbenzylidene camphor | 3.0 |
| Zinc oxide. neutral | Zinc oxide | 5.0 |
| Water. Distilled | Water (aqua) | ad 100 |
| EDETA BD | Disodium EDTA | 0.1 |
| Glycerol | Glycerol | 4.0 |
| Magnesium sulfate | Magnesium sulfate | 0.5 |
| Perfume oil PO1, PO2, PO3, PO4, or PO5 | Perfume | 0.3 |
| Symdiol ® 68 | Hexanediol, Caprylylglycol | 0.5 |
| 1,2-heptanediol | 1,2-heptanediol | 0.15 |

TABLE 58

After sun balm

| Ingredients | INCI | Amount |
|---|---|---|
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | 3.0 |
| Glycerol 99.5 P. | Glycerol | 5.0 |
| Vitamin E | Tocopherol | 0.3 |
| Sunflower Oil | Helianthus Annuus (Sunflower) Oil | 1.0 |
| SymUrban ® | Benzylidene Dimethoxydimethylin danone | 0.1 |
| Water | Water (Aqua) | ad 100 |
| Pemulen ® TR-2 | Acrylates/C10-30 Alkyl Acrylate Crosspolymer | 1.0 |
| D-Panthenol 75 W | Panthenol | 0.5 |
| SymFinity ® 1298 | Echinacea Purpurea Extract | 0.1 |
| Extrapone ® Pearl GW | Water (Aqua), Glycerol, Hydrolyzed Pearl, Xanthan Gum | 1.0 |
| Tinogard TT | Pentaerythrityl Tetra-di-t-butyl Hydroxyhydrocinnamate | 0.1 |
| Sodium Hydroxide 10% solution | Sodium Hydroxide | 2.5 |
| Ethanol 96% | Alcohol | 15.0 |
| Perfume oil PO1, PO2, PO3, PO4, or PO5 | Perfume | 0.2 |
| SymOcide ® PS | Phenoxyethanol. 1.2-Hexanediol. Decyleneglycol | 0.8 |
| 1,2-heptanediol | 1,2-heptanediol | 0.15 |
| 2,3-octanediol | 2,3-octanediol | 0.05 |

TABLE 59

After Sun Lotion

| Ingredients | Amount |
|---|---|
| Acrylate/C10-30 alkylacrylate crosspolymer | 0.4 |
| Cetearylethyl hexanoate | 15.0 |
| Bisabolol | 0.2 |
| Helianthus Annuus (Sunflower) Oil | 0.3 |
| Tocopheryl acetate | 1.0 |
| Panthenol | 1.0 |
| Alcohol | 15.0 |
| Glycerol | 3.0 |
| Perfume oil PO1, PO2, PO3, PO4, or PO5 | 0.30 |
| 1,2-Hexanediol | 1.0 |
| 4-Hydroxyacetophenone | 0.3 |
| Pentylene glycol | 4.0 |
| Aqua dem. | ad 100 |
| Triethanolamine | 0.2 |
| 1,2-heptanediol | 0.2 |
| 2,3-octanediol | 0.1 |

TABLE 60

Syndet Antimicrobial Soap Bar

| Ingredients | INCI | Amount |
|---|---|---|
| Zetesap 813 A | Disodium Lauryl Sulfosuccinate, Sodium Lauryl Sulfate, Corn Starch, Cetearyl Alcohol, Paraffin, Titanium Dioxide | ad 100 |
| Amphotensid GB 2009 | Disodium Cocoamphodiacetate | 6.0 |
| Allantoin | Allantoin | 1.0 |
| Vitamin E | Tocopherol | 0.3 |
| Perfume oil PO1, PO2, PO3, PO4, or PO5 | Perfume | 1.0 |
| Tinogard DA | Dilauryl Thiodipropionate | 0.3 |
| SymOcide C | o-cymen-5-ol | 0.1 |
| 1,2-heptanediol/2,3-heptanediol blend (95:5 w/w %) | 1,2-heptanediol/2,3-heptanediol blend (95:5 w/w %) | 5.0 |

TABLE 61

Syndet Soap Bar

| Ingredients | INCI | Amount |
|---|---|---|
| Fenopon AC-78 | Sodium Cocoyl Isethionate | 20.0 |
| Natriumlaurylsulfoacetate | Sodium Lauryl Sulfoacetate | 16.0 |
| Paraffin | Paraffin | 19.0 |
| Wax. Microcrystalline | Microcrystalline Wax | 1.0 |
| Corn Starch | Corn Starch | 8.0 |
| Coconut oil | Coconut oil | 2.0 |
| Tocopherol | Tocopherol | 0.3 |
| Lauric acid diethanol amide | Lauramide DEA | 2.0 |
| Dextrin | Dextrin | 21.0 |
| Lactic acid. 88% | Lactic Acid | 1.0 |
| SymGuard CD | 3-Phenylpropanol, o-cymen-5-ol, Decylene glycol | 0.3 |
| Thymol | Thymol | 0.05 |
| Water | Water | ad 100 |
| Perfume oil PO1, PO2, PO3, PO4, or PO5 | Perfume | 1.0 |
| 1,2-heptanediol/2,3-heptanediol blend (95:5 w/w %) | 1,2-heptanediol/2,3-heptanediol blend (95:5 w/w %) | 3.0 |

TABLE 62

Antimicrobial Toilet Soap Bar

| Ingredients | Amount |
|---|---|
| Sodium soap from tallow | 60.0 |
| Sodium soap from palm oil | 27.0 |
| Glycerol | 2.0 |
| Sodium Chloride | 0.5 |
| 1-Hydroxyethane-1,1-diphosphonic acid, tetrasodium salt | 0.3 |
| Tocopherol | 0.1 |
| Pigment Yellow 1 | 0.02 |
| Water | ad 100 |

TABLE 62-continued

Antimicrobial Toilet Soap Bar

| Ingredients | Amount |
|---|---|
| Perfume oil PO1, PO2, PO3, PO4, or PO5 | 3.0 |
| Farnesol | 0.2 |
| 2,3-heptanediol | 1.0 |
| 2,3-octanediol | 1.0 |

TABLE 63

Shaving Foam

| Ingredients | Amount |
|---|---|
| Dem. Water | ad 100 |
| Triethanolamine | 4.0 |
| Edenor L2 SM (Stearinic acid. Palmitinic acid) (Cognis) | 5.3 |
| Laureth-23 | 3.0 |
| Stearylalcohol | 0.5 |
| Vitamin E | 0.2 |
| Tocopherol | |
| SymOcide BHO | 1.0 |
| (Hydroxacetophenone, Benzyl alcohol, Caprylyl glycol Water) | |
| 1,2-octanediol/2,3-octanediol blend (95:5 w/w %) | 0.3 |
| Sodium lauryl sulfate | 3.0 |
| Extrapone Seaweed (water, propylene glycol, potassium iodide, Fucus Vesiculosus Extract) | 1.0 |
| Dragosantol (Bisabolol, Farnesol) | 0.1 |
| Perfume oil PO1, PO2, PO3, PO4, or PO5 | 1.0 |
| Propane, butane 4.2 Bar | 4.0 |

TABLE 64

Skin Oil

| Ingredients | INCI | Amount |
|---|---|---|
| Neutral Oil | Caprylic Capric Triglyceride | ad 100 |
| Sunflower Oil | Helianthus Annuus (Sunflower) Seed Oil | 20.0 |
| PCL Liquid 100 | Cetearyl Ethylhexanoate | 15.0 |
| Dragosantol 100 | Bisabolol | 0.2 |
| Vitamin E Acetate | Tocopheryl Acetate | 0.3 |
| Perfume oil PO1, PO2, PO3, PO4, or PO5 | Perfume | 0.2 |
| 1,2-heptanediol/2,3-heptanediol blend (90:10 w/w %) | 1,2-heptanediol 2,3-heptanediol | 3.0 |

TABLE 65

Body, Face and Hair Care Oil

| Ingredients | INCI | Amount |
|---|---|---|
| Sweet Almond) Oil | Prunus Amygdalus Dulcis (Sweet Almond) Oil | 15.0 |
| Caprylic Capric Triglyceride | Caprylic Capric Triglyceride | ad 100 |
| Tegosoft OP | Ethylhexyl Palmitate | 14.0 |
| Covasilk 15 | Silica Dimethyl Silylate | 1.0 |
| Isoadipate | Diisopropyl Adipate | 20.0 |
| Dragosantol 100 | Bisabolol | 0.2 |
| Vitamin E Acetate | Tocopheryl Acetate | 0.3 |
| Perfume oil PO1, PO2, PO3, PO4, or PO5 | Perfume | 0.2 |
| 1,2-heptanediol | 1,2-heptanediol | 1.0 |
| 2,3-heptanediol | 2,3-heptanediol | 0.05 |

TABLE 66

Beard Care

| Ingredients | INCI | Amount |
|---|---|---|
| Eutanol G | Octyldodecanol | 16.0 |
| Gelling Agent GP-1 | Dibutyl Lauroyl Glutamide | 2.4 |
| Gelling Agent EB-21 | Dibutyl Ethylhexanoyl Glutamide | 1.6 |
| Jojoba Oil | Simmondsia Chinensis (Jojoba) Seed Oil | 10.0 |
| Sweet Almond Oil | Prunus Amygdalus Dulcis (Sweet Almond) Oil | ad 100 |
| SymClariol | Decylene Glycol | 0.1 |
| Dragoxat 89 | Ethylhexyl Isononanoate | 14.0 |
| Vitamin E Acetate | Tocopheryl Acetate | 0.3 |
| Perfume oil PO1, PO2, PO3, PO4, or PO5 | Perfume | 0.2 |
| SymMollient PDCC | Propanediol Caprylate Caprate | 10.0 |
| Symlite G8 | Glyceryl Caprylate | 0.5 |
| Hydrolite-5 | Pentylene Glycol | 0.5 |
| 1,2-heptanediol | 1,2-heptanediol | 1.5 |
| 2,3-heptanediol | 2,3-heptanediol | 0.05 |

TABLE 67

Solid Skin Care Concentrate

| Ingredients | INCI | Amount |
|---|---|---|
| Mango Butter | Mangifera Indica Seed Butter | ad 100 |
| Carnauba Wax | Copernicia Cerifera (Carnauba) Wax | 6.0 |
| Rice Bran Wax | Oryza Sativa (Rice) Bran Wax | 6.0 |
| Cannabis Sativa Seed Oil | Cannabis Sativa Seed Oil | 5.0 |
| Cacao Butter | Theobroma Cacao (Cocoa) Seed Butter | 5.0 |
| ImerCare Pharma 00T | Talc | 2.0 |
| Vitamin E | Tocoherol | 1.0 |
| SymReboot L 19 | Maltodextrin. *Lactobacillus Ferment* | 0.5 |
| Perfume oil PO1, PO2, PO3, PO4, or PO5 | Perfume | 0.2 |
| SymVital Age Repair 3040 | Zingiber Officinale (Ginegr) Root Extract | 0.2 |
| Sunflower Oil | Helianthus Annuus (Sunflower) Seed Oil | 20.0 |
| Symlite G8 | Glyceryl Caprylate | 0.5 |
| Argan Oil | Argania Spinosa Kernel Oil | 6.0 |
| 1,2-octanediol/2,3-octanediol blend (95:5 w/w %) | 1,2-octanediol/2,3-octanediol blend (95:5 w/w %) | 2.0 |
| 1,2-heptanediol | 1,2-heptanediol | 1.0 |

TABLE 68

Solid Shampoo

| Ingredients | INCI | Amount |
|---|---|---|
| Amisoft MS-11 | Sodium Myriostoyl Glutamate | ad 100 |
| Elfan AT 84 | Sodium Cocoyl Isethionate | 15.0 |
| ImerCare 02K-S | Kaolin | 18.8 |
| Hydrolite-5 Green | Pentylene Glycol | 1.0 |
| Cetiol SB45 | Bytyrrospermum Parkii Butter | 20.0 |
| Sym Decanox HA | Caprylic Capric Triglycerides Hydroxymethoxyphenyl Decanone | 2.0 |
| Water | Water (Aqua) | 15.0 |
| Perfume oil PO1, PO2, PO3, PO4, or PO5 | Perfume | 1.0 |
| 1,2-heptanediol/2,3-heptanediol blend (98:2 w/w %) | 1,2-heptanediol 2,3-heptanediol | 3.0 |

TABLE 69

Fresh Hair Shampoo

| Ingredients | INCI | Amount |
|---|---|---|
| Aqua | Aqua | ad 100 |
| EDTA B Powder | Disodium EDTA | 0.1 |
| Carbopol ® Aqua SF-1 Polymer | Acrylates copolymer | 11.0 |
| Texapon ® NSO UP | Sodium Laureth sulfate | 35.0 |
| Dehyton ® K | Cocamidopropyl betaine | 8.0 |
| Plantacare ® 2000 UP | Decyl Glucoside | 4.0 |
| Perfume oil PO1, PO2, PO3, PO4, or PO5 | Perfume | 1.0 |
| SymSave ® H | Hydroxyacetophenone | 0.5 |
| Hydrolite ® 6 | 1,2-Hexanediol | 1.0 |
| 1,2-heptanediol, 2,3-heptanediol (w/w % 95:5) | 1,2-heptanediol, 2,3-heptanediol | 0.5 |
| 1,2-heptandiol | 1,2-heptanediol | 0.5 |
| SymClariol ® | Decylene Glycol | 0.5 |
| SymLite ® G8 | Glyceryl Caprylate | 0.2 |
| Frescolat ® ML cryst | Menthyl Lactate | 1.0 |
| SymCalmin ® | Pentylene Glycol, Butylene Glycol, Hydroxyphenyl | 0.2 |
| SymControl Scalp | Water (Aqua), Glycerin, Mannitol, Tetraselmis Suecica Extract | 1.0 |
| Crinipan ® AD | Climbazole | 0.2 |
| Propylene Glycol | Propylene Glycol | 2.0 |
| SymHair ® Shield | Pentylene Glycol, Aqua, Glycerin, Triticum vulgare bran extract, 1,2-Hexanediol, Caprylyl | 1.0 |
| Sodium Hydroxide 10% solution | Aqua, Sodium hydroxide | 2.2 |
| Actipone ® Alpha-Pulp | Aqua, Butylene Glycol, Malic acid, Actinidia chinensis fruit extract, citrus aurantium dulcis juice, citrus paradise juice, pyrus malus juice | 0.2 |

TABLE 70

Hair Refresher Mist

| Ingredients | INCI | Amount |
|---|---|---|
| SymDeo ® Plus | Lauryl alcohol, Phenoxyethanol, 2-Benzyleptanol, Decylene Glycol | 0.5 |
| Perfume oil PO1, PO2, PO3, PO4, or PO5 | Perfume | 0.1 |
| Frescolat ® ML nat | Mentyl Lactate | 0.3 |
| Crinipan ® PMC green | Propanediol Caprylate | 0.3 |
| Solubilizer | PEG-40 Hydrogenated Castor oil, Trideceth-9, Propylene glycol, Aqua | 5.0 |
| SymCalmin ® | Pentylene Glycol, Butylene Glycol, Hydroxyphenyl Propamidobenzoic acid | 0.2 |
| Rutin | Rutin | 0.05 |
| SymControl ® Scalp | Water (Aqua), Glycerin, Mannitol, Tetraselmis Suecica Extract | 2.0 |
| 1,2-octanediol, 2,3-octanediol (w/w % 98:2) | 1,2-octanediol, 2,3-octanediol | 0.3 |
| 1,2-heptanediol, 2,3-heptanediol (w/w % 95:5) | 1,2-heptanediol, 2,3-heptanediol | 0.6 |
| Propylene Glycol | Propylene Glycol | 3.0 |
| Butylene Glycol | Butylene Glycol | 3.0 |
| Aqua | Aqua | ad 100 |
| Edeta ® BD | Disodium EDTA | 0.1 |
| Symdiol 68 T | Hexanediol, Caprylyl Glycol, Tropolone | 0.5 |
| Color | Color | 0.5 |
| Actipone ® Rosemary GW | Glycerin, Aqua, Rosmarinus officinalis leaf extract | 0.5 |

TABLE 71

Sensi-SCALP (Green Solid Shampoo)

| Ingredients | INCI | Amount |
|---|---|---|
| AMISOFT ® MS-11 | Sodium Myristoyl Glutamate | 30.0 |
| ELFAN ® AT 84 | Sodium Cocoyl Isethionate | 15.0 |
| ImerCare ® 02K-S | Kaolin | 18.8 |
| Hydrolite ® 5 green | Pentylene Glycol | 1.5 |
| 1,2-octanediol, 2,3-octanediol (w/w % 95:5) | 1,2-octanediol, 2,3-octanediol | 0.3 |
| 1,2-heptanediol, 2,3-heptanediol (w/w % 99:1) | 1,2-heptanediol, 2,3-heptanediol | 0.5 |
| Dragosantol ® 100 | Bisabolol | 0.1 |
| SymSave H | Hydroxyacetophenone | 0.3 |
| Aqua/Water | Aqua | ad 100 |
| SymDecanox ™ HA | Caprylic/Capric Triglyceride, Hydroxymethoxyphenyl decanone | 2.0 |
| Cetiol ® SB45 | Butyrospermum parkii butter | 13.0 |
| Extrapone ® Rooibus GW | Aqua, Glycerin, Aspalathus Linearis leaf extract | 1.0 |
| SymReboot ™ L19 | Maltodextrin, *Lactobacillus Ferment* | 0.5 |
| SymOleo ® Vita7 | Glycine soja oil, Gossypium herbaceum seed oil, mangifera idica seed butter, olea europaea fruitoil, persea gratissima oil, prunus amygdalus dulcis (sweet almond) oil, Theobroma cacao seed butter | 1.0 |
| Perfume oil PO1, PO2, PO3, PO4, or PO5 | Perfume | 1.2 |

TABLE 72

Shampoo Sulfate-Free

| Ingredients | EU INCI | Amount |
|---|---|---|
| Aqua/Water | Aqua | ad 100 |
| Akypo ® Foam RL 40 | Sodium Laureth-5 Carboxylate | 15.0 |
| Plantacare ® 2000 UP | Decyl Glucoside | 5.0 |
| EDTA NA2 | Disodium EDTA | 0.1 |
| SymOcide ® PH | Phenoxyethanol, Hydroxyacetophenone, Caprylyl Glycol, Aqua | 1.5 |
| Aqua/Water | Aqua | 10.0 |
| Novethix ™ L-10 Polymer | Acrylates/Beheneth-25 Methacrylate Copolymer | 7.0 |
| Dehyton ® PK 45 | Cocamidopropyl Betaine | 10.0 |
| 1,2-octanediol, 2,3-octanediol (w/w % 98:2) | 1,2-octanediol, 2,3-octanediol | 0.1 |
| 1,2-heptanediol, 2,3-heptanediol (w/w % 95:5) | 1,2-heptanediol, 2,3-heptanediol | 0.1 |
| SymDecanox DPG | Dipropylene Glycol, Hydroxymethoxyphenyl Decanone | 1.0 |
| SymMollient ® W/S | Trideceth-9, PEG-5 Isononanoate, Aqua | 0.5 |
| SymCalmin ® | Pentylene Glycol, Butylene Glycol, Hydroxyphenyl Propamidobenzoic acid | 1.0 |
| Antil ® 141 Liquid | Propylene Glycol, PEG-55 Proplyene Glycol Oleate | 2.0 |

TABLE 72-continued

Shampoo Sulfate-Free

| Ingredients | EU INCI | Amount |
|---|---|---|
| Acusol™ OP 301 | Styrene/Acrylates Copolymer | 1.0 |
| SymHair ® Restore | Glycerin, Triticum Vulgare Protein, Aqua | 1.0 |
| Perfume oil PO1, PO2, PO3, PO4, or PO5 | Perfume | 1.0 |

TABLE 73

Air freshener (A/F spray water based)

| No | Ingredients | Amount |
|---|---|---|
| 1 | Fragrance | 4 |
| 2 | Ethanol | 8 |
| 3 | PEG-40 Hydrogenated Castor Oil | 5 |
| 4 | 1,2-heptanediol | 1 |
| 5 | Hydroxyacetophenone | 0.3 |
| 6 | Aqua | add to 100 |

Colorless Liquid, pH Neutral

TABLE 74

All-purpose cleaner

| No | Ingredients | Amount |
|---|---|---|
| 1 | Fettalkoholethoxylat | 4 |
| 2 | Sulfonic acid, C 13-17-sec-Alkyl-, Sodium salt | 6.2 |
| 3 | 2-octyl-2H-isothiazol-3-one | 0.1 |
| 4 | Fragrance | 3.5 |
| 5 | Tocopherol | 0.1 |
| 6 | 1,2-heptanediol | 1 |
| 7 | Aqua | add to 100 |

Colorless Liquid, pH 7

TABLE 75

All-purpose cleaner

| No | Ingredients | Amount |
|---|---|---|
| 1 | Fettalkoholethoxylat | 4 |
| 2 | Sulfonic acid, C 13-17-sec-Alkyl-, Sodium salt | 6.2 |
| 3 | 2-octyl-2H-isothiazol-3-one | 0.1 |
| 4 | Fragrance | 3.5 |
| 5 | 2,3-octanediol | 0.1 |
| 6 | 1,2-heptanediol | 0.9 |
| 7 | Tocopherol | 0.2 |
| 8 | Aqua | add to 100 |

Colorless Liquid, pH 7

TABLE 76

All-purpose cleaner, alkaline

| No | Ingredients | Amount |
|---|---|---|
| 1 | Coco-Glycoside | 1 |
| 2 | Benzalkonium Chloride | 0.2 |
| 3 | Sodiumbicarbonat | 0.1 |
| 4 | Tri-sodiumcitrate-dihydrate | 0.1 |
| 5 | Methylglycinediacetic acid | 0.1 |
| 6 | 1,2-Benzisothiazol-3(2H)-on | 0.1 |
| 7 | Fragrance | 0.1 |

TABLE 76-continued

All-purpose cleaner, alkaline

| No | Ingredients | Amount |
|---|---|---|
| 8 | 1,2-heptanediol | 0.5 |
| 9 | Aqua | add to 100 |

Colorless Liquid, pH 9

TABLE 77

Cleaner, liquid, citric acid

| No | Ingredients | Amount |
|---|---|---|
| 1 | Sulfonic acid, C 13-17-sec-Alkyl-, Sodium salt | 1 |
| 2 | Citric Acid | 5 |
| 3 | Xanthan Gum | 0.5 |
| 4 | 1,2-heptanediol | 0.5 |
| 5 | Fragrance | 0.3 |
| 6 | Tocopherol | 0.05 |
| 7 | Aqua | add 100 |

Liquid of Low Viscosity, pH 2

TABLE 78

Cleaner, liquid, citric acid

| No | Ingredient | Amount |
|---|---|---|
| 1 | Sulfonic acid, C 13-17-sec-Alkyl-, Sodium salt | 1 |
| 2 | Citric Acid | 5 |
| 3 | Xanthan Gum | 0.5 |
| 4 | 1,2-heptanediol/2,3 heptanediol 90:10 | 0.5 |
| 5 | Fragrance | 0.3 |
| 6 | Aqua | add 100 |

Liquid of Low Viscosity, pH 2

TABLE 79

Detergent liquid light duty

| No | Ingredients | Amount |
|---|---|---|
| 1 | Cocos fatty acid | 0.85 |
| 2 | potassium hydroxide | 0.45 |
| 3 | 2-octyl-2H-isothiazol-3-one | 0.2 |
| 4 | Sulfonic acid, C 13-17-sec-Alkyl-, Sodium salt | 20 |
| 5 | Sodium Laureth Sulfate | 3 |
| 6 | Trideceth-9 | 5 |
| 7 | Sodium Chloride | 1.3 |
| 8 | 2,3-octanediol | 0.1 |
| 9 | 1,2-heptanediol | 0.9 |
| 10 | Fragrance | 0.5 |
| 11 | Tocopherol | 0.1 |
| 12 | Aqua | add to 100 |

Liquid, pH 7.3

TABLE 80

Detergent liquid light duty

| No | Ingredients | Amount |
|---|---|---|
| 1 | Cocos fatty acid | 0.85 |
| 2 | potassium hydroxide | 0.45 |
| 3 | 2-octyl-2H-isothiazol-3-one | 0.2 |
| 4 | Sulfonic acid, C 13-17-sec-Alkyl-, Sodium salt | 20 |
| 5 | Sodium Laureth Sulfate | 3 |
| 6 | Trideceth-9 | 5 |
| 7 | Sodium Chloride | 1.3 |

TABLE 80-continued

Detergent liquid light duty

| No | Ingredients | Amount |
|----|-------------|--------|
| 8 | 2,3-heptanediol | 0.1 |
| 9 | 1,2-heptanediol | 0.9 |
| 10 | Fragrance | 0.5 |
| 11 | Aqua | add to 100 |

Liquid, pH 7.3

TABLE 81

Dishwash liquid manual

| No | Ingredients | Amount |
|----|-------------|--------|
| 1 | Sodium Laureth Sulfate | add 100 |
| 2 | Ethanol | 2.9 |
| 3 | lauramine oxide | 7.7 |
| 4 | propylene glycol | 1.9 |
| 5 | Phenoxyethanol | 0.1 |
| 6 | Benzisothiazolinone, Methylisothiazolinone, Laurylamine Dipropylenediamine | 0.1 |
| 7 | 1,2-heptanediol | 0.5 |
| 8 | sodium chloride | 3.85 |
| 9 | Tocopherol | 0.05 |
| 10 | Fragrance | 0.3 |

Colorless Liquid, pH 8.5

TABLE 82

Fabric softener

| No | Ingredients | Amount |
|----|-------------|--------|
| 1 | Di-(Talg Carboxyethyl) Hydroxyethyl methylammonium-methosulfat | 5.5 |
| 2 | Simethicone | 0.3 |
| 3 | 2-octyl-2H-isothiazol-3-one | 0.1 |
| 4 | 1,2-heptanediol | 0.5 |
| 5 | Fragrance | 0.2 |
| 6 | Tocopherol | 0.2 |
| 7 | Aqua | add 100 |

Liquid, pH 3

TABLE 83

Fabric softener concentrate, encapsulated

| No | Ingredients | Amount |
|----|-------------|--------|
| 1 | Di-(Talg Carboxyethyl) Hydroxyethyl methylammonium-methosulfat | 16.6 |
| 2 | 2-octyl-2H-isothiazol-3-one | 0.1 |
| 3 | Simethicone | 0.3 |
| 4 | magnesium chloride | 0.8 |
| 5 | encapsulated perfume oil | 0.3 |
| 6 | crosslinked cationic polymer | 0.15 |
| 7 | 1,2-heptanediol | 0.5 |
| 8 | Fragrance | 0.6 |
| 9 | Tocopherol | 0.2 |
| 10 | Aqua | add 100 |

White Liquid, pH 2.5

TABLE 84

Fabric softener concentrate, encapsulated

| No | Ingredients | Amount |
|----|-------------|--------|
| 1 | Di-(Talg Carboxyethyl) Hydroxyethyl methylammonium-methosulfat | 16.6 |
| 2 | 2-octyl-2H-isothiazol-3-one | 0.1 |
| 3 | Simethicone | 0.3 |
| 4 | magnesium chloride | 0.8 |
| 5 | encapsulated perfume oil | 0.3 |
| 6 | crosslinked cationic polymer | 0.15 |
| 7 | 2,3-heptanediol | 0.05 |
| 8 | 1,2-heptanediol | 0.5 |
| 9 | Fragrance | 0.6 |
| 10 | Tocopherol | 0.2 |
| 11 | Aqua | add 100 |

White Liquid, pH 2.5

TABLE 85

Hand soap, liquid

| No | Ingredients | Amount |
|----|-------------|--------|
| 1 | Sodium Laureth Sulfate | 18 |
| 2 | Cocoamidopropylbetaine | 6 |
| 3 | Cocamide DEA | 3 |
| 4 | citric acid | 0.5 |
| 5 | sodium chloride | 1.9 |
| 6 | Glycerol | 2 |
| 7 | Fragrance | 0.2 |
| 8 | 1,2-heptanediol | 0.25 |
| 9 | Tocopherol | 0.1 |
| 10 | Aqua | add 100 |

Slightly Colored Liquid, pH 6

TABLE 86

Rim block gel

| No | ingredients | Amount |
|----|-------------|--------|
| 1 | Sodium Laureth Sulfate | 11 |
| 2 | Trideceth-9 | 2 |
| 3 | Xanthan gum | 2 |
| 4 | Hydroxyethylcellulose | 0.5 |
| 5 | Citric Acid | 0.4 |
| 6 | Ethanol | 6 |
| 7 | Fragrance | 5 |
| 8 | 1,2-heptanediol | 0.5 |
| 9 | Aqua | add 100 |

Colorless Paste/Gel, pH=4.5

TABLE 87

Scent Lotion with capsules

| No | ingredients | Amount |
|----|-------------|--------|
| 1 | microcrystalline cellulose/cellulose gum | 1 |
| 2 | PEG-40 hydrogenated Castor oil/Trideceth-9 | 0.5 |
| 3 | encapsulated perfume oil | 1 |
| 4 | 2-octyl-2H-isothiazol-3-one | 0.1 |
| 5 | Fragrance | 5 |
| 6 | 1,2-heptanediol | 1 |
| 7 | Tocopherol | 0.15 |
| 8 | Aqua | add 100 |

White Emulsion, pH Neutral

TABLE 88

Cleaner, liquid, lactic acid

| No | ingredients | Amount |
|---|---|---|
| 1 | Sodium Laureth Sulfate | 1.8 |
| 2 | Trideceth-9 | 2.1 |
| 3 | Xanthan gum | 0.35 |
| 4 | Lactic Acid | 2.8 |
| 5 | 1,2-heptanediol | 1 |
| 6 | Fragrance | 0.3 |
| 7 | Hydroxyacetophenone | 0.3 |
| 8 | Aqua | add 100 |

Colorless Liquid, pH 2.0

TABLE 89

Cleaner, liquid, citric acid

| No | ingredients | Amount |
|---|---|---|
| 1 | Sulfonic acid, C 13-17-sec-Alkyl-, Sodium salt | 1 |
| 2 | Xanthan gum | 0-3 |
| 3 | citric acid | 5 |
| 4 | 1,2heptanediol | 0.25 |
| 5 | Fragrance | 0.3 |
| 6 | Aqua | add 100 |

Liquid, pH 2

The invention claimed is:

1. A cosmetic or pharmaceutical composition or homecare product, comprising:
   (a1) 1,2-heptanediol;
   (b1) at least one antioxidant; and
   (c1) optionally at least one active substance for a cosmetic or pharmaceutical composition or homecare product and/or additive;
   wherein the at least one antioxidant is selected e group consisting of arbutin, amino acids and their derivatives, tert-butylhydroquinone, caffeic acid, chlorogenic acid, imidazoles and their derivatives, cannabidiol and its extracts, kojic acid, peptides, hydroxyphenyl propamidobenzoic acid (dihydroavenanthramide D), diethylhexyl syringylidene malonate, phenylethyl resorcinol, gallic acid and their derivatives, quercetin, hydroxyacetophenone, rosmarinic acid, carotenoids, carotenes, phytoene, phytofluene and their derivatives, lipoic acid and its derivatives, aurothioglucose, propylthiouracil and other thiols and their salts dilauryl thiodipropionate pentaerythrityl tetra-di-t-butyl hydroxyhydrocinnamate, distearyl thiodipropionate, thiodipropionic acid and their derivatives as well as sulphoximine compounds, Lactobacillus, chelating agents and their derivatives, unsaturated fatty acids and their derivatives, folic acid and its derivatives, ubiquinone and ubiquinol and their derivatives, triethyl citrate, tocopherols and their derivatives, dexpanthenol, Vitamin A and its derivatives coniferyl benzoate of benzoin resin, rutinic acid and its derivatives, ferrulic acid and its derivatives, butylhydroxytoluene, butylhydroxyanisole hydroxymethoxyphenyl decanone, nordihydroguaiacic acid, nordihydroguaiaretic acid, allantoin, tropolone, trihydroxybutyrophenone, uric acid and its derivatives, urea, mannose and its derivatives, hydroxy acetophenone (ortho/para), zinc and its derivatives, beta-aspartyl arginine, selenium and its derivatives, Vitis Vinifera (Grape) seed extract, oat extract, Cichorium intubybus (chicory) leaf extract, Leon-topodium Alpinum extract, green tea extract, Curcumin Zingiber officinalis Extract, Silymarin, stilbenes and their derivatives, derivatives of said antioxidants, and mixtures of two or more of said antioxidants.

2. The cosmetic or pharmaceutical composition or homecare product according to claim 1, wherein the at least one active substance for a cosmetic or pharmaceutical composition or homecare product and/or additive is selected from the group consisting of agents against ageing of the skin, anti-microbial agents, antioxidants, chelating agents, emulsifiers, surfactants, preservatives, green and synthetic polymers, skin-cooling agents, rheology additives, oils, fragrances or perfume oils, polyols, and mixtures of two or more of the aforementioned substances.

3. The cosmetic or pharmaceutical composition or homecare product according to claim 1, comprising the 1,2-heptanediol in an amount of 0.001 to 15.0% by weight based on the total weight of the composition or homecare product.

4. The cosmetic or pharmaceutical composition or homecare product according to claim 1, comprising the at least one antioxidant in an amount of 0.0001 to 10.0% by weight, based on the total weight of the composition.

5. The cosmetic or pharmaceutical composition or homecare product according to claim 1, wherein
   the composition or homecare product is a dispersion comprising an oil component in an amount of ≥1% by weight, and wherein the composition or homecare product is in the form of an emulsion, a liquid, a lotion, as suspension, a milk, an ointment, a paste, a gel, a cream based formulation, an oil based formulation or a liposome-based formulation; or
   the composition or homecare product is a water free oil formulation; or
   the composition or homecare product is a liquid surfactant formulation; or
   the composition or homecare product is a solid surfactant formulation; or
   the composition or homecare product is an aqueous or aqueous/alcoholic or aqueous/glycolic based solution, comprising the alcohol or glycol in an amount of 0.1% to ≤50% by weight, based on the total weight of the solution.

6. A method of enhancing an effect of an antioxidant in a cosmetic or pharmaceutical composition or homecare product, comprising formulating the composition or homecare product as a composition or homecare product according to claim 1, wherein the effect is scavenging reactive oxygen species (ROS); inhibiting interleukin 8 (IL-8) secretion, inhibiting matrix metalloproteinases expression, the antioxidative effect, the antioxidative effect upon application, or a combination thereof.

7. A method of treating a dermatological or keratological disease in a patient in need thereof, comprising administering a therapeutically effective amount of the pharmaceutical composition of claim 1.

8. The method of claim 7, wherein the dermatological or keratological disease is selected from the group consisting of atopic dermatitis, psoriasis, acneiform exanthema, sebostasis, xerosis, eczema, hyper seborrhea and hypo seborrhea, dermatitis, rosacea, wheals, erythema, pruritus, inflammation, irritation, fibrosis, lichen planus, Pityriasis rosea, Pityriasis versicolor, autoimmune bullous diseases, urticaria, angioedema, allergic skin reactions, and inflammatory diseases.

* * * * *